(12) United States Patent
Kadoma et al.

(10) Patent No.: US 8,859,108 B2
(45) Date of Patent: Oct. 14, 2014

(54) BENZOXAZOLE DERIVATIVE, AND LIGHT-EMITTING ELEMENT, LIGHT-EMITTING DEVICE, AND ELECTRONIC DEVICE USING THE SAME

(75) Inventors: Hiroshi Kadoma, Kanagawa (JP); Sachiko Kawakami, Kanagawa (JP); Takahiro Ushikubo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 651 days.

(21) Appl. No.: 12/466,116

(22) Filed: May 14, 2009

(65) Prior Publication Data
US 2009/0286985 A1 Nov. 19, 2009

(30) Foreign Application Priority Data
May 16, 2008 (JP) .................................. 2008-129146

(51) Int. Cl.
*C07D 413/10* (2006.01)
*C07D 263/56* (2006.01)
*H01L 51/54* (2006.01)
*C07D 263/57* (2006.01)

(52) U.S. Cl.
CPC ............ *C07D 263/57* (2013.01); *C07D 413/10* (2013.01); *Y10S 428/917* (2013.01)
USPC ........... 428/690; 428/917; 313/504; 313/506; 546/173; 546/271.7; 548/224

(58) Field of Classification Search
None
See application file for complete search history.

(56) References Cited

U.S. PATENT DOCUMENTS

| | | | |
|---|---|---|---|
| 6,908,695 B2 | 6/2005 | Seo et al. | |
| 6,984,462 B2 * | 1/2006 | Kim et al. | ..................... 428/690 |
| 6,998,487 B2 * | 2/2006 | Kim et al. | ....................... 546/15 |
| 7,221,095 B2 | 5/2007 | Yamazaki et al. | |
| 7,332,857 B2 | 2/2008 | Seo et al. | |
| 7,541,099 B2 | 6/2009 | Yamagata et al. | |
| 7,598,666 B2 | 10/2009 | Hamada et al. | |
| 7,965,032 B2 | 6/2011 | Bae et al. | |
| 2002/0139303 A1 | 10/2002 | Yamazaki et al. | |

(Continued)

FOREIGN PATENT DOCUMENTS

| | | |
|---|---|---|
| EP | 1405893 A | 4/2004 |
| EP | 1645552 A | 4/2006 |
| EP | 2364964 A | 9/2011 |
| JP | 2003-055652 A | 2/2003 |
| JP | 2003-217856 A | 7/2003 |
| JP | 2004-529937 | 9/2004 |
| JP | 2009-529035 | 8/2009 |
| WO | WO-02/088274 | 11/2002 |
| WO | WO-2007/102683 | 9/2007 |

OTHER PUBLICATIONS

Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID 04 Digest: SID International Symposium Digest of Technical Papers, vol. 35, Book 2, May 2004, pp. 900-903.

*Primary Examiner* — Dawn L. Garrett
(74) *Attorney, Agent, or Firm* — Husch Blackwell LLP

(57) ABSTRACT

An object is to provide a novel benzoxazole derivative. Another object is to reduce driving voltage of a light-emitting element. Still another object is to reduce power consumption of a light-emitting element, a light-emitting device, and an electronic device. A benzoxazole derivative represented by General Formula (G1) is provided. The benzoxazole derivative represented by General Formula (G1) has an electron-injecting property and an electron-transporting property; accordingly, it can be favorably used for a light-emitting element, a light-emitting device, and an electronic device.

12 Claims, 73 Drawing Sheets

(56) References Cited

U.S. PATENT DOCUMENTS

| | | |
|---|---|---|
| 2003/0010288 A1 | 1/2003 | Yamazaki et al. |
| 2003/0143430 A1 | 7/2003 | Kawamura et al. |
| 2005/0260442 A1 | 11/2005 | Yu et al. |
| 2007/0049760 A1 | 3/2007 | Kawakami et al. |
| 2007/0205412 A1 | 9/2007 | Bae et al. |
| 2008/0093981 A1 | 4/2008 | Nakamura et al. |
| 2009/0072712 A1* | 3/2009 | Stoessel et al. ............... 313/504 |
| 2009/0146139 A1 | 6/2009 | Stoessel et al. |
| 2009/0267498 A1 | 10/2009 | Kawakami et al. |
| 2011/0127510 A1* | 6/2011 | Seo et al. ........................ 257/40 |

* cited by examiner

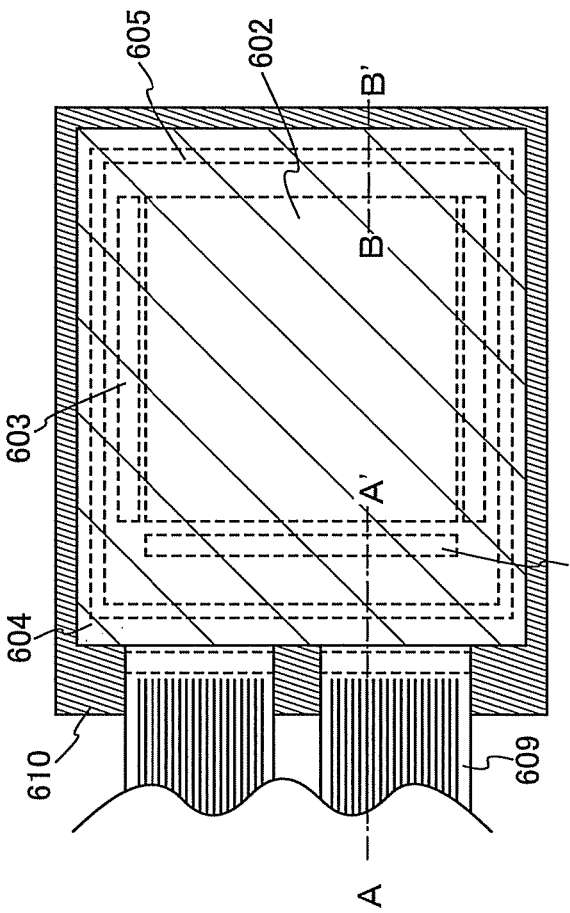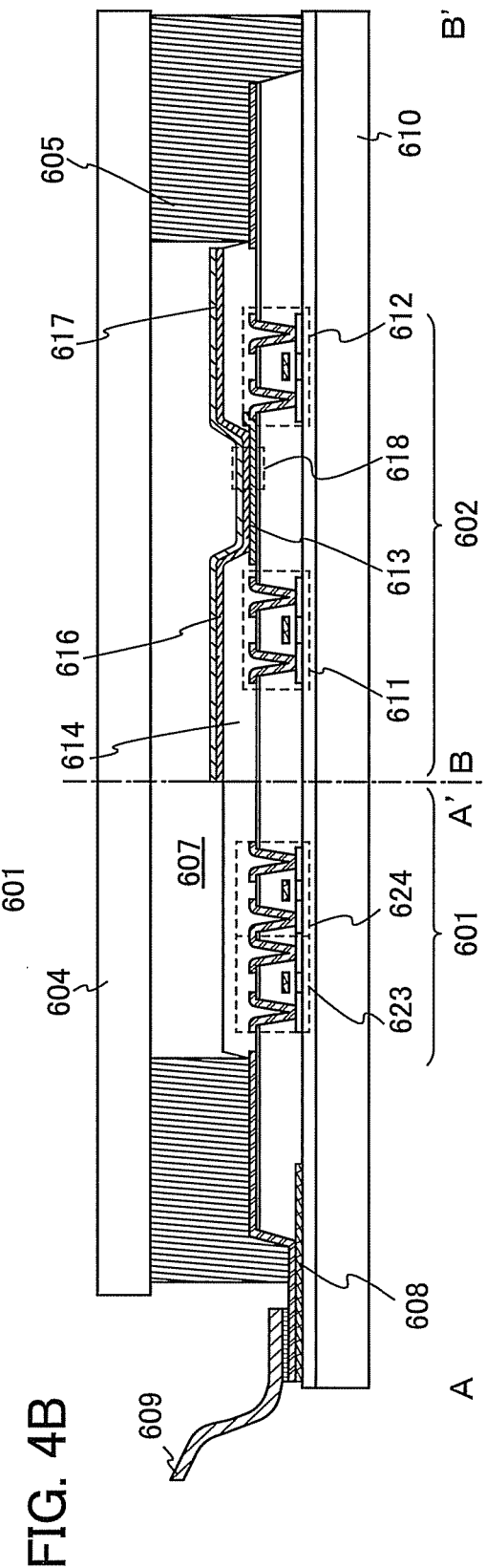
FIG. 4A
FIG. 4B

BENZOXAZOLE DERIVATIVE, AND LIGHT-EMITTING ELEMENT, LIGHT-EMITTING DEVICE, AND ELECTRONIC DEVICE USING THE SAME

BACKGROUND OF THE INVENTION

1. Field of the Invention

The present invention relates to benzoxazole derivatives. In addition, the present invention relates to light-emitting elements, light-emitting devices, and electronic devices using the benzoxazole derivatives.

2. Description of the Related Art

An organic compound can take various structures compared with an inorganic compound, and it is possible to synthesize a material having various functions by appropriate molecular-design of an organic compound. Owing to these advantages, photo electronics and electronics which use a functional organic material have been attracting attention in recent years.

For example, a solar cell, a light-emitting element, an organic transistor, and the like are exemplified as an electronic device which utilizes an organic compound as a functional material. These are devices taking advantage of electric properties and optical properties of the organic compound. Among them, in particular, a light-emitting element has been making remarkable development.

It is considered that the light emission mechanism of a light-emitting element is as follows: when a voltage is applied between a pair of electrodes which interpose a light-emitting layer, electrons injected from a cathode and holes injected from an anode are recombined in the emission center of the light-emitting layer to form a molecular exciton, and energy is released to emit light when the molecular exciton relaxes to the ground state. An excited singlet state and an excited triplet state are known as an excited state, and it is considered that light can be emitted through either state.

In an attempt to improve performance of such a light-emitting element, there are many problems which depend on the material, and in order to solve these problems, improvement of element structure, development of a material, and the like have been carried out.

For example, as an electron-transporting material for light-emitting elements, tris(8-quinolinolato)aluminum(III) (abbrev.: Alq) is widely used (see Non-Patent Document 1). However, in the case of using Alq for a light-emitting element, there is a problem in that driving voltage is high. In particular, in view of commercialization, less power consumption is an important issue, and various researches and developments for a material and a light-emitting element with more superior characteristics have been carried out (see Patent Document 1, for example).

[Patent Document 1] United States Published Patent Application No. 2007/0205412

[Non-Patent Document 1] Taishi TSUJI and five others, SID 04 DIGEST, 35, PP. 900-903 (2004)

SUMMARY OF THE INVENTION

In view of the aforementioned problems, it is an object of one embodiment of the present invention to provide a novel electron-transporting material.

Further, it is an object of one embodiment of the present invention to provide a light-emitting element, a light-emitting device, and an electronic device that use a novel electron-transporting material.

It is another object of one embodiment of the present invention to reduce driving voltage of a light-emitting element. Further, it is an object of one embodiment of the present invention to improve emission efficiency of a light-emitting element. In addition, it is still another object of one embodiment of the present invention to reduce power consumption of a light-emitting element, a light-emitting device, and an electronic device.

One embodiment of the present invention is a benzoxazole derivative represented by General Formula (G1).

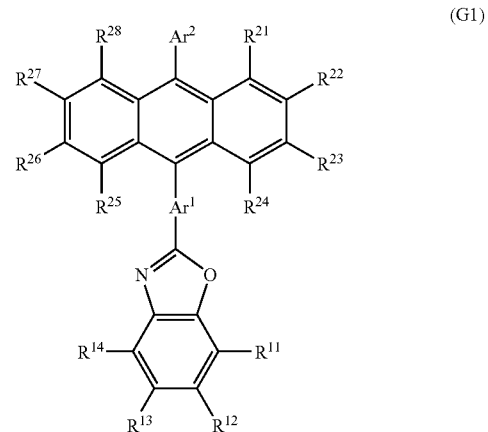

(G1)

In the formula, $Ar^1$ is a substituted or unsubstituted arylene group having 6 to 13 carbon atoms, $Ar^2$ is a substituted or unsubstituted aryl group having 6 to 13 carbon atoms or a substituted or unsubstituted heteroaryl group having 4 to 9 carbon atoms which is composed of a six-membered ring, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and $R^{21}$ to $R^{28}$ are independently either hydrogen or an alkyl group having 1 to 4 carbon atoms.

Another embodiment of the present invention is a benzoxazole derivative represented by General Formula (G2).

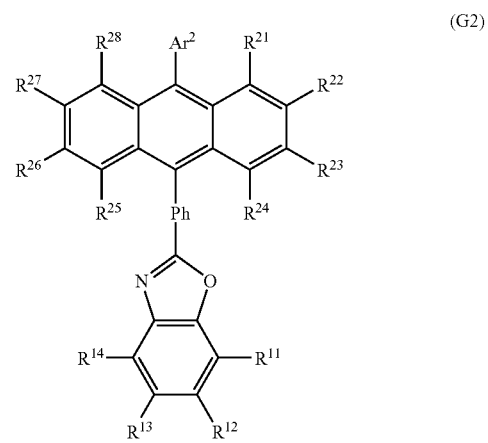

(G2)

In the formula, Ph is a substituted or unsubstituted phenylene group, $Ar^2$ is a substituted or unsubstituted aryl group having 6 to 13 carbon atoms or a substituted or unsubstituted heteroaryl group having 4 to 9 carbon atoms which is composed of a six-membered ring, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and $R^{21}$ to $R^{28}$ are independently either hydrogen or an alkyl group having 1 to 4 carbon atoms.

Further, another embodiment of the present invention is a benzoxazole derivative represented by General Formula (G3).

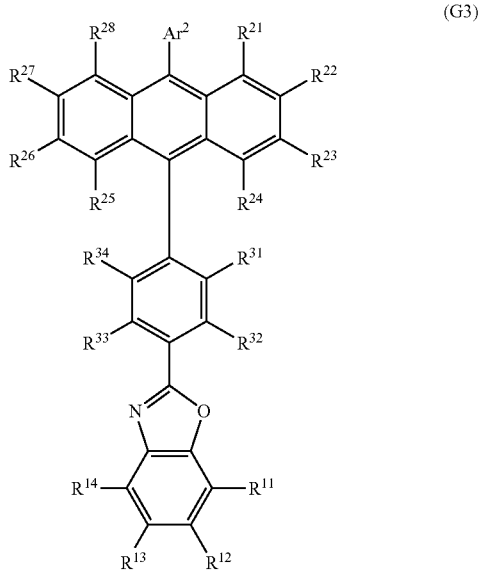

In the formula, $Ar^2$ is a substituted or unsubstituted aryl group having 6 to 13 carbon atoms or a substituted or unsubstituted heteroaryl group having 4 to 9 carbon atoms which is composed of a six-membered ring, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, $R^{21}$ to $R^{28}$ are independently either hydrogen or an alkyl group having 1 to 4 carbon atoms, and $R^{31}$ to $R^{34}$ are independently any of hydrogen, an alkyl group having 1 to 4 carbon atoms, and a substituted or unsubstituted aryl group having 6 to 10 carbon atoms.

Furthermore, another embodiment of the present invention is a benzoxazole derivative represented by General Formula (G4).

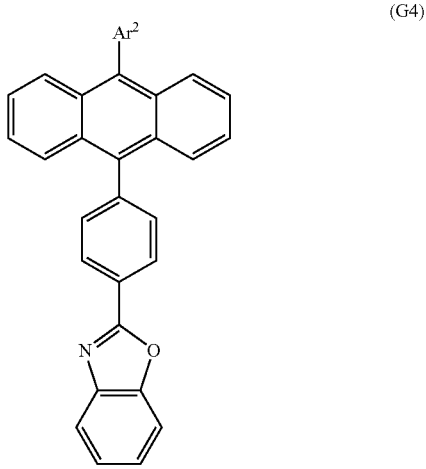

In the formula, $Ar^2$ is a substituted or unsubstituted aryl group having 6 to 13 carbon atoms or a substituted or unsubstituted heteroaryl group having 4 to 9 carbon atoms which is composed of a six-membered ring.

In any of the above-described structures, $Ar^2$ is preferably any of a substituted or unsubstituted phenyl group, a substituted or unsubstituted pyridyl group, a substituted or unsubstituted quinolyl group, a substituted or unsubstituted pyrimidinyl group, a substituted or unsubstituted pyrazinyl group, a substituted or unsubstituted naphthyl group, and a substituted or unsubstituted isoquinolyl group.

The above-described benzoxazole derivatives can be favorably used in light-emitting elements.

Thus, one embodiment of the present invention is a light-emitting element including any of the benzoxazole derivatives described above between a pair of electrodes.

The benzoxazole derivatives described above are superior in an electron-transporting property; thus, it is particularly preferable to use the benzoxazole derivatives for electron-transporting layers.

Therefore, another embodiment of the present invention is a light-emitting element having a light-emitting layer and a layer including any of the above-described benzoxazole derivatives between an anode and a cathode. The layer including any of the above-described benzoxazole derivatives is provided between the light-emitting layer and the cathode.

Moreover, the present invention includes light-emitting devices each having the above-described light-emitting element.

Thus, one embodiment of the present invention is a light-emitting device which includes a light-emitting element including any of the benzoxazole derivatives described above and a control circuit which controls light emission of the light-emitting element.

Note that the light-emitting device in this specification includes an image display device, a light-emitting device, or a light source (including a lighting device). Further, the following are all included in the category of a light-emitting device: a module in which a connector, for example, an FPC (flexible printed circuit), a TAB (tape automated bonding) tape, or a TCP (tape carrier package) is attached to a panel provided with a light-emitting element; a module provided with a printed wiring board at the end of the TAB tape or the TCP; and a module in which an IC (integrated circuit) is directly mounted on a light-emitting element by a COG (chip on glass) method.

Further, an electronic device using a light-emitting element of the present invention in a display portion is also included in the scope of the present invention. Accordingly, an embodiment of the present invention is an electronic device which includes a display portion provided with the above-described light-emitting element and a control circuit which controls light emission of the light-emitting element.

Benzoxazole derivatives of the present invention are excellent in an electron-transporting property. Therefore, they can be favorably used in light-emitting elements.

In addition, by using benzoxazole derivatives of the present invention for light-emitting elements, light-emitting elements with low driving voltage can be obtained. In addition, by using the benzoxazole derivatives of the present invention for light-emitting elements, light-emitting elements with high emission efficiency can be obtained. In addition, light-emitting elements with low power consumption can be obtained.

Further, by applying light-emitting elements of the present invention to light-emitting devices and electronic devices, light-emitting devices and electronic devices having low power consumption can be obtained.

BRIEF DESCRIPTION OF THE DRAWINGS

In the accompanying drawings:

FIGS. 4A and 4B illustrate a light-emitting device according to an embodiment of the present invention;

DETAILED DESCRIPTION OF THE INVENTION

Figure 1:
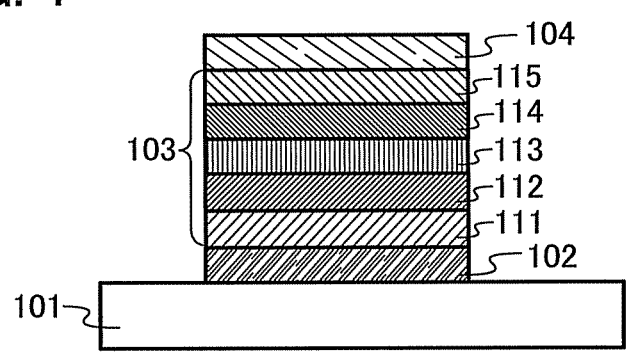
FIG. 1 illustrates a light-emitting element according to an embodiment of the present invention.

Hereinafter, embodiments of the present invention will be described in detail with reference to the accompanying drawings. However, the present invention is not limited to the following description, and various changes and modifications for the modes and details thereof will be apparent to those skilled in the art unless such changes and modifications depart from the spirit and scope of the present invention. Therefore, the present invention should not be interpreted as being limited to what is described in the embodiments below.

Embodiment 1

In Embodiment 1, benzoxazole derivatives of the present invention will be described. Each of the benzoxazole derivatives of the present invention includes an anthracene skeleton and a benzoxazole skeleton in its molecule.

More specifically, one benzoxazole derivative according to the present invention is a benzoxazole derivative represented by General Formula (G1).

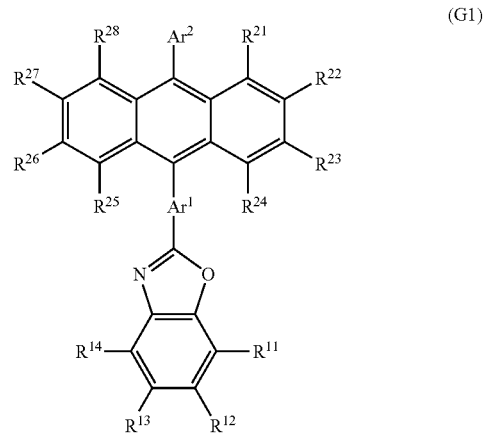

(G1)

In the formula, $Ar^1$ is a substituted or unsubstituted arylene group having 6 to 13 carbon atoms, $Ar^2$ is a substituted or unsubstituted aryl group having 6 to 13 carbon atoms or a substituted or unsubstituted heteroaryl group having 4 to 9 carbon atoms which is composed of a six-membered ring, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and $R^{21}$ to $R^{28}$ are independently either hydrogen or an alkyl group having 1 to 4 carbon atoms.

Note that the carbon atoms of an aryl group, a heteroaryl group, or an arylene group described in this specification represent carbon atoms which form a ring of the main skeleton, and carbon atoms of a substituent bonded to the main skeleton are not included therein. As a substituent bonded to an aryl group, a heteroaryl group, or an arylene group, an alkyl group having 1 to 4 carbon atoms or an aryl group having 6 to 13 carbon atoms can be given. Specifically, a methyl group, an ethyl group, a propyl group, a butyl group, a phenyl group, a naphthyl group, a fluorenyl group, or the like can be given. Further, the number of substituents that an aryl group, a heteroaryl group, or an arylene group has may be either one or more than one. In the case where the aryl group, the heteroaryl group, or the arylene group has two substituents, the substituents may be bonded to each other to form a ring. For example, when the aryl group is a fluorenyl group, carbon at a 9-position may have two phenyl groups, and the two phenyl groups may be bound to each other to form a spiro ring structure.

In General Formula (G1), for example, aryl groups represented by Structural Formulae (11-1) to (11-19), heteroaryl groups represented by Structural Formulae (12-1) to (12-38), and the like can be given as the substituted or unsubstituted aryl group having 6 to 13 carbon atoms or the substituted or unsubstituted heteroaryl group having 4 to 9 carbon atoms which is composed of a six-membered ring represented by $Ar^2$. As shown in Structural Formulae (11-2) to (11-8), Structural Formulae (11-11) to (11-19), and Structural Formulae (12-34) to (12-38), the substituent represented by $Ar^2$ may further have a substituent. Further, as shown in Structural Formulae (11-17) to (11-19), one carbon may have two substituents. As shown in Structural Formula (11-18), the two substituents may be bonded to each other to form a spiro ring structure.

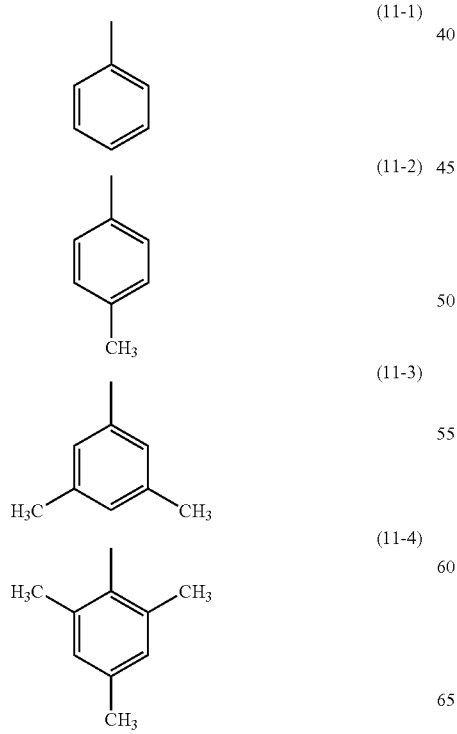

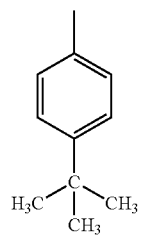 (11-5)

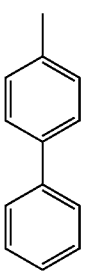 (11-6)

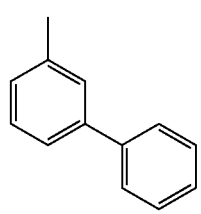 (11-7)

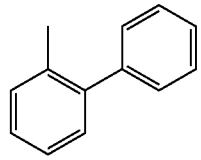 (11-8)

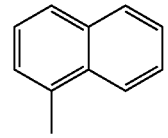 (11-9)

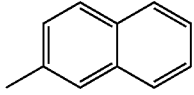 (11-10)

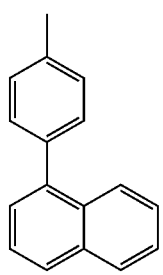 (11-11)

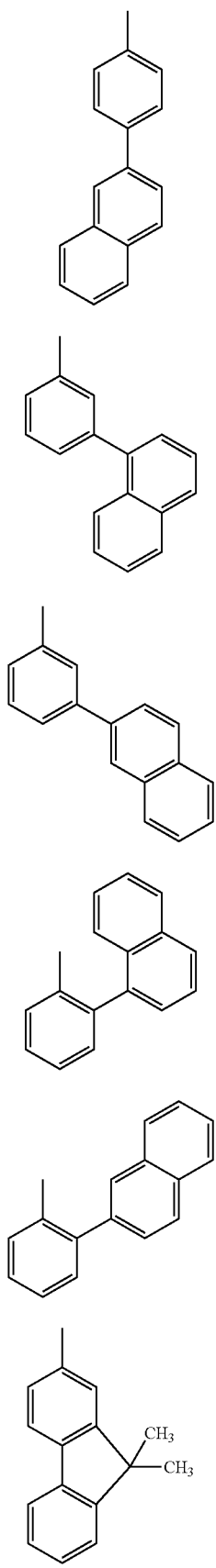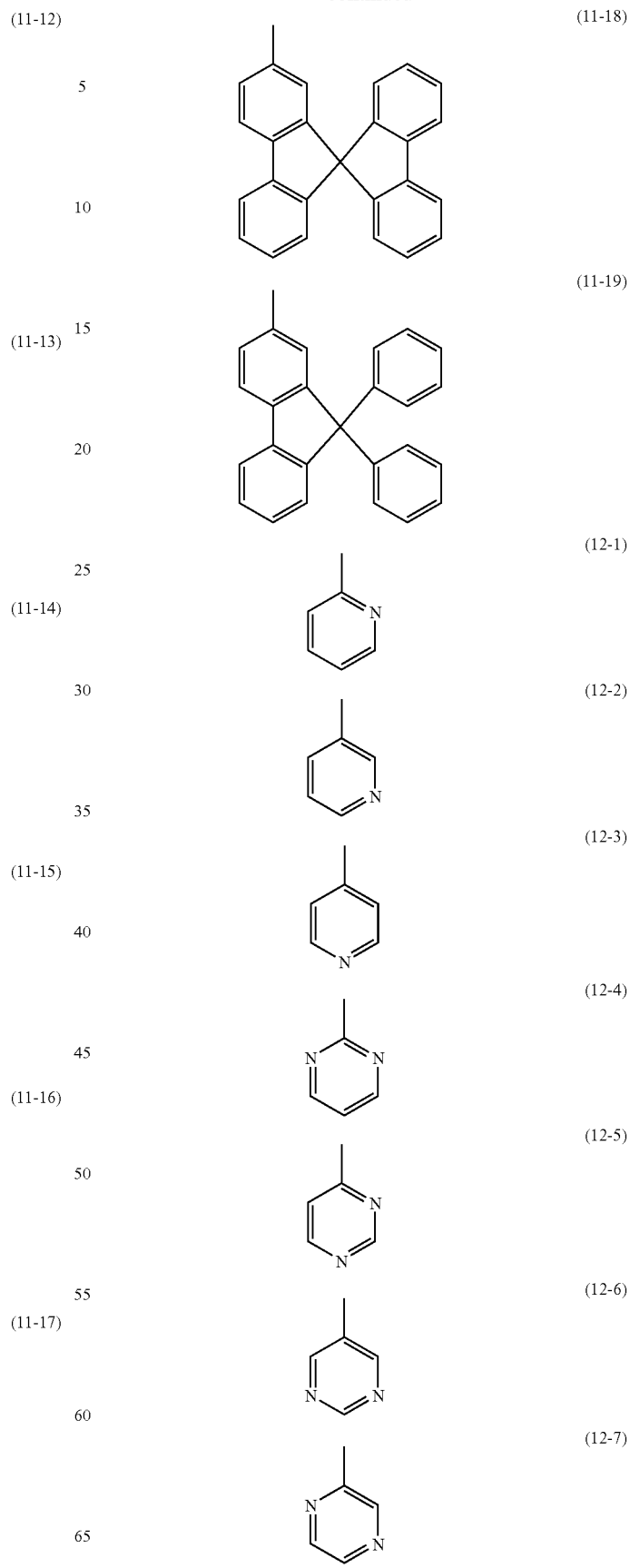

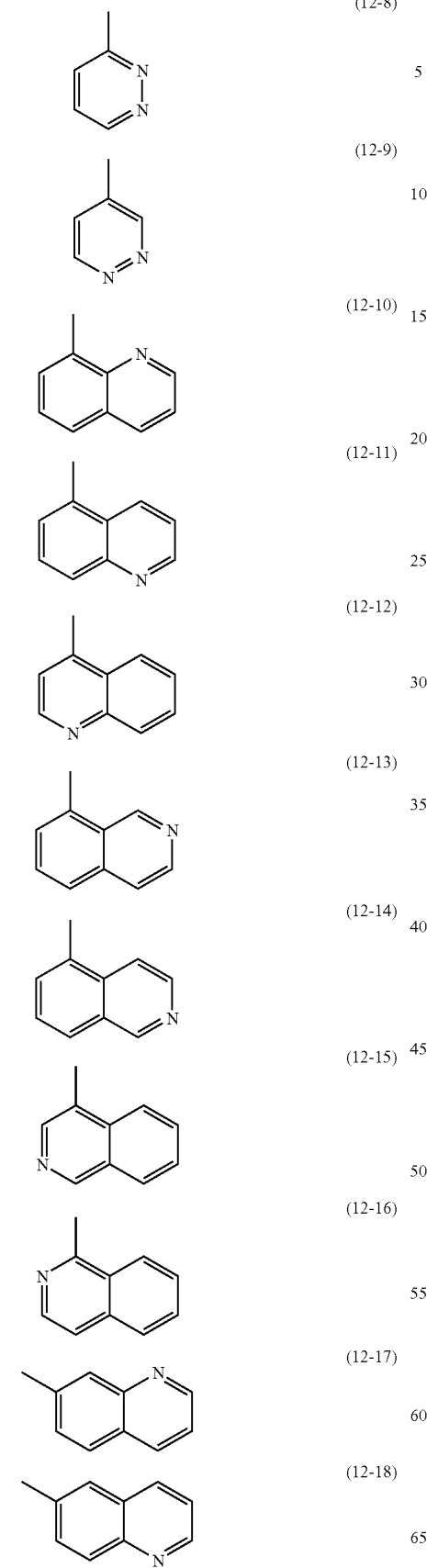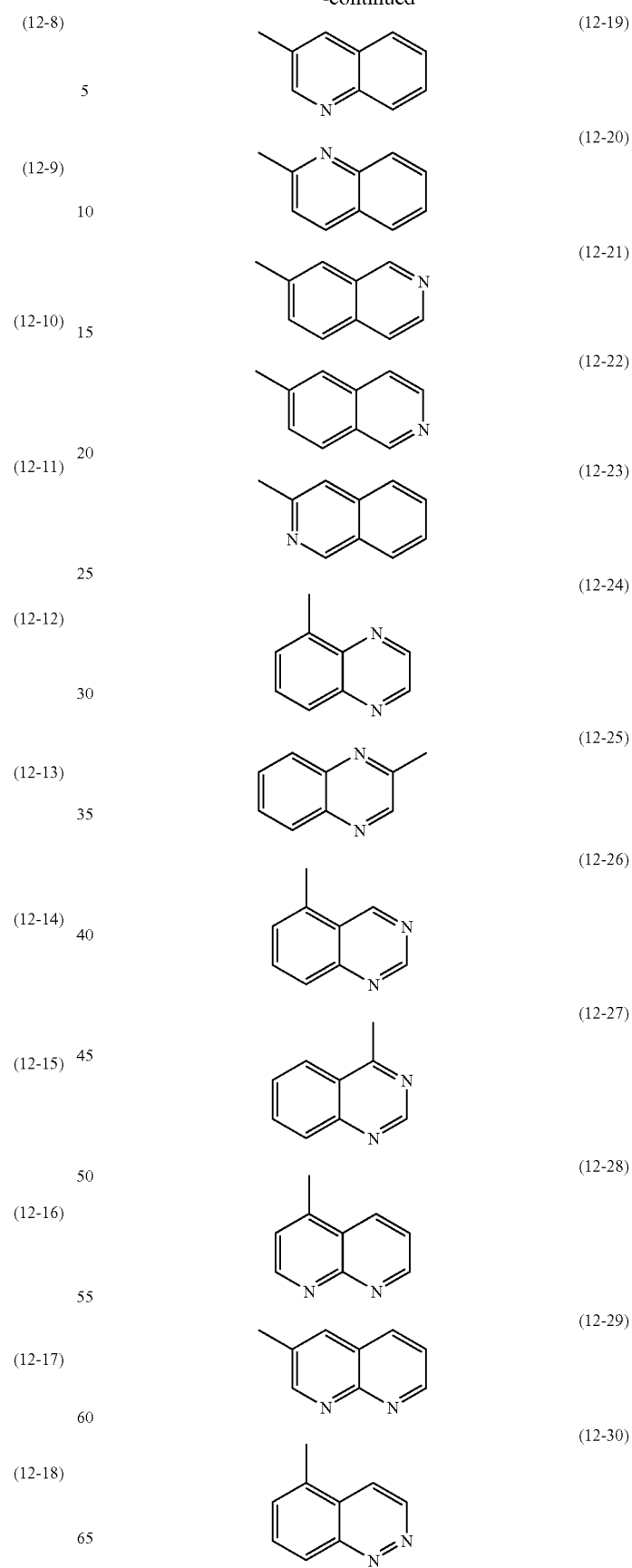

(12-31) 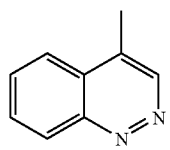
(12-32) 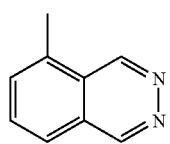
(12-33) 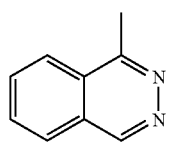
(12-34) 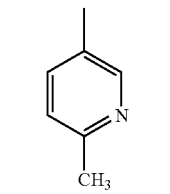
(12-35) 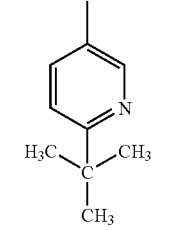
(12-36) 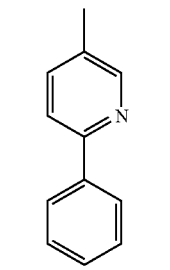
(12-37) 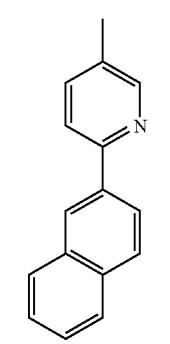
(12-38) 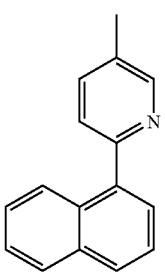
In addition, in General Formula (G1), for example, substituents represented by Structural Formulae (13-1) to (13-21) and the like can be given as hydrogen, the alkyl group having 1 to 4 carbon atoms, the haloalkyl group having 1 to 4 carbon atoms, the substituted or unsubstituted aryl group having 6 to 13 carbon atoms, or the halogen which is represented by $R^{11}$ to $R^{14}$.
(13-1) H
(13-2) $CH_3$
(13-3) 
(13-4) 
(13-5) 
(13-6) 
(13-7) 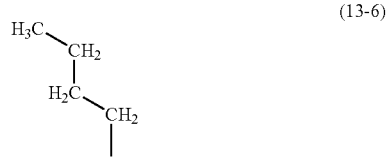
(13-8) 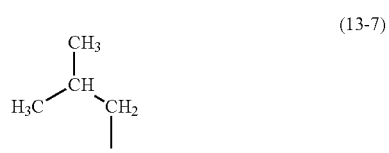
(13-9) 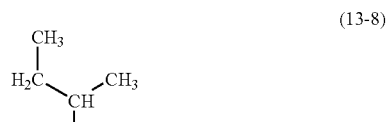
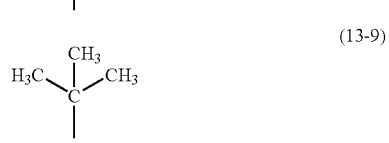

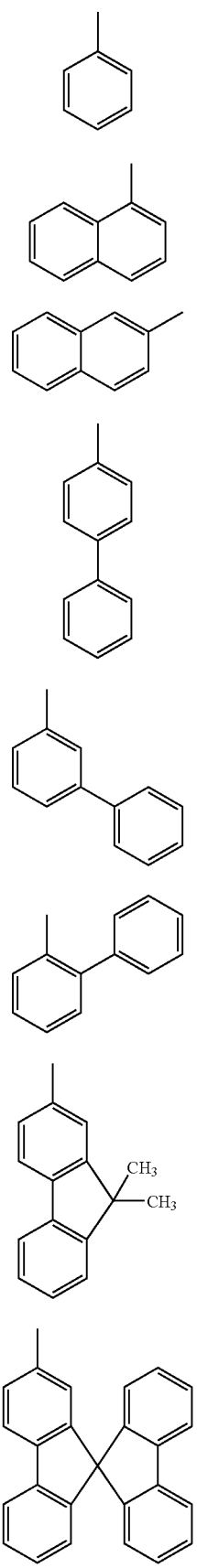
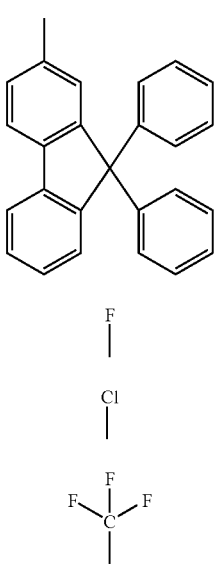
Further, in General Formula (G1), for example, substituents represented by Structural Formulae (14-1) to (14-9) and the like can be given as hydrogen or the alkyl group having 1 to 4 carbon atoms which is represented by $R^{21}$ to $R^{28}$.

(14-9)
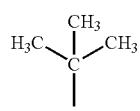
Further, in General Formula (G1), for example, arylene groups represented by Structural Formulae (15-1) to (15-21) can be given as the substituted or unsubstituted arylene group having 6 to 13 carbon atoms which is represented by $Ar^1$. As shown in Structural Formulae (15-7) to (15-17) and Structural Formulae (15-19) to (15-21), the arylene group represented by $Ar^1$ may have a substituent.
(15-1)
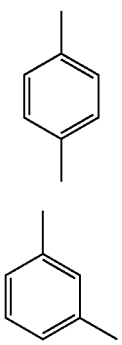
(15-2)
(15-3)
(15-4)
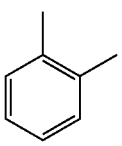
(15-5)
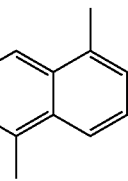
(15-6)
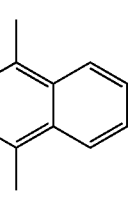
(15-7)
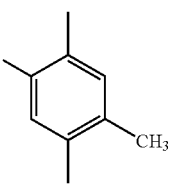
(15-8)
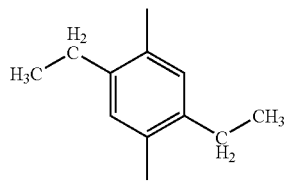
(15-9)
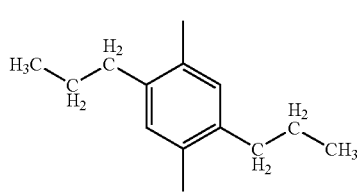
(15-10)
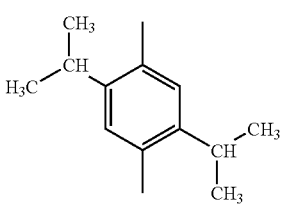
(15-11)
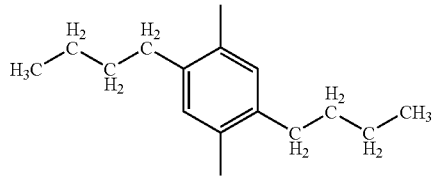
(15-12)
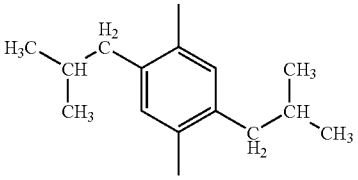
(15-13)
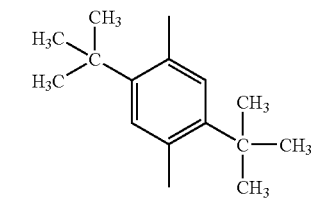
(15-14)
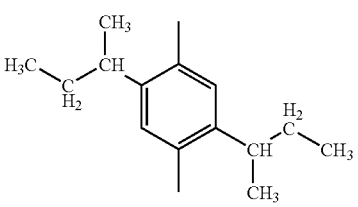
(15-15)
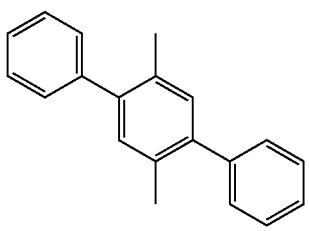

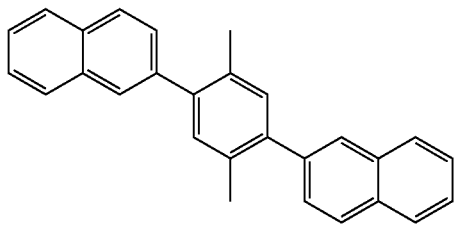
(15-16)

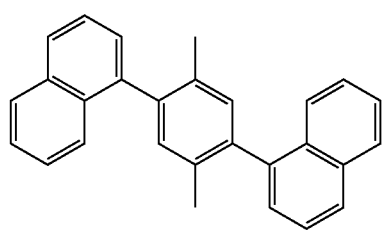
(15-17)

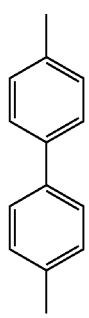
(15-18)

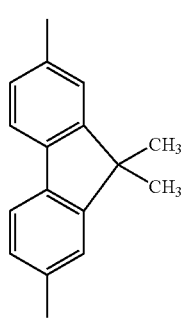
(15-19)

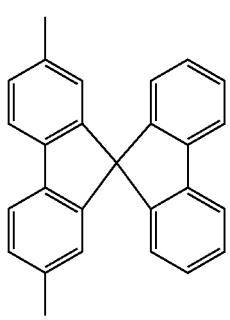
(15-20)

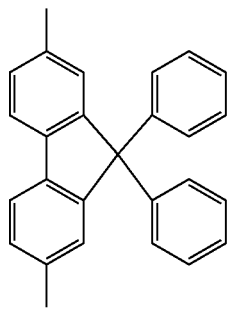
(15-21)

In particular, $Ar^1$ in the benzoxazole derivative represented by General Formula (G1) is preferably a substituted or unsubstituted phenylene group. Specifically, $Ar^1$ is preferably any of a substituted or unsubstituted 1,2-phenylene group, a substituted or unsubstituted 1,3-phenylene group, and a substituted or unsubstituted 1,4-phenylene group. When $Ar^1$ is a substituted or unsubstituted phenylene group, synthesis or refinement (high purification) can be facilitated.

In other words, one benzoxazole derivative according to the present invention is a benzoxazole derivative represented by General Formula (G2).

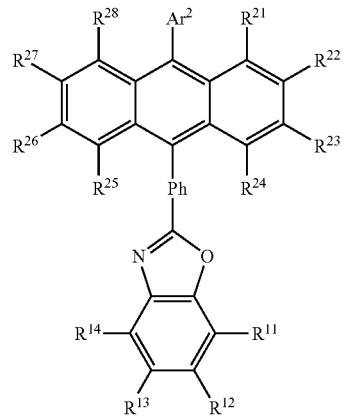
(G2)

In the formula, Ph is a substituted or unsubstituted phenylene group, $Ar^2$ is a substituted or unsubstituted aryl group having 6 to 13 carbon atoms or a substituted or unsubstituted heteroaryl group having 4 to 9 carbon atoms which is composed of a six-membered ring, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and $R^{21}$ to $R^{28}$ are independently either hydrogen or an alkyl group having 1 to 4 carbon atoms.

In the benzoxazole derivative represented by General Formula (G1) and the benzoxazole derivative represented by General Formula (G2), $Ar^1$ is preferably a substituted or unsubstituted 1,4-phenylene group in terms of synthesis or refinement (high purification) easiness.

In other words, one benzoxazole derivative according to the present invention is a benzoxazole derivative represented by General Formula (G3).

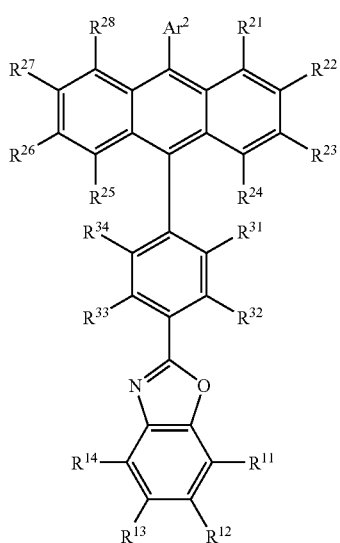
(G3)

In the formula, Ar² is a substituted or unsubstituted aryl group having 6 to 13 carbon atoms or a substituted or unsubstituted heteroaryl group having 4 to 9 carbon atoms which is composed of a six-membered ring, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, $R^{21}$ to $R^{28}$ are independently either hydrogen or an alkyl group having 1 to 4 carbon atoms, and $R^{31}$ to $R^{34}$ are independently any of hydrogen, an alkyl group having 1 to 4 carbon atoms, and a substituted or unsubstituted aryl group having 6 to 10 carbon atoms.

In General Formula (G3), for example, substituents represented by Structural Formulae (16-1) to (16-9) and the like can be given as hydrogen or the alkyl group having 1 to 4 carbon atoms which is represented by $R^{31}$ to $R^{34}$.

(16-1)
H (16-2)
CH₃

(16-3)
H₃C—CH₂

(16-4)
H₂C—CH₂
    |
    CH₃

(16-5)
H₃C     CH₃
    \CH/

(16-6)
H₃C—CH₂
      |
      H₂C—CH₂

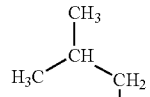
(16-7)

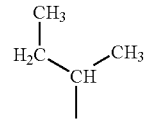
(16-8)

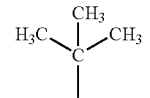
(16-9)

In the benzoxazole derivatives represented by General Formula (G1) to (G3), Ar¹ is preferably an unsubstituted 1,4-phenylene group in terms of synthesis or refinement (high purification) easiness. Further, $R^{11}$ to $R^{14}$, $R^{21}$ to $R^{28}$, and $R^{31}$ to $R^{34}$ are preferably hydrogen in terms of synthesis or refinement (high purification) easiness.

Accordingly, one benzoxazole derivative according to the present invention is a benzoxazole derivative represented by General Formula (G4).

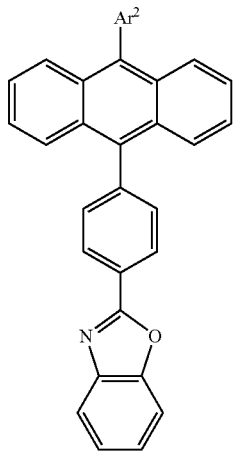
(G4)

In the formula, Ar² is a substituted or unsubstituted aryl group having 6 to 13 carbon atoms or a substituted or unsubstituted heteroaryl group having 4 to 9 carbon atoms which is composed of a six-membered ring.

In the benzoxazole derivatives represented by General Formula (G1) to (G4), Ar² may be a substituted or unsubstituted phenyl group, a substituted or unsubstituted pyridyl group, a substituted or unsubstituted quinolyl group, a substituted or unsubstituted pyrimidinyl group, a substituted or unsubstituted pyrazinyl group, or a substituted or unsubstituted naphthyl group, a substituted or unsubstituted isoquinolyl group, a substituted or unsubstituted quinoxalyl group, a substituted or unsubstituted fluorenyl group, or the like. Among them, any of a substituted or unsubstituted phenyl group, a substituted or unsubstituted pyridyl group, a substituted or unsubstituted quinolyl group, a substituted or unsubstituted pyrimidinyl group, a substituted or unsubstituted pyrazinyl group, a substituted or unsubstituted naphthyl group, and a substituted or unsubstituted isoquinolyl group is preferable in terms of synthesis or refinement (high purification) easiness and material cost.

As the benzoxazole derivative represented by General Formula (G1), benzoxazole derivatives represented by Structural Formulae (101) to (233) can be given, for example. However, the present invention is not limited to the derivatives represented by these structural formulae.

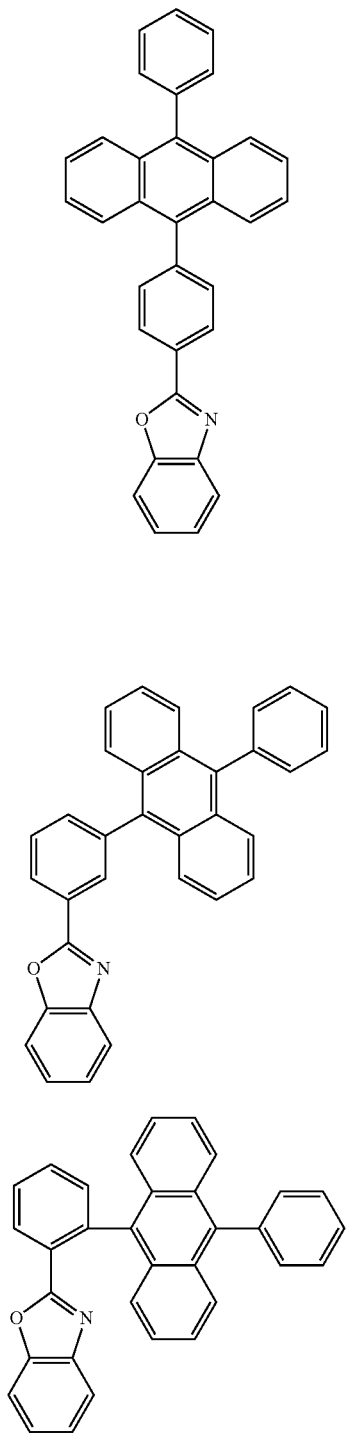

(101)

(102)

(103)

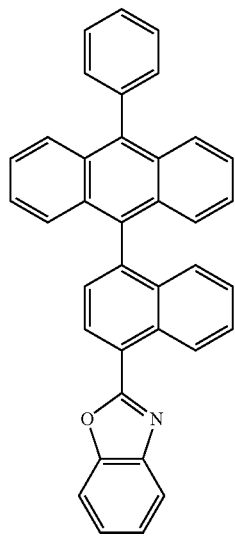

(104)

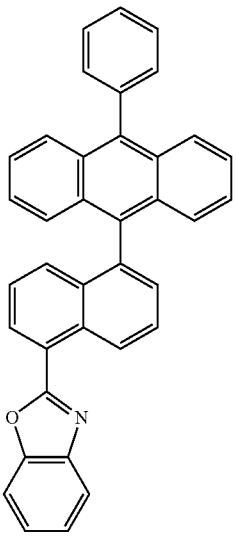

(105)

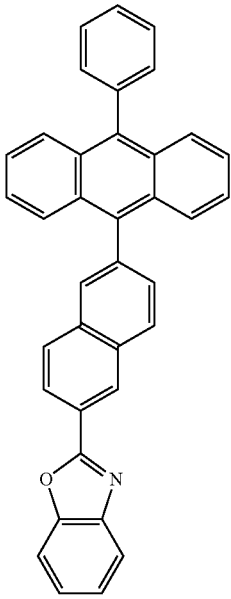

(106)

(107)
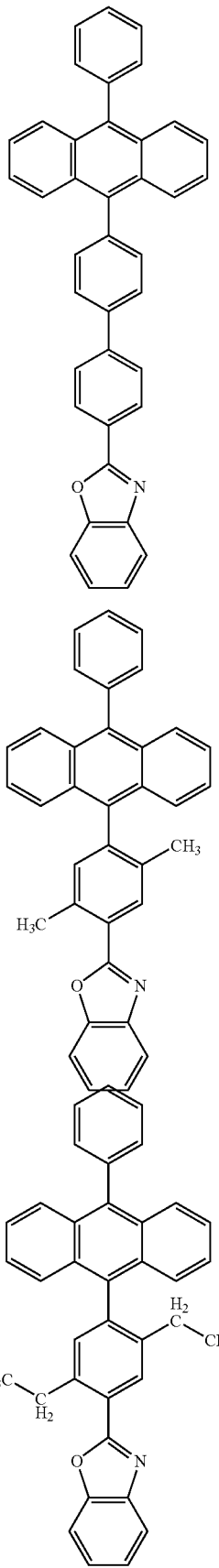
(108)
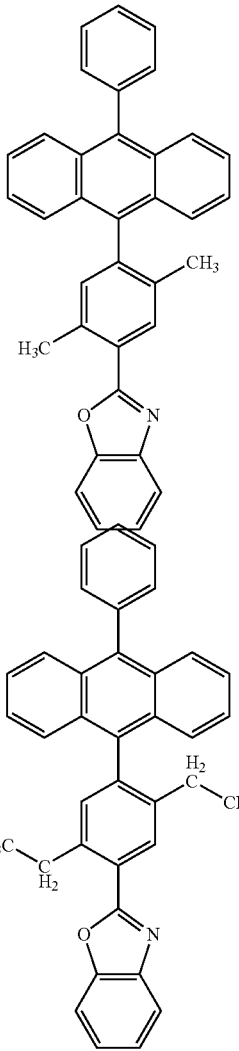
(110)
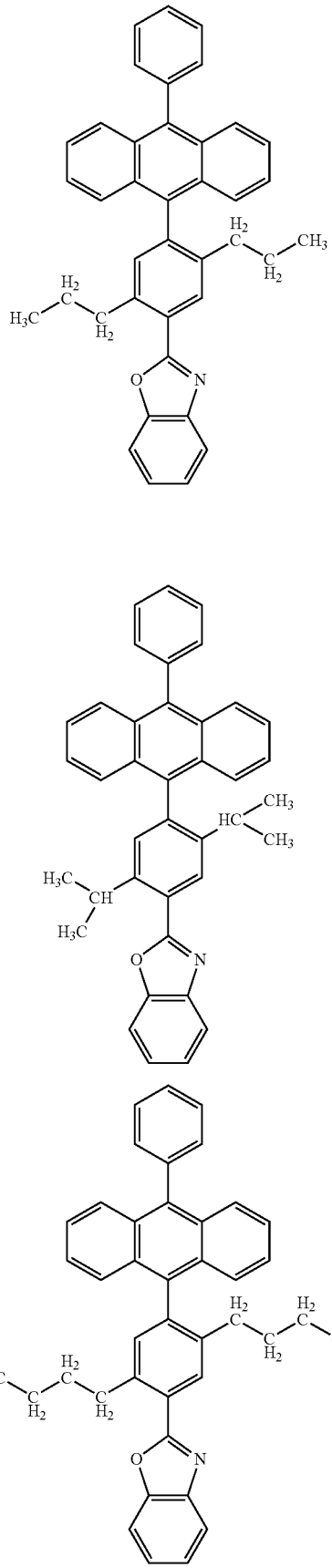
(111)
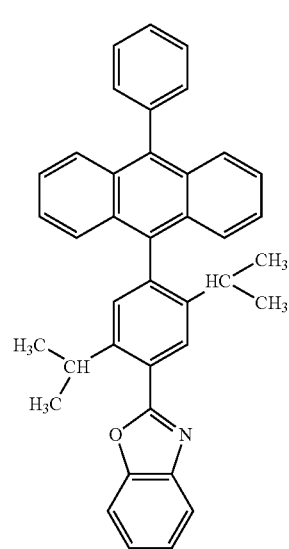
(109)
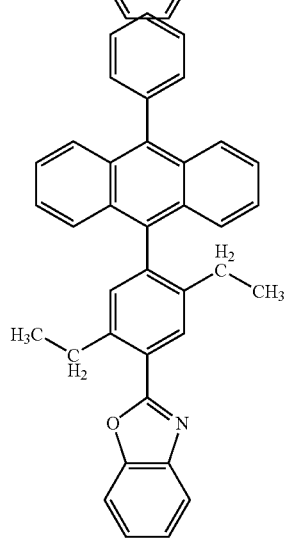
(112)
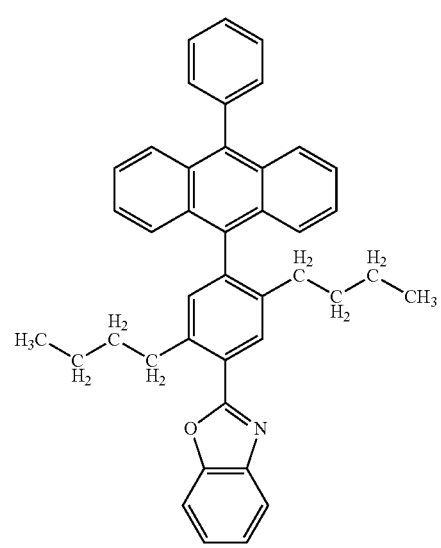

(113)
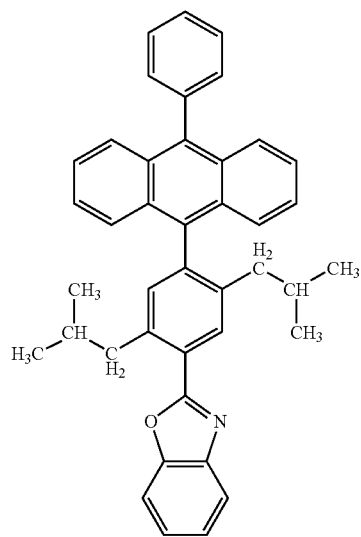
(114)
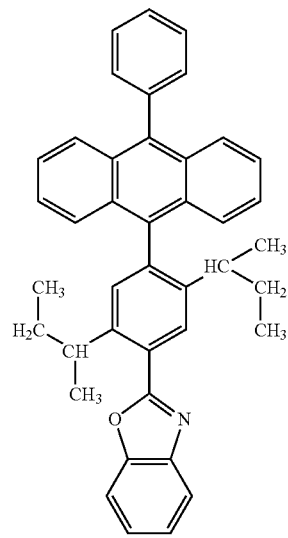
(115)
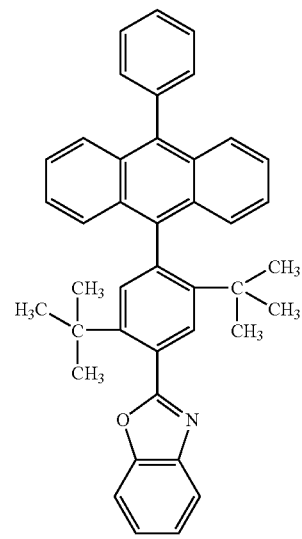
(116)
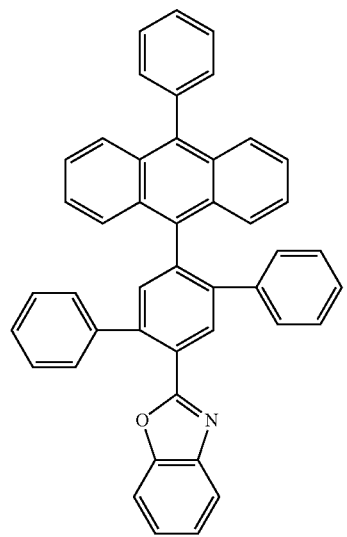
(117)
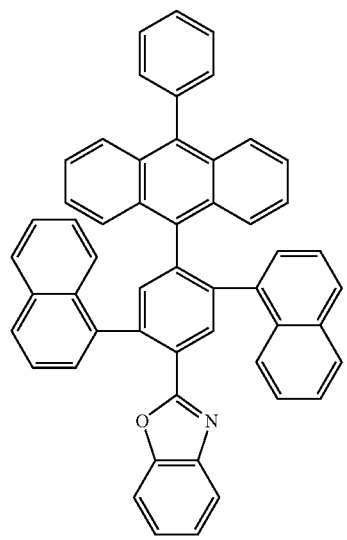
(118)

(119)
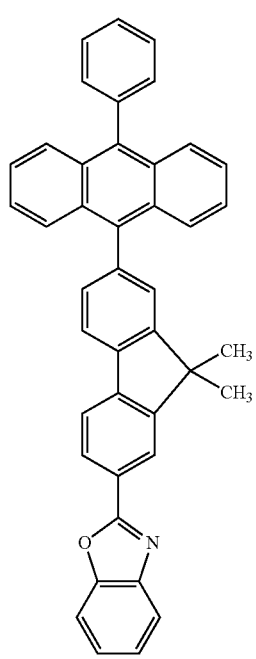
(120)
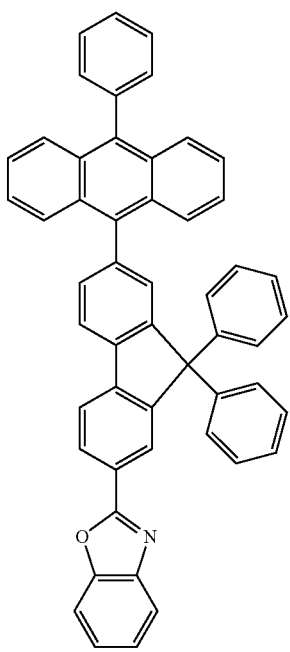
(121)
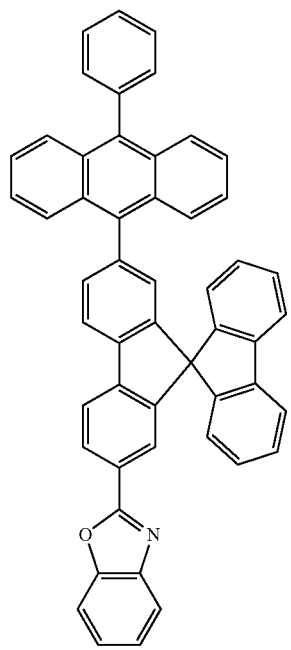
(122)
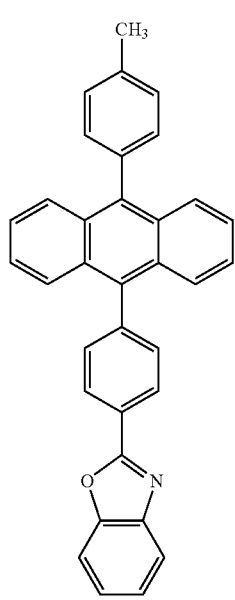

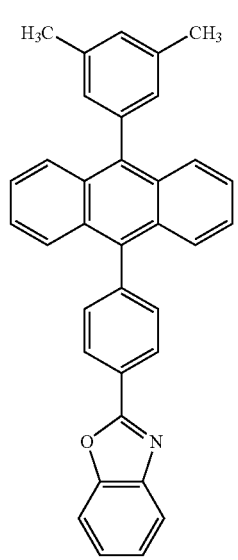
(123)
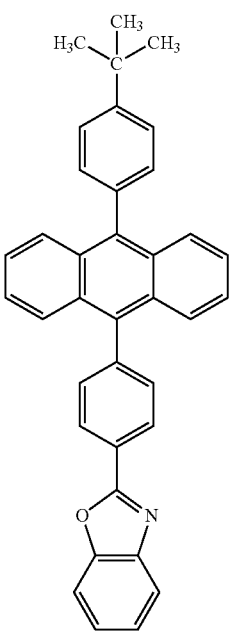
(125)
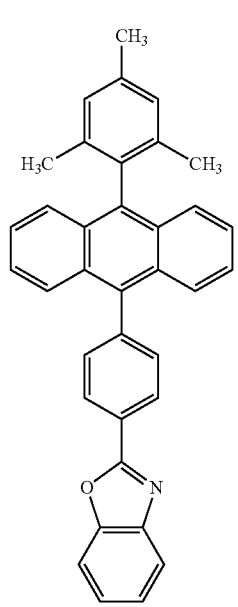
(124)
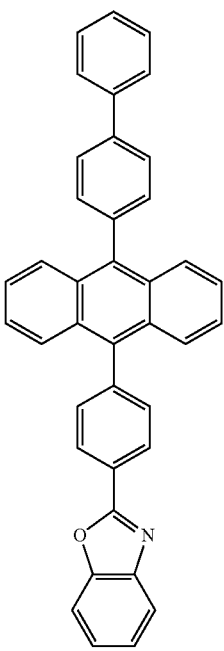
(126)

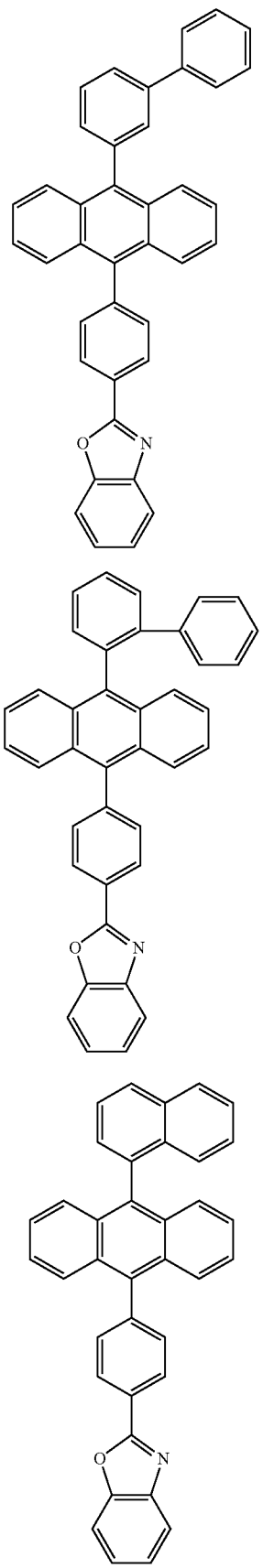

(132) 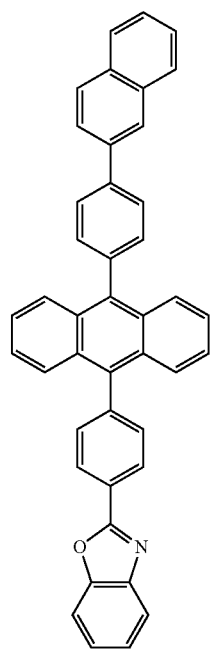
(134) 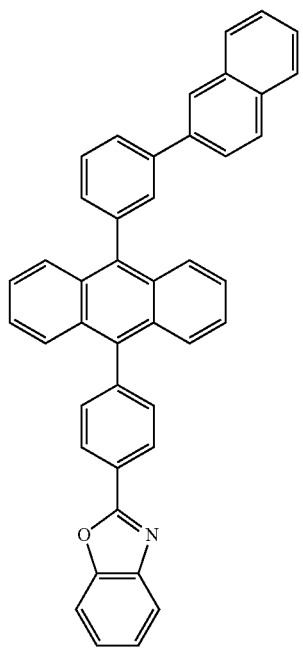
(133) 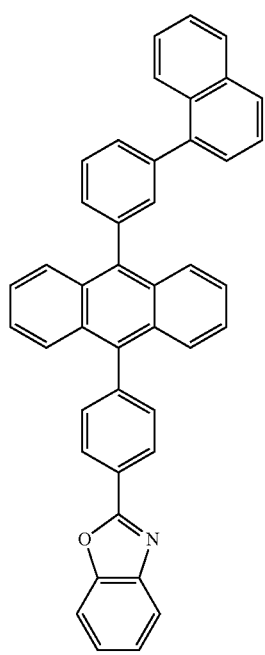
(135) 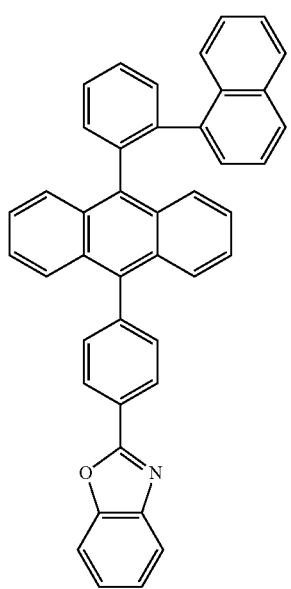

(136)
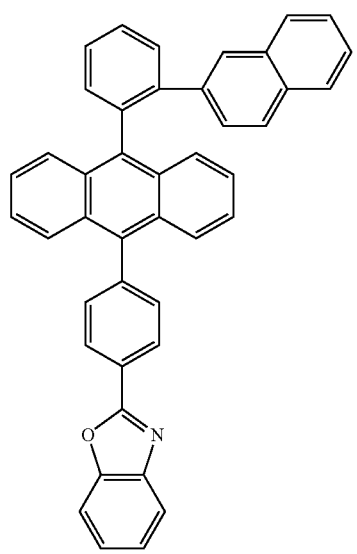
(137)
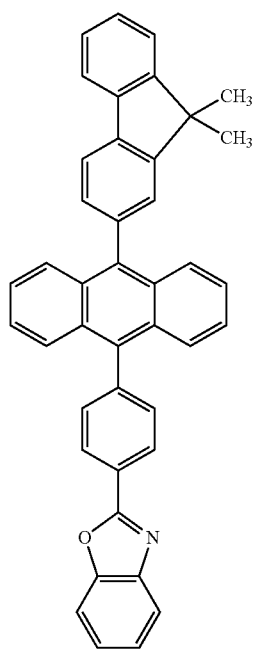
(138)
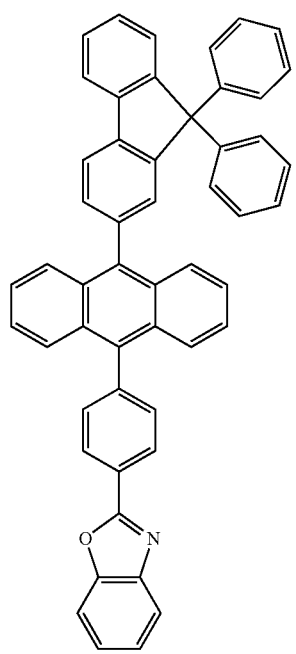
(139)
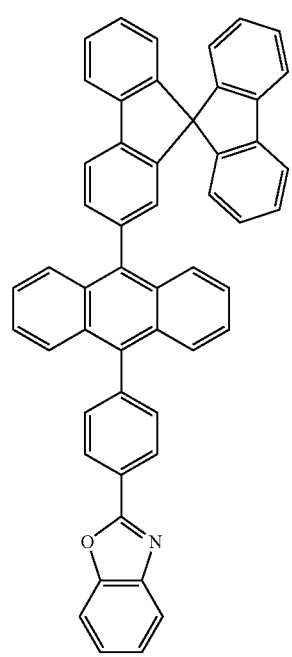

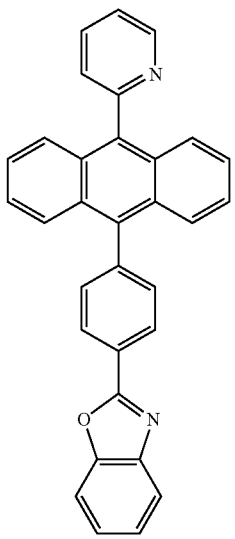
(140)
(141)
(142)
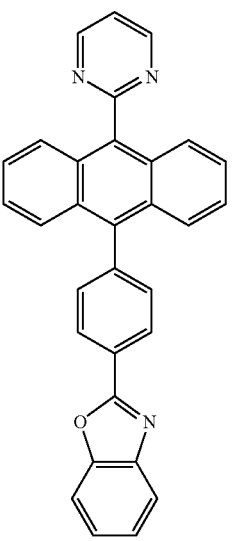
(143)
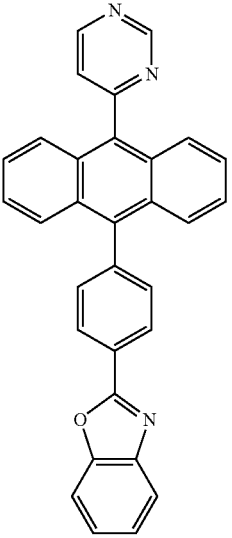
(144)
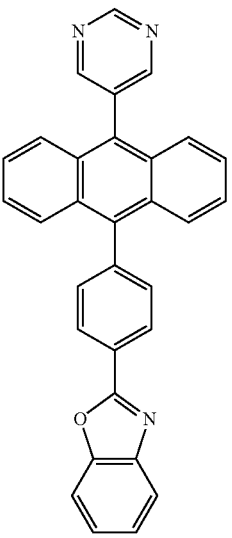
(145)

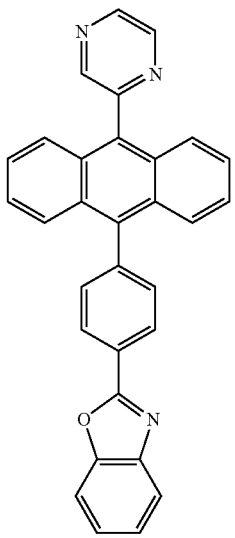
(146)
(147)
(148)
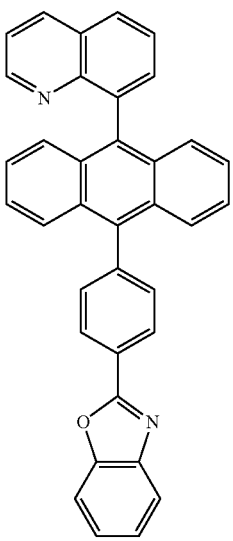
(149)
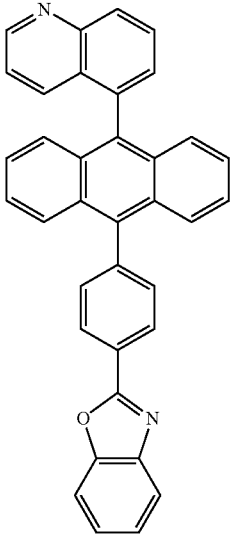
(150)
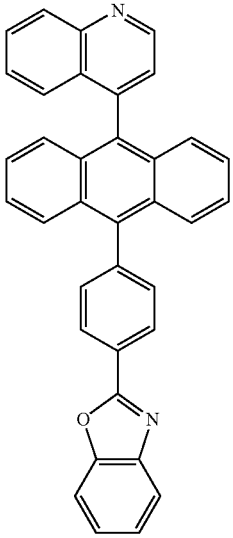
(151)

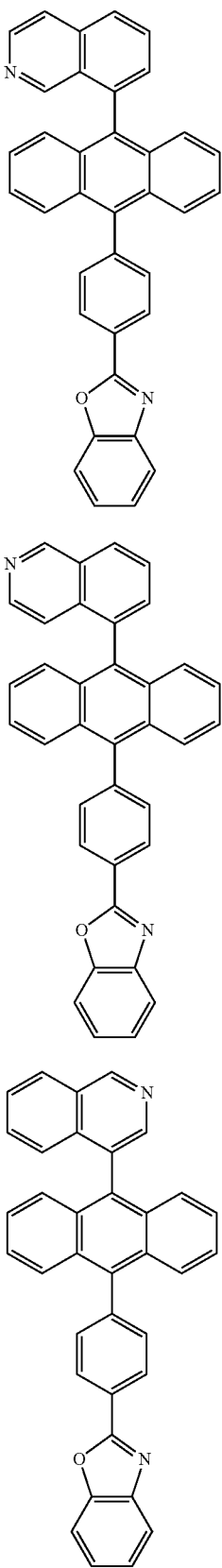
(152)
(153)
(154)
(155)
(156)

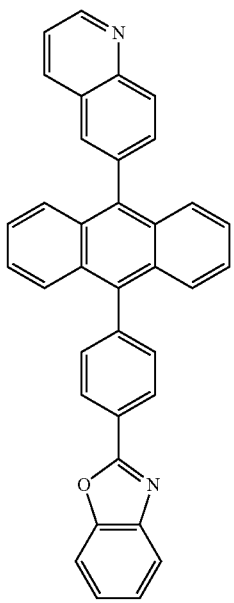
(157)
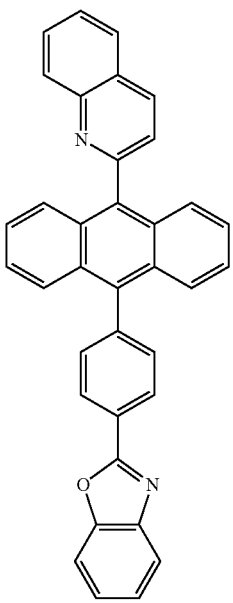
(159)
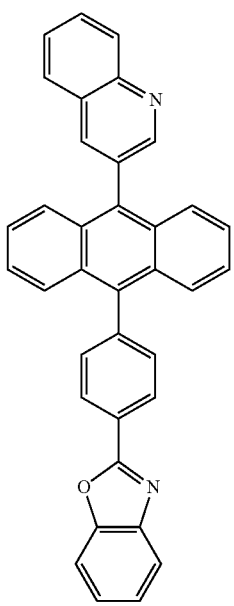
(158)
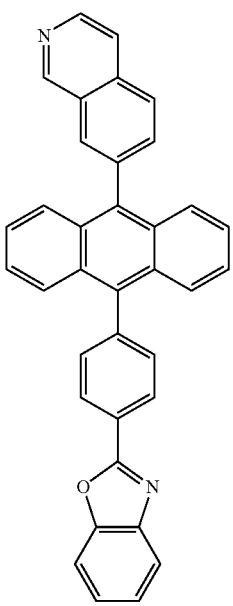
(160)

(161)
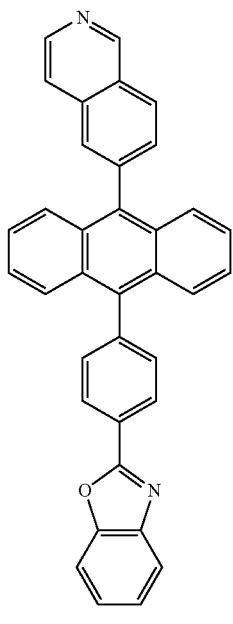
(162)
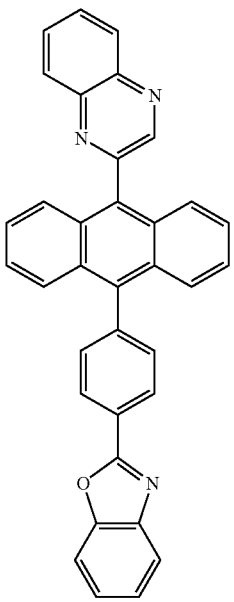
(163)
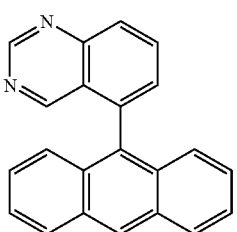
(164)
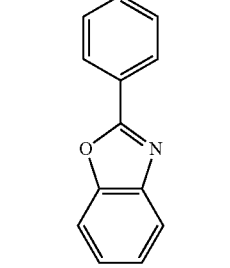
(165)
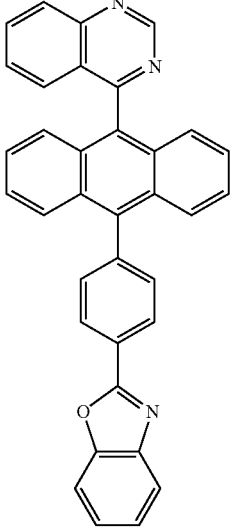

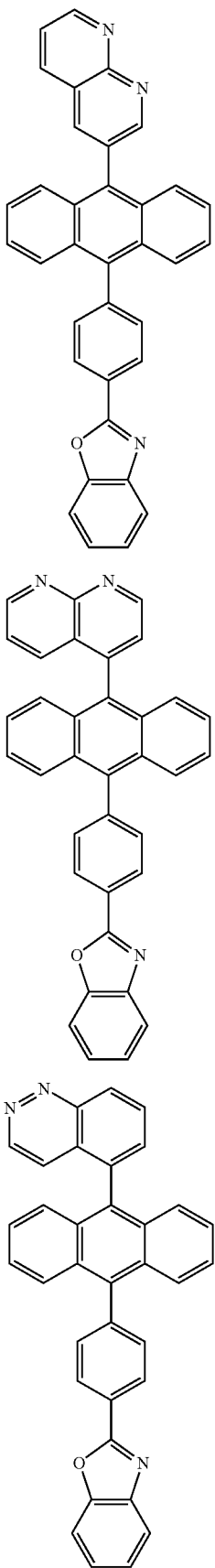
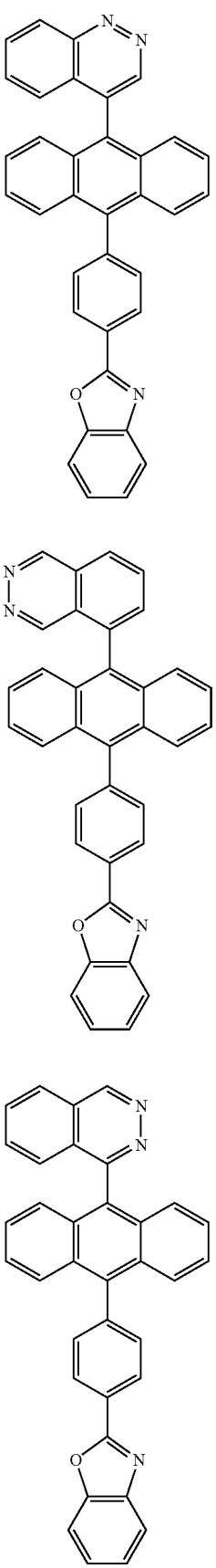

(172)
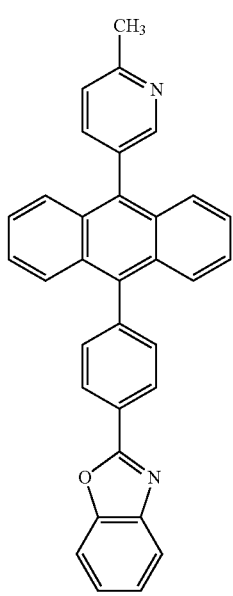
(174)
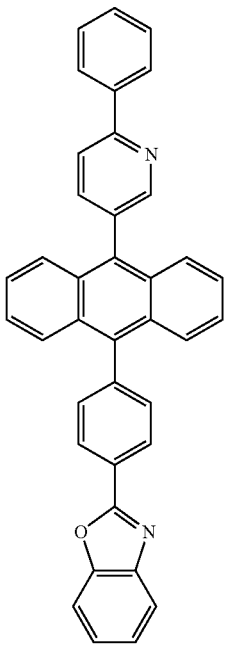
(173)
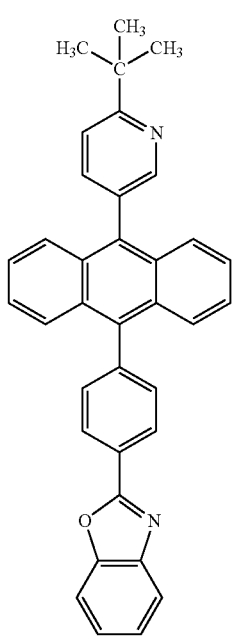
(175)
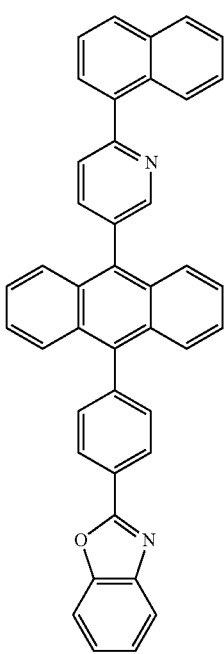

(176)
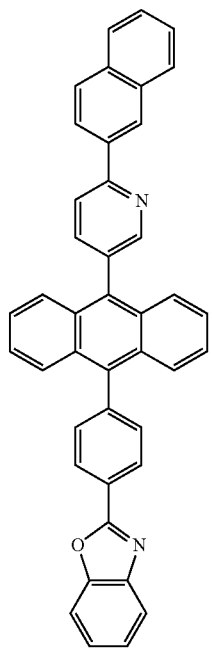
(177)
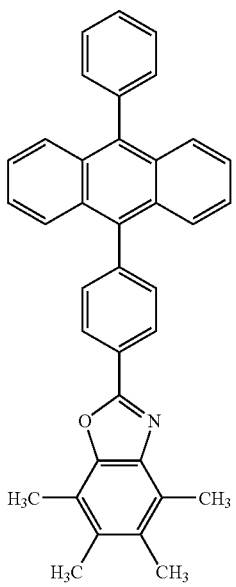
(178)
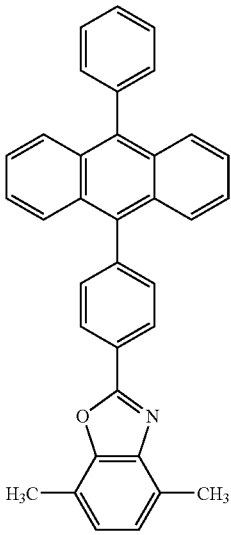
(179)
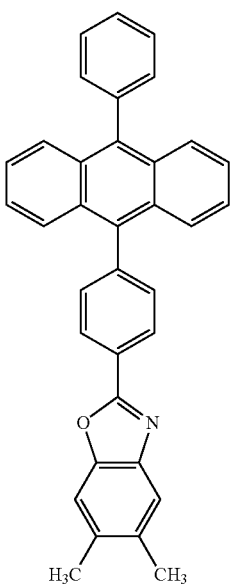
(180)
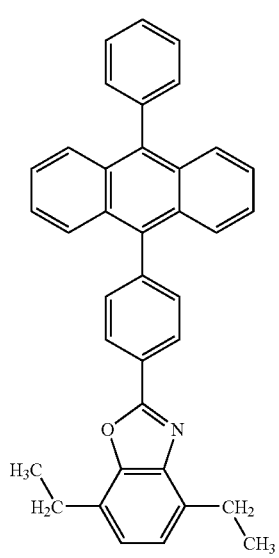

(181)
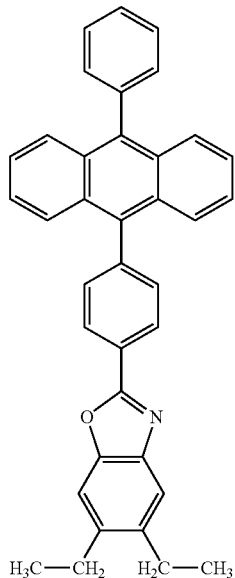
(183)
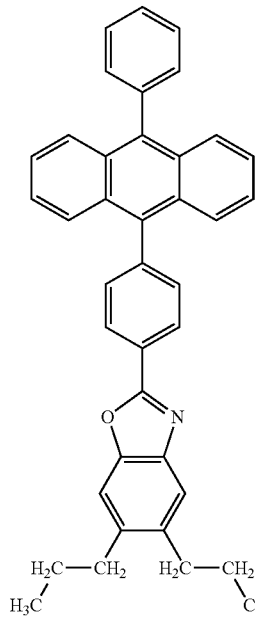
(182)
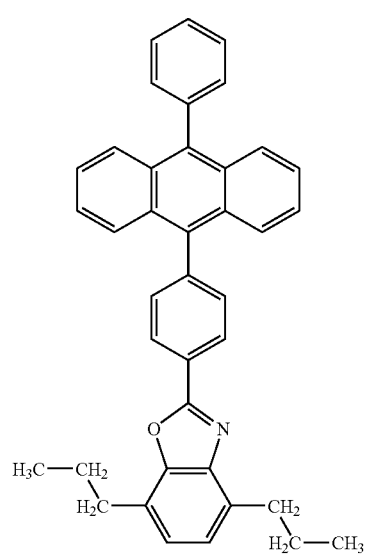
(184)

(185)
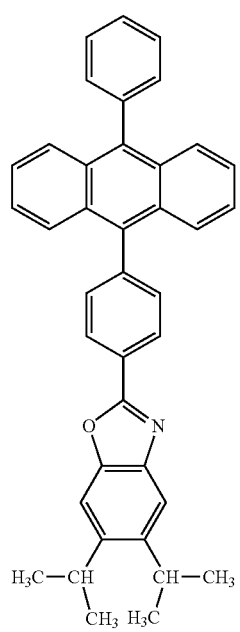
(187)
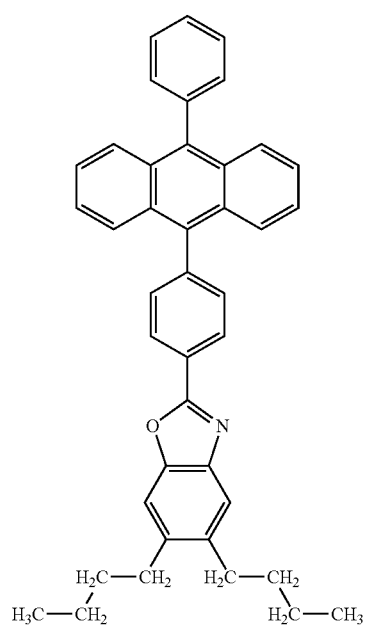
(186)
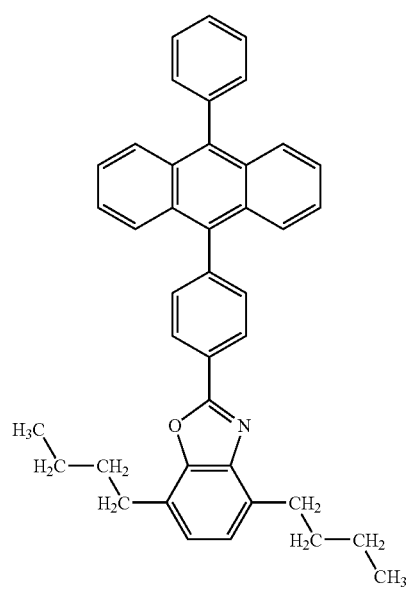
(188)
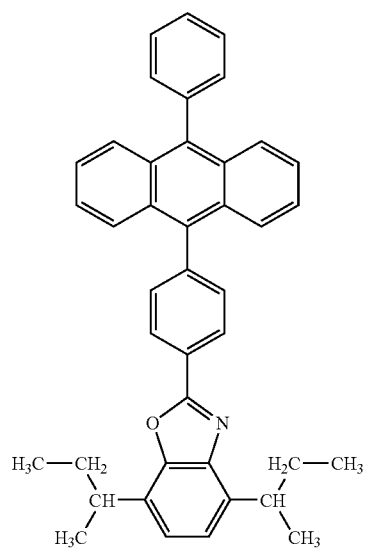

(189)
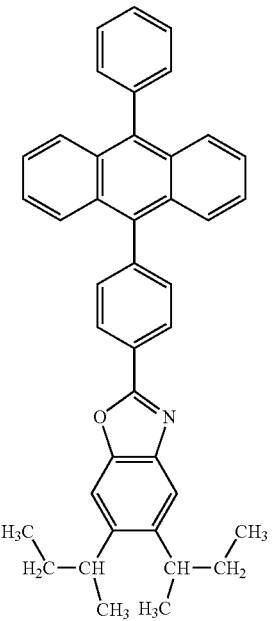
(190)
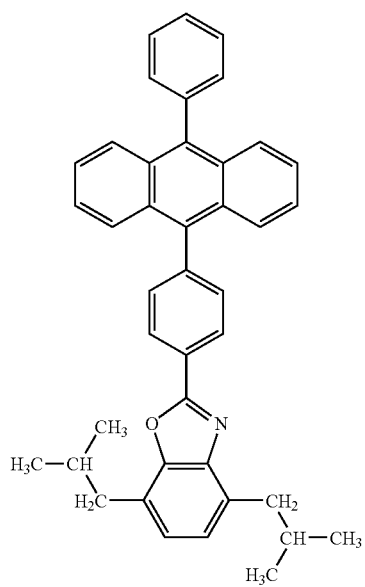
(191)
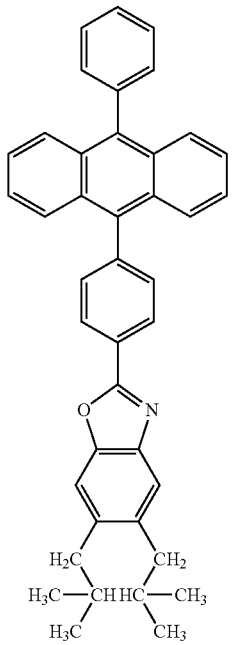
(192)
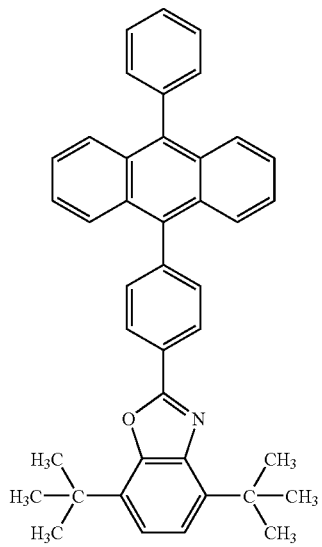

(193)
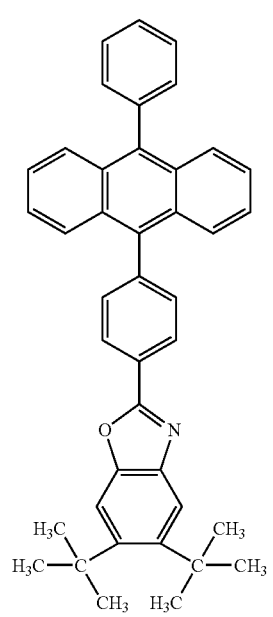
(194)
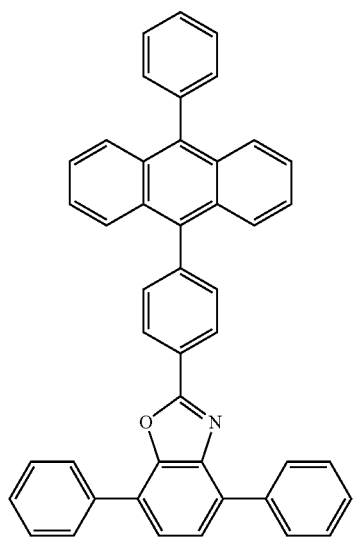
(195)
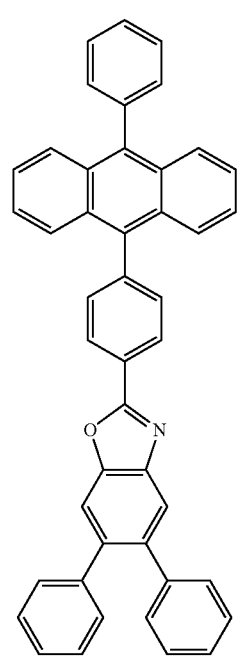
(196)
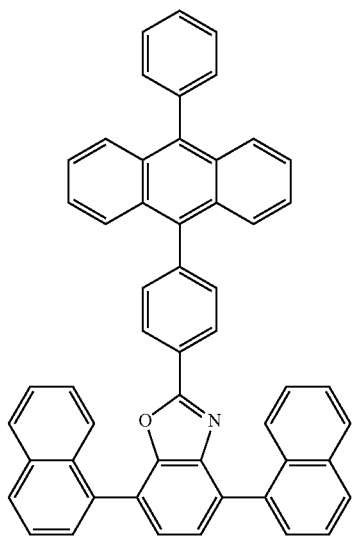

(197)
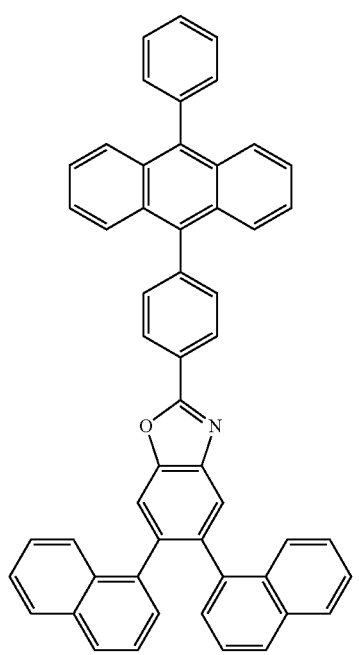
(199)
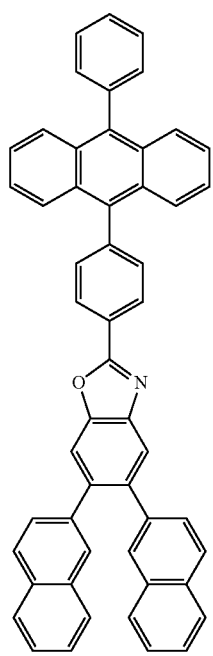
(198)
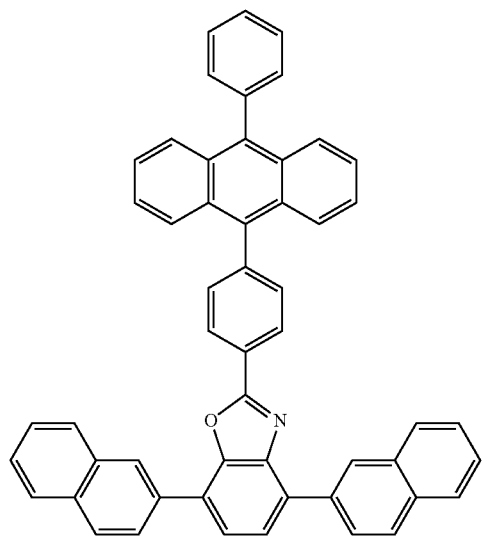
(200)
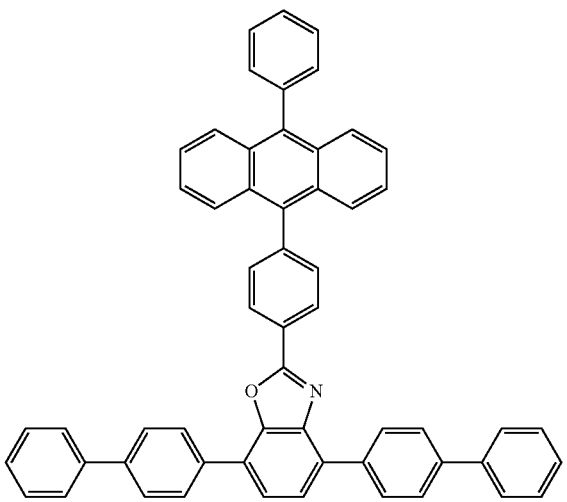

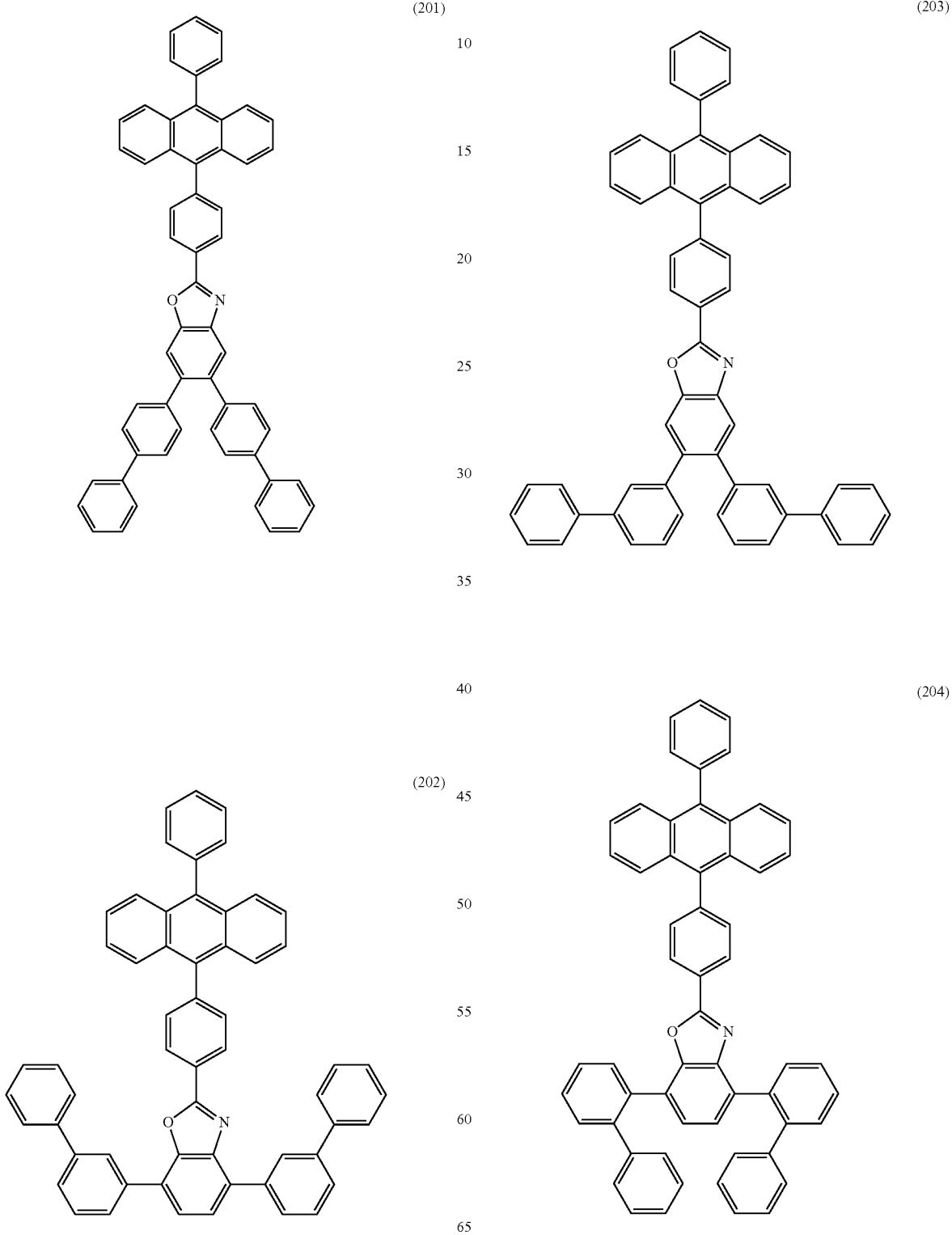

(205)
(206)
(207)
(208)
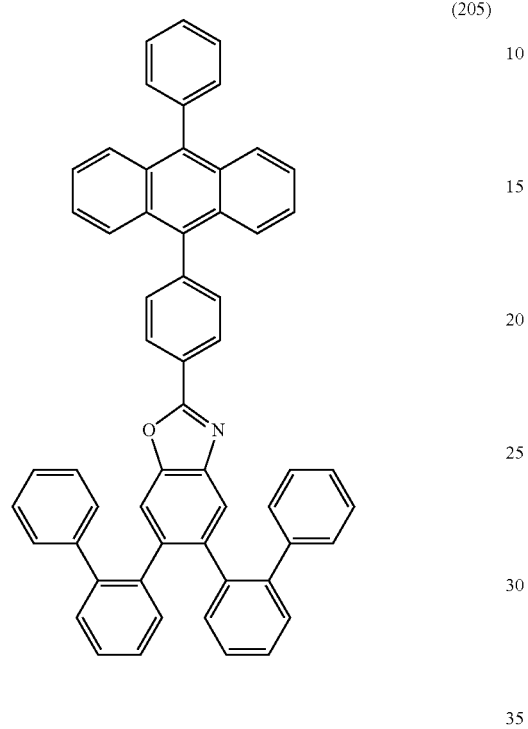
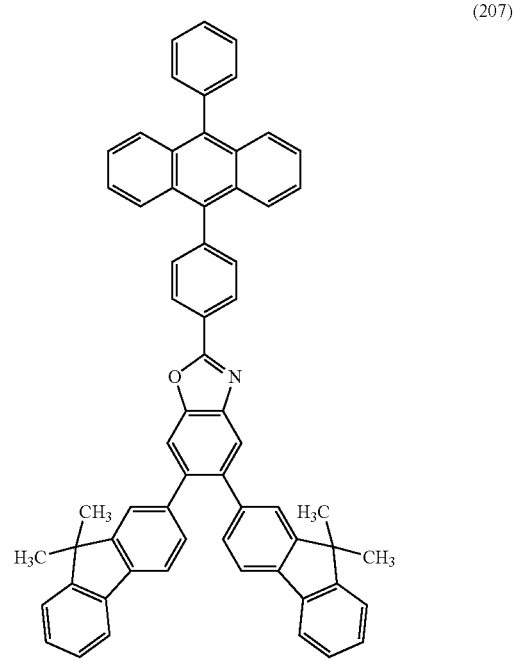
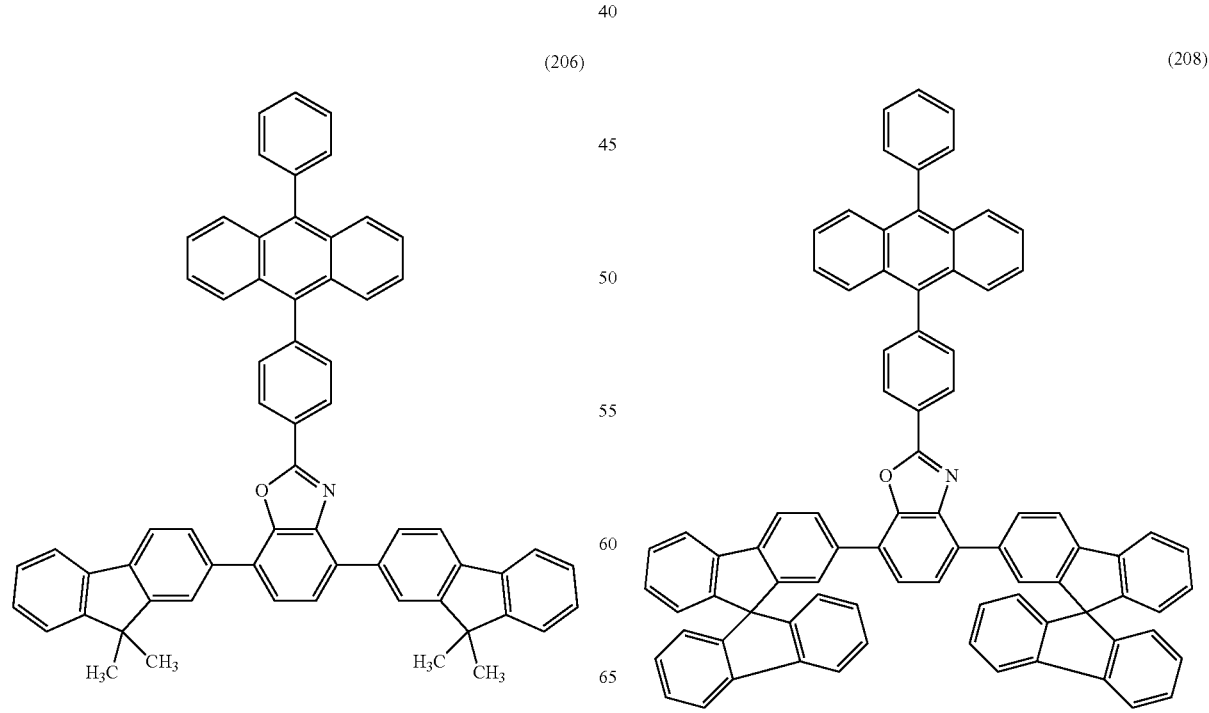

(209)
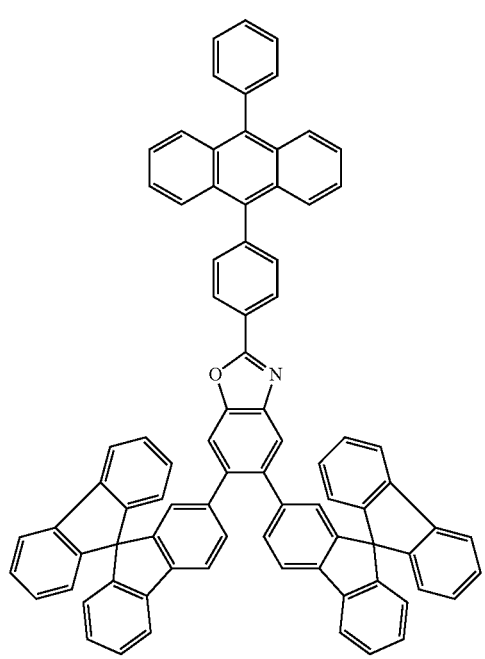
(210)
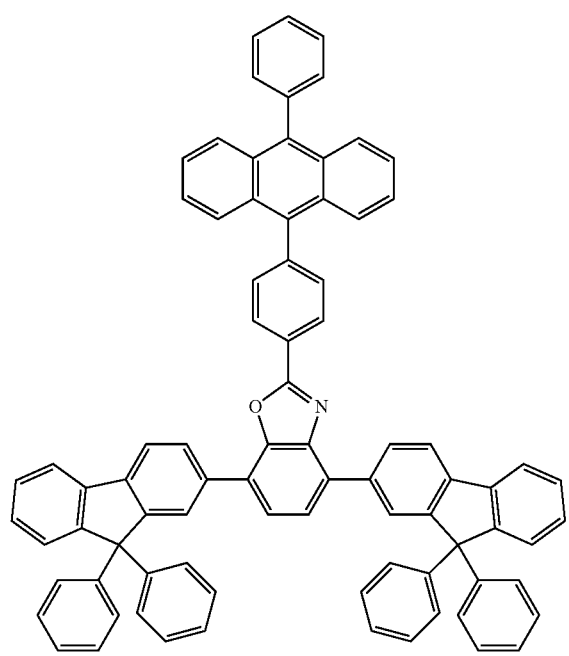
(211)
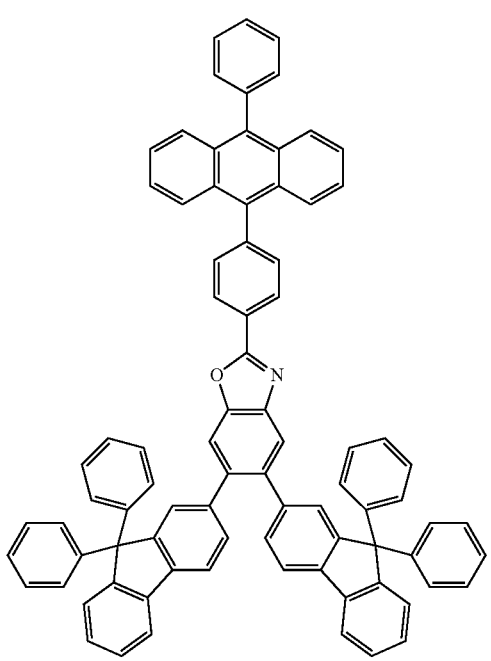
(212)
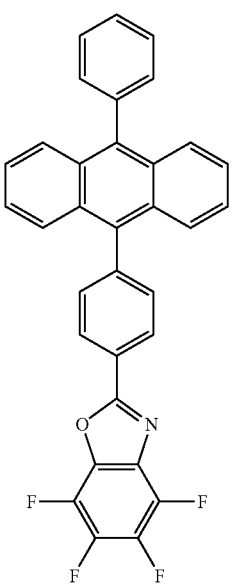

(213)
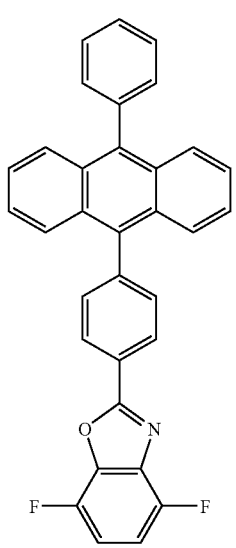
(214)
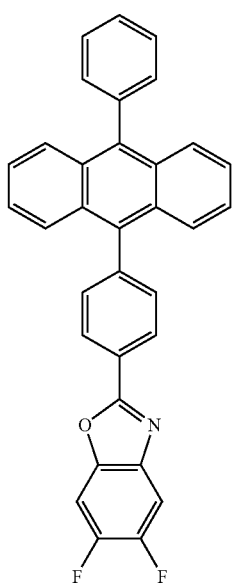
(215)
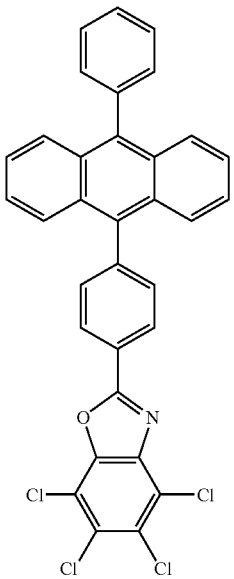
(216)
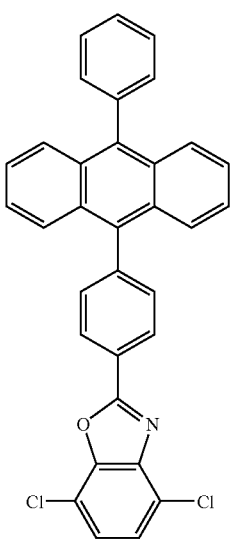

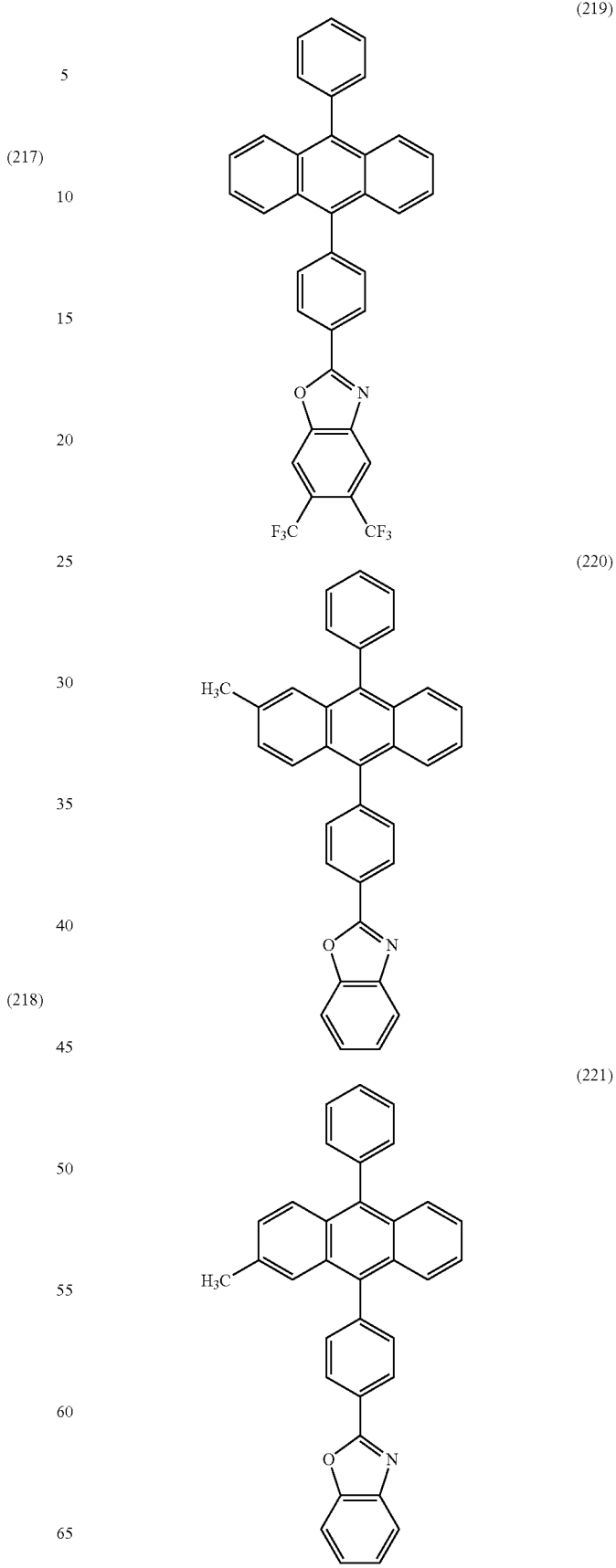

(222) 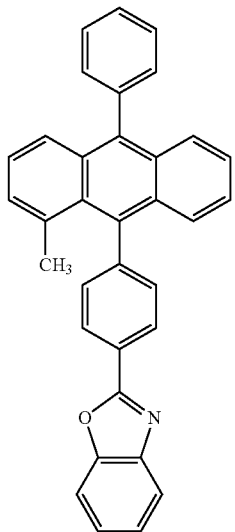
(223) 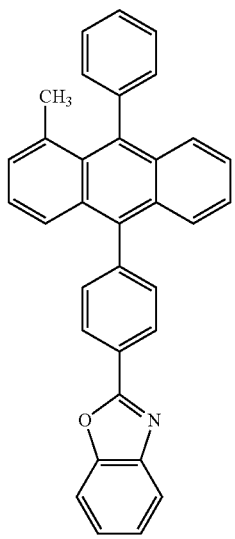
(224) 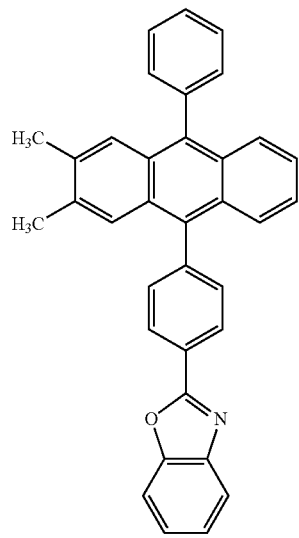
(225) 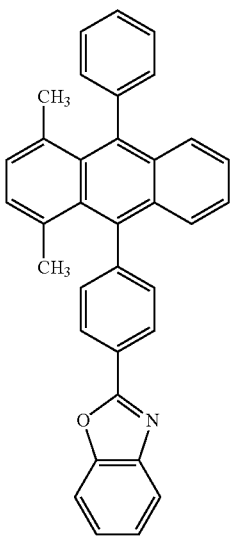
(226) 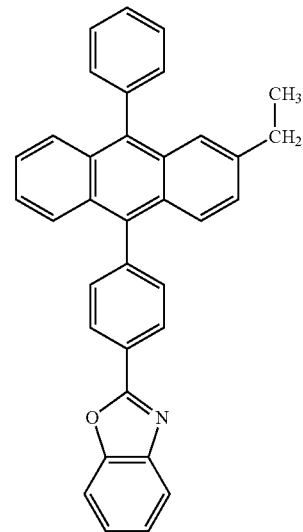
(227) 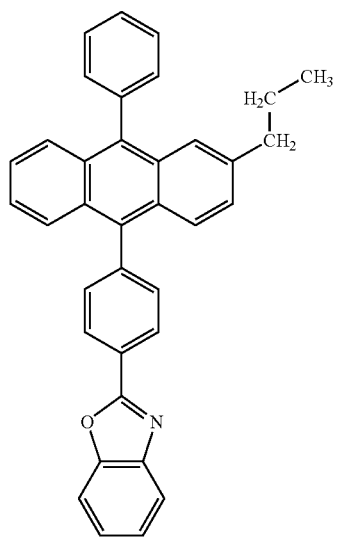

(228)
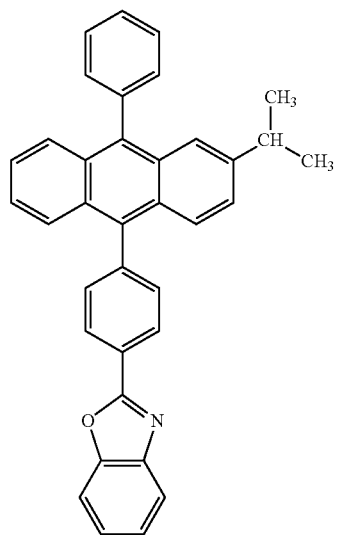
(229)
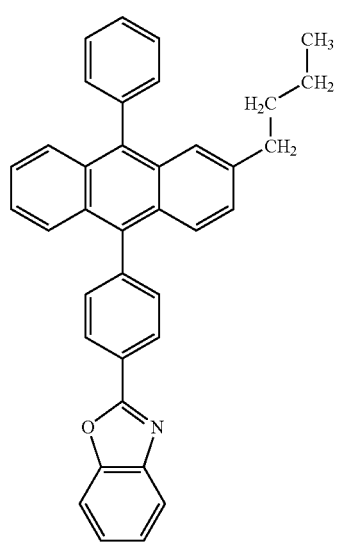
(230)
(231)
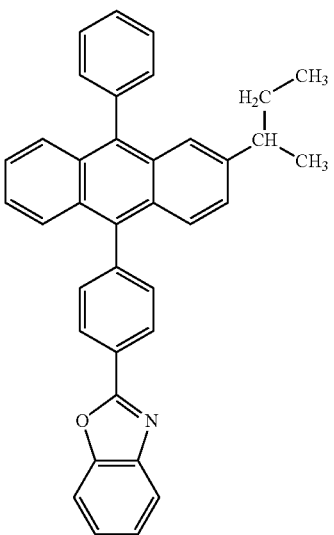
(232)
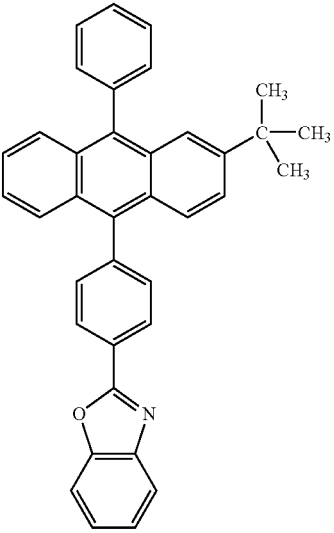
(233)
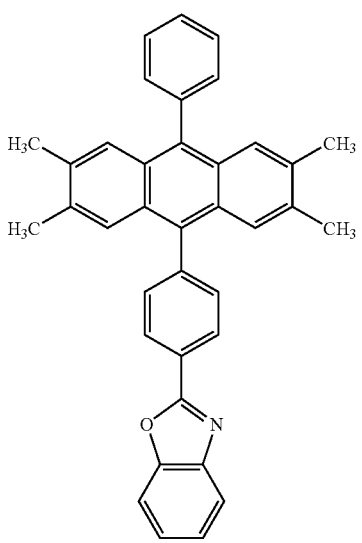
As a synthesis method of the benzoxazole derivatives of the present invention, various reactions can be applied. For example, the benzoxazole derivatives of the present invention can be synthesized by synthetic reactions shown below. Note that the synthesis method of the benzoxazole derivatives of the present invention is not limited to the following synthesis method.

<Synthesis Method of Compound Represented by General Formula (G1)>

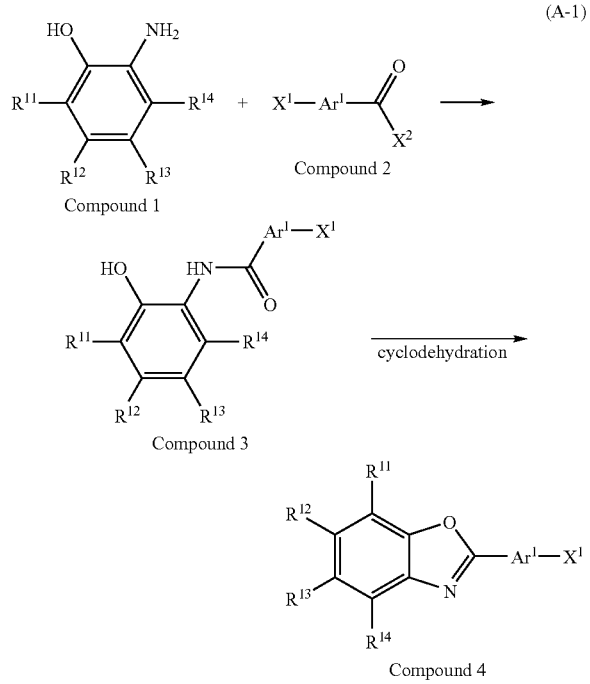

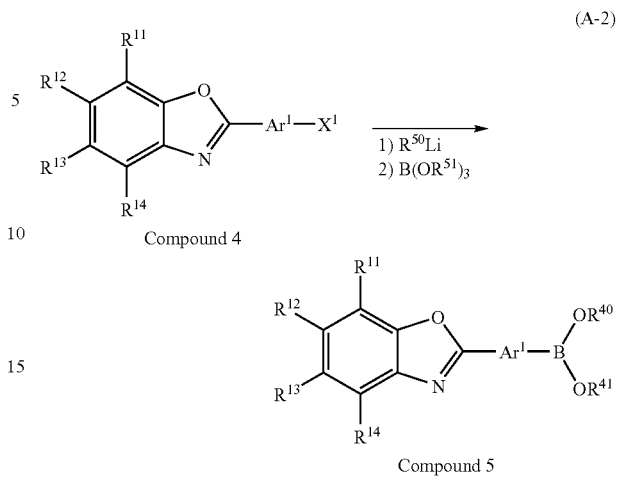

First of all, a benzoxazole derivative (Compound 4) can be synthesized in accordance with a synthesis scheme (A-1). In this scheme, $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen. $Ar^1$ is a substituted or unsubstituted arylene group having 6 to 13 carbon atoms. Further, $X^1$ represents halogen or a triflate group. In the case where $X^1$ is halogen, bromine or iodine is preferable. Furthermore, $X^2$ represents halogen and is preferably chlorine.

First, an ortho-aminophenol derivative (Compound 1) is acylated with an acyl halide (Compound 2), whereby a N-(2-hydroxyphenyl)-arylenamide derivative (Compound 3) can be obtained. A solvent used here can be, but not limited to, an ether-based solvent such as diethyl ether or tetrahydrofuran or a halogen-based solvent such as chloroform, dichloromethane, or carbon tetrachloride.

Next, cyclodehydration of the N-(2-hydroxyphenyl)-arylenamide derivative (Compound 3) is performed, whereby a benzoxazole ring is formed. A dehydrating agent used here can be, but not limited to, inorganic acid such as hydrochloric acid, sulfuric acid, or phosphoric acid or organic acid such as para-toluenesulfonic acid or trifluoroacetic acid. A solvent used here can be, but not limited to, a halogen-based solvent such as chloroform, dichloromethane, or carbon tetrachloride or hydrocarbon such as benzene, toluene, or xylene. In this manner, the benzoxazole derivative (Compound 4) can be obtained.

Next, Compound 5 can be synthesized in accordance with a synthesis scheme (A-2). Boron oxidation or organoboration of the benzoxazole derivative (Compound 4) is performed using an alkyllithium reagent and a boron reagent, whereby a boronic acid of the benzoxazole derivative or an organoboron compound of the benzoxazole derivative (Compound 5) can be obtained. In the synthesis scheme (A-2), $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen. $Ar^1$ is a substituted or unsubstituted arylene group having 6 to 13 carbon atoms. Further, $X^1$ represents halogen and is preferably bromine or iodine in particular. In addition, $R^{50}$ represents an alkyl group having 1 to 6 carbon atoms, $R^{51}$ represents an alkyl group having 1 to 6 carbon atoms, and $R^{40}$ and $R^{41}$ are independently either hydrogen or an alkyl group having 1 to 6 carbon atoms. In the synthesis scheme (A-2), $R^{40}$ and $R^{41}$ may be bonded to each other to form a ring.

In the synthesis scheme (A-2), an ether-based solvent such as diethyl ether, tetrahydrofuran (THF), or cyclopentyl methyl ether can be used. However, the solvent that can be used is not limited to these solvents. The alkyllithium reagent may be, but not limited to, n-butyllithium in which $R^{50}$ is an n-butyl group, tert-butyllithium in which $R^{50}$ is a tert-butyl group, methyllithium in which $R^{50}$ is a methyl group, or the like. The boron reagent may be, but not limited to, trimethyl borate in which $R^{51}$ is a methyl group, triisopropyl borate in which $R^{51}$ is an isopropyl group, or the like.

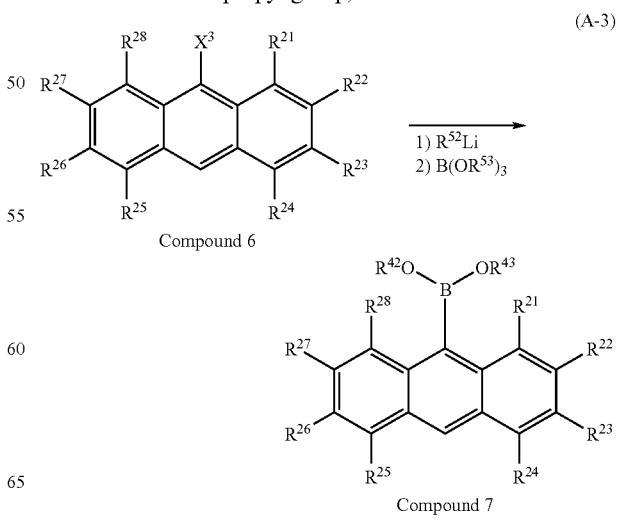

Next, boron oxidation or organoboration of a halide of an anthracene derivative (Compound 6) is performed using an alkyllithium reagent and a boron reagent in accordance with a synthesis scheme (A-3), whereby a boronic acid of the anthracene derivative or an organoboron compound of the anthracene derivative (Compound 7) can be obtained. In the synthesis scheme (A-3), $R^{21}$ to $R^{28}$ are independently either hydrogen or an alkyl group having 1 to 4 carbon atoms. Further, $X^3$ represents halogen and is preferably chlorine, bromine, or iodine in particular. In addition, $R^{52}$ represents an alkyl group having 1 to 6 carbon atoms, $R^{53}$ represents an alkyl group having 1 to 6 carbon atoms, and $R^{42}$ and $R^{43}$ are independently either hydrogen or an alkyl group having 1 to 6 carbon atoms. In the synthesis scheme (A-3), $R^{42}$ and $R^{43}$ may be bonded to each other to form a ring.

In the synthesis scheme (A-3), an ether-based solvent such as diethyl ether, tetrahydrofuran (THF), or cyclopentyl methyl ether can be used. However, the solvent that can be used is not limited to these solvents. The alkyllithium reagent may be, but not limited to, n-butyllithium in which $R^{52}$ is an n-butyl group, tert-butyllithium in which $R^{52}$ is a tert-butyl group, methyllithium in which $R^{52}$ is a methyl group, or the like. The boron reagent may be, but not limited to, trimethyl borate in which $R^{53}$ is a methyl group, triisopropyl borate in which $R^{53}$ is an isopropyl group, or the like.

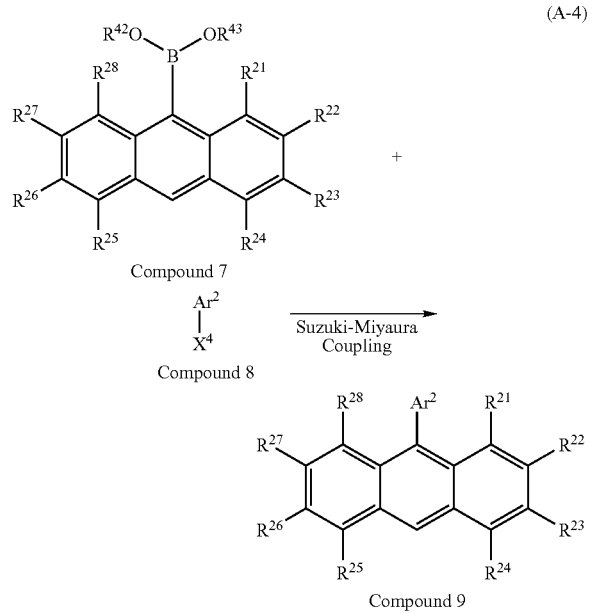

Next, as shown in a synthesis scheme (A-4), the boronic acid of the anthracene derivative or the organoboron compound of the anthracene derivative (Compound 7) and an aryl derivative (Compound 8) are coupled by Suzuki-Miyaura Coupling, whereby an arylanthracene derivative (Compound 9) can be obtained. In the synthesis scheme (A-4), $R^{21}$ to $R^{28}$ are independently either hydrogen or an alkyl group having 1 to 4 carbon atoms. $R^{42}$ and $R^{43}$ are independently either hydrogen or an alkyl group having 1 to 6 carbon atoms. In the synthesis scheme (A-4), $R^{42}$ and $R^{43}$ may be bonded to each other to form a ring. Further, $Ar^2$ is a substituted or unsubstituted aryl group having 6 to 13 carbon atoms or a substituted or unsubstituted heteroaryl group having 4 to 9 carbon atoms which is composed of a six-membered ring. Furthermore, $X^4$ represents halogen or a triflate group. In the case where $X^4$ is halogen, chlorine, bromine, or iodine is preferable, and in particular, bromine or iodine is more preferable.

A palladium catalyst that can be used in the synthesis scheme (A-4) may be, but not limited to, palladium(II) acetate, tetrakis(triphenylphosphine)palladium(0), bis(triphenylphosphine)palladium(II) dichloride, or the like. A ligand of the palladium catalyst that can be used in the synthetic scheme (A-4) may be, but not limited to, tri(ortho-tolyl)phosphine, triphenylphosphine, tricyclohexylphosphine, or the like. A base which can be used in the synthesis scheme (A-4) may be, but not limited to, an organic base such as sodium tert-butoxide, an inorganic base such as potassium carbonate or sodium carbonate, or the like. A solvent that can be used in the synthetic scheme (A-4) may be, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like. Further, a mixed solvent of toluene and water; a mixed solvent of toluene, ethanol, and water; or a mixed solvent of ether such as ethylene glycol dimethyl ether and water is more preferable.

In Suzuki-Miyaura Coupling shown in the synthesis scheme (A-4), cross coupling using organoaluminum, organozirconium, organozinc, organotin, or the like may be used instead of the boronic acid or the organoboron compound represented by Compound 7. However, the present invention is not limited thereto.

Further, in this coupling reaction, a boronic acid of the aryl derivative or an organoboron compound of the aryl derivative may be coupled with a halide of the anthracene derivative or the anthracene derivative substituted with a triflate group by Suzuki-Miyaura Coupling. However, in the case where $Ar^2$ is heteroaryl, it is preferable to couple Compound 7 and Compound 8 in terms of yield.

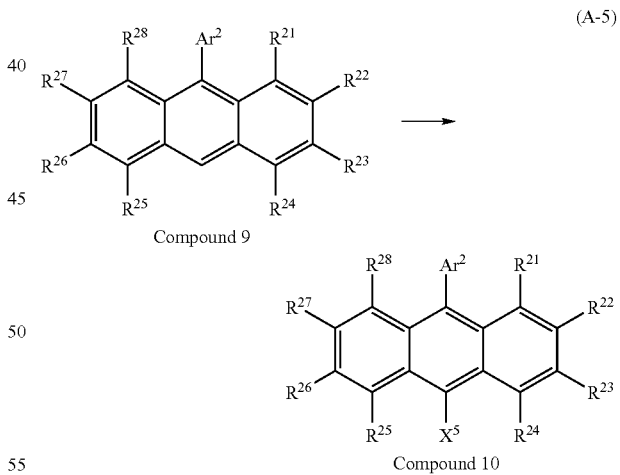

Next, as shown in a synthesis scheme (A-5), the arylanthracene derivative (Compound 9) is halided, whereby a halide of the arylanthracene derivative (Compound 10) can be obtained.

In the synthesis scheme (A-5), $R^{21}$ to $R^{28}$ are independently either hydrogen or an alkyl group having 1 to 4 carbon atoms. Further, $Ar^2$ is a substituted or unsubstituted aryl group having 6 to 13 carbon atoms or a substituted or unsubstituted heteroaryl group having 4 to 9 carbon atoms which is composed of a six-membered ring. Furthermore, $X^5$ represents halogen.

A halogenating agent that can be used in the synthesis scheme (A-5) may be, but not limited to, N-iodosuccinimide (NIS), bromine ($Br_2$), or N-bromosuccinimide (NBS). As a solvent that can be used, the following can be used alone or in combination: water; a carboxylic acid such as acetic acid (glacial acetic acid) or propionic acid; aromatic hydrocarbon such as benzene, toluene, or xylene; ether such as 1,2-dimethoxyethane, diethyl ether, tetrahydrofuran, or dioxane; saturated hydrocarbon such as pentane, hexane, heptane, or cyclohexane; a halogen-based solvent such as dichloromethane, chloroform, carbon tetrachloride, or 1,2-dichloroethane; nitrile such as acetonitrile or benzonitrile; ester such as ethyl acetate, methyl acetate, or butyl acetate; or the like. In the case where water is used, it is preferable to mix water and an organic solvent. Further, in the case where NIS is used, 1.5 to 2 equivalents of NIS are preferably used with respect to one equivalent of Compound 9, and more preferably, an acid such as acetic acid, sulfuric acid, or trifluoroacetic acid is used.

In the synthesis scheme (A-5), in the case where NBS is used as the halogenating agent, a polar solvent such as ethyl acetate, DMF, or acetic acid (glacial acetic acid) is preferably used; however, the present invention is not limited thereto.

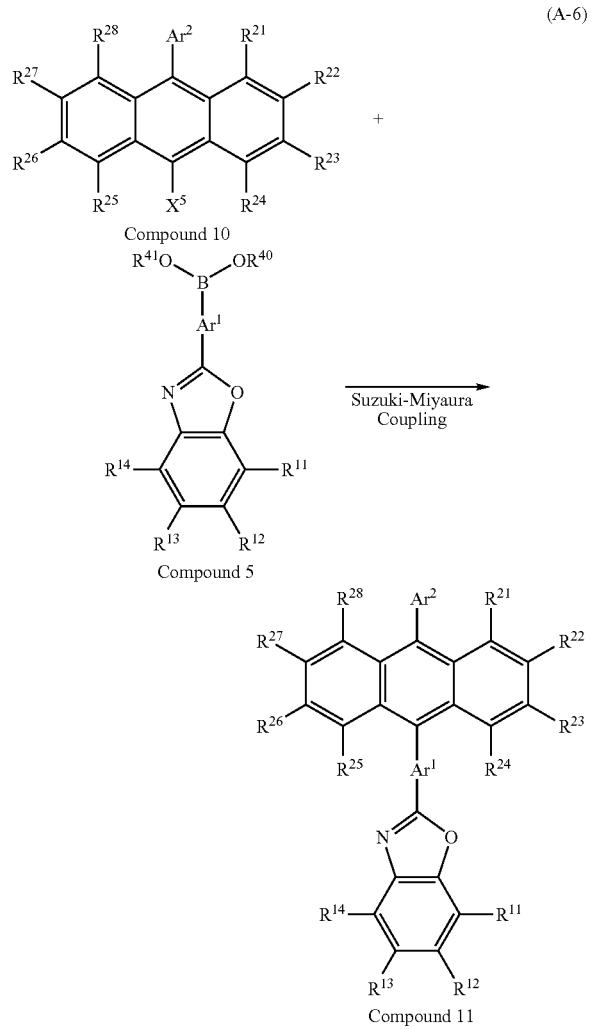

As shown in a synthesis scheme (A-6), the boronic acid of the benzoxazole derivative or the organoboron compound of the benzoxazole derivative (Compound 5) and the halide of the arylanthracene derivative (Compound 10) are coupled by Suzuki-Miyaura Coupling, whereby the target Compound 11 can be obtained. In the synthesis scheme (A-6), $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen. $R^{21}$ to $R^{28}$ are independently either hydrogen or an alkyl group having 1 to 4 carbon atoms. $R^{40}$ and $R^{41}$ are independently either hydrogen or an alkyl group having 1 to 6 carbon atoms. In the synthesis scheme (A-6), $R^{40}$ and $R^{41}$ may be bonded to each other to form a ring. Further, $Ar^2$ is a substituted or unsubstituted aryl group having 6 to 13 carbon atoms or a substituted or unsubstituted heteroaryl group having 4 to 9 carbon atoms which is composed of a six-membered ring. Furthermore, $X^5$ represents halogen and is preferably bromine or iodine in particular.

A palladium catalyst that can be used in the synthesis scheme (A-6) may be, but not limited to, palladium(II) acetate, tetrakis(triphenylphosphine)palladium(0), bis(triphenylphosphine)palladium(II) dichloride, or the like. A ligand of the palladium catalyst that can be used in the synthetic scheme (A-6) may be, but not limited to, tri(ortho-tolyl)phosphine, triphenylphosphine, tricyclohexylphosphine, or the like. A base which can be used in the synthesis scheme (A-6) may be, but not limited to, an organic base such as sodium tert-butoxide, an inorganic base such as potassium carbonate or sodium carbonate, or the like. A solvent that can be used in the synthetic scheme (A-6) may be, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like. Further, a mixed solvent of toluene and water; a mixed solvent of toluene, ethanol, and water; or a mixed solvent of ether such as ethylene glycol dimethyl ether and water is more preferable.

In Suzuki-Miyaura Coupling shown in the synthesis scheme (A-6), cross coupling using organoaluminum, organozirconium, organozinc, organotin, or the like may be used instead of using the boronic acid or the organoboron compound represented by Compound 10. However, the present invention is not limited thereto. Further, in this coupling, a triflate group or the like may be used other than halogen; however, the present invention is not limited thereto.

In Suzuki-Miyaura Coupling shown in the synthesis scheme (A-6), a boronic acid of the arylanthracene derivative or an organoboron compound of the arylanthracene derivative may be coupled with a halide of the benzoxazole derivative or the benzoxazole derivative substituted with a triflate group by Suzuki-Miyaura Coupling.

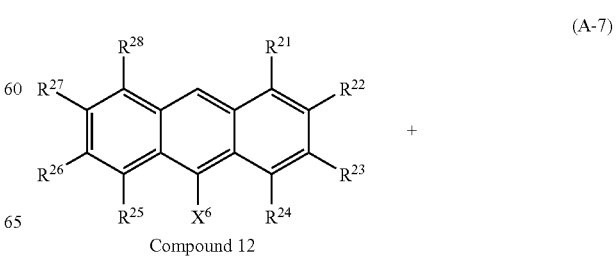

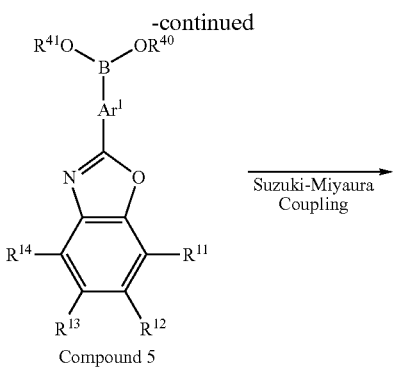

Compound 5

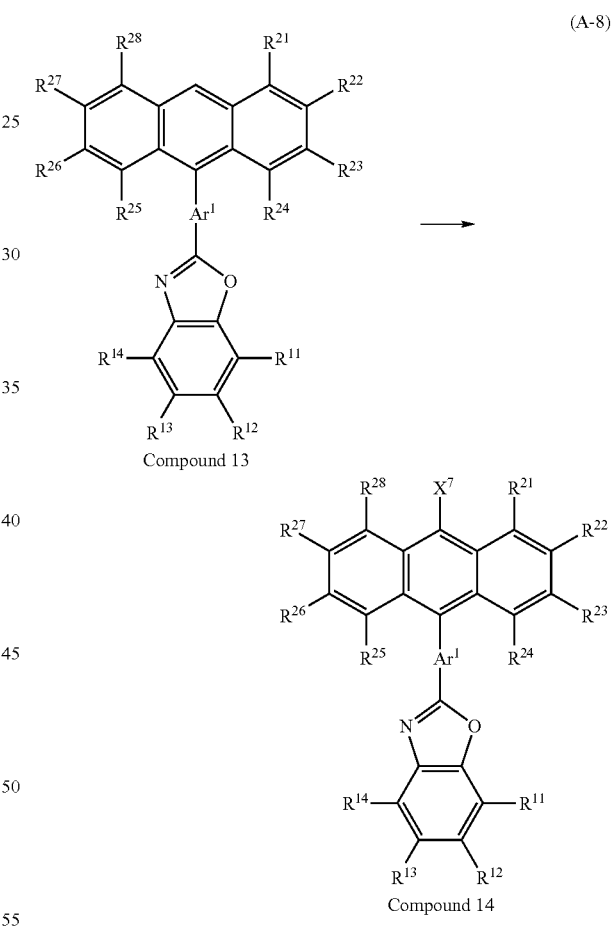

As shown in the synthesis scheme (A-7), the boronic acid of the benzoxazole derivative or the organoboron compound of the benzoxazole derivative (Compound 5) and an anthracene derivative (Compound 12) are coupled by Suzuki-Miyaura Coupling, whereby Compound 13 can be obtained. In the synthesis scheme (A-7), $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen. $R^{21}$ to $R^{28}$ are independently either hydrogen or an alkyl group having 1 to 4 carbon atoms. $R^{40}$ and $R^{41}$ are independently either hydrogen or an alkyl group having 1 to 6 carbon atoms. In the synthesis scheme (A-7), $R^{40}$ and $R^{41}$ may be bonded to each other to form a ring. $Ar^1$ is a substituted or unsubstituted arylene group having 6 to 13 carbon atoms. Further, $X^6$ represents halogen or a triflate group. In the case where $X^6$ is halogen, chlorine, bromine, or iodine is preferable, and in particular, bromine or iodine is more preferable.

A palladium catalyst that can be used in the synthesis scheme (A-7) may be, but not limited to, palladium(II) acetate, tetrakis(triphenylphosphine)palladium(0), bis(triphenylphosphine)palladium(II) dichloride, or the like. A ligand of the palladium catalyst that can be used in the synthetic scheme (A-7) may be, but not limited to, tri(ortho-tolyl)phosphine, triphenylphosphine, tricyclohexylphosphine, or the like. A base which can be used in the synthesis scheme (A-7) may be, but not limited to, an organic base such as sodium tert-butoxide, an inorganic base such as potassium carbonate or sodium carbonate, or the like. A solvent that can be used in the synthetic scheme (A-7) may be, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like. Further, a mixed solvent of toluene and water; a mixed solvent of toluene, ethanol, and water; or a mixed solvent of ether such as ethylene glycol dimethyl ether and water is more preferable.

In Suzuki-Miyaura Coupling shown in the synthesis scheme (A-7), cross coupling using organoaluminum, organozirconium, organozinc, organotin, or the like may be performed instead of using the boronic acid or the organoboron compound. However, the present invention is not limited thereto.

In Suzuki-Miyaura Coupling shown in the synthesis scheme (A-7), a boronic acid of the anthracene derivative or an organoboron compound of the anthracene derivative may be coupled with a halide of the benzoxazole derivative or the benzoxazole derivative substituted with a triflate group by Suzuki-Miyaura Coupling.

(A-8)

Next, as shown in a synthesis scheme (A-8), the anthracene derivative (Compound 13) is halided, whereby a halide anthracene derivative (Compound 14) can be obtained.

In the synthesis scheme (A-8), $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen. $R^{21}$ to $R^{28}$ are independently either hydrogen or an alkyl group having 1 to 4 carbon atoms. $Ar^1$ is a substituted or unsubstituted arylene group having 6 to 13 carbon atoms. Further, $X^7$ represents halogen.

A halogenating agent that can be used in the synthesis scheme (A-8) may be, but not limited to, N-iodosuccinimide (NIS), bromine (Br$_2$), or N-bromosuccinimide (NBS). As a solvent that can be used, the following can be used alone or in combination: water; a carboxylic acid such as acetic acid (glacial acetic acid) or propionic acid; aromatic hydrocarbon such as benzene, toluene, or xylene; ether such as 1,2-dimethoxyethane, diethyl ether, tetrahydrofuran, or dioxane; saturated hydrocarbon such as pentane, hexane, heptane, or cyclohexane; a halogen-based solvent such as dichloromethane, chloroform, carbon tetrachloride, or 1,2-dichloroethane; nitrile such as acetonitrile or benzonitrile; ester such as ethyl acetate, methyl acetate, or butyl acetate; or the like. In the case where water is used, it is preferable to mix water and an organic solvent. Further, in the case where NIS is used, 1.5 to 2 equivalents of NIS are preferably used with respect to one equivalent of Compound 13, and more preferably, an acid such as acetic acid, sulfuric acid, or trifluoroacetic acid is used.

In the synthesis scheme (A-8), in the case where NBS is used as the halogenating agent, a polar solvent such as ethyl acetate, DMF, or acetic acid (glacial acetic acid) is preferably used; however, the present invention is not limited thereto.

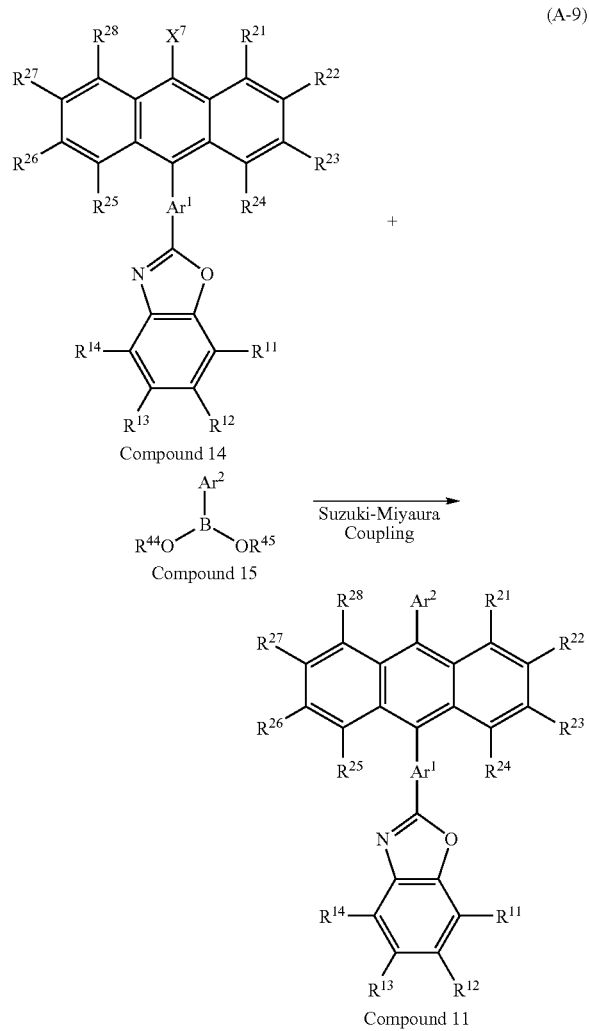

As shown in a synthesis scheme (A-9), the halide anthracene derivative (Compound 14) and an arylboronic acid or an arylboron compound (Compound 15) are coupled by Suzuki-Miyaura Coupling, whereby the target Compound 11 can be obtained. In the synthesis scheme (A-9), $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen. $R^{21}$ to $R^{28}$ are independently either hydrogen or an alkyl group having 1 to 4 carbon atoms. $R^{44}$ and $R^{45}$ are independently either hydrogen or an alkyl group having 1 to 6 carbon atoms. In the synthesis scheme (A-9), $R^{44}$ and $R^{45}$ may be bonded to each other to form a ring. $Ar^1$ is a substituted or unsubstituted arylene group having 6 to 13 carbon atoms. Further, $Ar^2$ is a substituted or unsubstituted aryl group having 6 to 13 carbon atoms or a substituted or unsubstituted heteroaryl group having 4 to 9 carbon atoms which is composed of a six-membered ring. Furthermore, $X^7$ represents halogen and is preferably bromine or iodine in particular.

A palladium catalyst that can be used in the synthesis scheme (A-9) may be, but not limited to, palladium(II) acetate, tetrakis(triphenylphosphine)palladium(0), bis(triphenylphosphine)palladium(II) dichloride, or the like. A ligand of the palladium catalyst that can be used in the synthetic scheme (A-9) may be, but not limited to, tri(ortho-tolyl)phosphine, triphenylphosphine, tricyclohexylphosphine, or the like. A base which can be used in the synthesis scheme (A-9) may be, but not limited to, an organic base such as sodium tert-butoxide, an inorganic base such as potassium carbonate or sodium carbonate, or the like. A solvent that can be used in the synthetic scheme (A-9) may be, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of an ether such as ethylene glycol dimethyl ether and water; or the like. Further, a mixed solvent of toluene and water; a mixed solvent of toluene, ethanol, and water; or a mixed solvent of ether such as ethylene glycol dimethyl ether and water is more preferable.

In Suzuki-Miyaura Coupling shown in the synthesis scheme (A-9), cross coupling using organoaluminum, organozirconium, organozinc, organotin, or the like may be used instead of using the boronic acid or the organoboron compound represented by Compound 15. However, the present invention is not limited thereto. Further, in this coupling, a triflate group or the like may be used other than halogen; however, the present invention is not limited thereto.

In Suzuki-Miyaura Coupling shown in the synthesis scheme (A-9), a boronic acid of the benzoxazole derivative or an organoboron compound of the benzoxazole derivative may be coupled with a halide of the aryl derivative or the aryl derivative substituted with a triflate group by Suzuki-Miyaura Coupling.

Benzoxazole derivatives according to the present invention have a benzoxazole skeleton. The benzoxazole skeleton contributes to easiness of accepting electrons. Further, the benzoxazole derivatives according to the present invention have a diaryl (heteroaryl) anthracene skeleton. The diaryl anthracene skeleton contributes to hopping of carriers. Therefore, the benzoxazole derivatives according to the present invention are excellent in an electron-transporting property.

In addition, it is preferable that benzoxazole derivatives according to the present invention do not have a substituent with high molecular weight, which might disturb hopping. In particular, in the case of providing a substituent with high molecular weight for Ar², the substituent might disturb hopping and reduce an electron-transporting property.

Further, the benzoxazole derivatives according to the present invention are excellent in an electron-transporting property. Thus, when the benzoxazole derivatives according to the present invention are used for electronics devices such as a light-emitting element and an organic transistor, favorable electric characteristics can be obtained.

Furthermore, benzoxazole derivatives according to the present invention are excellent in thermal stability. Thus, such electronic devices with high reliability that are not easily deteriorated even under a high temperature condition can be obtained by using the benzoxazole derivatives according to the present invention.

Embodiment 2

In Embodiment 2, an embodiment of light-emitting elements using any of the benzoxazole derivatives described in Embodiment 1 will be described with reference to FIG. 1 and FIG. 2.

A light-emitting element of the present invention has a plurality of layers between a pair of electrodes. The plurality of layers are stacked by combining layers formed with a substance having a high carrier-injecting property and a substance having a high carrier-transporting property so that a light-emitting region is formed apart from the electrodes, or so that carriers are recombined in a portion apart from the electrodes.

In this embodiment, the light-emitting element includes a first electrode 102, a second electrode 104, and an EL layer which is provided between the first electrode 102 and the second electrode 104. Note that in this embodiment, description will be made below in such conditions that the first electrode 102 functions as an anode and the second electrode 104 functions as a cathode. In other words, the description will be made below regarding light emission as being obtained when voltage is applied to the first electrode 102 and the second electrode 104 so that the potential of the first electrode 102 is higher than that of the second electrode 104.

A substrate 101 is used as a support of the light-emitting element. The substrate 101 can be formed of, for example, glass, plastic, metal, or the like. Note that materials other than glass or plastic can also be used as long as they can function as a support of a light-emitting element. Note that in the case where light from the light-emitting element is extracted outside through the substrate, the substrate 101 preferably has a light-transmitting property.

The first electrode 102 is preferably formed using any of metals, alloys, conductive compounds, a mixture thereof, and the like with a high work function (specifically, a work function of 4.0 eV or higher is preferable). For example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. Films of such conductive metal oxide are usually formed by sputtering method, but may also be formed by an ink-jet method, a spin coating method, or the like by application of sol-gel method or the like. For example, indium oxide-zinc oxide (IZO) can be formed by a sputtering method using indium oxide into which zinc oxide of 1 to 20 wt % is added, as a target. Indium oxide containing tungsten oxide and zinc oxide (IWZO) can be formed by a sputtering method using a target in which 0.5 to 5 wt % of tungsten oxide and 0.1 to 1 wt % of zinc oxide are mixed with indium oxide. Other than these, gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of the metal materials (such as titanium nitride), and the like can be given.

In the case where a layer including a composite material described below is used as a layer in contact with the first electrode 102, various metals, alloys, electrically conductive compounds, a mixture thereof, or the like can be used for the first electrode 102 regardless of the work function. For example, aluminum (Al), silver (Ag), an aluminum alloy (AlSi), or the like can be used. Besides, an element belonging to Group 1 or 2 of the periodic table which has a low work function, i.e., alkali metals such as lithium (Li) and cesium (Cs) and alkaline-earth metals such as magnesium (Mg), calcium (Ca), and strontium (Sr); alloys of them (e.g., MgAg and AlLi); rare-earth metals such as europium (Eu) and ytterbium (Yb); alloys of them; and the like can also be used. A film of an alkali metal, an alkaline-earth metal, or an alloy including these can be formed by a vacuum evaporation method. Alternatively, a film of an alloy including an alkali metal or an alkaline-earth metal can be formed by a sputtering method. Further, a film of silver paste or the like can be formed by an ink-jet method or the like.

The EL layer 103 described in this embodiment includes a hole-injecting layer 111, a hole-transporting layer 112, a light-emitting layer 113, an electron-transporting layer 114, and an electron-injecting layer 115. Note that it is acceptable as long as the EL layer 103 include a benzoxazole derivative described in Embodiment 1. Thus, the structure of other stacked layers is not specifically limited. That is, there is no particular limitation on the stacked structure of the EL layer 103, and any of the benzoxazole derivatives described in Embodiment 1 may be combined as appropriate with a layer formed of a substance having a high electron-transporting property, a substance having a high hole-transporting property, a substance having a high electron-injecting property, a substance having a high hole-injecting property, a bipolar substance (a substance having high electron-transporting and hole-transporting properties), a substance having a high light-emitting property, or the like. For example, the EL layer 103 can be formed by an appropriate combination of a hole-injecting layer, a hole-transporting layer, a light-emitting layer, an electron-transporting layer, an electron-injecting layer, and the like. Specific materials to form each of the layers will be given below.

The hole-injecting layer 111 is a layer including a substance having a high hole-injecting property. As the substance having a high hole-injecting property, molybdenum oxide, vanadium oxide, ruthenium oxide, tungsten oxide, manganese oxide, or the like can be used. In addition, as a low-molecular organic compound, the following compounds are given: phthalocyanine-based compounds such as phthalocyanine (abbrev.: H₂Pc), copper(II) phthalocyanine (abbrev.: CuPc), and vanadyl phthalocyanine (abbrev.: VOPc); aromatic amine compounds such as 4,4',4''-tris(N,N-diphenylamino)triphenylamine (abbrev.: TDATA), 4,4',4''-tris[N-(3-methylphenyl)-N-phenylamino]triphenylamine (abbrev.: MTDATA), 4,4'-bis[N-(4-diphenylaminophenyl)-N-phenylamino]biphenyl (abbrev.: DPAB), 4,4'-bis(N-{4-[N'-(3-methylphenyl)-N'-phenylamino]phenyl}-N-phenylamino)biphenyl (abbrev.: DNTPD), 1,3,5-tris[N-(4-diphenylaminophenyl)-N-phenylamino]benzene (abbrev.: DPA3B); 3-[N-(9-phenylcarbazol-3-yl)-N-phenylamino]-9-phenylcarbazole (abbrev.: PCzPCA1), 3,6-bis[N-(9-phenylcarbazol-3-yl)-N-phenylamino]-9-phenylcarbazole (abbrev.:

PCzPCA2), and 3-[N-(1-naphthyl)-N-(9-phenylcarbazol-3-yl)amino]-9-phenylcarbazole (abbrev.: PCzPCN1); and the like.

As a further alternative, a composite material formed by mixing an acceptor substance into a substance having a high hole-transporting property can also be used for the hole-injecting layer 111. Note that, by using the material formed by mixing an acceptor substance into a substance having a high hole-transporting property, a material used to form an electrode may be selected regardless of its work function. In other words, besides a material with a high work function, a material with a low work function may also be used for the first electrode 102. Such composite materials can be formed by co-evaporation of a substance having a high hole-transporting property and an acceptor substance.

It is to be noted that, in this specification, "composition" means not only a simple mixture of two materials but also a mixture of a plurality of materials in a condition where an electric charge is donated and accepted among the materials.

As an organic compound used for the composite material, various compounds such as an aromatic amine compound, a carbazole derivative, aromatic hydrocarbon, and a high molecular compound (oligomer, dendrimer, polymer, or the like) can be used. The organic compound used for the composite material is preferably an organic compound having a high hole-transporting property. Specifically, a substance having a hole mobility of $10^{-6}$ cm$^2$/Vs or higher is preferably used. However, a substance other than the above substances may be used as long as it has a higher hole-transporting property than an electron-transporting property. The organic compounds that can be used for the composite material are specifically listed below.

For example, the following organic compounds can be used for the composite material: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbrev.: NPB or α-NPD), and N,N'-bis(3-methylphenyl)-N,N'-diphenyl-[1,1'-biphenyl]-4,4'-diamine (abbrev.: TPD); carbazole derivatives such as 4,4'-di(N-carbazolyl)biphenyl (abbrev.: CBP), 1,3,5-tris[4-(N-carbazolyl)phenyl]benzene (abbrev.: TCPB), 9-[4-(10-phenyl-9-anthryl)phenyl]-9H-carbazole (abbrev.: CzPA), and 1,4-bis[4-(N-carbazolyl)phenyl-2,3,5,6-tetraphenylbenzene; and aromatic hydrocarbon compounds such as 2-tert-butyl-9,10-di(2-naphthyl)anthracene (abbrev.: t-BuDNA), 2-tert-butyl-9,10-di(1-naphthyl)anthracene, 9,10-bis(3,5-diphenylphenyl)anthracene (abbrev.: DPPA), 2-tert-butyl-9,10-bis(4-phenylphenyl)anthracene (abbrev.: t-BuDBA), 9,10-di(2-naphthyl)anthracene (abbrev.: DNA), 9,10-diphenylanthracene (abbrev.: DPAnth), 2-tert-butylanthracene (abbrev.: t-BuAnth), 9,10-bis(4-methyl-1-naphthyl)anthracene (abbrev.: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbrev.: DPVBi), and 9,10-bis[4-(2,2-diphenylvinyl)phenyl]anthracene (abbrev.: DPVPA).

As the acceptor substance, organic compounds such as 7,7,8,8-tetracyano-2,3,5,6-tetrafluoroquinodimethane (abbrev.: F$_4$-TCNQ) and chloranil and a transition metal oxide can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of a high electron accepting property. Among these, molybdenum oxide is especially preferable since it is stable in air and its hygroscopic property is low so that it can be easily treated.

For the hole-injecting layer 111, a high molecular compound (e.g., an oligomer, a dendrimer, or a polymer) can be used. For example, the following high molecular compounds can be given: poly(N-vinylcarbazole) (abbrev.: PVK); poly (4-vinyltriphenylamine) (abbrev.: PVTPA); poly[N-(4-{1'-[4-(4-diphenylamino)phenyl]phenyl-N'-phenylamino}phenyl)methacrylamide] (abbrev.: PTPDMA); and poly[N,N'-bis(4-butylphenyl)-N,N'-bis(phenyl)benzidine] (abbrev.: Poly-TPD). In addition, high molecular compounds doped with acid such as poly(3,4-ethylenedioxythiophene)/poly(styrenesulfonic acid) (PEDOT/PSS) and polyaniline/poly(styrenesulfonic acid) (PAni/PSS) can be used.

Note that the hole-injecting layer 111 may be formed using a composite material of the above-described high molecular compound, such as PVK, PVTPA, PTPDMA, or Poly-TPD, and the above-described acceptor substance.

The hole-transporting layer 112 is a layer which includes a substance having a high hole-transporting property. As a low molecular organic compound of a substance having a high hole-transporting property, aromatic amine compounds such as NPB (or α-NPD), TPD, 4,4'-bis[N-(9,9-dimethylfluoren-2-yl)-N-phenylamino]biphenyl (abbrev.: DFLDPBi), and 4,4'-bis[N-(spiro-9,9'-bifluoren-2-yl)-N-phenylamino]biphenyl (abbrev.: BSPB) can be used. The materials described here are mainly materials having a hole mobility of $10^{-6}$ cm$^2$/Vs or higher. It is to be noted that a substance other than the above substances may be used as long as it has a higher hole-transporting property than an electron-transporting property. Note that the layer containing a substance having a high hole-transporting property is not limited to a single layer, and two or more layers containing the aforementioned substances may be stacked.

Furthermore, for the hole-transporting layer 112, a composite material in which an acceptor substance is contained in the above-mentioned substance having a high hole-transporting property can be used.

For the hole-transporting layer 112, a high molecular compound such as PVK, PVTPA, PTPDMA, or Poly-TPD can be used alternatively.

The light-emitting layer 113 is a layer including a substance having a high light-emitting property, and various materials can be used for the light-emitting layer 113. As the substance having a high light-emitting property, for example, a fluorescent compound which emits fluorescence or a phosphorescent compound which emits phosphorescence can be used.

Examples of a phosphorescent compound which is used for the light-emitting layer are given below. As a blue light-emitting material, the following can be given: bis[2-(4',6'-difluorophenyl)pyridinato-N,C$^2$']iridium(III)tetrakis(1-pyrazolyl)borate (abbrev.: FIr6), bis[2-(4',6'-difluorophenyl)pyridinato-N,C$^2$']iridium(III)picolinate (abbrev.: FIrpic), bis[2-(3',5'bistrifluoromethylphenyl)pyridinato-N,C$^2$']iridium (III)picolinate (abbrev.: Ir(CF$_3$ ppy)$_2$(pic)), bis[2-(4',6'-difluorophenyl)pyridinato-N,C$^2$']iridium(III) acetylacetonate (abbrev.: FIracac), and the like. As a green light-emitting material, the following can be given: tris(2-phenylpyridinato-N,C$^2$')iridium(II) (abbrev.: Ir(ppy)$_3$); bis (2-phenylpyridinato-N,C$^2$')iridium(II)acetylacetonate (abbrev.: Ir(ppy)$_2$(acac)); bis(1,2-diphenyl-1H-benzimidazolato)iridium(II)acetylacetonate (abbrev.:

Ir(pbi)$_2$ (acac)); bis(benzo[h]quinolinato)iridium(III)acetylacetonate (abbrev.: Ir(bzq)$_2$(acac)); and the like. As a yellow light-emitting material, the following can be given: bis(2,4-diphenyl-1,3-oxazolato-N,C$^{2'}$)iridium(III)acetylacetonate (abbrev.: Ir(dpo)$_2$(acac)); bis[2-(4'-perfluorophenylphenyl) pyridinato]iridium(III)acetylacetonate (abbrev.: Ir(p-PF-ph)$_2$ (acac)); bis(2-phenylbenzothiazolato-N,C$^{2'}$)iridium(III) acetylacetonate (abbrev.: Ir(bt)$_2$(acac)); and the like. As an orange light-emitting material, the following can be given: tris(2-phenylquinolinato-N,C$^{2'}$)iridium(III) (abbrev.: Ir(Pq)$_3$); bis(2-phenylquinolinato-N,C$^{2'}$)iridium(III) acetylacetonate (abbrev.: Ir(pq)$_2$(acac)); and the like. As a red light-emitting material, the following organometallic complexes can be given: bis[2-(2'-benzo[4,5-α]thienyl)pyridinato-N,C$^{3'}$)iridium(II)acetylacetonate (abbrev.: Ir(btp)$_2$ (acac)); bis(1-phenylisoquinolinato-N,C$^{2'}$)iridium(II) acetylacetonate (abbrev.: Ir(piq)$_2$(acac)); (acetylacetonato) bis[2,3-bis(4-fluorophenyl)quinoxalinato]iridium(II) (abbrev.: Ir(Fdpq)$_2$(acac)); 2,3,7,8,12,13,17,18-octaethyl-21H,23H-porphyrinplatinum(II) (abbrev.: PtOEP); and the like. In addition, a rare-earth metal complex such as tris (acetylacetonato)(monophenanthroline)terbium(III) (abbrev.: Tb(acac)$_3$(Phen)); tris(1,3-diphenyl-1,3-propanedionato)(monophenanthroline)europium(III) (abbrev.: Eu(DBM)$_3$ (Phen)); or tris[1-(2-thenoyl)-3,3,3-trifluoroacetonato](monophenanthroline)europium(III) (abbrev.: Eu(TTA)$_3$(Phen)) performs light emission (electron transition between different multiplicities) from a rare-earth metal ion; therefore, such a rare-earth metal complex can be used as the phosphorescent compound.

Examples of a fluorescent compound which is used for the light-emitting layer are given below. As a blue light-emitting material, the following can be given:
N,N'-bis[4-(9H-carbazol-9-yl)phenyl]-N,N'-diphenylstilbene-4,4'-diamine (abbrev.: YGA2S), 4-(9H-carbazol-9-yl)-4'-(10-phenyl-9-anthryl)triphenylamine (abbrev.: YGAPA), 4-(9H-carbazol-9-yl)-4'-(9,10-diphenyl-2-anthryl)triphenylamine (abbrev.: 2YGAPPA); N,9-diphenyl-N-[4-(10-phenyl-9-anthryl)phenyl]-9H-carbazol-3-amine (PCAPA); perylene; 2,5,8,11-tetra-tert-butylperylene (TBP); 4-(10-phenyl-9-anthryl)-4'-(9-phenyl-9H-carbazol-3-yl)triphenylamine (PCBAPA); and the like. As a green light-emitting material, the following can be given:
N-(9,10-diphenyl-2-anthryl)-N,9-diphenyl-9H-carbazol-3-amine (abbrev.: 2PCAPA); N-[9,10-bis(1,1'-biphenyl-2-yl)-2-anthryl]-N,9-diphenyl-9H-carbazol-3-amine (abbrev.: 2PCABPhA); N-(9,10-diphenyl-2-anthryl)-N,N',N'-triphenyl-1,4-phenylenediamine abbrev.: 2DPAPA); N-[9,10-bis(1,1'-biphenyl-2-yl)-2-anthryl]-N,N',N'-triphenyl-1,4-phenylenediamine (abbrev.: 2DPABPhA); N-[9,10-bis(1,1'-biphenyl-2-yl)]-N-[4-(9H-carbazol-9-yl)phenyl]-N-phenylanthracen-2-amine (abbrev.: 2YGABPhA); N,N,9-triphenylanthracen-9-amine (abbrev.: DPhAPhA); and the like. As a yellow light-emitting material, the following can be given: rubrene, 5,12-bis(1,1'-biphenyl-4-yl)-6,11-diphenyltetracene (abbrev.: BPT), and the like. As a red light-emitting material, the following can be given: N,N,N',N'-tetrakis(4-methylphenyl)tetracene-5,11-diamine (abbrev.: p-mPhTD), 7,13-diphenyl-N,N,N',N'-tetrakis(4-methylphenyl)acenaphtho[1,2-a]fluoranthene-3,10-diamine (abbrev.: p-mPhAFD), and the like.

Note that the light-emitting layer may have a structure in which any of the above-described substances having a high light-emitting property (guest material) is dispersed in another substance (host material). As a substance in which the substance having a light-emitting property is dispersed, various kinds of substances can be used, and it is preferable to use a substance whose lowest unoccupied molecular orbital (LUMO) level is higher than that of the substance having a light-emitting property and whose highest occupied molecular orbital (HOMO) level is lower than that of the substance having a light-emitting property.

As the substance in which the substance having a light-emitting property is dispersed, specifically, the following can be used: a metal complex such as tris(8-quinolinolato)aluminum(III) (abbrev.: Alq), tris(4-methyl-8-quinolinolato)aluminum(III) (abbrev.: Almq$_3$), bis(10-hydroxybenzo[h]quinolinato)beryllium(II) (abbrev.: BeBq$_2$), bis(2-methyl-8-quinolinolato)(4-phenylphenolato)aluminum(III) (abbrev.: BAlq), bis(8-quinolinolato)zinc(II) (abbrev.: Znq), bis[2-(2-benzoxazolyl)phenolato]zinc(II) (abbrev.: ZnPBO), or bis[2-(2-benzothiazolyl)phenolato]zinc(II) (abbrev.: ZnBTZ); a heterocyclic compound such as 2-(4-biphenylyl)-5-(4-tert-butylphenyl)-1,3,4-oxadiazole (abbrev.: PBD), 1,3-bis[5-(p-tert-butylphenyl)-1,3,4-oxadiazol-2-yl]benzene (abbrev.: OXD-7), 3-(4-biphenylyl)-4-phenyl-5-(4-tert-butylphenyl)-1,2,4-triazole (abbrev.: TAZ), 2,2',2''-(1,3,5-benzenetriyl)tris (1-phenyl-1H-benzimidazole) (abbrev.: TPBI), bathophenanthroline (abbrev.: BPhen), or bathocuproine (BCP); a condensed aromatic compound such as 9-[4-(10-phenyl-9-anthryl)phenyl]-9H-carbazole (abbrev.: CzPA), 3,6-diphenyl-9-[4-(10-phenyl-9-anthryl)phenyl]-9H-carbazole (abbrev.: DPCzPA), 9,10-bis(3,5-diphenylphenyl)anthracene (abbrev.: DPPA), 9,10-di(2-naphthyl)anthracene (abbrev.: DNA), 2-tert-butyl-9,10-di(2-naphthyl)anthracene (abbrev.: t-BuDNA), 9,9'-bianthryl (abbrev.: BANT), 9,9'-(stilbene-3, 3'-diyl)diphenanthrene (abbrev.: DPNS), 9,9'-(stilbene-4,4'-diyl)diphenanthrene (abbrev.: DPNS2), 3,3',3''-(benzene-1,3, 5-triyl)tripyrene (abbrev.: TPB3), 9,10-diphenylanthracene (abbrev.: DPAnth), or 6,12-dimethoxy-5,11-diphenylchrysene; an aromatic amine compound such as N,N-diphenyl-9-[4-(10-phenyl-9-anthryl)phenyl]-9H-carbazol-3-amine (abbrev.: CZA1PA), 4-(10-phenyl-9-anthryl)triphenylamine (abbrev.: DPhPA), N,9-diphenyl-N-[4-(10-phenyl-9-anthryl) phenyl]-9H-carbazol-3-amine (abbrev.: PCAPA), N,9-diphenyl-N-{4-[4-(10-phenyl-9-anthryl)phenyl]phenyl}-9H-carbazol-3-amine (abbrev.: PCAPBA), N-(9,10-diphenyl-2-anthryl)-N,9-diphenyl-9H-carbazol-3-amine (abbrev.: 2PCAPA), NPB (or α-NPD), TPD, DFLDPBi, or BSPB; or the like.

As a substance in which the substance having a light-emitting property is dispersed, plural kinds of substances can be used. For example, in order to suppress crystallization, a substance such as rubrene which suppresses crystallization may be further added. In addition, NPB, Alq, or the like may be further added in order to transfer energy to the substance having a light-emitting property more efficiently.

When the light-emitting layer 113 has a structure in which the substance having a high light-emitting property is dispersed into another substance, crystallization of the light-emitting layer 113 can be suppressed. Further, concentration quenching due to high concentration of the substance having a high light-emitting property can be suppressed.

For the light-emitting layer 113, a high molecular compound can also be used. Specifically, as a blue light-emitting material, the following can be given: poly(9,9-dioctylfluorene-2,7-diyl) (abbrev.: PFO), poly[(9,9-dioctylfluorene-2,7-diyl-co-(2,5-dimethoxybenzene-1,4-diyl)] (abbrev.: PF-DMOP), poly {(9,9-dioctylfluorene-2,7-diyl)-co-[N,N'-di-(p-butylphenyl)-1,4-diaminobenzene]} (abbrev.: TAB-PFH), and the like. As a green light-emitting material, the following can be given: poly(p-phenylenevinylene) (abbrev.: PPV), poly[(9,9-dihexylfluorene-2,7-diyl)-alt-co-(benzo[2, 1,3]thiadiazol-4,7-diyl)] (abbrev.: PFBT), poly[(9,9-dioctyl- 2,7-divinylenfluorenylene)-alt-co-(2-methoxy-5-(2-ethylhexyloxy)-1,4-phenylene)], and the like. As a light-emitting material which exhibits orange to red light emission, the following can be given: poly[2-methoxy-5-(2'-ethylhexoxy)-1,4-phenylenevinylene] (abbrev.: MEH-PPV), poly(3-butylthiophene-2,5-diyl) (abbrev.: R4-PAT), poly{[9,9-dihexyl-2,7-bis(1-cyanovinylene)fluorenylene]-alt-co-[2,5-bis(N,N'-diphenyl amino)-1,4-phenylene]}, poly {[2-methoxy-5-(2-ethylhexyloxy)-1,4-bis(1-cyanovinylenephenylene)]-alt-co-[2,5-bis(N,N'-diphenylamino)-1,4-phenylene]} (abbrev.: CN-PPV-DPD), and the like.

The electron-transporting layer 114 is a layer including a substance having a high electron-transporting property. The benzoxazole derivatives described in Embodiment 1 are excellent in an electron-transporting property; therefore, any of the benzoxazole derivatives can be suitably used for the electron-transporting layer 114. Note that the electron-transporting layer is not limited to a single layer, and may be a stack of two or more layers.

In the case where the electron transporting layer has a stacked structure of two or more layers, as another substance having a high electron-transporting property, for example, as a low molecular organic compound, a metal complex such as tris(8-quinolinolato)aluminum(III) (abbrev.: Alq), tris(4-methyl-8-quinolinolato)aluminum(III) (abbrev.: Almq$_3$), bis(10-hydroxybenzo[h]quinolinato)beryllium(II) (abbrev.: BeBq$_2$), bis(2-methyl-8-quinolinolato)(4-phenylphenolato)aluminum(III) (abbrev.: BAlq), bis(8-quinolinolato)zinc(II) (abbrev.: Znq), bis[2-(2-benzoxazolyl)phenolato]zinc(II) (abbrev.: ZnPBO), or bis[2-(2-benzothiazolyl)phenolato]zinc(II) (abbrev.: ZnBTZ), can be used. Further, the following heterocyclic compound, as well as the aforementioned metal complexes, can also be used: 2-(4-biphenylyl)-5-(4-tert-butylphenyl)-1,3,4-oxadiazole (abbrev.: PBD); 1,3-bis[5-(p-tert-butylphenyl)-1,3,4-oxadiazol-2-yl]benzene (abbrev.: OXD-7); 3-(4-biphenylyl)-4-phenyl-5-(4-tert-butylphenyl)-1,2,4-triazole (abbrev.: TAZ01); 2,2',2''-(1,3,5-benzenetriyl)tris(1-phenyl-1H-benzimidazole) (abbrev.: TPBI); bathophenanthroline (abbrev.: BPhen); bathocuproine (abbrev.: BCP); or the like. The materials described here are mainly materials having an electron mobility of $10^{-6}$ cm$^2$/Vs or higher. Note that a substance other than the above substances may be used as long as it has a higher electron-transporting property than a hole-transporting property. Note that the electron transporting layer is not limited to a single layer, and two or more layers containing the aforementioned substances may be stacked.

In the case where the electron-transporting layer has a stacked structure of two or more layers, a high molecular compound can be used as another substance having a high electron-transporting property. For example, poly[(9,9-dihexylfluorene-2,7-diyl)-co-(pyridine-3,5-diyl)] (abbrev.: PF-Py), poly[(9,9-dioctylfluorene-2,7-diyl)-co-(2,2'-bipyridine-6,6'-diyl)] (abbrev.: PF-BPy), or the like can be used.

The electron-injecting layer 115 is a layer including a substance having a high electron-injecting property. As the substance having a high electron-injecting property, an alkali metal or an alkaline-earth metal such as lithium (Li) or magnesium (Mg), or a compound thereof such as lithium fluoride (LiF), cesium fluoride (CsF), or calcium fluoride (CaF$_2$) can be used. For example, a layer of a substance having an electron-transporting property containing an alkali metal, an alkaline-earth metal, or a compound thereof, such as Alq which contains magnesium (Mg), may be used. With the use of a layer of a substance having an electron-transporting property containing an alkali metal or an alkaline-earth metal as the electron injecting layer, electron injection from the second electrode 104 is performed efficiently, which is preferable.

As a substance for forming the second electrode 104, a metal, an alloy, an electrically conductive compound, a mixture thereof, or the like with a low work function (specifically, a work function of 3.8 eV or lower is preferable) can be used. As a specific example of such a cathode material, an element belonging to Group 1 or 2 of the periodic table, that is, an alkali metal such as lithium (Li) or cesium (Cs); an alkaline-earth metal such as magnesium (Mg), calcium (Ca), or strontium (Sr); an alloy thereof (MgAg, AlLi); a rare-earth metal such as europium (Eu) or ytterbium (Yb); an alloy thereof; and the like can be used. A film of an alkali metal, an alkaline-earth metal, or an alloy including these can be formed by a vacuum evaporation method. In addition, a film of an alloy including an alkali metal or an alkaline-earth metal can be formed by a sputtering method. Further, a film of silver paste or the like can be formed by an ink-jet method.

In the case where the electron-injecting layer 115 that is a layer functioning to promote electron injection is provided between the second electrode 104 and the electron-transporting layer 114, the second electrode 104 can be formed using any of various conductive materials such as Al, Ag, ITO, and indium oxide-tin oxide containing silicon or silicon oxide, regardless of their work functions. A film of any of these conductive materials can be formed by a sputtering method, an inkjet method, a spin coating method, or the like.

As a formation method of the EL layer, various methods can be used regardless of a dry method or a wet method. For example, a vacuum evaporation method, an ink-jet method, a spin coating method, or the like may be used. Further, different formation methods may be employed for each electrode or layer.

For example, the EL layer may be formed by a wet method using a high molecular compound selected from the above-described materials. Further, the EL layer can also be formed by a wet method using a low molecular organic compound. Furthermore, the EL layer may be formed by a dry method such as a vacuum evaporation method using a low molecular organic compound.

The electrode may be formed by a wet method using sol-gel method, or by a wet method using a paste of a metal material. Further, the electrode may be formed by a dry method such as a sputtering method or a vacuum evaporation method.

For example, in the case where a light-emitting element of the present invention is applied to a display device and the display device is manufactured using a large-sized substrate, it is preferable to form the light-emitting layer by a wet method. When the light-emitting layer is formed by an ink-jet method, it becomes easy to form the light-emitting layers separately for different colors even when a large-sized substrate is used.

The light-emitting element of the present invention that has a structure as the one described above emits light when a current flows due to a potential difference generated between the first electrode 102 and the second electrode 104 and holes and electrons are recombined in the EL layer 103.

The emitted light is extracted outside through one or both of the first electrode 102 and the second electrode 104. Therefore, one or both of the first electrode 102 and the second electrode 104 have a light-transmitting property. For example, when only the first electrode 102 has a light-transmitting property, the emitted light is extracted from the substrate side through the first electrode 102. Meanwhile, when only the second electrode 104 has a light-transmitting property, the emitted light is extracted from the side opposite to the substrate side through the second electrode 104. In the case where each of the first electrode 102 and the second electrode 104 has a light-transmitting property, the emitted light is extracted from both of the substrate side and the side opposite to the substrate through the first electrode 102 and the second electrode 104.

The structure of the layers provided between the first electrode 102 and the second electrode 104 is not limited to the aforementioned one. Any structure other than the above structure can be employed as long as a light-emitting region for recombination of holes and electrons is positioned away from the first electrode 102 and the second electrode 104 so as to prevent quenching caused by proximity of the light-emitting region to metal, and any of the benzoxazole derivatives shown in Embodiment 1 is provided.

That is, there is no particular limitation on the stacked structure of the layers, and any of the benzoxazole derivatives shown in Embodiment 1 may be combined as appropriate with a layer containing a substance having a high electron-transporting property, a substance having a high hole-transporting property, a substance having a high electron-injecting property, a substance having a high hole-injecting property, a bipolar substance (a substance having high electron-transporting and hole-transporting properties), or the like.

Figure 2:
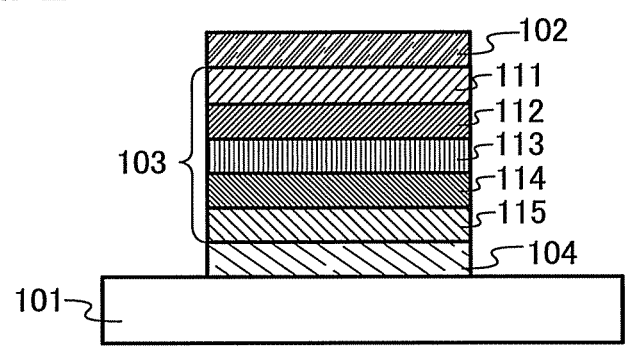
FIG. 2 illustrates a light-emitting element according to an embodiment of the present invention.

Alternatively, as illustrated in FIG. 2, a structure may be employed in which the second electrode 104 serving as a cathode, the EL layer 103, and the first electrode 102 serving as an anode are stacked sequentially over the substrate 101. In FIG. 2, a structure is employed in which the electron-injecting layer 115, the electron-transporting layer 114, the light-emitting layer 113, the hole-transporting layer 112, and the hole-injecting layer 111 are stacked sequentially over the second electrode 104.

In this embodiment, the light-emitting element is formed over a substrate made of glass, plastic, or the like. By forming a plurality of such light-emitting elements over a substrate, a passive-matrix light-emitting device can be manufactured. Alternatively, for example, a thin film transistor (TFT) may be formed over a substrate made of glass, plastic, or the like, and a light-emitting element may be manufactured over an electrode that is electrically connected to the TFT. Thus, an active-matrix light-emitting device which controls the driving of a light-emitting element by a TFT can be manufactured. The structure of the TFT is not particularly limited. The TFT may be either of staggered type or inversely staggered type. In addition, a driver circuit formed over a TFT substrate may be formed using both an N-type and P-type TFTs, or using either an N-type or P-type TFTs. In addition, the crystallinity of a semiconductor film used for the TFT is not particularly limited. Either an amorphous semiconductor film or a crystalline semiconductor film may be used for the TFT. Further, a single crystal semiconductor film may be used. The single crystal semiconductor film can be formed by a Smart Cut (registered trademark) method or the like.

Because the benzoxazole derivatives described in Embodiment 1 have an excellent electron-transporting property, any of the benzoxazole derivatives can be suitably used for an electron-transporting layer of a light-emitting element. By using any of the benzoxazole derivatives described in Embodiment 1, a light-emitting element with low driving voltage can be obtained. In addition, a light-emitting element with low power consumption can be obtained.

In many cases, light-emitting elements which use an organic compound have excessive holes when they are driven. Accordingly, in order to improve emission efficiency, it is important to donate more electrons by using a material having an excellent electron-transporting property. The benzoxazole derivatives described in Embodiment 1 are excellent in an electron-transporting property; accordingly, by using any of the benzoxazole derivatives for a light-emitting element, carrier balance can be improved, whereby emission efficiency can be improved.

The benzoxazole derivatives described in Embodiment 1 are excellent in thermal stability. Therefore, when any of the benzoxazole derivatives described in Embodiment 1 is used, such a light-emitting element with high reliability that is not easily deteriorated even under a high temperature condition can be obtained.

Note that this embodiment can be implemented in combination with any of the other embodiments as appropriate.

Embodiment 3

In Embodiment 3, a structure in which any of the benzoxazole derivatives described in Embodiment 1 is used for a light-emitting layer will be described as one embodiment of a light-emitting element according to the present invention.

Because the benzoxazole derivatives described in Embodiment 1 are excellent in an electron-transporting property, the benzoxazole derivatives can each be used as a host material in a light-emitting layer having a structure in which a substance having a high light-emitting property (guest material) is dispersed in another substance (host material).

In the case where any of the benzoxazole derivatives described in Embodiment 1 is used as a host material and where a guest material emits fluorescence, it is preferable to use, as the guest material, a substance whose lowest unoccupied molecular orbital (LUMO) level is lower than that of the benzoxazole derivative and whose highest occupied molecular orbital (HOMO) level is higher than that of the benzoxazole derivative. As a blue light-emitting material, the following can be used: N,N'-bis[4-(9H-carbazol-9-yl)phenyl]-N,N'-diphenylstilbene-4,4'-diamine (abbrev.: YGA2S), 4-(9H-carbazol-9-yl)-4'-(10-phenyl-9-anthryl)triphenylamine (abbrev.: YGAPA), or the like. As a green light-emitting material, the following can be used: N-(9,10-diphenyl-2-anthryl)-N,9-diphenyl-9H-carbazol-3-amine (abbrev.: 2PCAPA); N-[9,10-bis(1,1'-biphenyl-2-yl)-2-anthryl]-N,9-diphenyl-9H-carbazol-3-amine (abbrev.: 2PCABPhA); N-(9,10-diphenyl-2-anthryl)-N,N',N'-triphenyl-1,4-phenylenediamine (abbrev.: 2DPAPA); N-[9,10-bis(1,1'-biphenyl-2-yl)-2-anthryl]-N,N',N'-triphenyl-1,4-phenylenediamine (abbrev.: 2DPABPhA); N-[9,10-bis(1,1'-biphenyl-2-yl)]-N-[4-(9H-carbazol-9-yl)phenyl]-N-phenylanthracen-2-amine (abbrev.: 2YGABPhA); N,N,9-triphenylanthracen-9-amine (abbrev.: DPhAPhA); or the like. As a yellow light-emitting material, the following can be used: rubrene, 5,12-bis(1,1'-biphenyl-4-yl)-6,11-diphenyltetracene (abbrev.: BPT), or the like. As a red light-emitting material, the following can be used: N,N,N',N'-tetrakis(4-methylphenyl)tetracene-5,11-diamine (abbrev.: p-mPhTD), 7,13-diphenyl-N,N,N',N'-tetrakis(4-methylphenyl)acenaphtho[1,2-a]fluoranthene-3,10-diamine (abbrev.: p-mPhAFD), or the like.

Alternatively, in the case where any of the benzoxazole derivatives described in Embodiment 1 is used as a host material and where a guest material emits phosphorescence, it is preferable to use, as the guest material, a substance having lower triplet excitation energy than the benzoxazole derivative.

Since the benzoxazole derivatives described in Embodiment 1 are excellent in an electron-transporting property, by using any of the benzoxazole derivatives for a light-emitting layer, a light-emitting layer having a high electron-transporting property can be obtained. Such a light-emitting layer can provide light emission with high efficiency when a guest material having a high electron-trapping property is used.

As the substance (host material) into which the substance having a light-emitting property (guest material) is dispersed, plural kinds of substances can be used. Therefore, the light-emitting layer may contain a second host material in addition to the benzoxazole derivative described in Embodiment 1. Since the benzoxazole derivatives described in Embodiment 1 are excellent in an electron-transporting property, it is preferable to use a material having an excellent hole-transporting property as the second host material. With such a structure, the light-emitting layer has a hole-transporting property and an electron-transporting property, and the recombination probability of holes and electrons in the light-emitting layer is increased, so that light emission with high efficiency can be obtained. Further, a light-emitting element with low-voltage driving can be obtained.

The benzoxazole derivatives described in Embodiment 1 are excellent in thermal stability. Therefore, when any of the benzoxazole derivatives described in Embodiment 1 is used, such a light-emitting element with high reliability that is not easily deteriorated even under a high temperature condition can be obtained.

Note that this embodiment can be implemented in combination with any of the other embodiments as appropriate.

Embodiment 4

In Embodiment 4, a structure in which any of the benzoxazole derivatives described in Embodiment 1 is used for an electron-injecting layer will be described as one embodiment of a light-emitting element according to the present invention.

Since the benzoxazole derivatives described in Embodiment 1 are excellent in an electron-injecting property as well, any of the benzoxazole derivatives can be used for an electron-injecting layer of a light-emitting element. In the case where any of the benzoxazole derivatives described in Embodiment 1 is used for an electron-injecting layer, it is preferable that the electron-injecting layer include an alkali metal, an alkaline-earth metal, or a compound thereof in addition to any of the benzoxazole derivatives described in Embodiment 1. With such a structure, a property of injecting electrons from an electrode serving as a cathode is increased, and a light-emitting element with low-voltage driving can be obtained.

The benzoxazole derivatives described in Embodiment 1 are excellent in thermal stability. Therefore, when any of the benzoxazole derivatives described in Embodiment 1 is used, such a light-emitting device with high reliability that is not easily deteriorated even under a high temperature condition can be obtained.

Note that this embodiment can be implemented in combination with any of the other embodiments as appropriate.

Embodiment 5

In Embodiment 5, an embodiment of a light-emitting element having a structure in which a plurality of light-emitting units according to the present invention is stacked (hereinafter, referred to as a stack-type element) will be described with reference to FIG. 3. This light-emitting element is a stacked-type element including a plurality of light-emitting units between a first electrode and a second electrode. The structure of each light-emitting unit can be similar to any of the structures described in Embodiments 2 to 4. In other words, the light-emitting element described in Embodiment 2 is a light-emitting element having one light-emitting unit. In this embodiment, a light-emitting element having a plurality of light-emitting units will be described.

Figure 3:
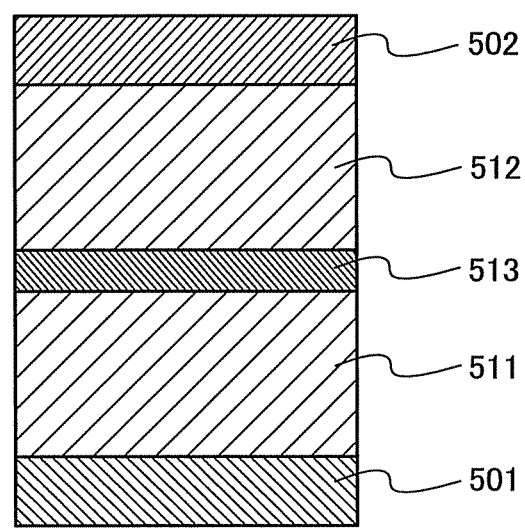
FIG. 3 illustrates a light-emitting element according to an embodiment of the present invention.

In FIG. 3, a first light-emitting unit 511 and a second light-emitting unit 512 are stacked between a first electrode 501 and a second electrode 502. The first electrode 501 and the second electrode 502 may be similar to the electrodes described in Embodiment 1. In addition, the first light-emitting unit 511 and the second light-emitting unit 512 may have the same structure or different structures. Structures of the first light-emitting unit 511 and the second light-emitting unit 512 may be similar to any of the structures described in Embodiments 2 to 4.

A charge-generating layer 513 is a layer which injects electrons into a light-emitting unit on one side and injects holes into a light-emitting unit on the other side when voltage is applied to the first electrode 501 and the second electrode 502, and may have either a single-layer structure or a stacked structure of plural layers. As a stacked structure of plural layers, a structure in which a hole-injecting layer and an electron-injecting layer are stacked is preferable.

As the hole-injecting layer, a semiconductor or an insulator, such as molybdenum oxide, vanadium oxide, rhenium oxide, or ruthenium oxide, can be used. Alternatively, the hole-injecting layer may have a structure in which an acceptor substance is added to a substance having a high hole-transporting property. The layer including a substance having a high hole-transporting property and an acceptor substance is formed of the composite material described in Embodiment 2 and includes, as an acceptor substance, 7,7,8,8-tetracyano-2,3,5,6-tetrafluoroquinodimethane (abbrev.: $F_4$-TCNQ) or metal oxide such as vanadium oxide, molybdenum oxide, or tungsten oxide. As the substance having a high hole-transporting property, various compounds such as an aromatic amine compound, a carbazole derivative, aromatic hydrocarbon, a high-molecular compound, oligomer, dendrimer, polymer, and the like can be used. Note that a substance having a hole mobility of $10^{-6}$ $cm^2/Vs$ or higher is preferably employed as the substance having a high hole-transporting property. It is to be noted that a substance other than the above substances may be used as long as it has a higher hole-transporting property than an electron-transporting property. Since the composite material of the substance having a high hole-transporting property and the acceptor substance is excellent in a carrier-injecting property and a carrier-transporting property, low-voltage driving and low-current driving can be realized.

As the electron-injecting layer, an insulator or a semiconductor, such as lithium oxide, lithium fluoride, or cesium carbonate, can be used. Alternatively, the electron-injecting layer may have a structure in which a donor substance is added to a substance having a high electron-transporting property. As the donor substance, an alkali metal, an alkaline-earth metal, a rare-earth metal, a metal that belongs to Group 13 of the periodic table, or an oxide or carbonate thereof may be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transporting property, the materials described in Embodiment 2 may be used. Note that a substance having an electron mobility of $10^{-6}$ $cm^2/Vs$ or higher is preferably employed as the substance having a high electron-transporting property. It is to be noted that a substance other than the above substances may be used as long as it has a higher electron-transporting property than a hole-transporting property. Since the composite material of the substance having a high electron-transporting property and the donor substance is excellent in a carrier-injecting property and a carrier-transporting property, low-voltage driving and low-current driving can be realized.

Further, the electrode materials described in Embodiment 2 can be used for the charge-generating layer 513. For example, the charge-generating layer 513 may be formed by combining a layer including a substance having a high hole-transporting property and metal oxide with a transparent conductive film. It is preferable that the charge-generating layer be a highly light-transmitting layer so that light extraction efficiency is increased.

In any cases, the charge-generating layer 513 interposed between the first light-emitting unit 511 and the second light-emitting unit 512 may have any structure as long as electrons are injected to a light-emitting unit on one side and holes are injected to a light-emitting unit on the other side when voltage is applied to the first electrode 501 and the second electrode 502. For example, any structure is acceptable for the charge-generating layer 513 as long as the layer 513 injects electrons and holes into the first light-emitting unit 511 and the second light-emitting unit 512, respectively, when voltage is applied so that the potential of the first electrode is higher than the potential of the second electrode.

Although the light-emitting element having two light-emitting units is described in this embodiment, a light-emitting element in which three or more light-emitting units are stacked can be employed in a similar way. By arranging a plurality of light-emitting units between a pair of electrodes so as to be partitioned by a charge-generating layer as in the light-emitting element of this embodiment, the element can perform light emission in a high luminance region while keeping a current density low; whereby the element can have long life. In the case where the light-emitting element is applied to a lighting device, voltage drop due to resistance of an electrode material can be reduced. Accordingly, uniform emission in a large area is possible. Furthermore, a light-emitting device of low power consumption, which can be driven at low voltage, can be realized.

When light-emitting units have different emission colors, light emission of desired color can be obtained as a whole light-emitting element. For example, in the light-emitting element having two light-emitting units, when emission color of the first light-emitting unit and emission color of the second light-emitting unit are complementary colors, a light-emitting element emitting white light as a whole light-emitting element can be obtained. Note that "complementary color" means a relation between colors which becomes an achromatic color when they are mixed. That is, white light emission can be obtained by mixture of lights obtained from substances emitting the lights of complementary colors. Also in a light-emitting element including three light-emitting units, white light emission can be similarly obtained as a whole light-emitting element in the case where emission color of the first light-emitting unit is red, emission color of the second light-emitting unit is green, and emission color of the third light-emitting unit is blue, for example. Note that this embodiment can be implemented in combination with any of the other embodiments as appropriate.

Embodiment 6

In Embodiment 6, an embodiment of a light-emitting device including a light-emitting element according to the present invention will be described.

In this embodiment, a light-emitting device which has a light-emitting element according to the present invention in a pixel portion will be described with reference to FIGS. 4A and 4B. FIG. 4A is a top view of the light-emitting device, and FIG. 4B is a cross-sectional view taken along A-A' and B-B' in FIG. 4A. This light-emitting device includes a driver circuit portion (source side driver circuit) 601, a pixel portion 602, and a driver circuit portion (gate side driver circuit) 603, which are indicated by dotted lines, for controlling light emission from the light-emitting element. Also, a reference numeral 604 represents a sealing substrate, a reference numeral 605 represents a sealant, and the inside that is surrounded by the sealant 605 is a space 607.

A lead wiring 608 is used to transmit signals to be inputted to the source side driver circuit 601 and the gate side driver circuit 603 and receives a video signal, a clock signal, a start signal, a reset signal, and the like from a flexible printed circuit (FPC) 609 which is an external input terminal. Although only the FPC is illustrated here, this FPC may be provided with a printed wiring board (PWB). The light-emitting device in this specification includes not only a main body of a light-emitting device but also a light-emitting device with an FPC or a PWB attached thereto.

Next, a sectional structure of the light-emitting device will be described with reference to FIG. 4B. Although the driver circuit portion and the pixel portion are formed over an element substrate 610, FIG. 4B illustrates the source side driver circuit 601, which is one of the driver circuit portions, and one pixel in the pixel portion 602.

The source driver circuit 601 includes a CMOS circuit formed by combining an N-channel TFT 623 and a P-channel TFT 624. Alternatively, the driver circuit may be formed by various CMOS circuits, PMOS circuits, or NMOS circuits. In this embodiment, a driver-integrated type in which a driver circuit is formed over a substrate provided with a pixel portion is described; however, the present invention is not limited to this type, and the driver circuit can be formed outside the substrate.

The pixel portion 602 is formed of a plurality of pixels each of which includes a switching TFT 611, a current control TFT 612, and a first electrode 613 which is electrically connected to a drain of the current control TFT 612. Note that an insulator 614 is formed so as to cover an end portion of the first electrode 613. Here, the insulator 614 is formed using a positive photosensitive acrylic resin film.

In order to improve the coverage, the insulator 614 is formed to have a curved surface with curvature at its upper or lower end portion. For example, in the case of using positive photosensitive acrylic as a material of the insulator 614, it is preferable that the insulator 614 be formed so as to have a curved surface with a curvature radius (0.2 μm to 3 μm) only at its upper end portion. The insulator 614 can be formed using either a negative type which becomes insoluble in an etchant by light irradiation or a positive type which becomes soluble in an etchant by light irradiation. An EL layer 616 and a second electrode 617 are formed over the first electrode 613. Here, the first electrode 613 can be formed using any of various metals, alloys, electrically conductive compounds, and mixtures thereof. If the first electrode is used as an anode, it is preferable to use, among those materials, a metal, an alloy, an electrically conductive compound, a mixture thereof, or the like with a high work function (preferably, a work function of 4.0 eV or higher). For example, the first electrode 613 can be formed using a single-layer film of an indium tin oxide film containing silicon, an indium zinc oxide film, a titanium nitride film, a chromium film, a tungsten film, a Zn film, a Pt film, or the like; or a stacked film such as a stack of a titanium nitride film and a film containing aluminum as its main component or a three-layer structure of a titanium nitride film, a film containing aluminum as its main component, and a titanium nitride film. When the first electrode 613 has a stacked structure, the first electrode 613 can have a resistance low enough to serve as a wiring, giving a good ohmic contact, and can function as an anode.

The EL layer 616 is formed by various methods such as an evaporation method using an evaporation mask, an inkjet method, and a spin coating method. The EL layer 616 includes any of the benzoxazole derivatives described in Embodiment 1. Any of low molecular compounds, high molecular compounds, oligomers, and dendrimers may be employed as a material used for the EL layer 616. As the material for the EL layer, not only an organic compound but also an inorganic compound may be used.

As a material used for the second electrode 617, any of various metals, alloys, electrically conductive compounds, and mixtures thereof can be used. If the second electrode is used as a cathode, it is preferable that the second electrode be formed using a metal, an alloy, an electrically conductive compound, a mixture thereof, or the like with a low work function (preferably, a work function of 3.8 eV or lower) among such materials. For example, an element belonging to Group 1 or Group 2 of the periodic table, that is, an alkali metal such as lithium (Li) or cesium (Cs), an alkaline-earth metal such as magnesium (Mg), calcium (Ca), or strontium (Sr), an alloy containing these (e.g., MgAg, AlLi), and the like can be given. If light generated in the EL layer 616 is transmitted through the second electrode 617, the second electrode 617 can be formed using a stack of a metal thin film and a transparent conductive film (indium tin oxide (ITO), indium tin oxide containing silicon or silicon oxide, indium zinc oxide (IZO), indium oxide containing tungsten oxide and zinc oxide (IWZO), or the like). The sealing substrate 604 is attached using the sealant 605 to the element substrate 610; thus, a light-emitting element 618 is provided in the space 607 surrounded by the element substrate 610, the sealing substrate 604, and the sealant 605. The space 607 is filled with a filler. There are cases where the space 607 may be filled with an inert gas (such as nitrogen or argon), or where the space 607 may be filled with the sealant 605.

An epoxy based resin is preferably used for the sealant 605. In addition, it is desirable to use a material that allows permeation of moisture or oxygen as little as possible. As the sealing substrate 604, a plastic substrate formed of FRP (fiberglass-reinforced plastics), PVF (polyvinyl fluoride), polyester, acrylic, or the like can be used other than a glass substrate or a quartz substrate.

As thus described, a light-emitting device having a light-emitting element of the present invention can be obtained.

A light-emitting device of the present invention includes any of the light-emitting elements described in Embodiments 2 to 5. The light-emitting elements described in Embodiments 2 to 5 each have low driving voltage; therefore, a light-emitting device with low power consumption can be obtained.

The benzoxazole derivatives described in Embodiment 1 are excellent in thermal stability. Therefore, when any of the benzoxazole derivatives described in Embodiment 1 is used, such a light-emitting device with high reliability that is not easily deteriorated even under a high temperature condition can be obtained.

Figure 5A:
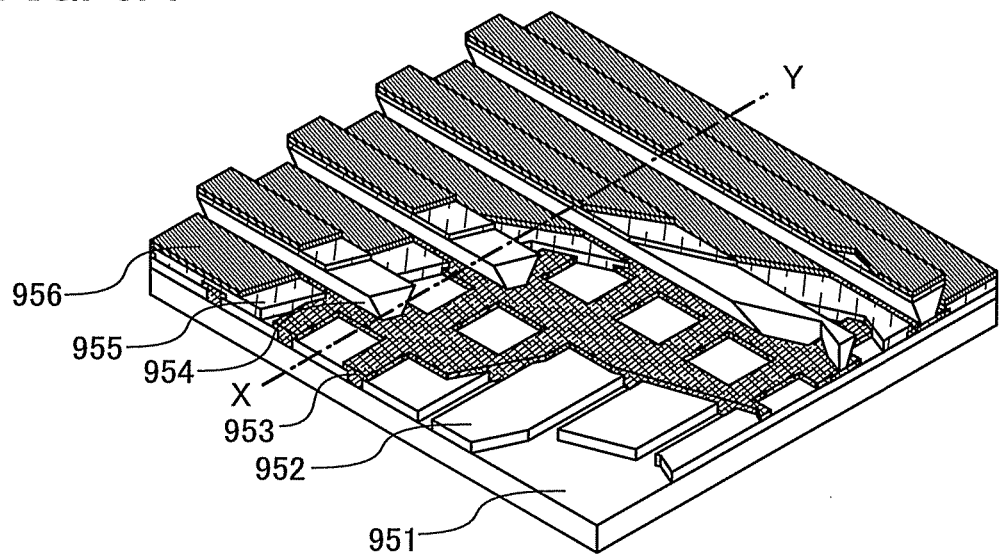
FIGS. 5A and 5B illustrate a light-emitting device according to an embodiment of the present invention.
Figure 5B:
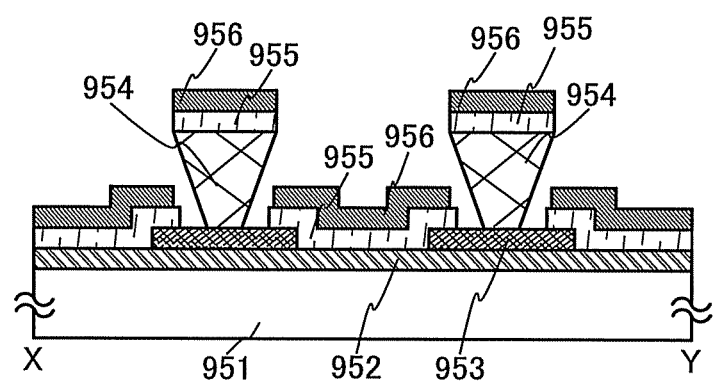

As described above, an active-matrix light-emitting device that controls driving of a light-emitting element with a transistor is described in this embodiment; however, a passive-matrix light-emitting device may be used. FIGS. 5A and 5B illustrate a passive-matrix light-emitting device which is manufactured by application of the present invention. FIG. 5A is a perspective view of the light-emitting device, and FIG. 5B is a cross-sectional view of FIG. 5A taken along the line X-Y. In FIGS. 5A and 5B, an EL layer 955 is provided between an electrode 952 and an electrode 956 over a substrate 951. An edge portion of the electrode 952 is covered with an insulating layer 953. A partition layer 954 is provided over the insulating layer 953. The sidewalls of the partition layer 954 are a slope so that a distance between both sidewalls is gradually narrowed toward the surface of the substrate. That is, a cross section in a short side direction of the partition layer 954 is a trapezoidal shape, and a lower side (the side facing the same direction as the plane direction of the insulating layer 953 and touching the insulating layer 953) is shorter than an upper side (the side facing the same direction as the plane direction of the insulating layer 953, and not touching the insulating layer 953). Fabrication of the partition layer 954 in this manner allows patterning of the cathode. In addition, in a passive-matrix light-emitting device, a light-emitting device with low power consumption can be obtained by including a light-emitting element with low driving voltage according to the present invention.

Note that this embodiment can be implemented in combination with any of the other embodiments as appropriate.

Embodiment 7

In Embodiment 7, an embodiment of an electronic device of the present invention including the light-emitting device described in Embodiment 6 as a part will be described. An electronic device of the present invention includes any of the light-emitting elements described in Embodiments 2 to 5 and a display portion with low power consumption.

As an electronic device manufactured using the light-emitting device of the present invention, a video camera, a digital camera, a goggle-type display, a navigation system, an audio reproducing device (car audio set, audio component set, or the like), a computer, a game machine, a portable information terminal (mobile computer, mobile phone, portable game machine, electronic book, or the like), and an image reproducing device provided with a recording medium (specifically, a device provided with a display device that can reproduce the content of a recording medium such as a Digital Versatile Disc (DVD) and display the image), and the like are given. Specific examples of these electronic devices are illustrated in FIGS. 6A to 6D.

Figure 6A:
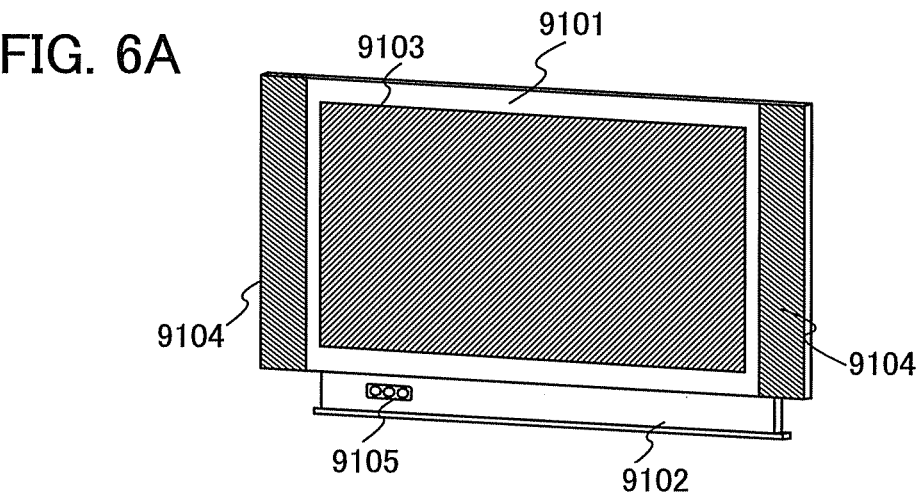
FIGS. 6A to 6D illustrate electronic devices according to an embodiment of the present invention.

FIG. 6A illustrates a television device of this embodiment, which includes a housing 9101, a support 9102, a display portion 9103, speaker portions 9104, a video input terminal 9105, and the like. In the display portion 9103 of the television device, light-emitting elements that are similar to those described in Embodiments 2 to 5 are arranged in matrix. Features of the light-emitting elements are that driving voltage is low and power consumption is low. Since the display portion 9103 which includes such light-emitting elements has similar features, this television device consumes low power. With such features, the number or scale of power supply circuits in the television device can be drastically reduced, and therefore, the size and weight of the housing 9101 and the support 9102 can be reduced. In the television device of this embodiment, reduction in power consumption and reduction in size and weight are achieved; accordingly, a product which is suitable for living environment can be provided.

Figure 6B:
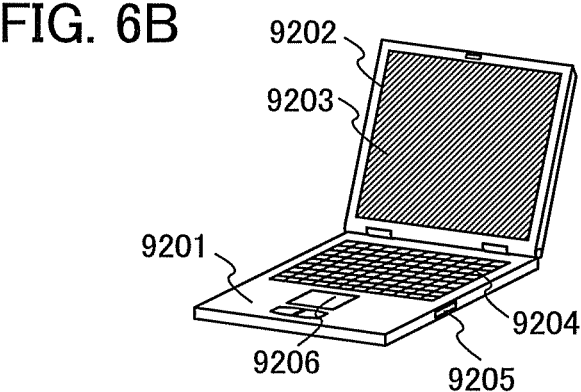

FIG. 6B illustrates a computer of this embodiment, which includes a main body 9201, a housing 9202, a display portion 9203, a keyboard 9204, an external connection port 9205, a pointing device 9206, and the like. In the display portion 9203 of this computer, light-emitting elements that are similar to those described in Embodiments 2 to 5 are arranged in matrix. Features of the light-emitting elements are that driving voltage is low and power consumption is low. Since the display portion 9203 which includes such light-emitting elements has similar features, this computer consumes low power. With such features, the number or scale of power supply circuits in the computer can be drastically reduced, and therefore, the size and weight of the main body 9201 and the housing 9202 can be reduced. In the computer of this embodiment, reduction in power consumption and reduction in size and weight are achieved; accordingly, a product which is suitable for environment can be provided.

Figure 6C:
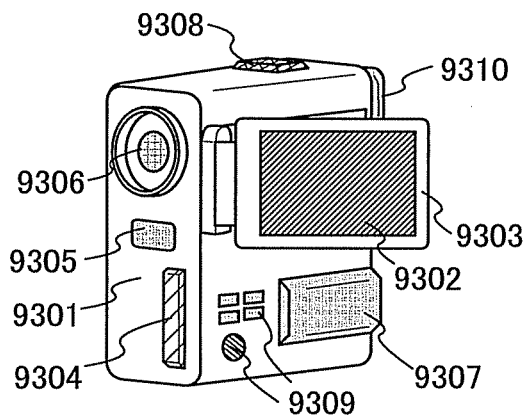

FIG. 6C illustrates a camera that includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiments 2 to 5 are arranged in matrix. Features of the light-emitting elements are that driving voltage is low and power consumption is low. The display portion 9302 which includes such light-emitting elements has similar features. Therefore, this camera consumes low power. With such features, the number or scale of power supply circuits in the camera can be drastically reduced, and therefore, the size and weight of the main body 9301 can be reduced. In the camera of this embodiment, reduction in power consumption and reduction in size and weight are achieved; therefore, a product which is suitable for being carried around can be provided.

Figure 6D:
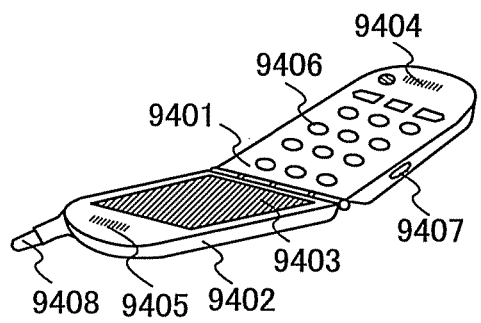

FIG. 6D illustrates a mobile phone of this embodiment, which includes a main body 9401, a housing 9402, a display portion 9403, an audio input portion 9404, an audio output portion 9405, operation keys 9406, an external connection port 9407, an antenna 9408, and the like. In the display portion 9403 of the mobile phone, light-emitting elements that are similar to those described in Embodiments 2 to 5 are arranged in matrix. Features of the light-emitting elements are that driving voltage is low and power consumption is low. Since the display portion 9403 which includes such light-emitting elements has similar features, this mobile phone consumes low power. With such features, the number or scale of power supply circuits in the mobile phone can be drastically reduced, and therefore, the size and weight of the main body 9401 and the housing 9402 can be reduced. In the mobile phone of this embodiment, reduction in power consumption and reduction in size and weight are achieved; therefore, a product which is suitable for being carried around can be provided.

Figure 12A:
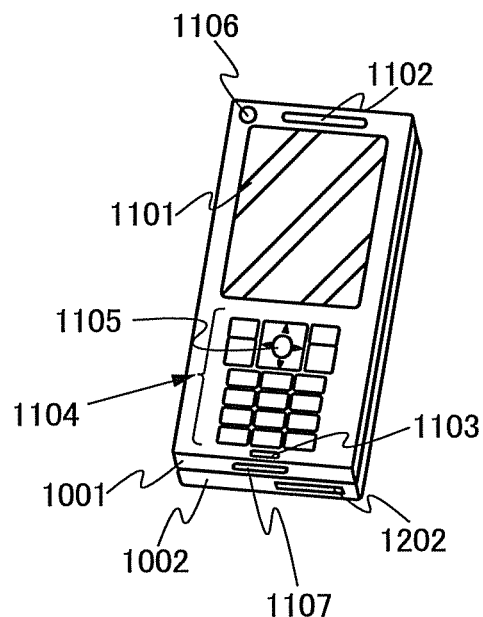
FIGS. 12A to 12C illustrate an electronic device according to an embodiment of the present invention.
Figure 12B:
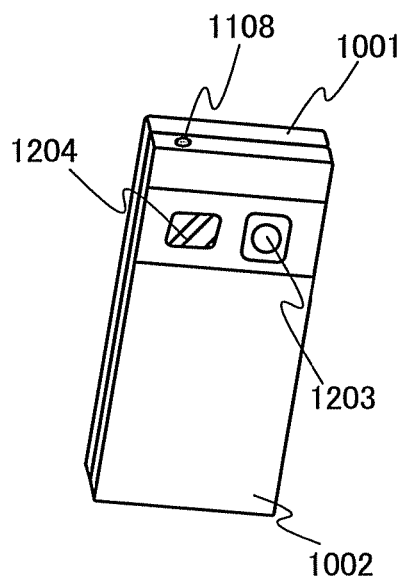
Figure 12C:
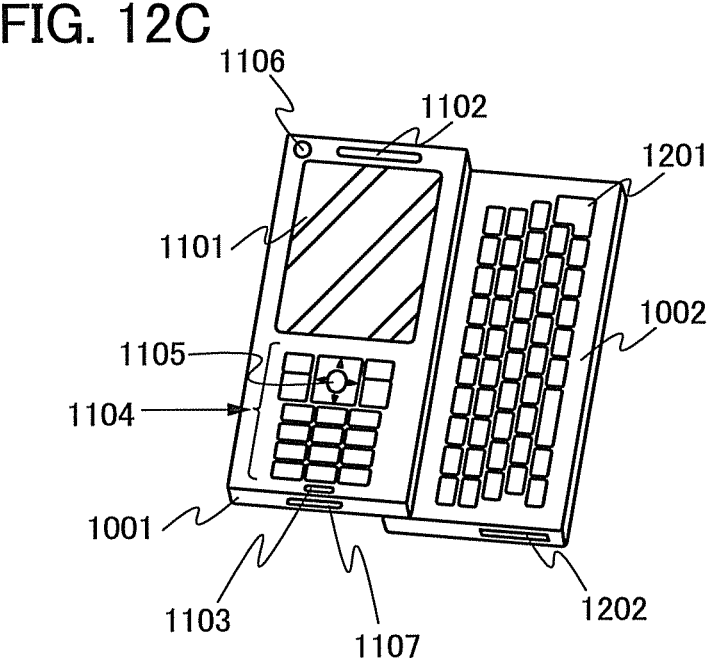

FIGS. 12A to 12C illustrate an example of a structure of a mobile phone, which is different from the structure of the mobile phone of FIG. 6D. FIG. 12A is a front view, FIG. 12B is a rear view, and FIG. 12C is a development view. The mobile phone in FIGS. 12A to 12C is a so-called smartphone which has both a function as a phone and a function as a portable information terminal, and incorporates a computer to conduct a variety of data processing in addition to voice calls.

The mobile phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, an earphone terminal 1108, and the like, while the housing 1002 includes a keyboard 1201, an external memory slot 1202, a camera lens 1203, a light 1204, and the like. In addition, an antenna is incorporated in the housing 1001.

Further, in addition to the above-described structure, the smartphone may incorporate a non-contact IC chip, a small size memory device, or the like.

In the display portion 1101, the light-emitting device described in Embodiment 6 can be incorporated, and a display direction can be appropriately changed depending on the usage mode. Because the camera lens 1106 is provided in the same plane as the display portion 1101, the smartphone can be used as a videophone. Further, a still image and a moving image can be taken with the camera lens 1203 and the light 1204 by using the display portion 1101 as a viewfinder. The speaker 1102 and the microphone 1103 can be used for video calling, recording and playing sound, and the like without being limited to voice calls. With the use of the operation keys 1104, making and receiving calls, inputting simple information of e-mails or the like, scrolling of the screen, moving the cursor and the like are possible. Furthermore, the housing 1001 and the housing 1002, which are overlapped with each other (FIG. 12A), can be developed by sliding as illustrated in FIG. 12C and can be used as a portable information terminal. At this time, smooth operation can be conducted using the keyboard 1201 and the pointing device 1105. The external connection terminal 1107 can be connected to an AC adaptor and various types of cables such as a USB cable, and charging and data communication with a computer or the like are possible. Furthermore, a large amount of data can be stored and moved by inserting a recording medium into the external memory slot 1202.

In addition to the above-described functions, the smartphone may have an infrared communication function, a television receiver function, and the like.

Figure 7:
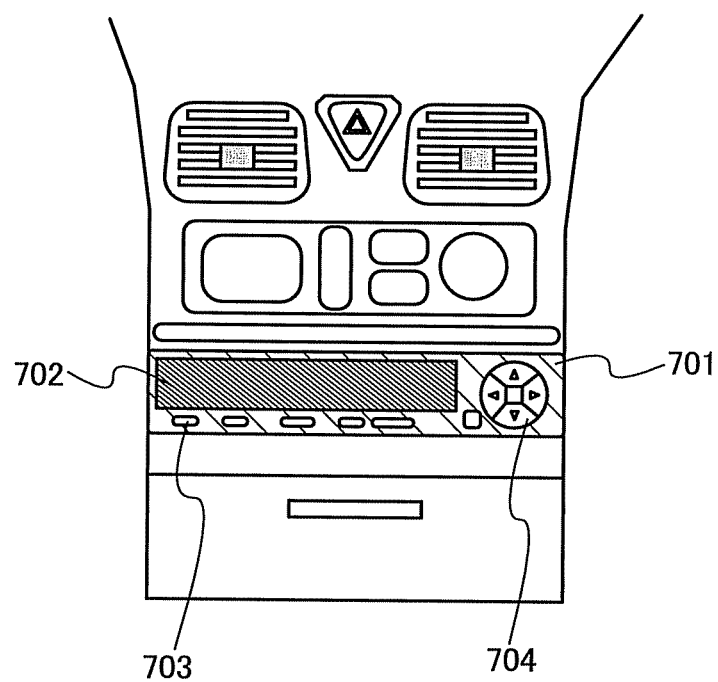
FIG. 7 illustrates an electronic device according to an embodiment of the present invention.

FIG. 7 illustrates an audio reproducing device, specifically, a car audio system, which includes a main body 701, a display portion 702, and operation switches 703 and 704. The display portion 702 can be realized using the light-emitting device (passive-matrix type or active-matrix type) described in Embodiment 6. Further, the display portion 702 may employ a segment type light-emitting device. In any case, the use of a light-emitting element of the present invention makes it possible to form a bright display portion while achieving low power consumption, with the use of a vehicle power source (12 V to 42 V). Although an in-car audio system is illustrated in this embodiment, the present invention may be used for a portable audio device or an audio device for household use.

Figure 8:
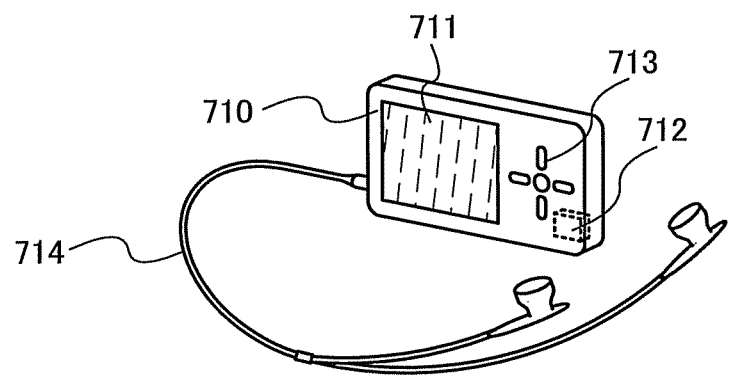
FIG. 8 illustrates an electronic device according to an embodiment of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that a pair of headphones or a wireless pair of earphones can be used instead of the pair of earphones 714. The display portion 711 can be realized using the light-emitting device (passive-matrix type or active-matrix type) described in Embodiment 6. Further, the display portion 711 may employ a segment type light-emitting device. In any case, the use of a light-emitting element of the present invention makes it possible to form a bright display portion which can display images even when using a secondary battery (a nickel-hydrogen battery or the like) while achieving low power consumption. As the memory portion 712, a hard disk or a nonvolatile memory is used. For example, a NAND type flash memory with a recording capacity of 20 to 200 gigabytes (GB) is used, and by operating the operation portion 713, an image or a sound (e.g., music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying the present invention is so wide that the light-emitting device is applicable to electronic devices in various fields. By applying the present invention, an electronic device which has a display portion consuming low power can be manufactured.

The light-emitting device to which the present invention is applied has a light-emitting element with high emission efficiency, and can also be used as a lighting device. One mode of using a light-emitting element to which the present invention is applied as a lighting device is described with reference to FIG. 9.

Figure 9:
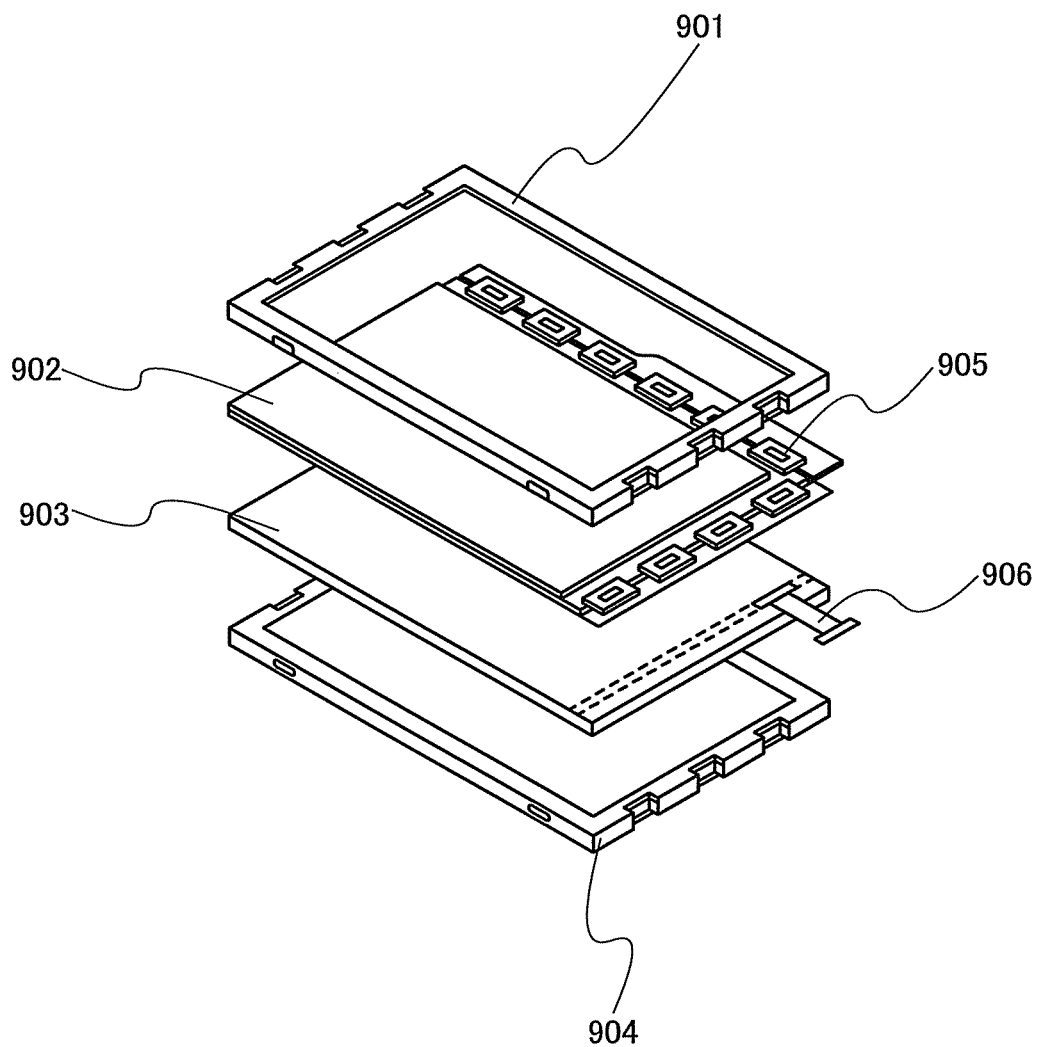
FIG. 9 illustrates an electronic device according to an embodiment of the present invention.

FIG. 9 illustrates a liquid crystal display device using the light-emitting device to which the present invention is applied as a backlight, as an example of the electronic device using a light-emitting device according to the present invention as a lighting device. The liquid crystal display device illustrated in FIG. 9 includes a housing 901, a liquid crystal layer 902, a backlight 903, and a housing 904. The liquid crystal layer 902 is connected to a driver IC 905. The light-emitting device to which the present invention is applied is used as the backlight 903, and current is supplied through a terminal 906.

Because the light-emitting device according to the present invention is thin and consumes low power, reduction in thickness and power consumption of a liquid crystal display device is possible by using a light-emitting device according to the present invention as a backlight of the liquid crystal display device. Moreover, a light-emitting device according to the present invention is a plane-emission lighting device and can have a large area. Thus, the backlight can have a large area, and a liquid crystal display device having a large area can also be obtained.

Figure 10:
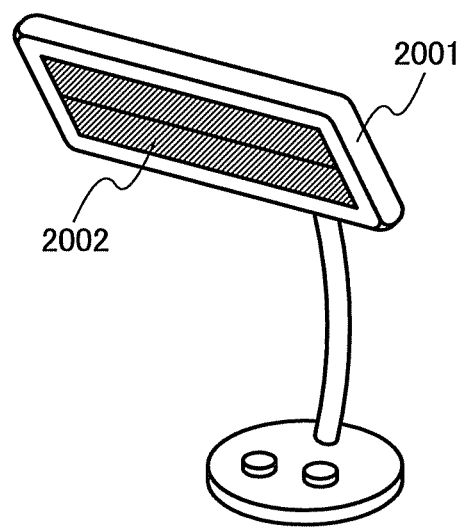
FIG. 10 illustrates a lighting device according to an embodiment of the present invention.

FIG. 10 illustrates an example in which a light-emitting device according to the present invention is used for a desk lamp, which is one of lighting devices. The desk lamp illustrated in FIG. 10 includes a housing 2001 and a light source 2002, and a light-emitting device according to the present invention is used as the light source 2002. Because a light-emitting device of the present invention consumes low power, the desk lamp also consumes low power.

Figure 11:
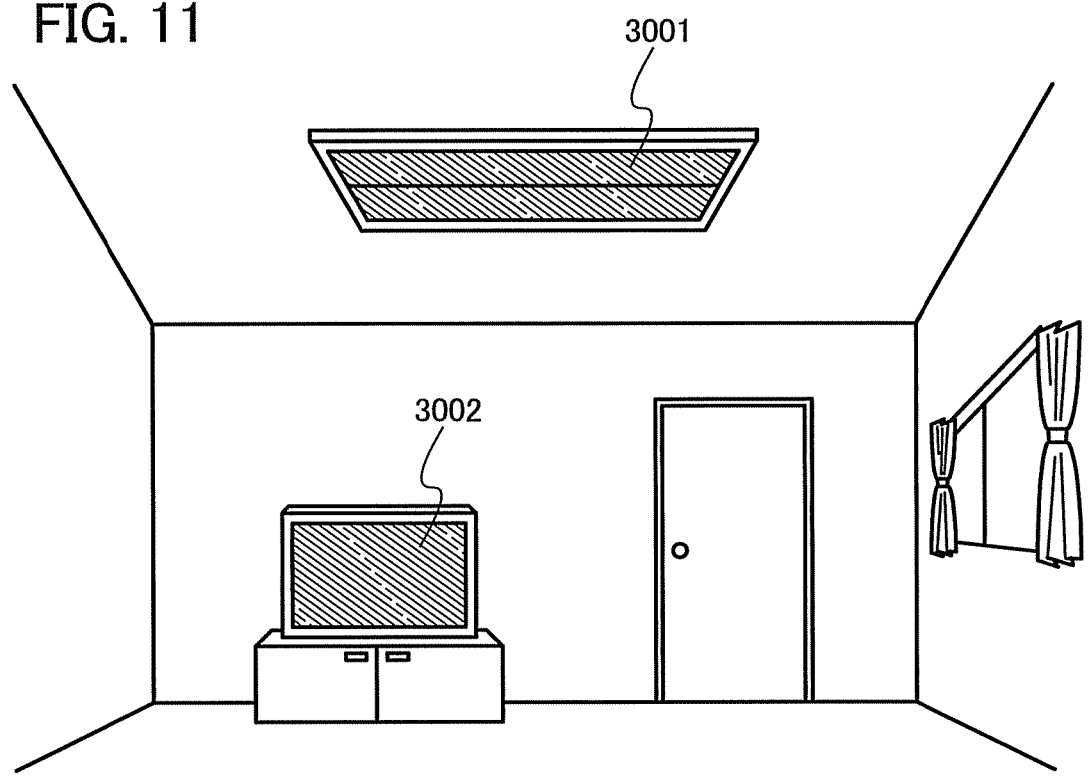
FIG. 11 illustrates a lighting device according to an embodiment of the present invention.

FIG. 11 illustrates an example in which the light-emitting device to which the present invention is applied is used for an indoor lighting device 3001. Because a light-emitting device according to the present invention can have a large area, it can be used for a lighting device having a large area. Moreover, because a light-emitting device according to the present invention consumes low power, it can be used for a lighting device which consumes low power. A television device 3002 according to the present invention as illustrated in FIG. 6A is placed in a room where the light-emitting device to which the present invention is applied is used as the indoor lighting device 3001. Thus, public broadcasting and movies can be watched. In such a case, since both devices consume low power, environmental load can be reduced.

Note that this embodiment can be implemented in combination with any of the other embodiments as appropriate.

Example 1

In Example 1, a synthesis method of 2-[4-(10-phenyl-9-anthryl)phenyl]benzoxazole (abbrev.: PABOx) represented by Structural Formula (101) will be described.

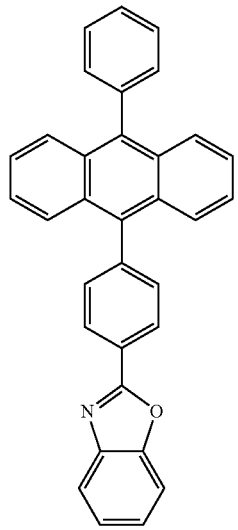

(101)

Step 1: Synthesis of 4-(benzoxazol-2-yl)phenylboronic acid (i) 4-bromo-N-(2-hydroxyphenyl)benzamide A synthesis scheme of 4-bromo-N-(2-hydroxyphenyl)benzamide is shown in (B-1).

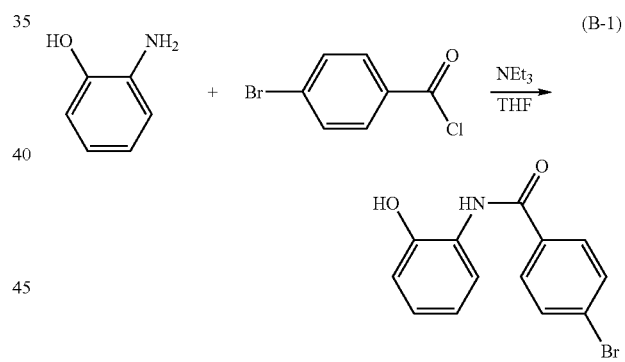

(B-1)

In a 200 mL three-neck flask, 2.2 g (20 mmol) of 2-aminophenol, 3.0 mL (22 mmol) of triethylamine, and 50 mL of tetrahydrofuran (THF) were placed. Then, the mixture was cooled to 0° C. After cooling, 50 mL of a THF solution containing 4.5 g (20 mmol) of 4-bromobenzoyl chloride was dripped under nitrogen stream. This solution was stirred at 0° C. for 4 hours under nitrogen stream. After a certain period, the solution was added to water, and an aqueous layer was extracted with ethyl acetate. The resulting extracted solution and the organic layer were combined and washed with 0.2 M hydrochloric acid and a saturated aqueous solution of sodium hydrogen carbonate, and then the organic layer was dried with magnesium sulfate. The mixture was subjected to suction filtration through Celite (produced by Wako Pure Chemical Industries, Ltd., Catalog No. 531-16855), and the filtrate was condensed to give a solid. The solid was recrystallized with ethyl acetate/hexane, so that 5.3 g of target white powder was obtained in a yield of 88%.

(ii) Synthesis of 2-(4-bromophenyl)benzoxazole

A synthesis scheme of 2-(4-bromophenyl)benzoxazole is shown in (B-2).

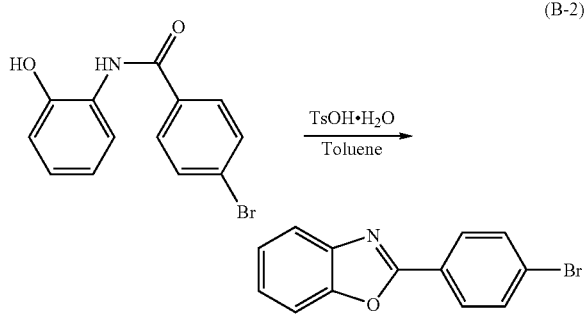

(B-2)

In a 300 mL three-neck flask, 5.3 g (18 mmol) of 4-bromo-N-(2-hydroxyphenyl)benzamide, 8.0 g (46 mmol) of para-toluenesulfonic acid monohydrate, and 200 mL of toluene were placed. This mixture was stirred for 4 hours under nitrogen stream. After a certain period, water was added to the mixture, and an aqueous layer was extracted with ethyl acetate. The resulting extracted solution and the organic layer were combined and washed with a saturated aqueous solution of sodium hydrogen carbonate and saturated saline, and then the organic layer was dried with magnesium sulfate. The mixture obtained was subjected to suction filtration through Celite (produced by Wako Pure Chemical Industries, Ltd., Catalog No. 531-16855), and the filtrate was condensed to give a solid. The solid was recrystallized with ethyl acetate/hexane, so that 3.1 g of target white powder was obtained in a yield of 61%.

(iii) Synthesis of 4-(benzoxazol-2-yl)phenylboronic acid

A synthesis scheme of 4-(benzoxazol-2-yl)phenylboronic acid is shown in (B-3).

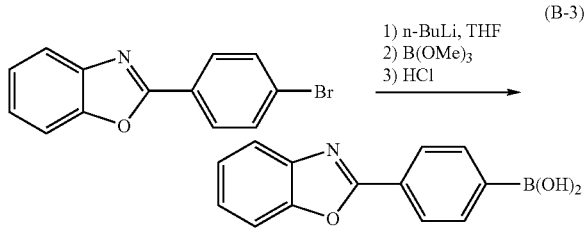

(B-3)

In a 300 mL three-neck flask, 5.5 g (20 mmol) of 2-(4-bromophenyl)benzoxazole was placed, and the air in the flask was replaced with nitrogen. Then, 120 mL of THF was added in the flask, and the mixture was cooled to −78° C. under nitrogen stream. After cooling, 13 mL (22 mmol) of 1.6 M n-butyllithium was dripped into the solution, and the mixture was stirred at the same temperature for 2 hours. After a certain period, 4.4 mL (40 mmol) of trimethyl borate was added to the solution, and the temperature was raised to room temperature, and then, the solution was stirred for 16 hours. After a certain period, 100 mL of 1 M hydrochloric acid was added to the solution, and stirred for 1 hour. An aqueous layer of the obtained mixture was extracted with ethyl acetate. The resulting extracted solution and the organic layer were combined and washed with saturated saline, and then dried with magnesium sulfate. The mixture was gravity filtered, and the obtained filtrate was condensed to give a solid. The solid was recrystallized with ethyl acetate/hexane, so that 3.3 g of target white powder was obtained in a yield of 69%.

Step 2: Synthesis of 9-bromo-10-phenylanthracene

(i) Synthesis of 9-phenylanthracene

A synthesis scheme of 9-phenylanthracene is shown in (B-4).

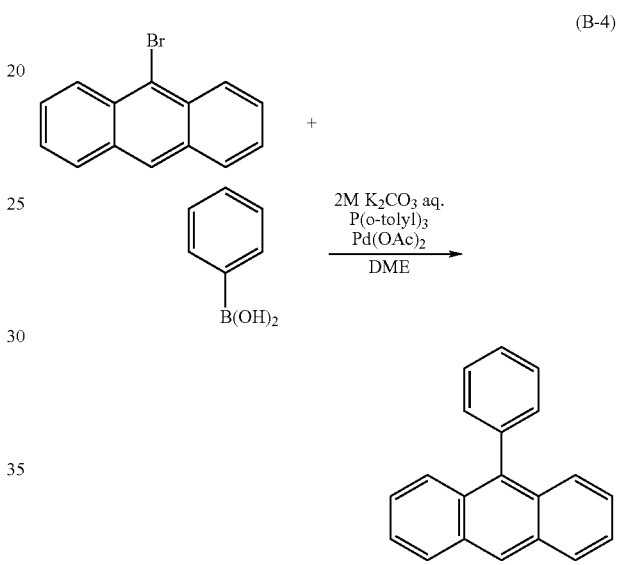

(B-4)

In a 200 mL three-neck flask, 6.4 g (25 mmol) of 9-bromoanthracene, 3.0 g (25 mmol) of phenylboronic acid, 0.76 g (2.5 mmol) of tri(ortho-tolyl)phosphine, 60 mL of ethylene glycol dimethyl ether (DME), and 25 mL of a 2.0 M potassium carbonate solution were placed. The mixture was degassed by being stirred under reduced pressure, and the air in the flask was replaced with nitrogen. To the mixture, 0.11 g (0.50 mmol) of palladium(II) acetate was added and stirred under nitrogen stream at 80° C. for 3 hours. After a certain period, water was added to the mixture, and an aqueous layer was extracted with toluene. The obtained extracted solution and the organic layer were combined and washed with saturated saline, and the organic layer was dried with magnesium sulfate. The mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was condensed to give a solid. The solid was recrystallized with toluene/methonol, so that 5.8 g of target white powder was obtained in a yield of 92%.

(ii) Synthesis of 9-bromo-10-phenylanthracene

A synthesis scheme of 9-bromo-10-phenylanthracene is shown in (B-5).

(B-5)

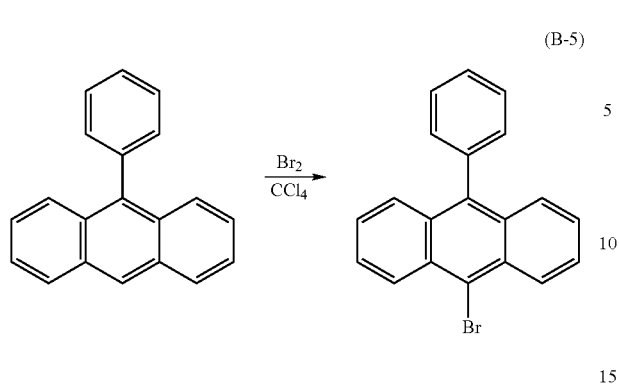

In a 300 mL three-neck flask, 5.8 g (23 mmol) of 9-phenylanthracene and 100 mL of carbon tetrachloride were placed. Then, 30 mL of a carbon tetrachloride solution containing 4.0 g (25 mmol) of bromine was dripped into the mixture under nitrogen stream. After dripping, the solution was stirred for 12 hours at room temperature. After a certain period, 100 mL of a 1.0 M sodium thiosulfate solution was added and stirred for 1 hour, and an aqueous layer of the mixture was extracted with chloroform. The obtained extracted solution and the organic layer were combined and washed with a 0.10 M sodium thiosulfate solution, a saturated aqueous solution of sodium hydrogen carbonate, and saturated saline in this order, and then, the organic layer was dried with magnesium sulfate. The mixture was gravity filtered, and the obtained filtrate was condensed to give a solid. A toluene solution of the solid was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was condensed to give a solid. Methanol was added to the solid, and this suspension was irradiated with ultrasonic waves. Then, 6.4 g of a solid substance, which was target pale yellow powder, was obtained by suction filtration in a yield of 84%.

Step 3: Synthesis of
2-[4-(10-phenyl-9-anthryl)phenyl]benzoxazole

A synthesis scheme of 2-[4-(10-phenyl-9-anthryl)phenyl]benzoxazole is shown in (B-6).

(B-6)

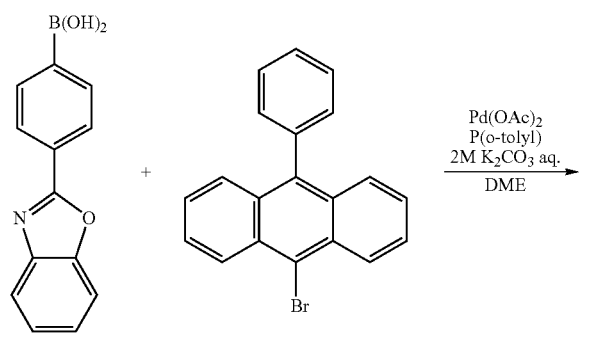

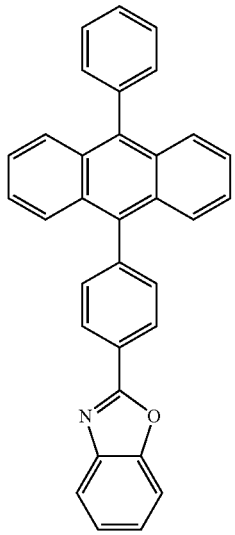

In a 50 mL three-neck flask, 1.0 g (3.0 mmol) of 9-bromo-10-phenylanthracene, 0.72 g (3.0 mmol) of 4-(benzoxazol-2-yl)phenylboronic acid, 0.10 g (0.32 mmol) of tri(ortho-tolyl)phosphine, 20 mL of ethylene glycol dimethyl ether (DME), and 3.0 mL (6.0 mmol) of a 2.0 M potassium carbonate solution were placed. The mixture was degassed by being stirred under reduced pressure, and the air in the flask was replaced with nitrogen. To the mixture, 14 mg (0.062 mmol) of palladium(II) acetate was added, and the mixture was stirred under nitrogen stream at 80° C. for 6 hours. After a certain period, water was added to the mixture, and an aqueous layer was extracted with toluene. The obtained extracted solution and the organic layer were combined and washed with saturated saline, and the organic layer was dried with magnesium sulfate. The mixture was gravity filtered, and the obtained filtrate was condensed to give an oily substance. The oily substance was purified by silica gel column chromatography (toluene:hexane=2:1) and recrystallized with toluene/methanol, giving 1.1 g of the target pale yellow powder in a yield of 81%.

Then, 1.1 g of the target substance was subjected to sublimation purification at 230° C. under argon stream (flow rate: 3.0 mL/min) and a pressure of 10 Pa for 17 hours; thus, 0.96 g of the target substance was recovered in a yield of 69%. This compound was measured by nuclear magnetic resonance (NMR) spectrometry and identified as 2-[4-(10-phenyl-9-anthryl)phenyl]benzoxazole (abbrev.: PABOx).

The $^1$H NMR data and the $^{13}$C NMR data are shown below.

$^1$H NMR (300 MHz, CDCl$_3$): δ (ppm)=7.32-7.43 (m, 6H), 7.47-7.50 (m, 2H), 7.58-7.73 (m, 100H), 7.83-7.87 (m, 1H), 8.51 (d, J=8.1 Hz, 2H).

$^{13}$C NMR (75 MHz, CDCl$_3$): δ (ppm)=110.67, 120.12, 124.67, 125.10, 125.22, 125.38, 126.43, 126.52, 127.11, 127.55, 127.72, 128.43, 129.61, 129.84, 131.25, 132.06, 135.76, 137.70, 138.87, 142.23, 142.82, 150.88, 163.01.

Figure 13A:
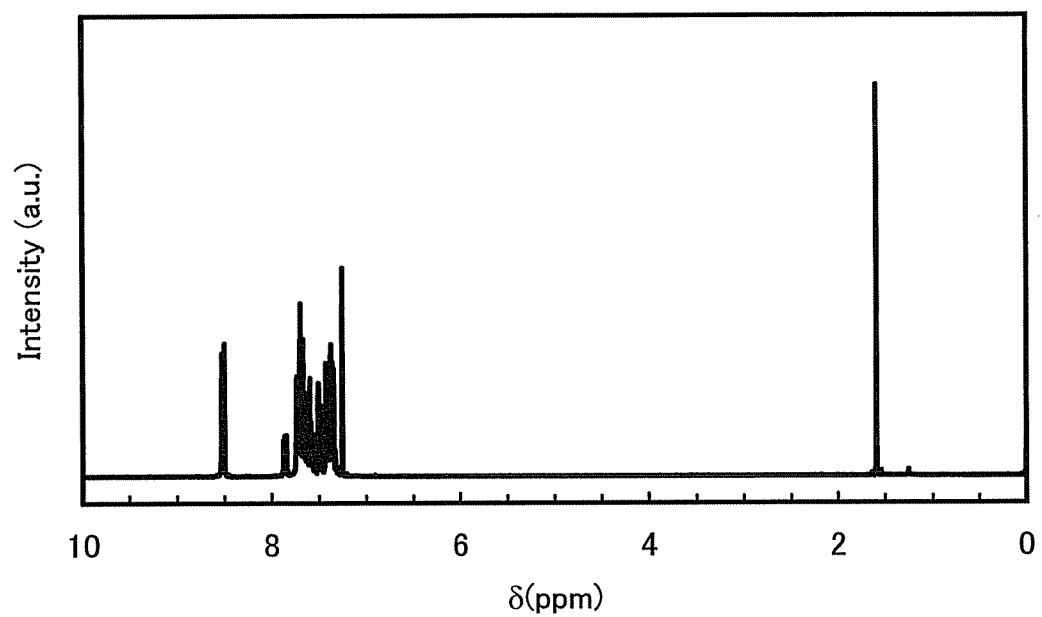
FIGS. 13A and 13B are each a $^1$H NMR chart of 2-[4-(10-phenyl-9-anthryl)phenyl]benzoxazole (abbrev.: PABOx)
Figure 13B:
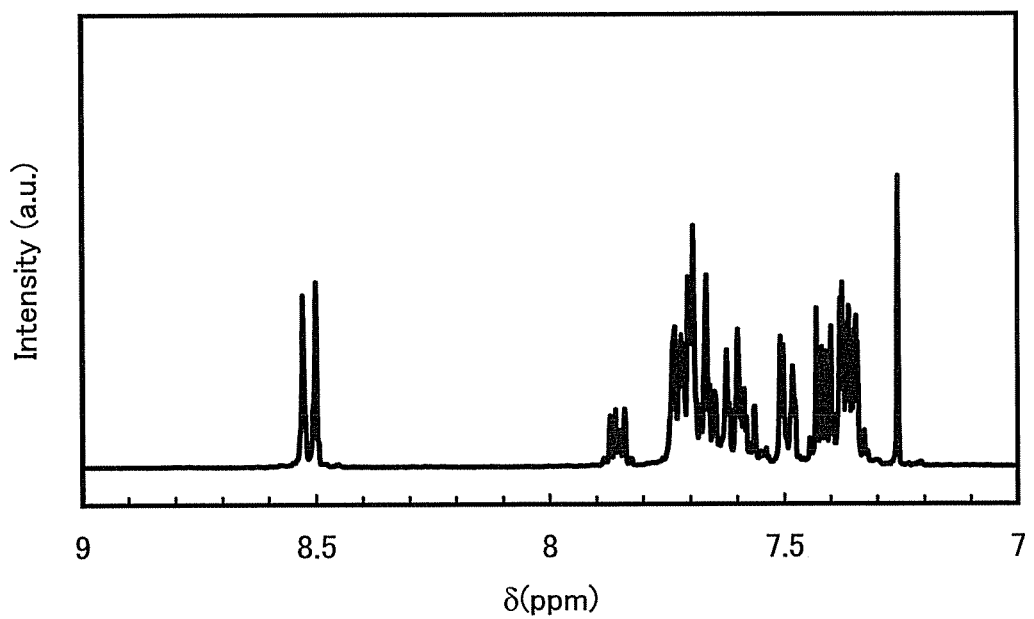
Figure 14A:
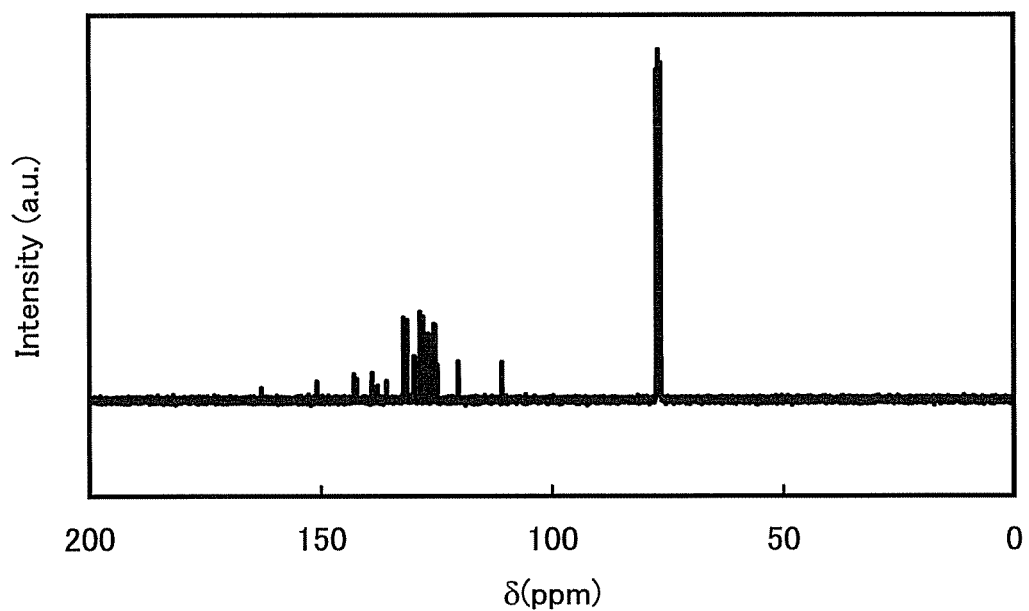
FIGS. 14A and 14B are each a $^{13}$C NMR chart of 2-[4-(10-phenyl-9-anthryl)phenyl]benzoxazole (abbrev.: PABOx)
Figure 14B:
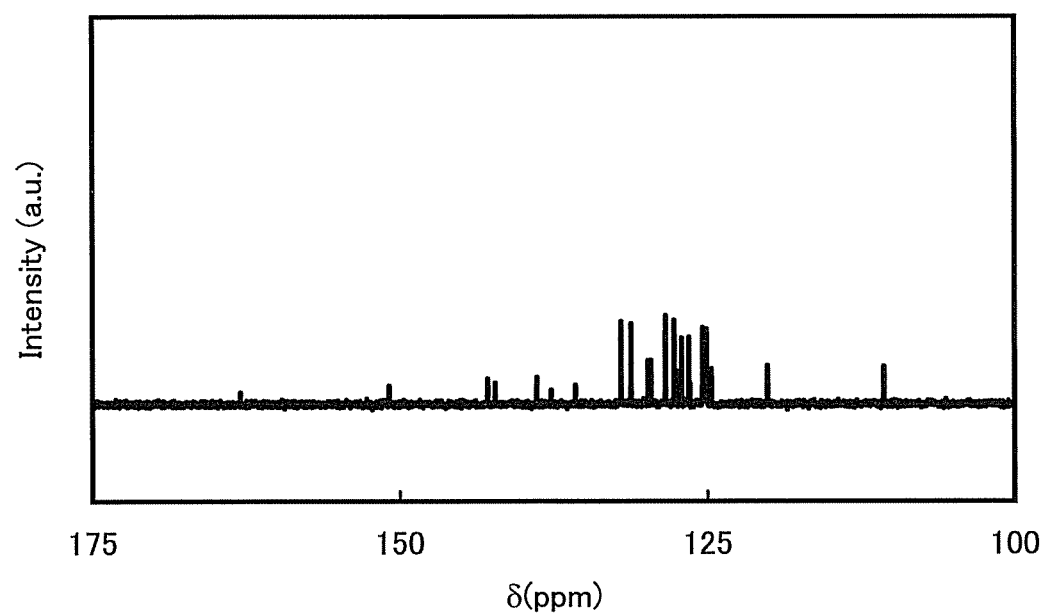

The $^1$H NMR chart is shown in FIGS. 13A and 13B. Note that FIG. 13B is an enlarged chart showing the range from 7.0 ppm to 9.0 ppm in FIG. 13A. In addition, the $^{13}$C NMR chart is shown in FIGS. 14A and 14B. Note that FIG. 14B is an enlarged chart showing the range from 100.0 ppm to 175.0 ppm in FIG. 14A.

Thermogravimetry-differential thermal analysis (TG-DTA) of PABOx obtained was performed. The measurement was performed using a high vacuum differential type differential thermal balance (TG-DTA2410SA, manufactured by Bruker AXS K.K.). The measurement was carried out under nitrogen stream (flow rate: 200 mL/min) and a normal pressure at a temperature rising rate of 10° C./min. From the relationship between the weight and the temperature (thermogravimetry), it was understood that the 5% weight loss temperature was 369° C. and the melting point was 256° C., which is indicative of high thermal stability.

Figure 15:
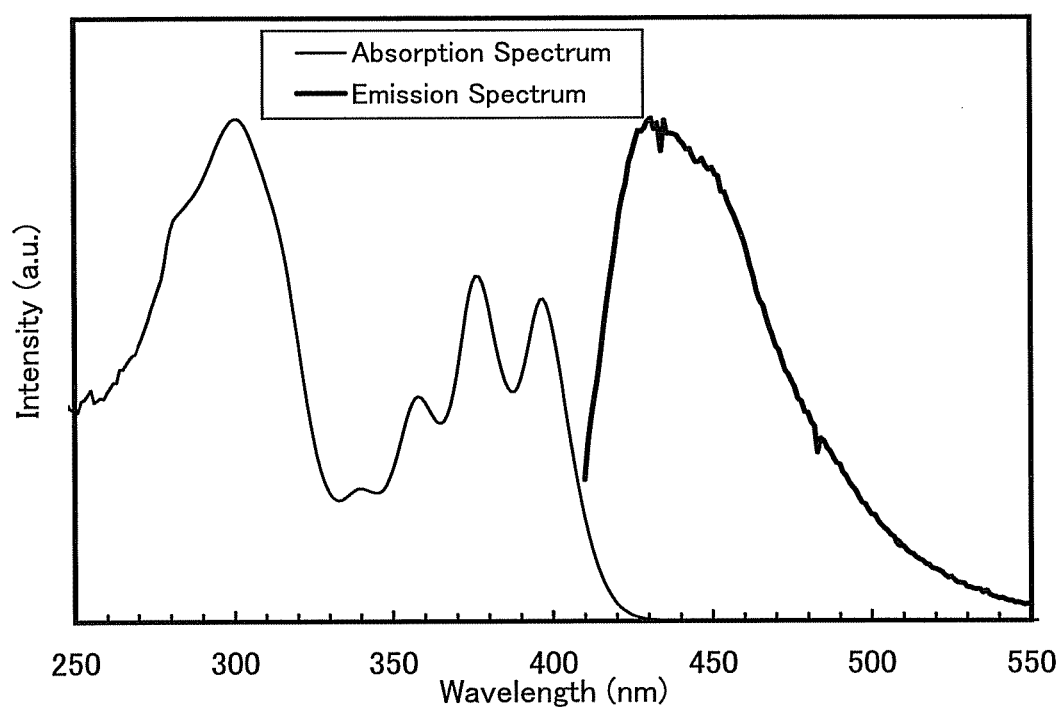
FIG. 15 shows an absorption spectrum and an emission spectrum of 2-[4-(10-phenyl-9-anthryl)phenyl]benzoxazole in a toluene solution (abbrev.: PABOx)

FIG. 15 shows an absorption spectrum and an emission spectrum of PABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 15. In FIG. 15, the horizontal axis indicates wavelength (nm) and the vertical axis indicates intensity (arbitrary unit). In the case of the toluene solution, absorptions were observed at around 301 nm, 358 nm, 376 nm, and 397 nm. In addition, the maximum emission wavelength was 431 nm (excitation wavelength: 396 nm) in the case of the toluene solution.

Figure 16:
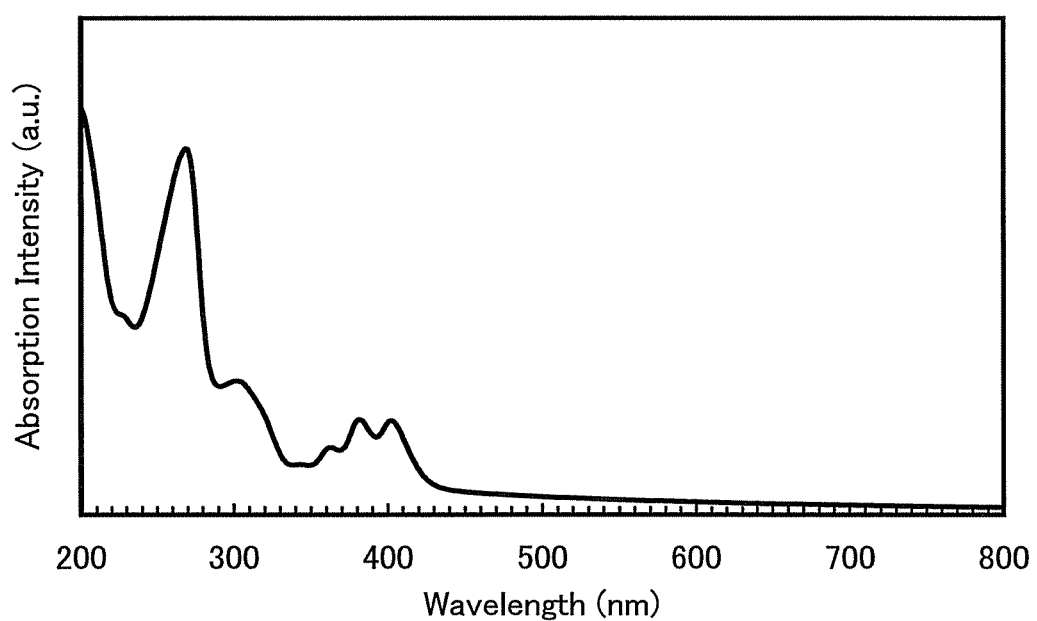
FIG. 16 shows an absorption spectrum of a thin film of 2-[4-(10-phenyl-9-anthryl)phenyl]benzoxazole (abbrev.: PABOx)
Figure 17:
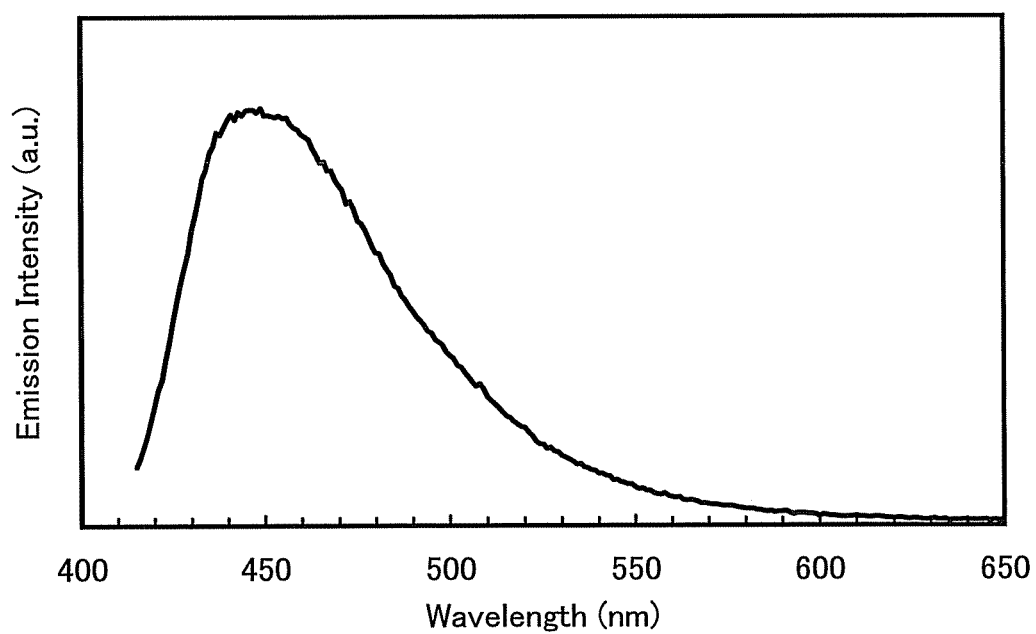
FIG. 17 shows an emission spectrum of a thin film of 2-[4-(10-phenyl-9-anthryl)phenyl]benzoxazole (abbrev.: PABOx)

FIG. 16 shows an absorption spectrum of a thin film of PABOx, and FIG. 17 shows an emission spectrum of a thin film of PABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 16. In FIG. 16, the horizontal axis indicates wavelength (nm) and the vertical axis indicates absorption intensity (arbitrary unit). In FIG. 17, the horizontal axis indicates wavelength (nm) and the vertical axis indicates emission intensity (arbitrary unit). In the case of the thin film, absorptions were observed at around 269 nm, 302 nm, 363 nm, 382 nm, and 396 nm. In addition, the maximum emission wavelength was 451 nm (excitation wavelength: 371 nm) in the case of the thin film.

In addition, the ionization potential of PABOx in the thin film state was 5.64 eV, which was measured by a photoelectron spectrometer (AC-2, manufactured by Riken Keiki Co., Ltd.) in air. As a result, the HOMO level was found to be −5.64 eV. Further, an absorption edge was obtained from a Tauc plot assuming direct transition with use of the data of the absorption spectrum of PABOx in the thin film state, and when the absorption edge was regarded as an optical energy gap, the energy gap was 2.93 eV. A LUMO level of −2.71 eV was obtained from the obtained value of the energy gap and the HOMO level.

Further, oxidation-reduction characteristics of PABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, PABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristics of PABOx were measured as follows. The potential of the working electrode with respect to the reference electrode was changed from −0.33 V to 1.20 V, and then changed from 1.20 V to −0.33 V. This change in potential was regarded as one cycle, and measurement was carried out for 100 cycles. The reduction characteristics of PABOx were examined as follows. The potential of the working electrode with respect to the reference electrode was changed from −1.13 V to −2.65 V, and then changed from −2.65 V to −1.13 V. This change in potential was regarded as one cycle, and measurement was performed for 100 cycles. Further, the scanning speed of the CV measurement was set to be 0.1 V/s.

Figure 18:
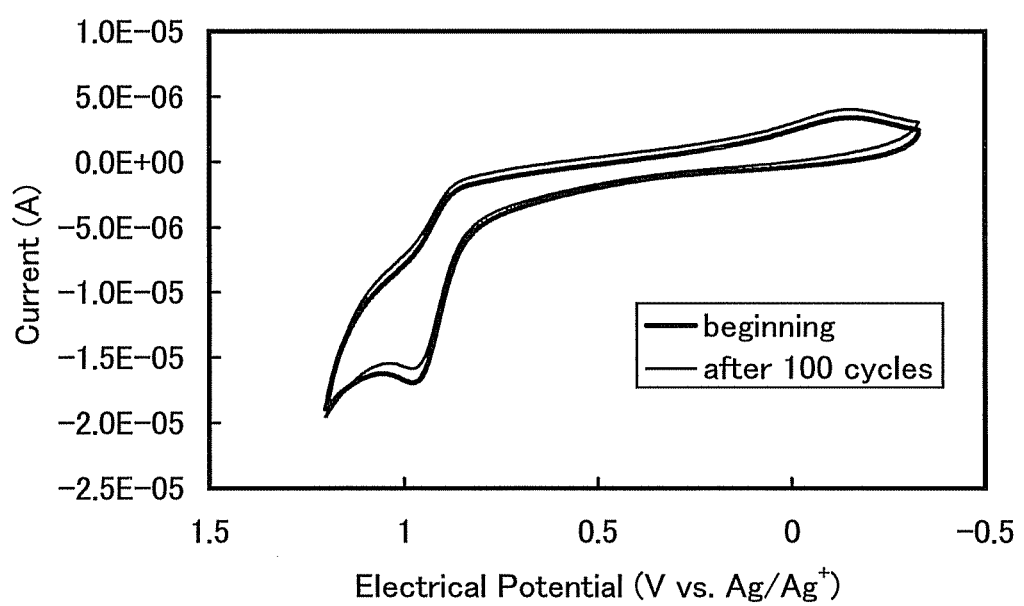
FIG. 18 shows CV measurement results of 2-[4-(10-phenyl-9-anthryl)phenyl]benzoxazole (abbrev.: PABOx)
Figure 19:
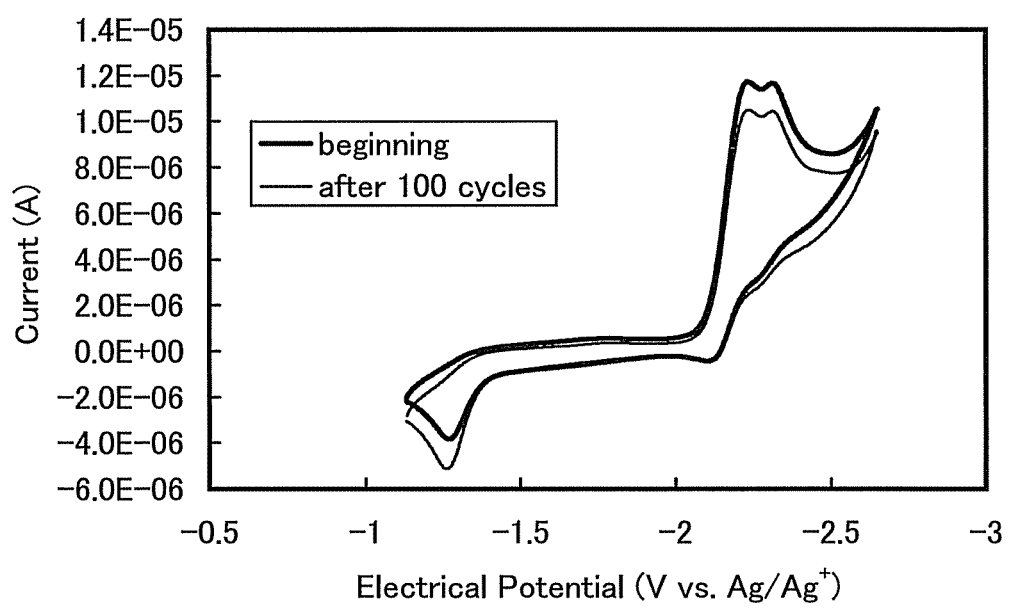
FIG. 19 shows CV measurement results of 2-[4-(10-phenyl-9-anthryl)phenyl]benzoxazole (abbrev.: PABOx)

FIG. 18 shows results of the CV measurement of PABOx on the oxidation side, and FIG. 19 shows results of the CV measurement of PABOx on the reduction side. In each of FIG. 18 and FIG. 19, the horizontal axis indicates a potential (V) of the working electrode with respect to the reference electrode, and the vertical axis indicates a current value (A) flowing between the working electrode and the auxiliary electrode. From FIG. 18, a current indicating oxidation was observed around 0.98 V (vs. Ag/Ag$^+$ electrode). In addition, from FIG. 19, a current indicating reduction was observed around −2.24 V (vs. Ag/Ag$^+$ electrode).

Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 2

In Example 2, a synthesis method of 2-{4-[10-(3-pyridyl)-9-anthryl]phenyl}benzoxazole (abbrev.: PyABOx) represented by Structural Formula (141) will be described.

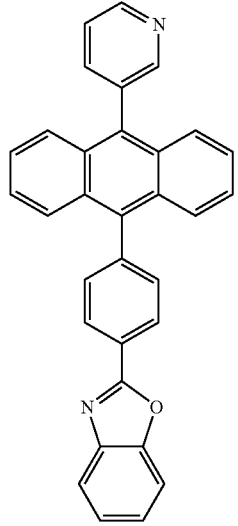

(141)

Step 1: Synthesis of 3-(10-bromo-9-anthryl)pyridine (i) 9-anthrylboronic acid

A synthesis scheme of 9-anthrylboronic acid is shown in (C-1).

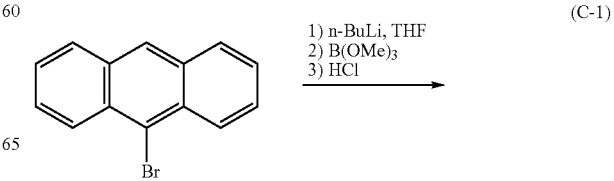

(C-1)

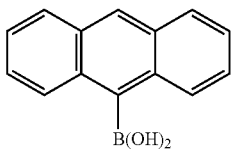

In a 500 mL three-neck flask, 7.7 g (30 mmol) of 9-bromoanthracene was placed, and the air in the flask was replaced with nitrogen. Then, 200 mL of THF was added into the flask and the solution was cooled to −80° C. under nitrogen stream. After cooling, 18 mL (30 mmol) of 1.6 M n-butyllithium was dripped into the solution and stirred at the same temperature for 2 hours. After a certain period, 6.8 mL (60 mmol) of trimethyl borate was added into the solution, the temperature of the solution was raised to room temperature, and then, the solution was stirred for 17 hours. After a certain period, 100 mL of 1.0 M hydrochloric acid was added to the solution and stirred for 1 hour. An aqueous layer of the obtained mixture was extracted with ethyl acetate. The resulting extracted solution and the organic layer were combined and washed with saturated saline, and then the organic layer was dried with magnesium sulfate. The obtained mixture was gravity filtered, and the filtrate was condensed to give a solid. The solid was recrystallized with toluene, so that 5.2 g of target white powder was obtained in a yield of 80%.

(ii) Synthesis of 3-(9-anthryl)pyridine

A synthesis scheme of 3-(9-anthryl)pyridine is shown in (C-2).

(C-2)

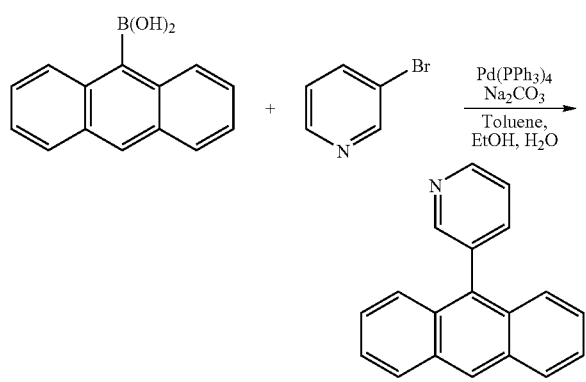

In a 200 mL three-neck flask, 5.2 g (23 mmol) of 9-anthrylboronic acid, 4.0 g (25 mmol) of 3-bromopyridine, 5.2 g (50 mmol) of sodium carbonate, 50 mL of toluene, 25 μL of ethanol, and 25 mL of water were placed. The mixture was degassed by being stirred under reduced pressure, and the air in the flask was replaced with nitrogen. To the mixture, 0.28 g (0.25 mmol) of tetrakis(triphenylphosphine)palladium(0) was added, and the mixture was stirred under nitrogen stream at 80° C. for 7 hours. After a certain period, water was added to the mixture, and an aqueous layer was extracted with toluene. The obtained extracted solution and the organic layer were combined, washed with saturated saline, and dried with magnesium sulfate. The obtained mixture was gravity filtered, and the filtrate was condensed to give an oily substance.

The oily substance was recrystallized with toluene/hexane, so that 2.8 g of target yellow powder was obtained in a yield of 46%.

(iii) Synthesis of 3-(10-bromo-9-anthryl)pyridine

A synthesis scheme of 3-(10-bromo-9-anthryl)pyridine is shown in (C-3).

(C-3)

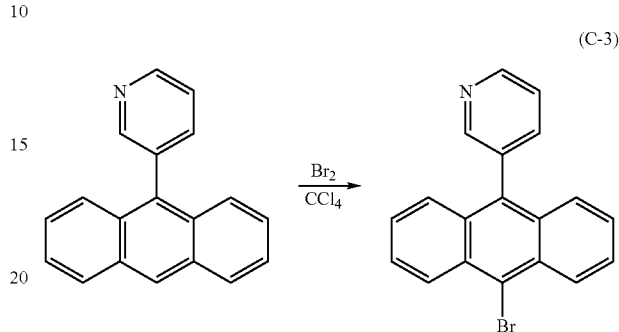

In a 200 μL three-neck flask, 1.0 g (4.0 mmol) of 3-(9-anthryl)pyridine and 25 mL of carbon tetrachloride were placed. Then, 10 μL of a carbon tetrachloride solution containing 0.83 g (5.1 mmol) of bromine was dripped into the solution under nitrogen stream, and the solution was stirred for 26 hours at room temperature. After a certain period, 100 mL of a 1.0 M sodium thiosulfate solution was added into the mixture. Then, an aqueous layer of the mixture was extracted with chloroform. The obtained extracted solution and the organic layer were combined, washed with a saturated aqueous solution of sodium hydrogen carbonate and saturated saline, and dried with magnesium sulfate. The mixture was gravity filtered, and the obtained filtrate was condensed to give a solid. A chloroform solution of the solid was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was condensed to give a solid. The solid was recrystallized with ethyl acetate/hexane, so that 0.74 g of target pale yellow powder was obtained in a yield of 53%.

Step 2: Synthesis of 2-{4-[10-(3-pyridyl)-9-anthryl]phenyl}benzoxazole

A synthesis scheme of 2-{4-[10-(3-pyridyl)-9-anthryl]phenyl}benzoxazole is shown in (C-4).

(C-4)

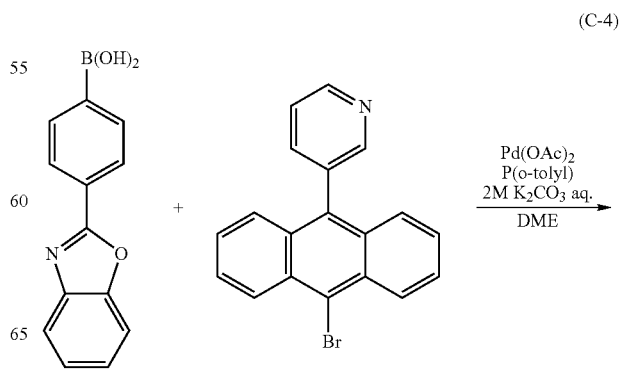

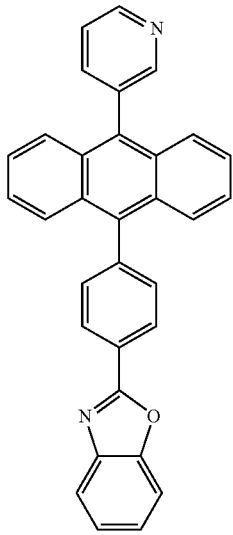

In a 50 mL three-neck flask, 0.70 g (2.1 mmol) of 3-(10-bromo-9-anthryl)pyridine, 0.52 g (2.1 mmol) of 4-(benzoxazol-2-yl)phenylboronic acid, 65 mg (0.21 mmol) of tri(ortho-tolyl)phosphine, 20 mL of ethylene glycol dimethyl ether (DME), and 2.5 mL (5.0 mmol) of a 2.0 M potassium carbonate solution were placed. The mixture was degassed by being stirred under reduced pressure, and the air in the flask was replaced with nitrogen. To the mixture, 10 mg (0.047 mmol) of palladium(II) acetate was added, and the mixture was refluxed under nitrogen stream at 120° C. for 10 hours. After a certain period, water was added to the mixture, and an aqueous layer was extracted with toluene. The obtained extracted solution and the organic layer were combined and washed with saturated saline, and the organic layer was dried with magnesium sulfate. The mixture was gravity filtered, and the obtained filtrate was condensed to give an oily substance. The oily substance was purified by silica gel column chromatography (toluene:ethyl acetate=4:1) and recrystallized with toluene/hexane, giving 0.58 g of the target pale yellow powder in a yield of 61%.

Then, 0.52 g of the target substance was subjected to sublimation purification at 230° C. under argon stream (flow rate: 3.0 mL/min) and a pressure of 10 Pa for 17 hours; thus, 0.41 g of the target substance was recovered in a yield of 78%. This compound was measured by nuclear magnetic resonance (NMR) spectrometry and identified as 2-{4-[10-(3-pyridyl)-9-anthryl]phenyl}benzoxazole (abbrev.: PyABOx).

The $^1$H NMR data is shown below.

$^1$H NMR (300 MHz, CDCl$_3$): δ (ppm)=7.38-7.45 (m, 6H), 7.57-7.76 (m, 8H), 7.83-7.87 (m, 2H), 8.52 (dd, J=7.5 Hz, 1.5 Hz, 211), 8.76 (d, J=1.8 Hz, 1H), 8.85 (dd, J=4.8 Hz, 1.5 Hz, 1H).

Figure 20A:
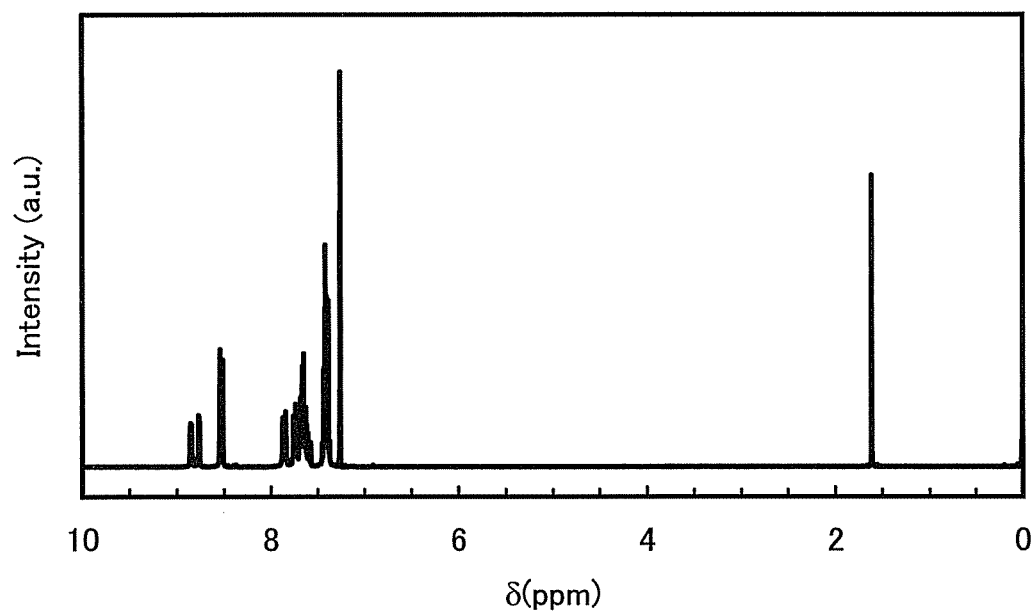
FIGS. 20A and 20B are each a $^1$H NMR chart of 2-{4-[10-(3-pyridyl)-9-anthryl]phenyl}benzoxazole (abbrev.: PyABOx)
Figure 20B:
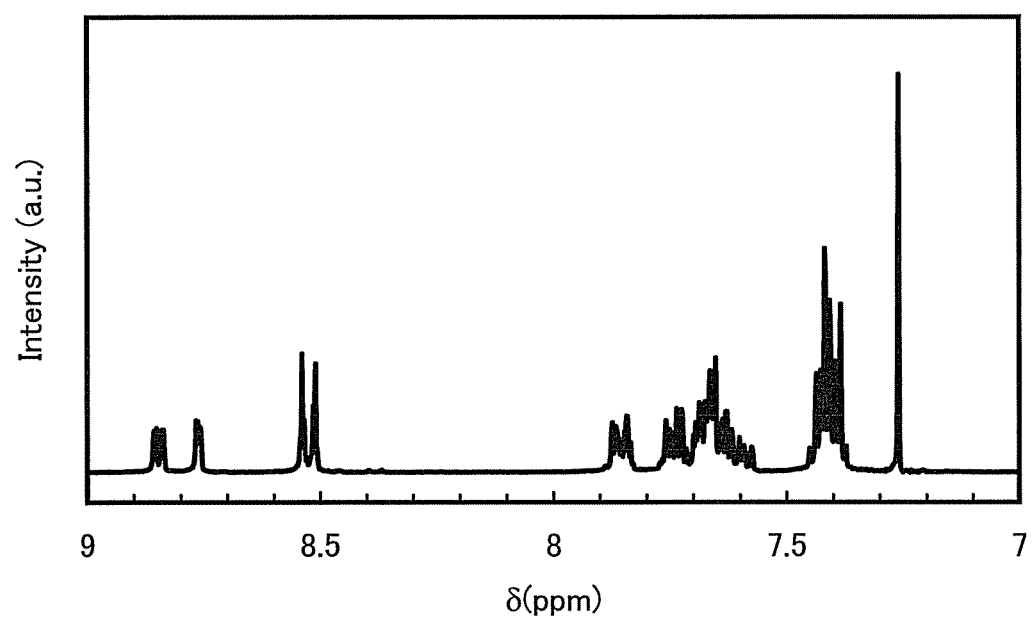

Further, the $^1$H NMR chart is shown in FIGS. 20A and 20B. Note that FIG. 20B is an enlarged chart showing the range from 7.0 ppm to 9.0 ppm in FIG. 20A.

Thermogravimetry-differential thermal analysis (TG-DTA) of PyABOx obtained was performed. The measurement was performed using a high vacuum differential type differential thermal balance (TG-DTA2410SA, manufactured by Bruker AXS K.K.). The measurement was carried out under nitrogen stream (flow rate: 200 mL/min) and a normal pressure at a temperature rising rate of 10° C./min. From the relationship between the weight and the temperature (thermogravimetry), it was understood that the 5% weight loss temperature was 380° C. and the melting point was 242° C., which is indicative of high thermal stability.

Figure 21:
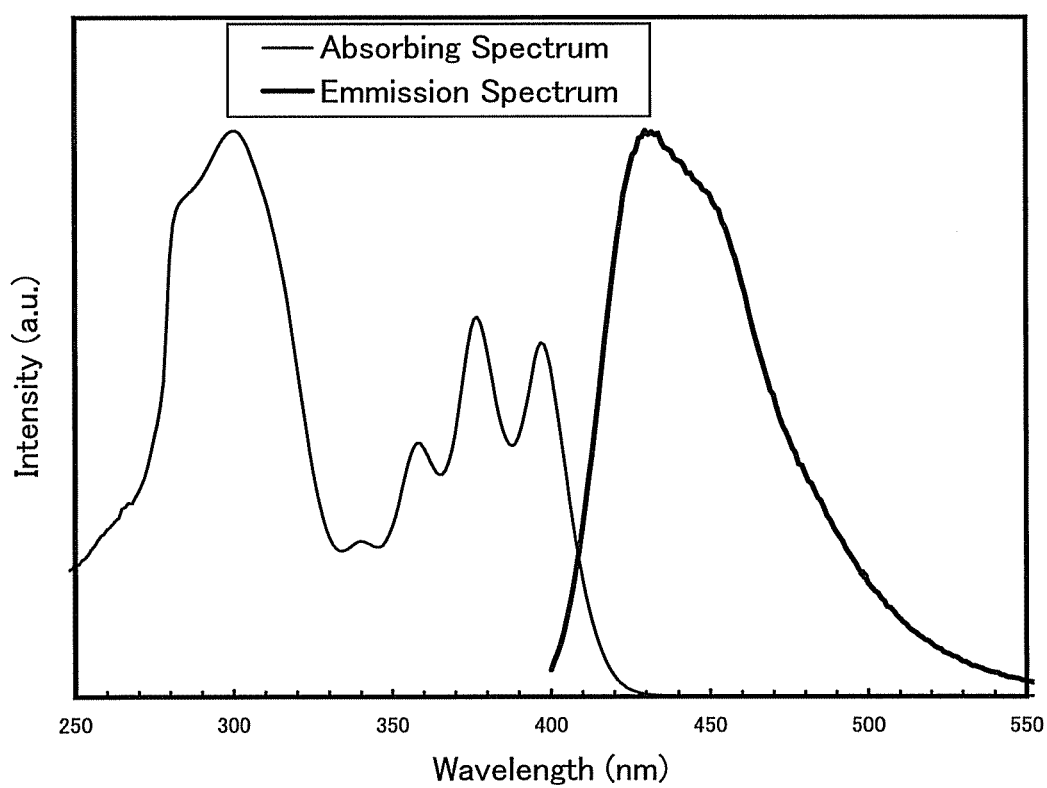
FIG. 21 shows an absorption spectrum and an emission spectrum of 2-{4-[10-(3-pyridyl)-9-anthryl]phenyl}benzoxazole in a toluene solution (abbrev.: PyABOx)

FIG. 21 shows an absorption spectrum and an emission spectrum of PyABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 21. In FIG. 21, the horizontal axis indicates wavelength (nm) and the vertical axis indicates intensity (arbitrary unit). In the case of the toluene solution, absorptions were observed at around 300 nm, 358 nm, 377 nm, and 397 nm. In addition, the maximum emission wavelength was 431 nm (excitation wavelength: 394 nm) in the case of the toluene solution.

Figure 22:
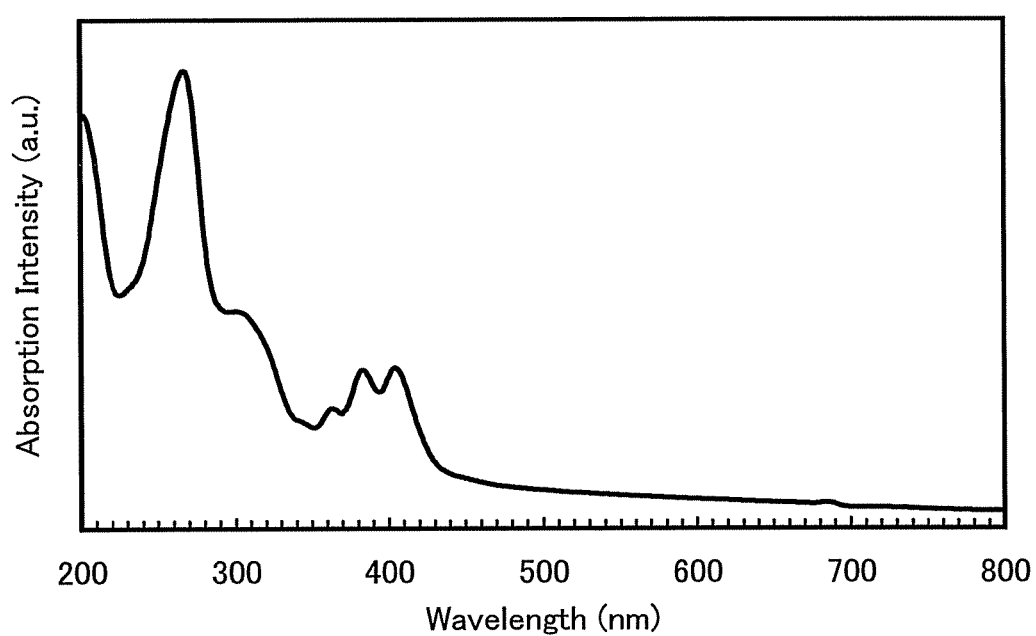
FIG. 22 shows an absorption spectrum of a thin film of 2-{4-[10-(3-pyridyl)-9-anthryl]phenyl}benzoxazole (abbrev.: PyABOx)
Figure 23:
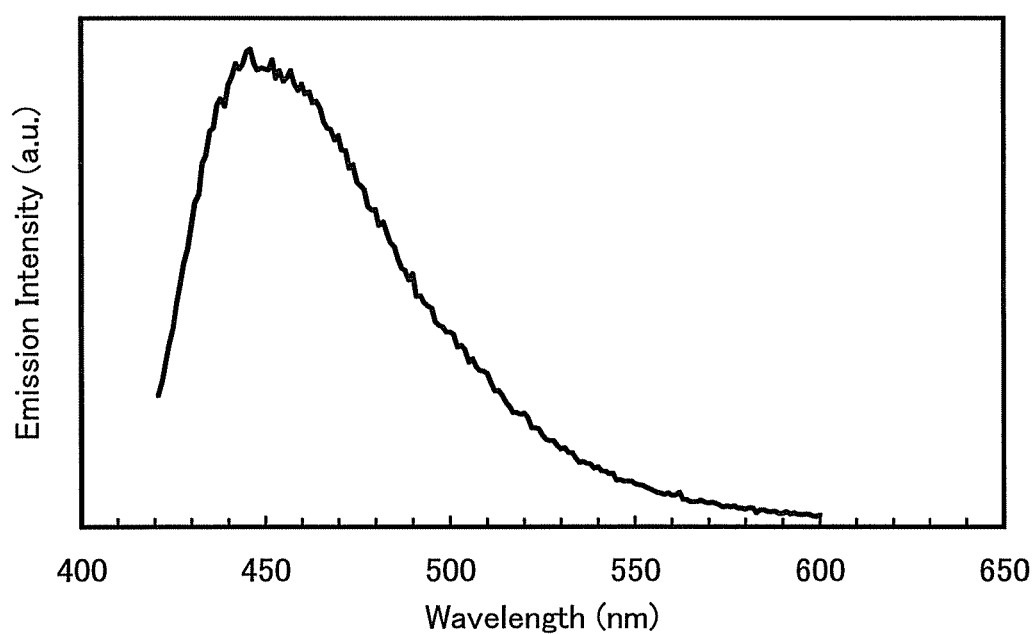
FIG. 23 shows an emission spectrum of a thin film of 2-{4-[10-(3-pyridyl)-9-anthryl]phenyl}benzoxazole (abbrev.: PyABOx)

FIG. 22 shows an absorption spectrum of a thin film of PyABOx, and FIG. 23 shows an emission spectrum of a thin film of PyABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 22. In FIG. 22, the horizontal axis indicates wavelength (nm) and the vertical axis indicates absorption intensity (arbitrary unit). In FIG. 23, the horizontal axis indicates wavelength (nm) and the vertical axis indicates emission intensity (arbitrary unit). In the case of the thin film, absorptions were observed at around 267 nm, 301 nm, 363 nm, 383 nm, and 404 nm. In addition, the maximum emission wavelength was 446 nm (excitation wavelength: 403 nm) in the case of the thin film.

In addition, the ionization potential of PyABOx in the thin film state was 5.81 eV, which was measured by a photoelectron spectrometer (AC-2, manufactured by Riken Keiki Co., Ltd.) in air. As a result, the HOMO level was found to be −5.81 eV. Further, an absorption edge was obtained from a Tauc plot assuming direct transition with use of the data of the absorption spectrum of PyABOx in the thin film state, and when the absorption edge was regarded as an optical energy gap, the energy gap was 2.90 eV A LUMO level of −2.91 eV was obtained from the obtained value of the energy gap and the HOMO level.

Further, oxidation-reduction characteristics of PyABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, PyABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristics of PyABOx were measured as follows. The potential of the working electrode with respect to the reference electrode was changed from −0.29 V to 1.20 V, and then changed from 1.20 V to −0.29 V. This change in potential was regarded as one cycle, and measurement was carried out for 100 cycles. The reduction characteristics of PyABOx were examined as follows. The potential of the working electrode with respect to the reference electrode was changed from −0.94 V to −2.60 V, and then changed from −2.60 V to −0.94 V. This change in potential was regarded as one cycle, and measurement was performed for 100 cycles. Further, the scanning speed of the CV measurement was set to be 0.1 V/s.

Figure 24:
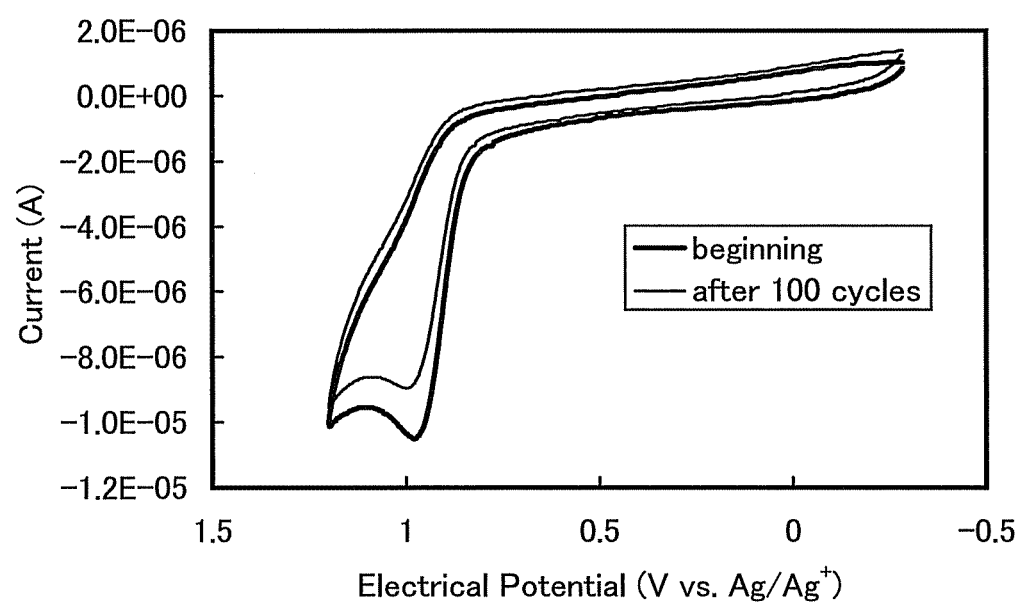
FIG. 24 shows CV measurement results of 2-{4-[10-(3-pyridyl)-9-anthryl]phenyl}benzoxazole (abbrev.: PyABOx)
Figure 25:
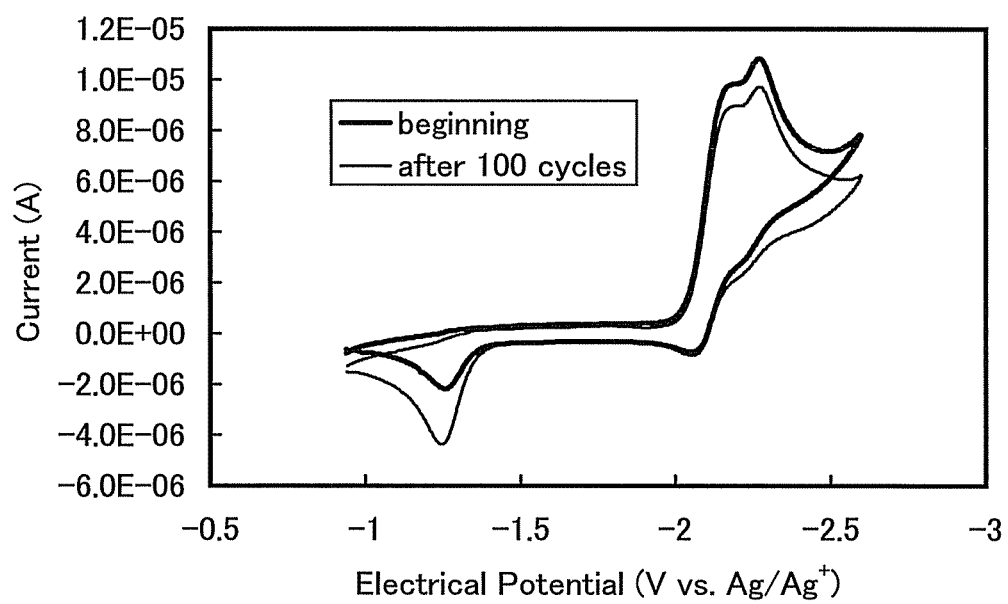
FIG. 25 shows CV measurement results of 2-{4-[10-(3-pyridyl)-9-anthryl]phenyl}benzoxazole (abbrev.: PyABOx)

FIG. 24 shows results of the CV measurement of PyABOx on the oxidation side, and FIG. 25 shows results of the CV measurement of PyABOx on the reduction side. In each of FIG. 24 and FIG. 25, the horizontal axis indicates a potential (V) of the working electrode with respect to the reference electrode, and the vertical axis indicates a current value (A) flowing between the working electrode and the auxiliary electrode. From FIG. 24, a current indicating oxidation was observed around 0.98 V (vs. Ag/Ag$^+$ electrode). In addition, from FIG. 25, a current indicating reduction was observed around −2.20 V (vs. Ag/Ag$^+$ electrode). Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 3

Figure 26:
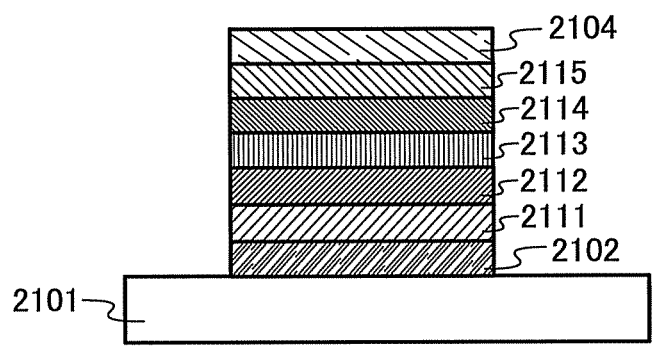
FIG. 26 illustrates a light-emitting element according to examples.

In Example 3, a light-emitting element of the present invention will be described with reference to FIG. 26. Structural formulae of materials used in this example are shown below. The structural formulae of the materials which have already been shown are omitted.

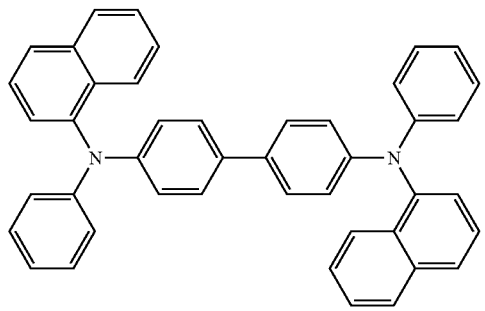

NPB

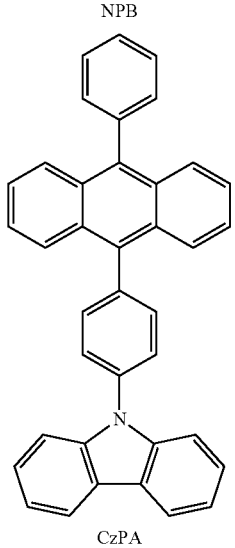

CzPA

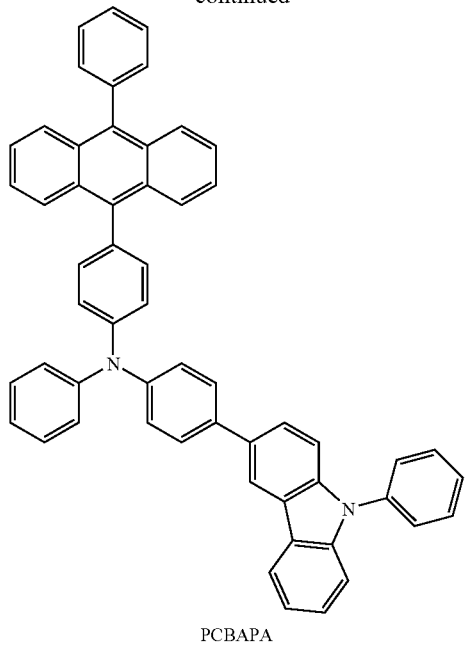

PCBAPA

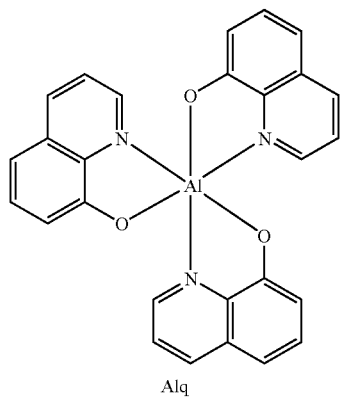

Alq

A manufacturing method of the light-emitting element of this example will be described below.
(Light-Emitting Element 1)

First, a film of indium tin oxide containing silicon oxide (ITSO) was formed by a sputtering method over a glass substrate 2101 to form a first electrode 2102. The thickness of the first electrode 2102 was set to be 110 nm, and the area thereof was set to be 2 mm×2 mm.

Next, the substrate provided with the first electrode 2102 was fixed to a substrate holder provided in a vacuum evaporation apparatus such that the side on which the first electrode 2102 was formed faced downward. After the pressure in a film formation chamber was reduced to approximately 104 Pa, a layer 2111 containing a composite material of an organic compound and an inorganic compound was formed on the first electrode 2102 by co-evaporation of 4,4'-bis[N-(1-naphthyl)-N-phenylamino]biphenyl (abbrev.: NPB) and molybdenum(VI) oxide. The film thickness of the layer 2111 containing a composite material was set to be 50 nm and the weight ratio between NPB and molybdenum(VI) oxide was adjusted to be 4:1 (=NPB:molybdenum oxide). Note that the co-evaporation is an evaporation method in which evaporation is performed simultaneously from a plurality of evaporation sources in one chamber.

Next, a film of 4,4'-bis[N-(1-naphthyl)-N-phenylamino]biphenyl (abbrev.: NPB) was formed to a thickness of 10 nm on the layer 2111 containing a composite material by an evaporation method employing resistance heating to form a hole-transporting layer 2112.

Then, a light-emitting layer 2113 was formed to a thickness of 30 nm on the hole-transporting layer 2112 by co-evaporation of 9-[4-(10-phenyl-9-anthryl)phenyl]-9H-carbazole (abbrev.: CzPA) and 4-(10-phenyl-9-anthryl)-4'-(9-phenyl-9H-carbazol-3-yl)triphenylamine (abbrev.: PCBAPA). The weight ratio between CzPA and PCBAPA was adjusted so as to be 1:0.1 (=CzPA:PCBAPA).

Then, a film of 2-[4-(10-phenyl-9-anthryl)phenyl]benzoxazole (abbrev.: PABOx) represented by Structural Formula (101) was formed to a thickness of 30 nm on the light-emitting layer 2113 by an evaporation method employing resistance heating, so that an electron-transporting layer 2114 was formed.

Furthermore, a film of lithium fluoride was formed to a thickness of 1 nm on the electron-transporting layer 2114, so that an electron-injecting layer 2115 was formed.

Lastly, a film of aluminum was formed to a thickness of 200 nm on the electron-injecting layer 2115 by an evaporation method employing resistance heating, so that a second electrode 2104 was formed. Accordingly, a light-emitting element 1 was fabricated.

(Light-Emitting Element 2)

A light-emitting element 2 was fabricated in a similar manner to that of the light-emitting element 1 by using the same substrate and using 2-{4-[10-(3-pyridyl)-9-anthryl]phenyl}benzoxazole (abbrev.: PyABOx) represented by Structural Formula (141) instead of PABOx. That is, a film of 2-{4-[10-(3-pyridyl)-9-anthryl]phenyl}benzoxazole (abbrev.: PyABOx) represented by Structural Formula (141) was formed to a thickness of 30 nm to form the electron-transporting layer 2114. Except for the electron-transporting layer 2114, the light-emitting element 2 was fabricated in a similar manner to that of the light-emitting element 1.

(Comparative Light-Emitting Element 3)

A comparative light-emitting element 3 was fabricated in a similar manner to that of the light-emitting element 1 by using the same substrate and using tris(8-quinolinolato)aluminum (III) (abbrev.: Alq) instead of PABOx. That is, a film of tris(8-quinolinolato)aluminum(III) (abbrev.: Alq) was formed to a thickness of 30 nm to form the electron-transporting layer 2114. Except for the electron-transporting layer 2114, the comparative light-emitting element 3 was formed in a similar manner to that of the light-emitting element 1.

The light-emitting element 1, the light-emitting element 2, and the comparative light-emitting element 3 obtained in the above-described manner were placed in a nitrogen-atmosphere glove box and were sealed so that the light-emitting elements were not exposed to air. Then, the operating characteristics of the light-emitting elements were measured. The measurement was carried out at room temperature (in the atmosphere kept at 25° C.).

Figure 27:
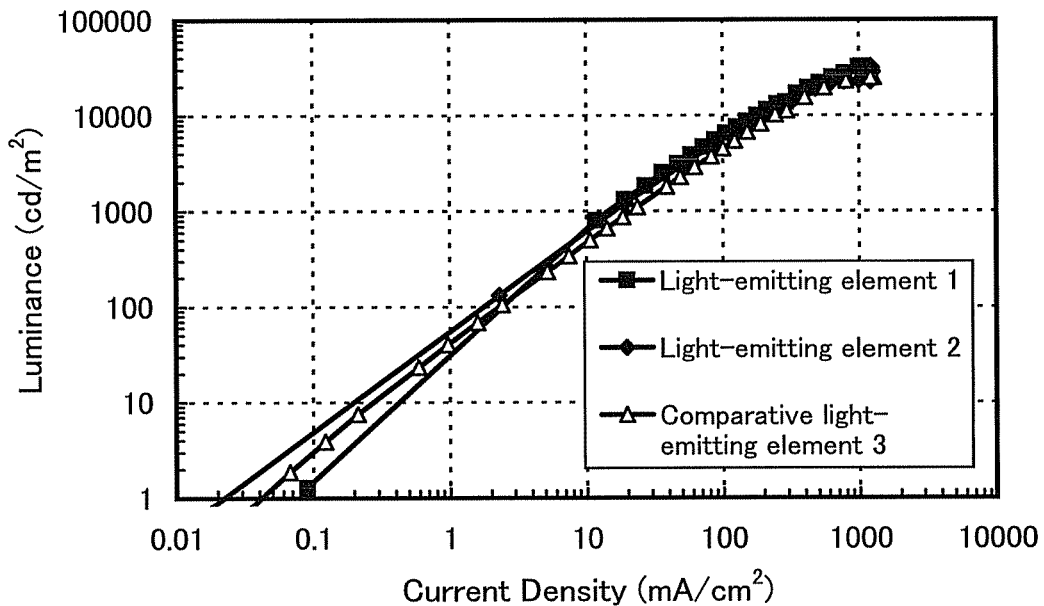
FIG. 27 shows current density-luminance characteristics of light-emitting elements fabricated in Example 3.
Figure 28:
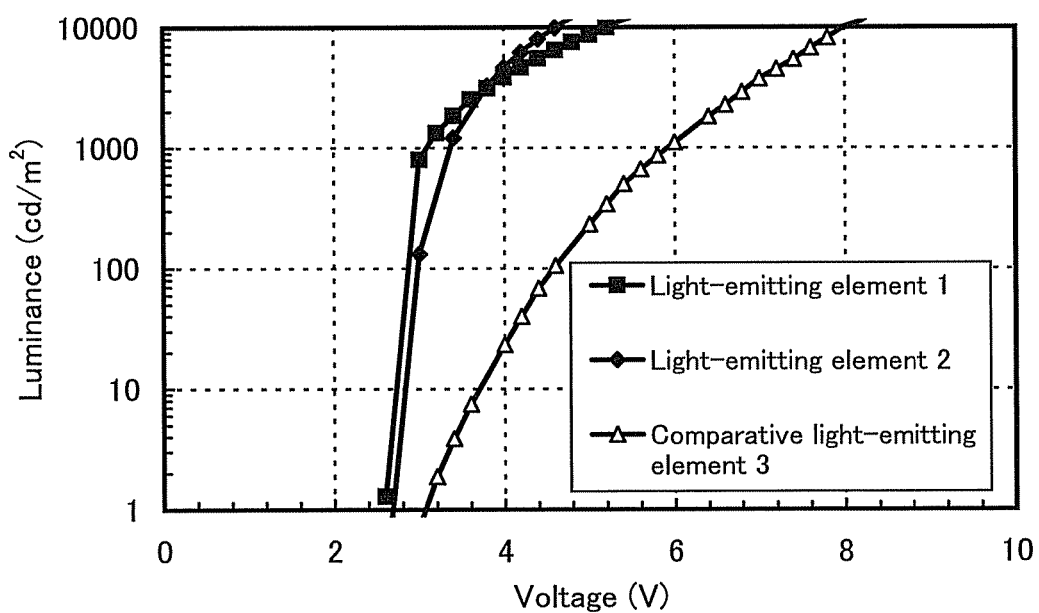
FIG. 28 shows voltage-luminance characteristics of the light-emitting elements fabricated in Example 3.
Figure 29:
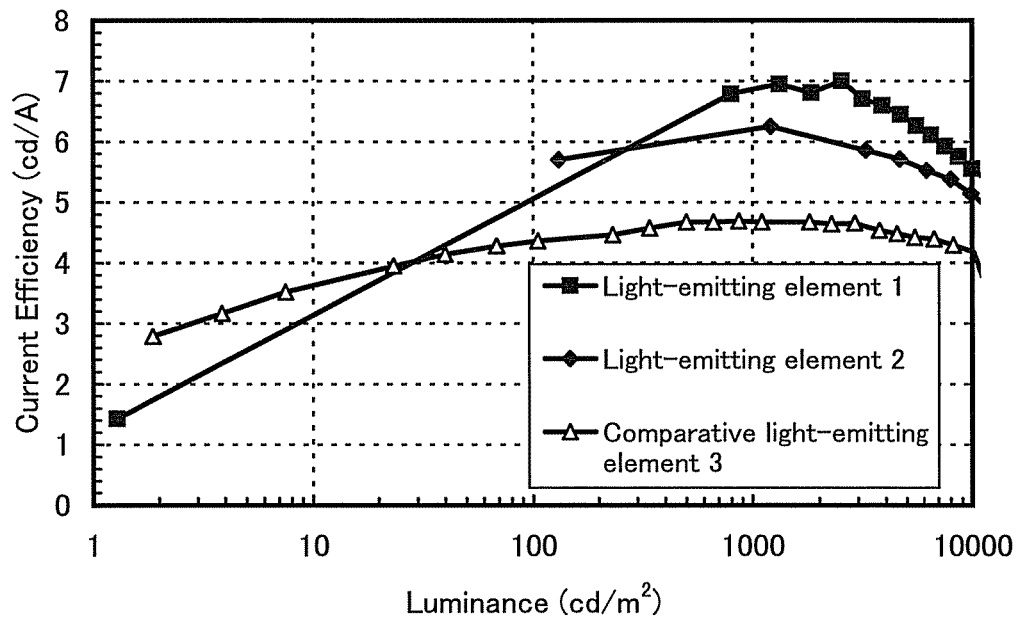
FIG. 29 shows luminance-current efficiency characteristics of the light-emitting elements fabricated in Example 3.
Figure 30:
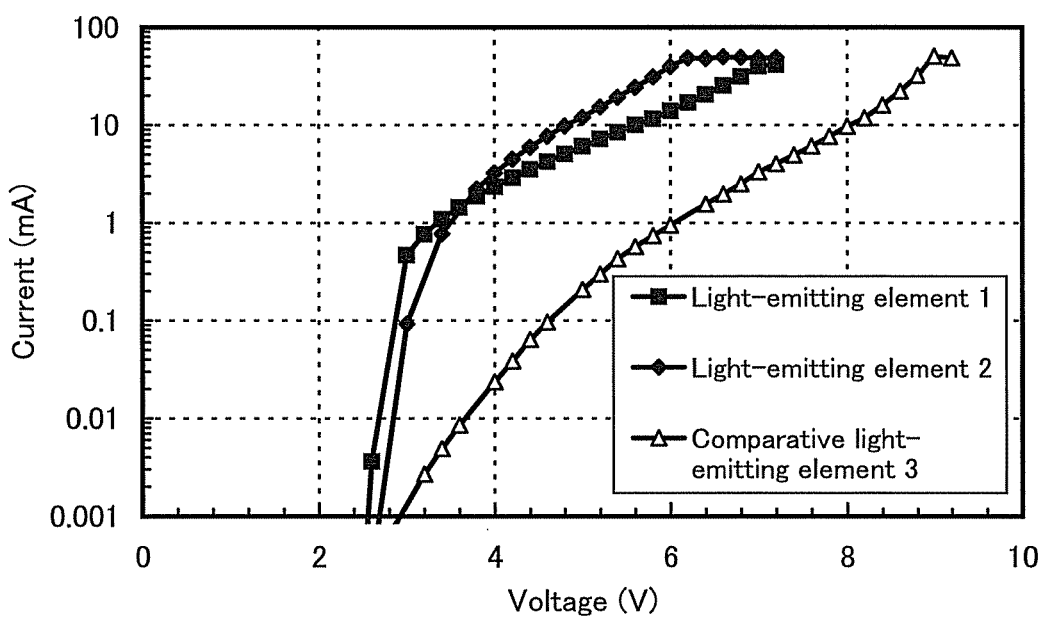
FIG. 30 shows voltage-current characteristics of the light-emitting elements fabricated in Example 3.

FIG. 27 shows current density-luminance characteristics of the light-emitting element 1, the light-emitting element 2, and the comparative light-emitting element 3. FIG. 28 shows voltage-luminance characteristics. FIG. 29 shows luminance-current efficiency characteristics. FIG. 30 shows voltage-current characteristics.

Figure 31:
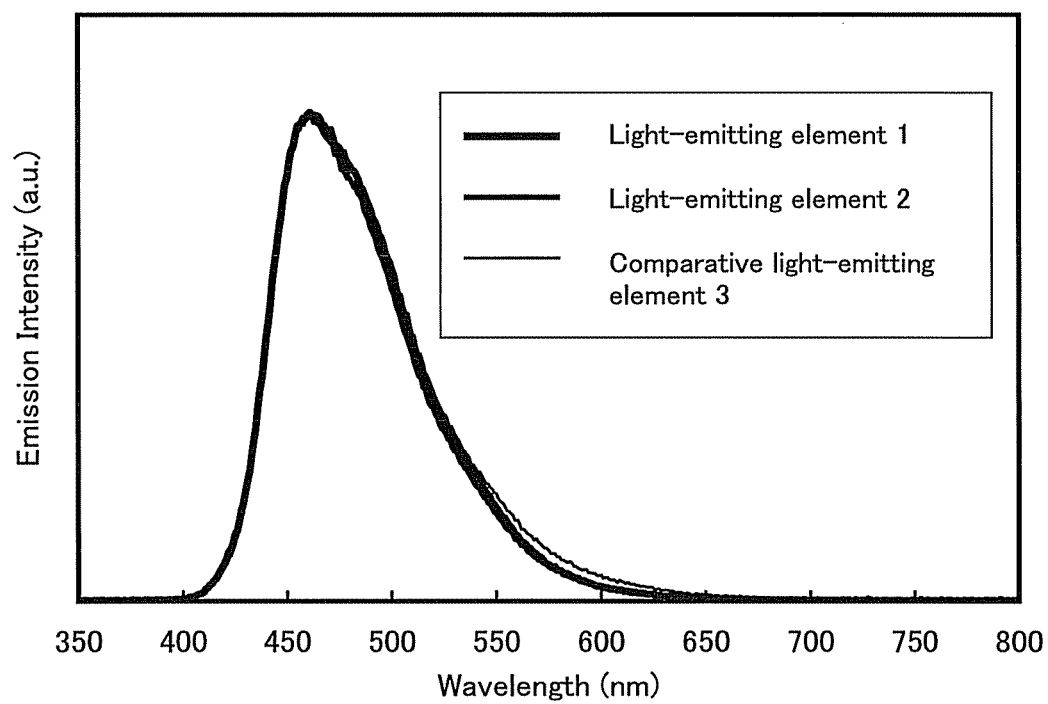
FIG. 31 shows emission spectra of the light-emitting elements fabricated in Example 3.

FIG. 31 shows the emission spectra when a current of 1 mA flows. It can be seen from FIG. 31 that light emission of each of the light-emitting element 1, the light-emitting element 2, and the comparative light-emitting element 3 results from PCBAPA.

The CIE chromaticity coordinates of the comparative light-emitting element 3 were x=0.16 and y=0.21 at a luminance of 1100 cd/m$^2$, and the comparative light-emitting element 3 emitted blue light. In addition, the current efficiency and the external quantum efficiency at a luminance of 1100 cd/m$^2$ were 4.7 cd/A and 3.0%, respectively. The voltage, the current density, and the power efficiency at a luminance of 1100 cd/m$^2$ were 6.0 V, 23.6 mA/cm$^2$, and 2.4 lm/W, respectively. On the contrary, the CIE chromaticity coordinates of the light-emitting element 1 were x=0.16 and y=0.20 at a luminance of 800 cd/m$^2$, and the light-emitting element 1 emitted blue light. In addition, the current efficiency and the external quantum efficiency at a luminance of 800 cd/m$^2$ were 6.8 cd/A and 4.5%, respectively, which shows that the light-emitting element 1 has higher emission efficiency than the comparative light-emitting element 3. Since the voltage at a luminance of 800 cd/m$^2$ was 3.0 V, it can be found that the driving voltage of the light-emitting element 1 is significantly lower than that of the comparative light-emitting element 3. Further, the current density was 11.8 mA/cm$^2$, and the power efficiency was as high as 7.1 lm/W.

The CIE chromaticity coordinates of the light-emitting element 2 were x=0.16 and y=0.19 at a luminance of 1210 cd/m$^2$, and the light-emitting element 2 emitted blue light. In addition, the current efficiency and the external quantum efficiency at a luminance of 1210 cd/m$^2$ were 6.3 cd/A and 4.3%, respectively, which shows that the light-emitting element 2 has higher emission efficiency than the comparative light-emitting element 3. Since the voltage at a luminance of 1210 cd/m$^2$ was 3.4 V, it can be found that the driving voltage of the light-emitting element 2 is significantly lower than that of the comparative light-emitting element 3. Further, the current density was 19.3 mA/cm$^2$, and the power efficiency was as high as 5.8 lm/W.

It can be seen from FIG. 30 that the light-emitting element 1 and the light-emitting element 2 require lower voltage than the comparative light-emitting element 3 to allow the same amount of current to flow. It can also be seen from FIG. 29 that the light-emitting element 1 and the light-emitting element 2 have higher current efficiency than the comparative light-emitting element 3. Accordingly, it can be understood that the light-emitting element 1 and the light-emitting element 2 require lower voltage and consume less power than the comparative light-emitting element 3 to provide the same luminance as shown in FIG. 28.

Therefore, the benzoxazole derivatives according to the present invention are excellent in an electron-transporting property. Further, by using the benzoxazole derivatives according to the present invention for light-emitting elements, light-emitting elements with low-voltage driving can be obtained. In addition, light-emitting elements with low power consumption can be obtained.

Example 4

Figure 32:
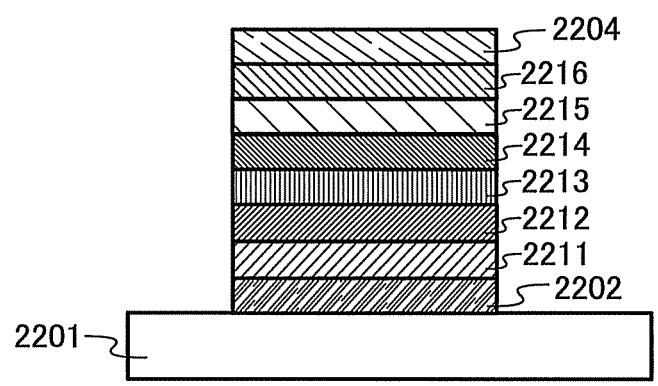
FIG. 32 illustrates a light-emitting element according to Example.

In Example 4, a light-emitting element of the present invention will be described with reference to FIG. 32. A manufacturing method of the light-emitting element of this example will be described below.

(Light-Emitting Element 4)

First, a film of indium tin oxide containing silicon oxide (ITSO) was formed by a sputtering method over a glass substrate 2201 to form a first electrode 2202. The thickness of the first electrode 2202 was set to be 110 nm, and the area thereof was set to be 2 mm×2 mm.

Next, the substrate provided with the first electrode 2202 was fixed to a substrate holder provided in a vacuum evaporation apparatus such that the side on which the first electrode 2102 was formed faced downward. After the pressure in a film formation chamber was reduced to approximately $10^{-4}$ Pa, a layer 2211 containing a composite material of an organic compound and an inorganic compound was formed on the first electrode 2202 by co-evaporation of 4,4'-bis[N-(1-naphthyl)-N-phenylamino]biphenyl (abbrev.: NPB) and molybdenum(VI) oxide. The film thickness of the layer 2211 containing a composite material was set to be 50 nm and the weight ratio between NPB and molybdenum(VI) oxide was adjusted to be 4:1 (=NPB:molybdenum oxide). Note that the co-evaporation is an evaporation method in which evaporation is performed simultaneously from a plurality of evaporation sources in one chamber.

Next, a film of 4,4'-bis[N-(1-naphthyl)-N-phenylamino]biphenyl (abbrev.: NPB) was formed to a thickness of 10 nm on the layer 2211 containing a composite material by an evaporation method employing resistance heating to form a hole-transporting layer 2212.

Then, a light-emitting layer 2213 was formed to a thickness of 30 nm on the hole-transporting layer 2112 by co-evaporation of 9-[4-(10-phenyl-9-anthryl)phenyl]-9H-carbazole (abbrev.: CzPA) and 4-(10-phenyl-9-anthryl)-4'-(9-phenyl-9H-carbazol-3-yl)triphenylamine (abbrev.: PCBAPA). The weight ratio between CzPA and PCBAPA was adjusted so as to be 1:0.1 (=CzPA:PCBAPA).

Then, a film of tris(8-quinolinolato)aluminum(III) (abbrev.: Alq) was formed to a thickness of 10 nm over the light-emitting layer 2213 by an evaporation method employing resistance heating, so that an electron-transporting layer (A) 2214 was formed. Further, a film of 2-[4-(10-phenyl-9-anthryl)phenyl]benzoxazole (abbrev.: PABOx) represented by Structural Formula (101) was formed to a thickness of 20 nm on the electron-transporting layer (A) 2214, so that an electron-transporting layer (B) 2215 was formed. Thus, the light-emitting element of this example has a structure in which two electron-transporting layers are stacked.

Furthermore, a film of lithium fluoride was formed to a thickness of 1 nm on the electron-transporting layer (B) 2215, so that an electron-injecting layer 2216 was formed.

Lastly, a film of aluminum was formed to a thickness of 200 nm on the electron-injecting layer 2216 by an evaporation method employing resistance heating, so that a second electrode 2204 was formed. Accordingly, a light-emitting element 4 was fabricated.

(Light-Emitting Element 5)

A light-emitting element 5 was fabricated in a similar manner to that of the light-emitting element 4 by using the same substrate and using 2-{4-[10-(3-pyridyl)-9-anthryl]phenyl}benzoxazole (abbrev.: PyABOx) represented by Structural Formula (141) instead of PABOx. That is, a film of 2-{4-[10-(3-pyridyl)-9-anthryl]phenyl}benzoxazole (abbrev.: PyABOx) represented by Structural Formula (141) was formed to a thickness of 20 nm to form the electron-transporting layer (B) 2215. Except for the electron-transporting layer (B) 2215, the light-emitting element 5 was formed in a similar manner to that of the light-emitting element 4.

The light-emitting element 4 and the light-emitting element 5 obtained in the above-described manner were placed in a nitrogen-atmosphere glove box and were sealed so that the light-emitting elements were not exposed to air. Then, the operating characteristics of the light-emitting elements were measured. The measurement was carried out at room temperature (in the atmosphere kept at 25° C.).

Figure 33:
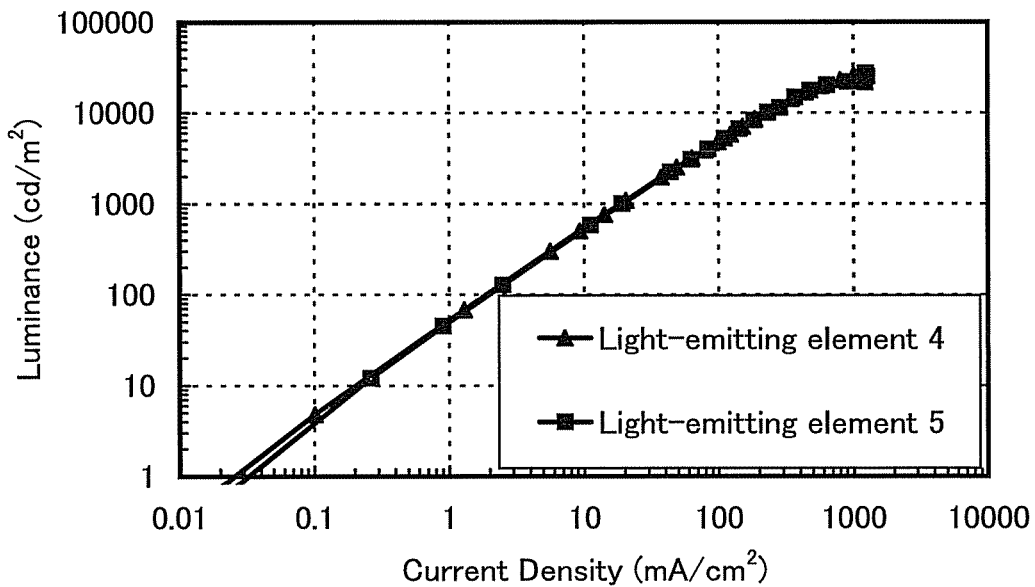
FIG. 33 shows current density-luminance characteristics of light-emitting elements fabricated in Example 4.
Figure 34:
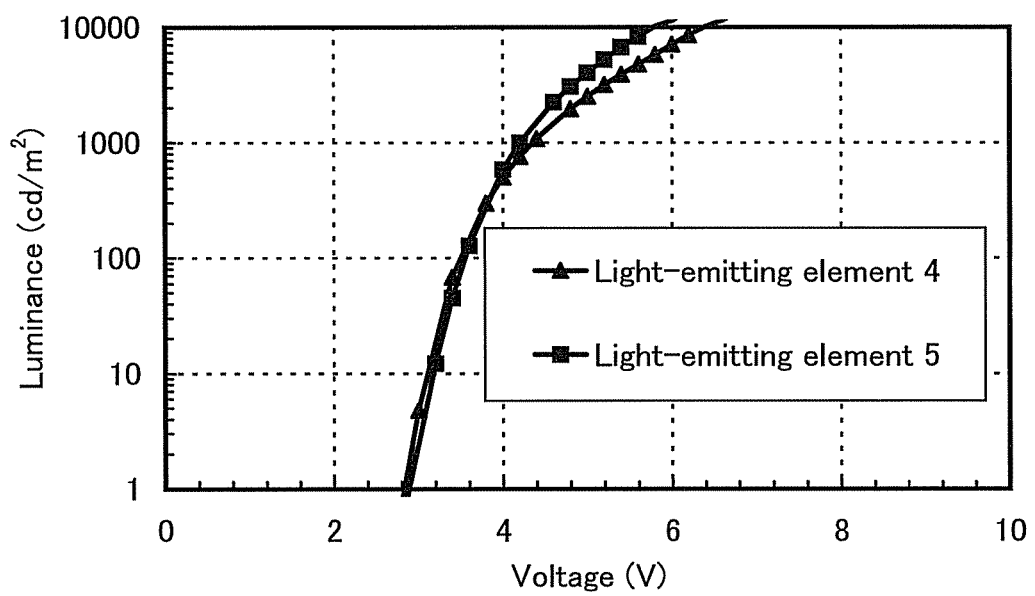
FIG. 34 shows voltage-luminance characteristics of the light-emitting elements fabricated in Example 4.
Figure 35:
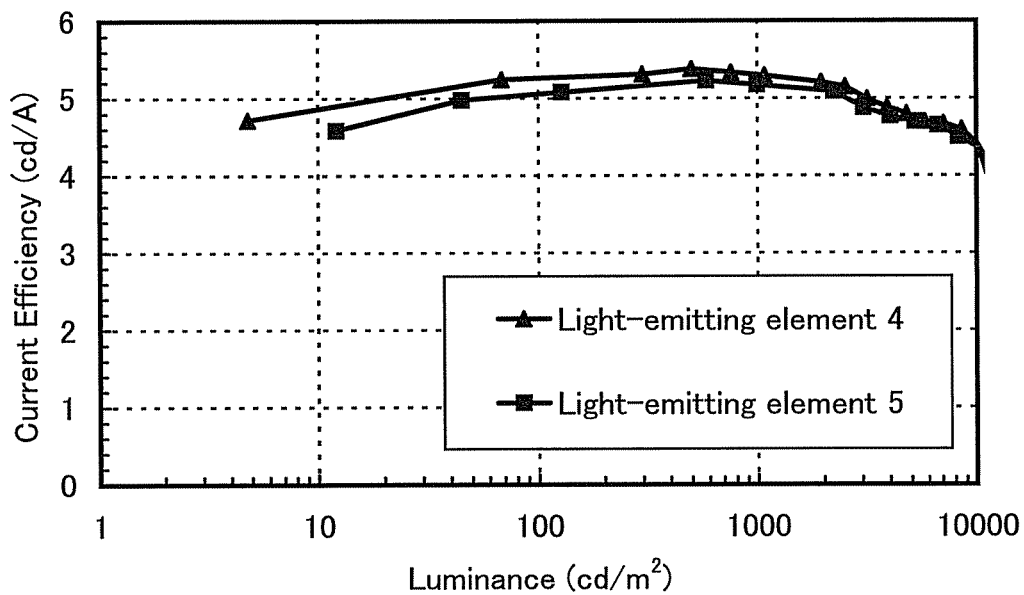
FIG. 35 shows luminance-current efficiency characteristics of the light-emitting elements fabricated in Example 4.
Figure 36:
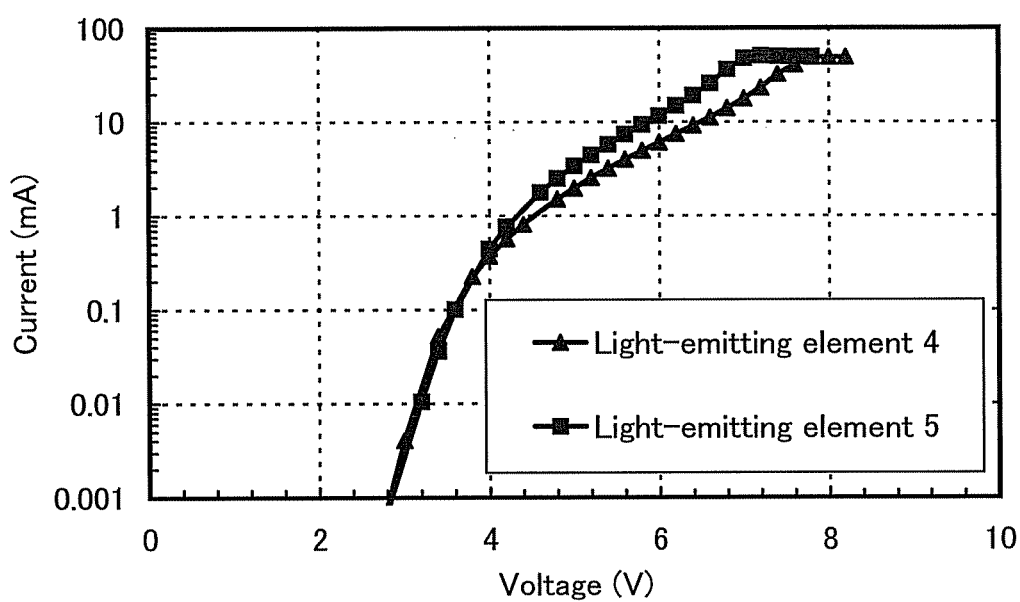
FIG. 36 shows voltage-current characteristics of the light-emitting elements fabricated in Example 4.

FIG. 33 shows current density-luminance characteristics of the light-emitting element 4 and the light-emitting element 5. FIG. 34 shows voltage-luminance characteristics. FIG. 35 shows luminance-current efficiency characteristics. FIG. 36 shows voltage-current characteristics.

Figure 37:
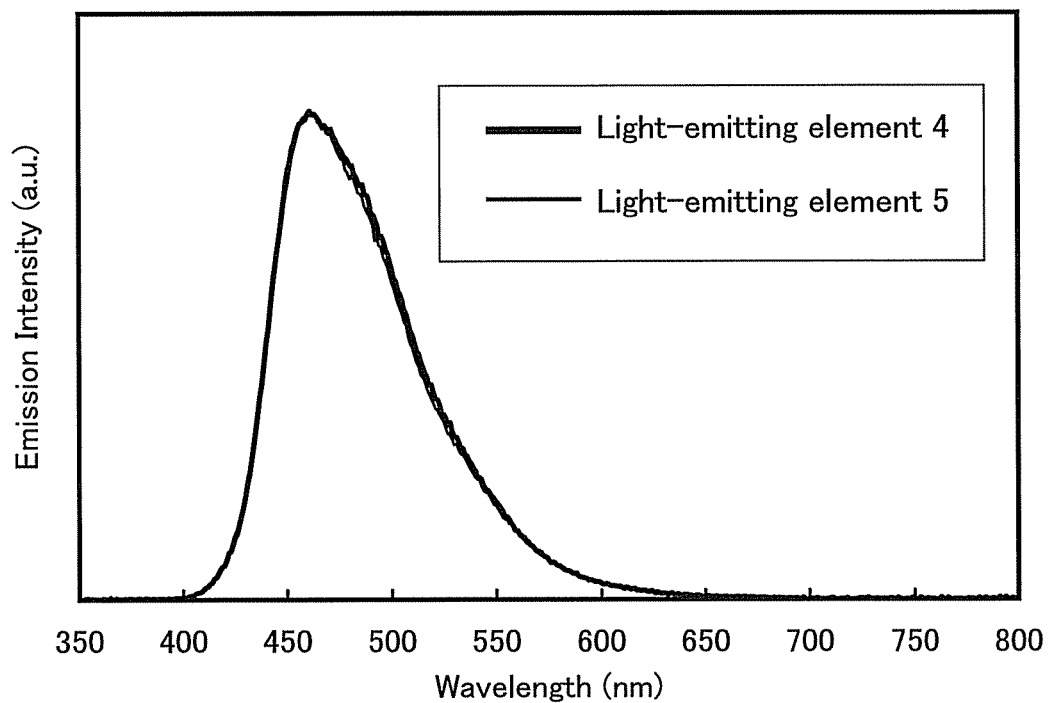
FIG. 37 shows emission spectra of the light-emitting elements fabricated in Example 4.

FIG. 37 shows the emission spectra when a current of 1 mA flows. It can be seen from FIG. 37 that light emission of each of the light-emitting element 4 and the light-emitting element 5 results from PCBAPA.

The CIE chromaticity coordinates of the light-emitting element 4 were x=0.16 and y=0.21 at a luminance of 1080 cd/m$^2$, and the light-emitting element 4 emitted blue light. In addition, the current efficiency and the external quantum efficiency at a luminance of 1080 cd/m$^2$ were 5.3 cd/A and 3.5%, respectively, which shows that the light-emitting element 4 has high emission efficiency. Since the voltage at a luminance of 1080 cd/m$^2$ was 4.4 V, it can be found that the driving voltage of the light-emitting element 4 is low. Further, the current density was 20.4 mA/cm$^2$, and the power efficiency was as high as 3.8 lm/W.

The CIE chromaticity coordinates of the light-emitting element 5 were x=0.16 and y=0.20 at a luminance of 1000 cd/m$^2$, and the light-emitting element 5 emitted blue light. In addition, the current efficiency and the external quantum efficiency at a luminance of 1000 cd/m$^2$ were 5.2 cd/A and 3.5%, respectively. Since the voltage at a luminance of 1000 cd/m$^2$ was 4.2 V, it can be found that the driving voltage of the light-emitting element 5 is low. Further, the current density was 19.3 mA/cm$^2$, and the power efficiency was as high as 3.9 lm/W.

Figure 38:
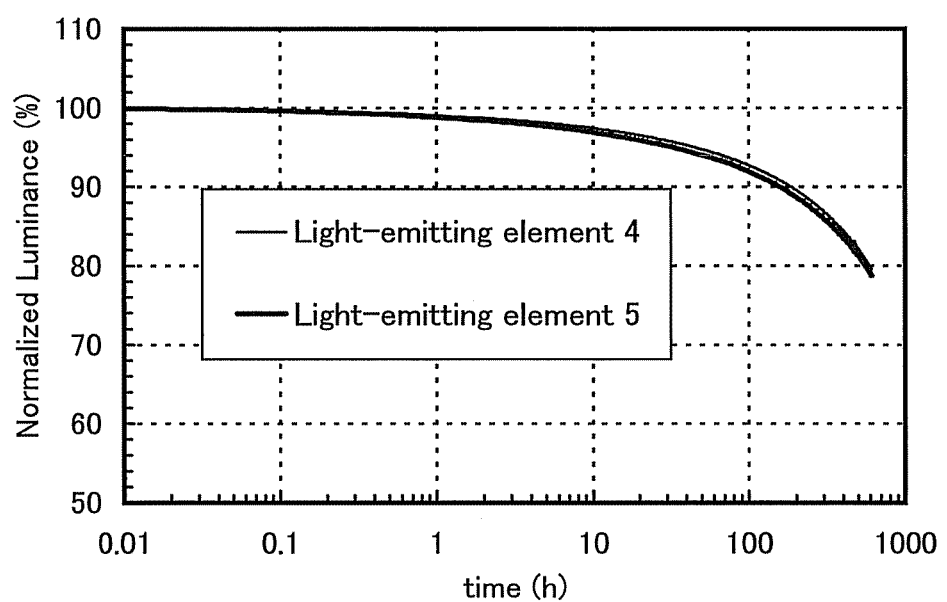
FIG. 38 shows changes in luminance with respect to driving time of the light-emitting elements fabricated in Example 4.

FIG. 38 shows the results of a continuous lighting test in which the light-emitting element 4 and the light-emitting element 5 were continuously lit by constant current driving with the initial luminance set at 1000 cd/m$^2$ (the vertical axis indicates the relative luminance on the assumption that 1000 cd/m$^2$ is 100%). From FIG. 38, it is seen that the light-emitting element 4 and the light-emitting element 5 exhibit 80% of the initial luminance even after 600 hours.

The light-emitting element 4 and the light-emitting element 5 use Alq for the electron-transporting layer (A). It can be found that by using the benzoxazole derivative of the present invention for the second electron-transporting layer (the electron-transporting layer (B)), the light-emitting element 4 and the light-emitting element 5 can each have a significantly lower driving voltage compared to that in the case of employing the structure where the electron-transporting layer is formed of only the Alq layer like the comparative light-emitting element 3 mentioned in Example 3. In addition, a light-emitting element with high emission efficiency can be obtained. Thus, power consumption can be reduced.

Therefore, the benzoxazole derivatives according to the present invention are excellent in an electron-transporting property. Further, by using the benzoxazole derivatives according to the present invention for light-emitting elements, light-emitting elements with low-voltage driving can be obtained. In addition, light-emitting elements with low power consumption can be obtained.

Example 5

In Example 5, a synthesis method of 2-{4-[10-(1-naphthyl)-9-anthryl]phenyl}benzoxazole (abbrev.: NABOx) represented by Structural Formula (129) will be described.

(129)

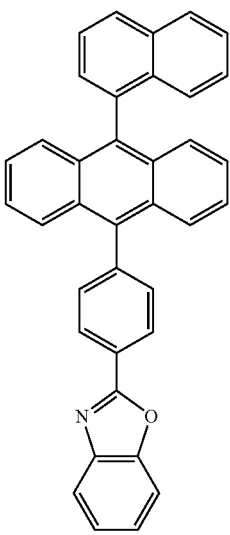

Step 1: Synthesis of
2-[4-(10-bromo-9-anthryl)phenyl]benzoxazole (i) 2-[4-(9-anthryl)phenyl]benzoxazole A synthesis scheme of 2-[4-(9-anthryl)phenyl]benzoxazole is shown in (D-1).

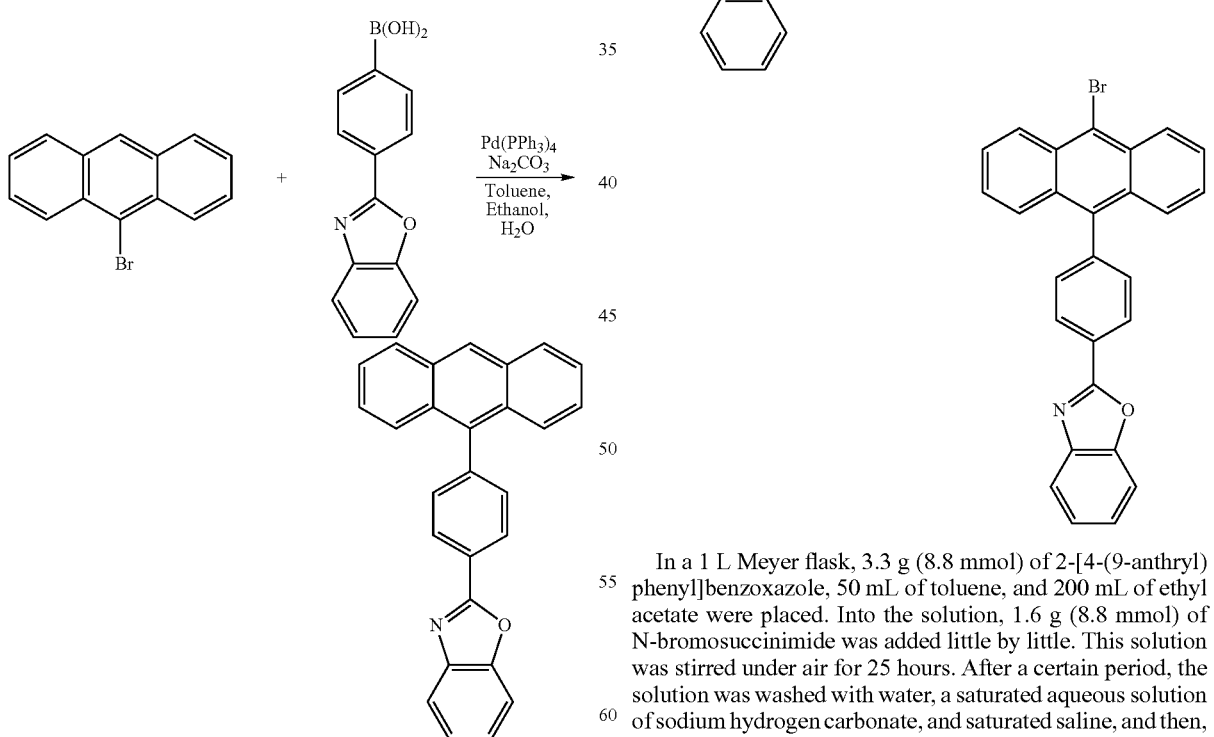

(D-1)

In a 200 mL three-neck flask, 3.7 g (15 mmol) of 4-(benzoxazol-2-yl)phenylboronic acid, 3.9 g (15 mmol) of 9-bromoanthracene, 3.3 g (31 mmol) of sodium carbonate, 60 mL of toluene, 15 mL of ethanol, and 15 mL of water were placed. The mixture was degassed by being stirred under reduced pressure, and the air in the flask was replaced with nitrogen. To the mixture, 0.16 g (0.14 mmol) of tetrakis(triphenylphosphine)palladium(0) was added, and the mixture was stirred under nitrogen stream at 110° C. for 6 hours. After a certain period, water was added to the mixture, and an aqueous layer was extracted with toluene. The obtained extracted solution and the organic layer were combined and washed with saturated saline, and the organic layer was dried with magnesium sulfate. The obtained mixture was gravity filtered, and the filtrate was condensed to give a solid. A toluene solution of the solid was subjected to suction filtration through Celite (produced by Wako Pure Chemical Industries, Ltd., Catalog No. 531-16855), and the filtrate was condensed. The solid was recrystallized with ethyl acetate/hexane, so that 3.3 g of target yellow powder was obtained in a yield of 57%.

(ii) 2-[4-(10-bromo-9-anthryl)phenyl]benzoxazole

A synthesis scheme of 2-[4-(10-bromo-9-anthryl)phenyl]benzoxazole is shown in (D-2).

(D-2)

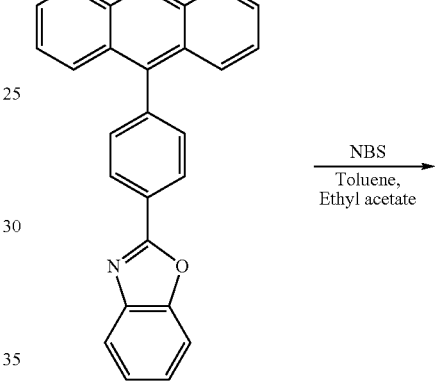

In a 1 L Meyer flask, 3.3 g (8.8 mmol) of 2-[4-(9-anthryl)phenyl]benzoxazole, 50 mL of toluene, and 200 mL of ethyl acetate were placed. Into the solution, 1.6 g (8.8 mmol) of N-bromosuccinimide was added little by little. This solution was stirred under air for 25 hours. After a certain period, the solution was washed with water, a saturated aqueous solution of sodium hydrogen carbonate, and saturated saline, and then, the organic layer was dried with magnesium sulfate. The obtained mixture was gravity filtered, and the filtrate was condensed to give an oily substance. The oily substance was purified by silica gel column chromatography (toluene:hexane=5:1) to give a solid. The solid was recrystallized with toluene/methanol, giving 3.3 g of the target yellow powder in a yield of 82%.

Step 2: 2-{4-[10-(1-naphthyl)-9-anthryl]phenyl}benzoxazole

A synthesis scheme of 2-{4-[10-(1-naphthyl)-9-anthryl]phenyl}benzoxazole is shown in (D-3).

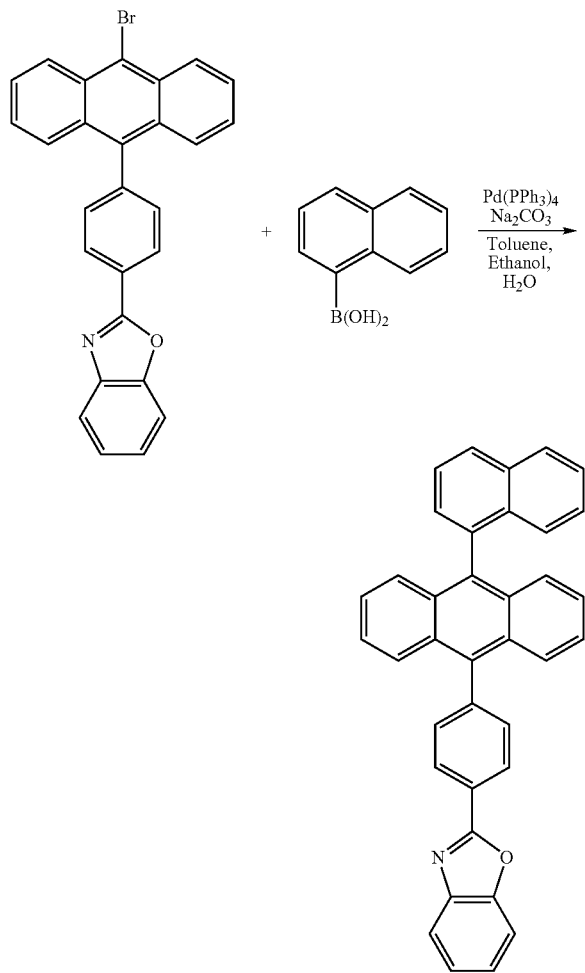

(D-3)

In a 50 mL three-neck flask, 0.90 g (2.0 mmol) of 2-[4-(10-bromo-9-anthryl)phenyl]benzoxazole, 0.37 g (2.2 mmol) of 1-naphthaleneboronic acid, 0.50 g (4.7 mmol) of sodium carbonate, 10 mL of toluene, 3 mL of ethanol, and 3 mL of water were placed. The mixture was degassed by being stirred under reduced pressure, and the air in the flask was replaced with nitrogen. To the mixture, 32 mg (0.027 mmol) of tetrakis(triphenylphosphine)palladium(0) was added, and the mixture was stirred under nitrogen stream at 80° C. for 7 hours. After a certain period, water was added to the mixture, and an aqueous layer was extracted with toluene. The obtained extracted solution and the organic layer were combined and washed with a saturated aqueous solution of sodium hydrogen carbonate and saturated saline, and the organic layer was dried with magnesium sulfate. The mixture was gravity filtered, and the obtained filtrate was condensed to give a solid. The solid was purified by silica gel column chromatograghy (toluene:hexane=2:1) and recrystallized with toluene/hexane, giving 0.78 g of the target pale yellow powder in a yield of 78%.

Then, 0.79 g of the target substance was subjected to sublimation purification at 240° C. under argon stream (flow rate: 3.0 mL/min) and a pressure of 10 Pa for 15 hours; thus, 0.67 g of the target substance was recovered in a yield of 84%. This compound was measured by nuclear magnetic resonance (NMR) spectrometry and identified as 2-{4-[10-(1-naphthyl)-9-anthryl]phenyl}benzoxazole (abbrev.: NABOx).

The $^1$H NMR data is shown below.

$^1$H NMR (300 MHz, CDCl$_3$): δ (ppm)=7.15-7.27 (m, 4H), 7.33-7.52 (m, 7H), 7.58 (d, J=6.3 Hz, 1H), 7.64-7.78 (m, 6H), 7.84-7.88 (m, 1H), 8.03 (d, J=8.1 Hz, 1H), 8.08 (d, J=8.1 Hz, 1H), 8.52-8.56 (m, 2H).

Figure 39A:
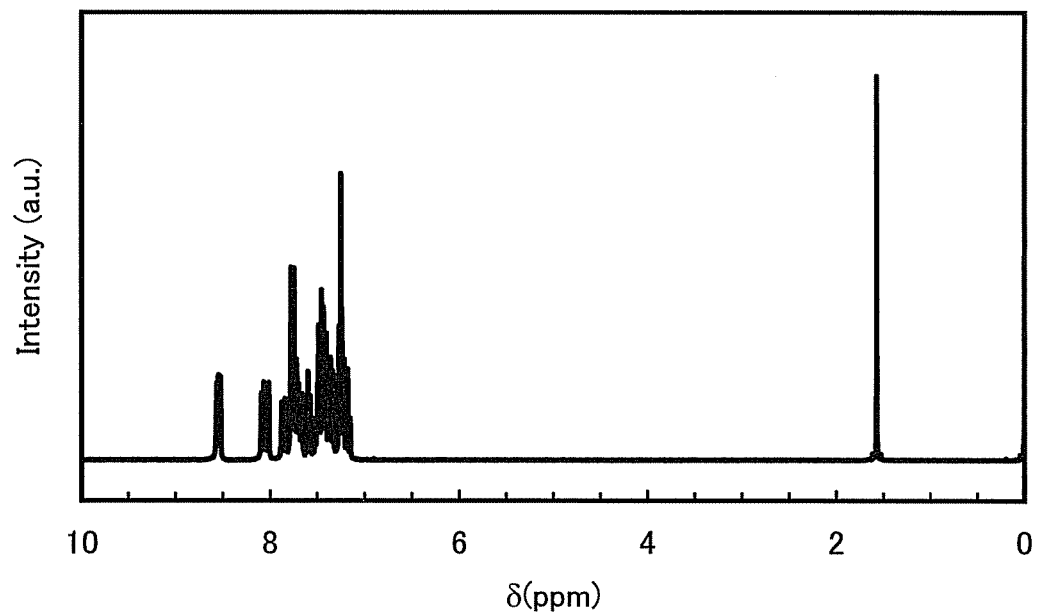
FIGS. 39A and 39B are each a $^1$H NMR chart of 2-{4-[10-(1-naphthyl)-9-anthryl]phenyl}benzoxazole (abbrev.: NABOx)
Figure 39B:
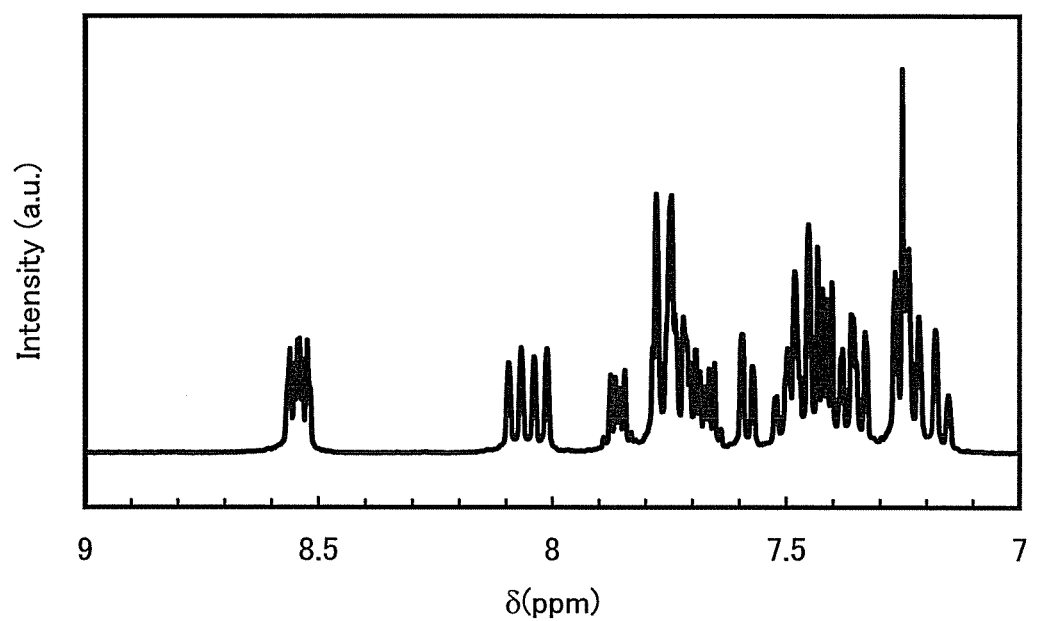

Further, the $^1$H NMR chart is shown in FIGS. 39A and 39B. Note that FIG. 39B is an enlarged chart showing the range from 7.0 ppm to 9.0 ppm in FIG. 39A.

Figure 40:
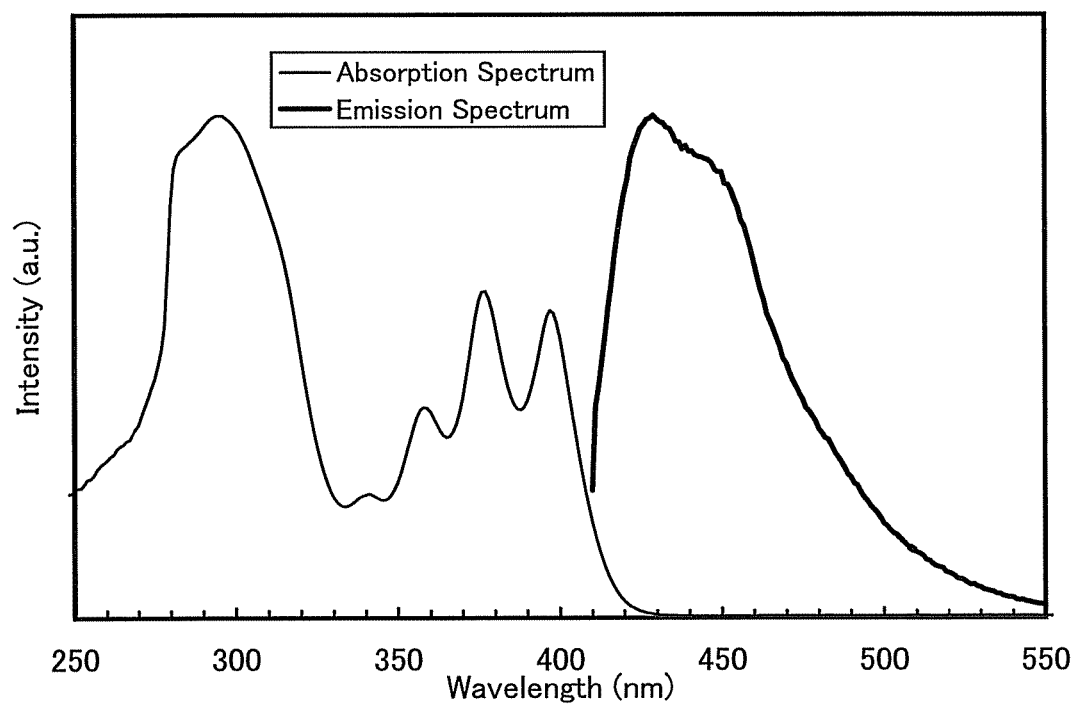
FIG. 40 shows an absorption spectrum and an emission spectrum of 2-{4-[10-(1-naphthyl)-9-anthryl]phenyl}benzoxazole in a toluene solution (abbrev.: NABOx)

Further, FIG. 40 shows an absorption spectrum and an emission spectrum of NABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 40. In FIG. 40, the horizontal axis indicates wavelength (nm) and the vertical axis indicates intensity (arbitrary unit). In the case of the toluene solution, absorptions were observed at around 341 nm, 358 nm, 377 nm, and 397 nm. In addition, the maximum emission wavelength was 429 nm (excitation wavelength: 398 nm) in the case of the toluene solution.

Figure 41:
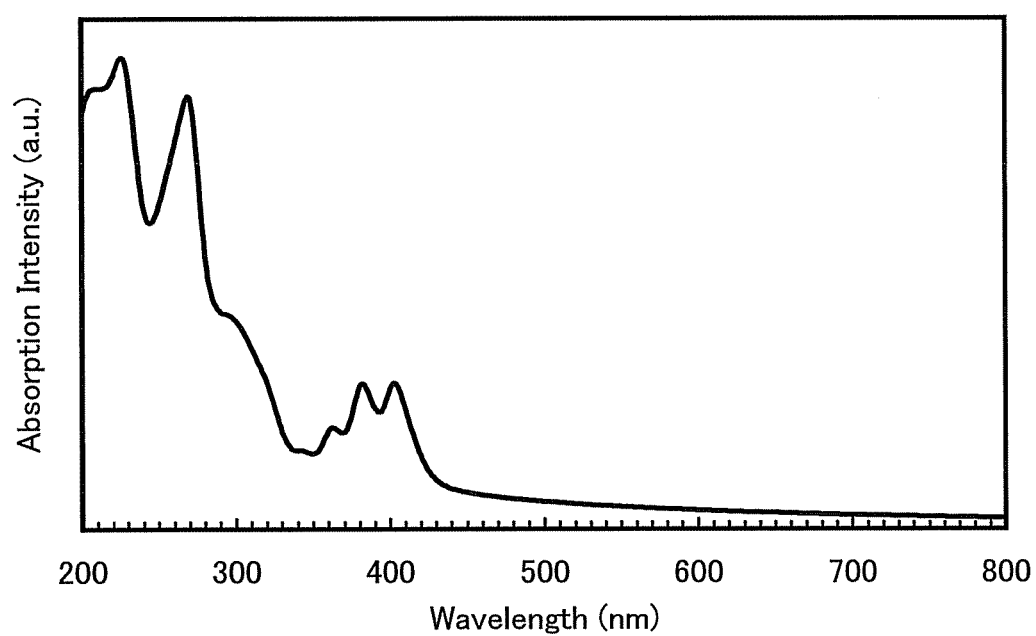
FIG. 41 shows an absorption spectrum of a thin film of 2-{4-[10-(1-naphthyl)-9-anthryl]phenyl}benzoxazole (abbrev.: NABOx)
Figure 42:
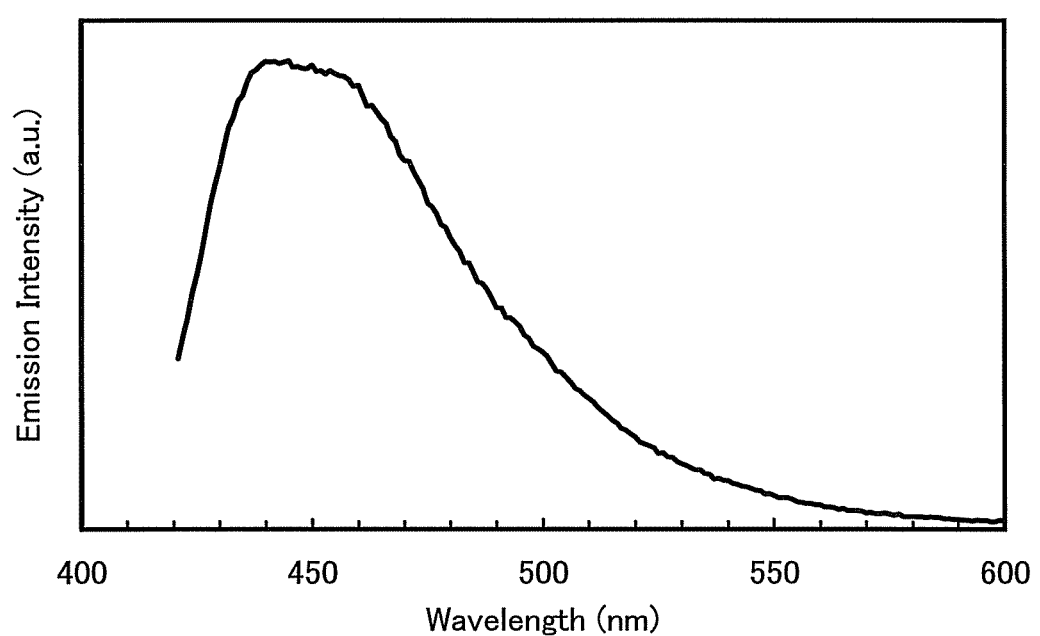
FIG. 42 shows an emission spectrum of a thin film of 2-{4-[10-(1-naphthyl)-9-anthryl]phenyl}benzoxazole (abbrev.: NABOx)

FIG. 41 shows an absorption spectrum of a thin film of NABOx, and FIG. 42 shows an emission spectrum of a thin film of NABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 41. In FIG. 41, the horizontal axis indicates wavelength (nm) and the vertical axis indicates absorption intensity (arbitrary unit). In FIG. 42, the horizontal axis indicates wavelength (nm) and the vertical axis indicates emission intensity (arbitrary unit). In the case of the thin film, absorptions were observed at around 226 nm, 269 nm, 296 nm, 363 nm, 382 nm, and 403 nm. In addition, the maximum emission wavelength was 441 nm (excitation wavelength: 403 nm) in the case of the thin film.

In addition, the ionization potential of NABOx in the thin film state was 5.85 eV, which was measured by a photoelectron spectrometer (AC-2, manufactured by Riken Keiki Co., Ltd.) in air. As a result, the HOMO level was found to be −5.85 eV. Further, an absorption edge was obtained from a Tauc plot assuming direct transition with use of the data of the absorption spectrum of NABOx in the thin film state, and when the absorption edge was regarded as an optical energy gap, the energy gap was 2.94 eV. A LUMO level of −2.91 eV was obtained from the obtained value of the energy gap and the HOMO level.

Further, oxidation-reduction characteristics of NABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, NABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag⁺ electrode (manufactured by BAS Inc., RE-7 reference electrode for nonaqueous solvent) was used as a reference electrode. The measurement was carried out at room temperature.

The oxidation characteristics of NABOx were measured as follows. The potential of the working electrode with respect to the reference electrode was changed from 0.22 V to 1.10 V, and then changed from 1.10 V to 0.22 V. This change in potential was regarded as one cycle, and measurement was carried out for 100 cycles. The reduction characteristics of NABOx were examined as follows. The potential of the working electrode with respect to the reference electrode was changed from −1.30 V to −2.45 V, and then changed from −2.45 V to −1.30 V. This change in potential was regarded as one cycle, and measurement was performed for 100 cycles. Further, the scanning speed of the CV measurement was set to be 0.1 V/s.

Figure 43:
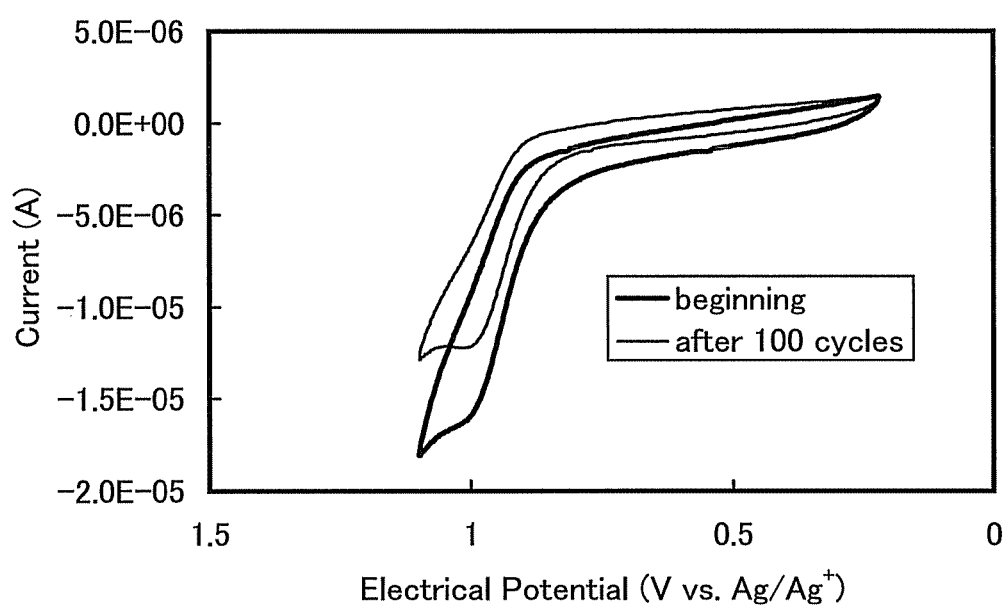
FIG. 43 shows CV measurement results of 2-{4-[10-(1-naphthyl)-9-anthryl]phenyl}benzoxazole (abbrev.: NABOx)
Figure 44:
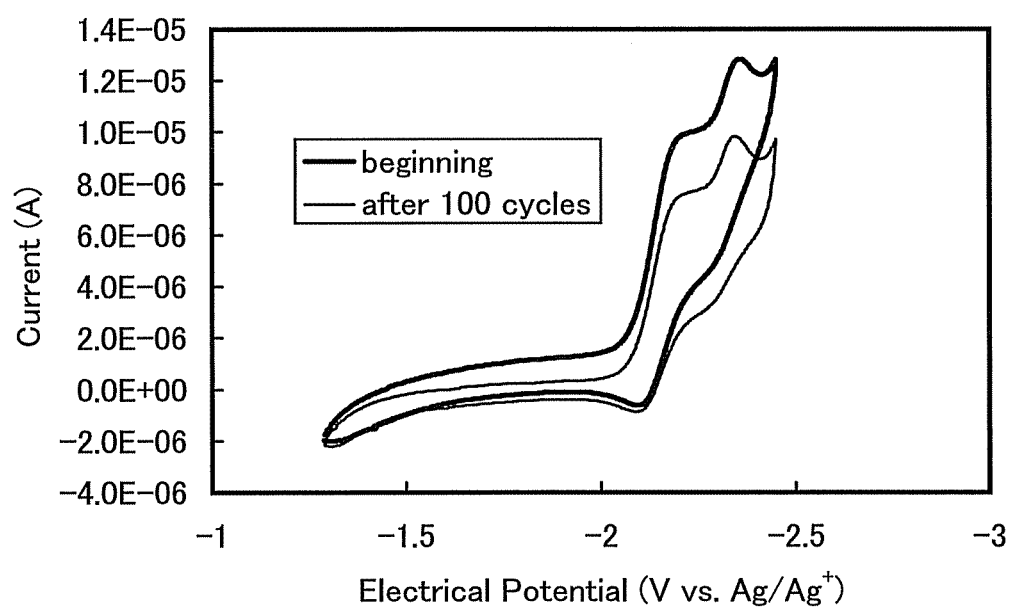
FIG. 44 shows CV measurement results of 2-{4-[10-(1-naphthyl)-9-anthryl]phenyl}benzoxazole (abbrev.: NABOx)

FIG. 43 shows results of the CV measurement of NABOx on the oxidation side, and FIG. 44 shows results of the CV measurement of NABOx on the reduction side. In each of FIG. 43 and FIG. 44, the horizontal axis indicates a potential (V) of the working electrode with respect to the reference electrode, and the vertical axis indicates a current value (A) flowing between the working electrode and the auxiliary electrode. From FIG. 43, a current indicating oxidation was observed around 1.02 V (vs. Ag/Ag⁺ electrode). In addition, from FIG. 44, a current indicating reduction was observed around −2.23 V (vs. Ag/Ag⁺ electrode).

Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 6

In Example 6, a synthesis method of 2-{4-[10-(biphenyl-4-yl)-9-anthryl]phenyl}benzoxazole (abbrev.: BPhABOx) represented by Structural Formula (126) will be described.

(126)

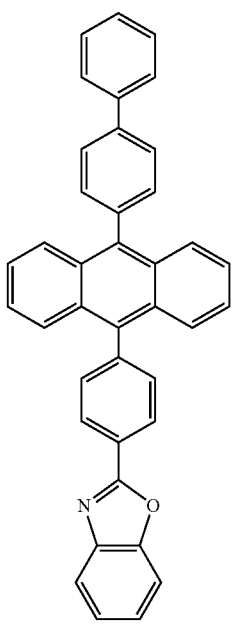

Step 1: Synthesis of 2-{4-[10-(biphenyl-4-yl)-9-anthryl]phenyl}benzoxazole

A synthesis scheme of 2-{4-[10-(biphenyl-4-yl)-9-anthryl]phenyl}benzoxazole is shown in (E-1).

(E-1)

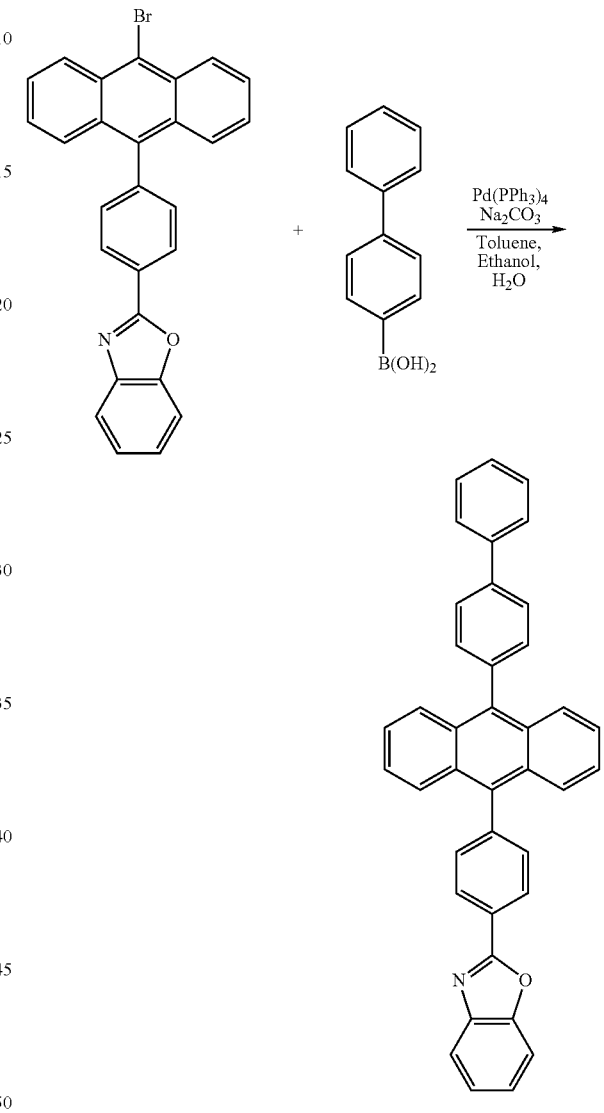

In a 100 mL three-neck flask, 0.91 g (2.0 mmol) of 2-[4-(10-bromo-9-anthryl)phenyl]benzoxazole, 0.44 g (2.2 mmol) of 4-biphenylboronic acid, 0.47 g (4.4 mmol) of sodium carbonate, 10 mL of toluene, 3 mL of ethanol, and 3 mL of water were placed. The mixture was degassed by being stirred under reduced pressure, and the air in the flask was replaced with nitrogen. To the mixture, 29 mg (0.025 mmol) of tetrakis(triphenylphosphine)palladium(0) was added, and the mixture was stirred under nitrogen stream at 80° C. for 13 hours. After a certain period, the mixture was cooled to room temperature, and the precipitated solid was obtained by suction filtration and washed with water. A toluene solution of the obtained solid was subjected to suction filtration through Celite (produced by Wako Pure Chemical Industries, Ltd., Catalog No. 531-16855) and alumina, and the filtrate was condensed to give a solid. The solid was recrystallized with toluene/hexane, giving 0.52 g of the target white powder. Further, an aqueous layer of the filtrate which was obtained through suction filtration after stirring was extracted with toluene. The obtained extracted solution was washed with a saturated aqueous solution of sodium hydrogen carbonate and saturated saline, and the organic layer was dried with magnesium sulfate. The mixture was gravity filtered, and the filtrate was condensed to give a solid. A toluene solution of the solid was subjected to suction filtration through Celite (produced by Wako Pure Chemical Industries, Ltd., Catalog No. 531-16855) and alumina, and the filtrate was condensed to give a solid. The solid was recrystallized with toluene/hexane, giving 0.47 g of the target white powder. In this manner, a total of 0.99 g of the target white solid was obtained in a yield of 93%.

Then, 0.97 g of the obtained target substance was subjected to sublimation purification at 290° C. under argon stream (flow rate: 3.0 mL/min) and a pressure of 10 Pa for 15 hours; thus, 0.88 g of the target substance was recovered in a yield of 90%. This compound was measured by nuclear magnetic resonance (NMR) spectrometry and identified as 2-{4-[10-(biphenyl-4-yl)-9-anthryl]phenyl}benzoxazole (abbrev.: BPhABOx).

The $^1$H NMR data is shown below.

$^1$H NMR (300 MHz, CDCl$_3$): δ (ppm)=7.36-7.45 (m, 7H), 7.51-7.59 (m, 4H), 7.65-7.87 (m, 12H), 8.52 (d, J=8.1 Hz, 2H).

Figure 45A:
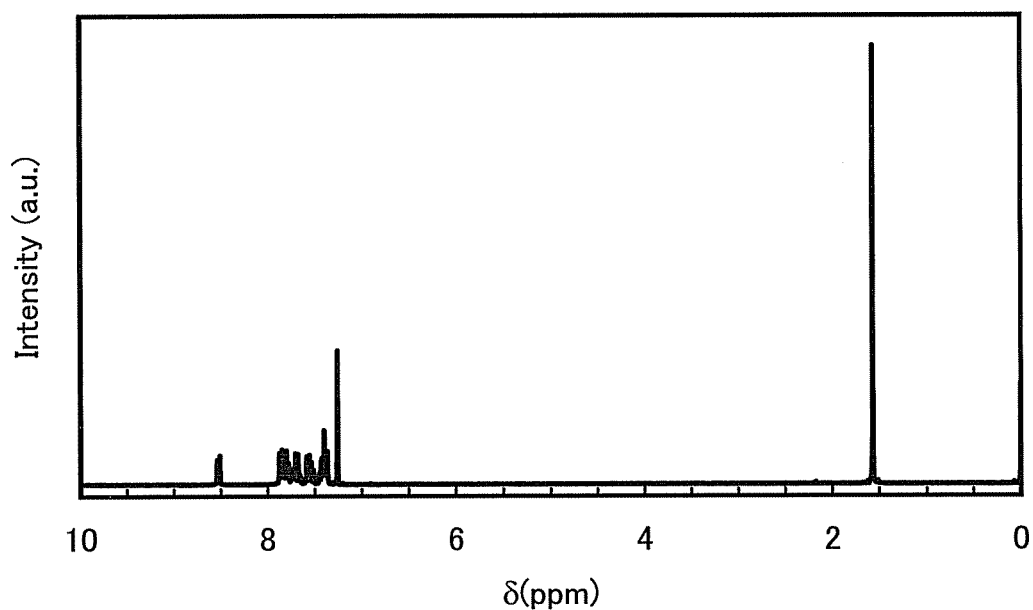
FIGS. 45A and 45B are each a $^1$H NMR chart of 2-{4-[10-(biphenyl-4-yl)-9-anthryl]phenyl}benzoxazole (abbrev.: BPhABOx)
Figure 45B:
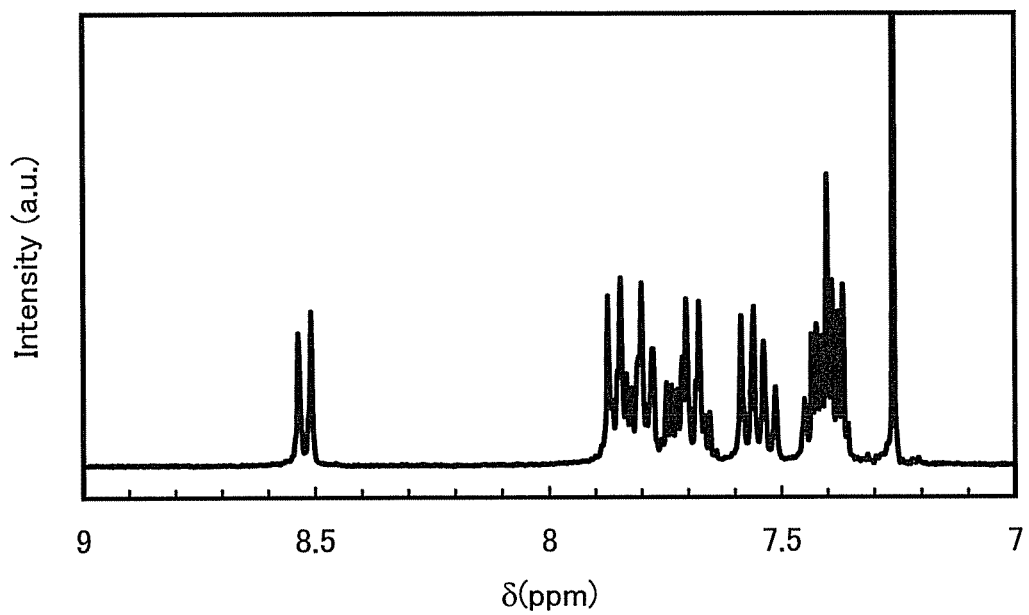
Figure 46:
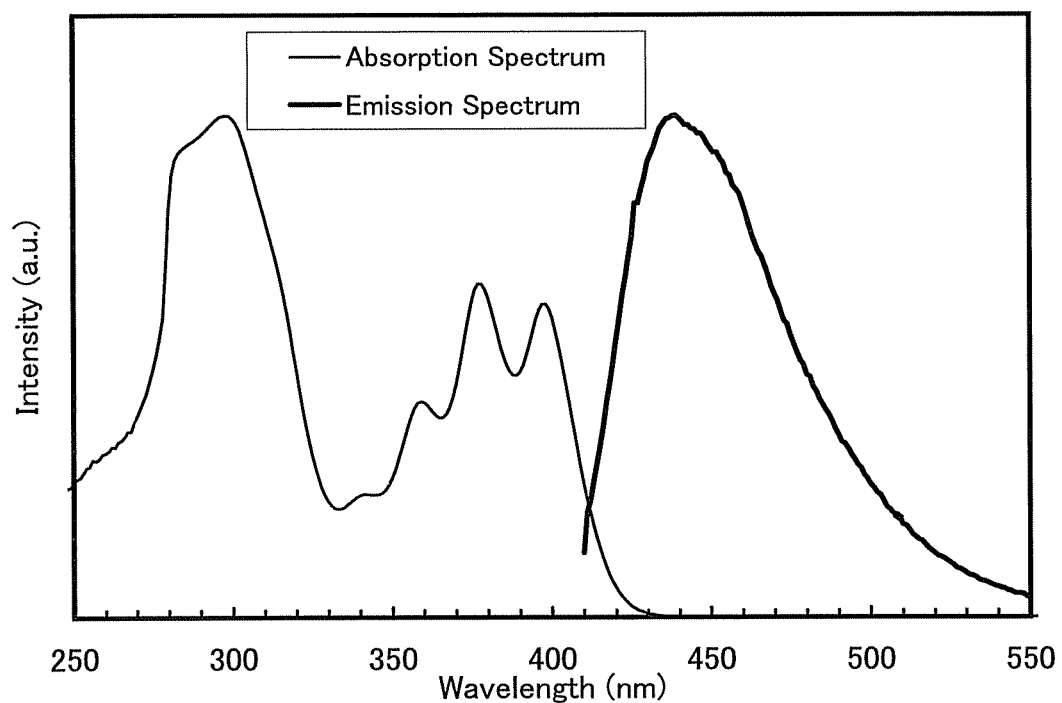
FIG. 46 shows an absorption spectrum and an emission spectrum of 2-{4-[10-(biphenyl-4-yl)-9-anthryl]phenyl}benzoxazole in a toluene solution (abbrev.: BPhABOx)

Further, the $^1$H NMR chart is shown in FIGS. 45A and 45B. Note that FIG. 45B is an enlarged chart showing the range from 7.0 ppm to 9.0 ppm in FIG. 45A. Further, FIG. 46 shows an absorption spectrum and an emission spectrum of BPhABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 46. In FIG. 46, the horizontal axis indicates wavelength (nm) and the vertical axis indicates intensity (arbitrary unit). In the case of the toluene solution, absorptions were observed at around 340 nm, 358 nm, 376 nm, and 397 nm. In addition, the maximum emission wavelength was 438 nm (excitation wavelength: 398 nm) in the case of the toluene solution.

Figure 47:
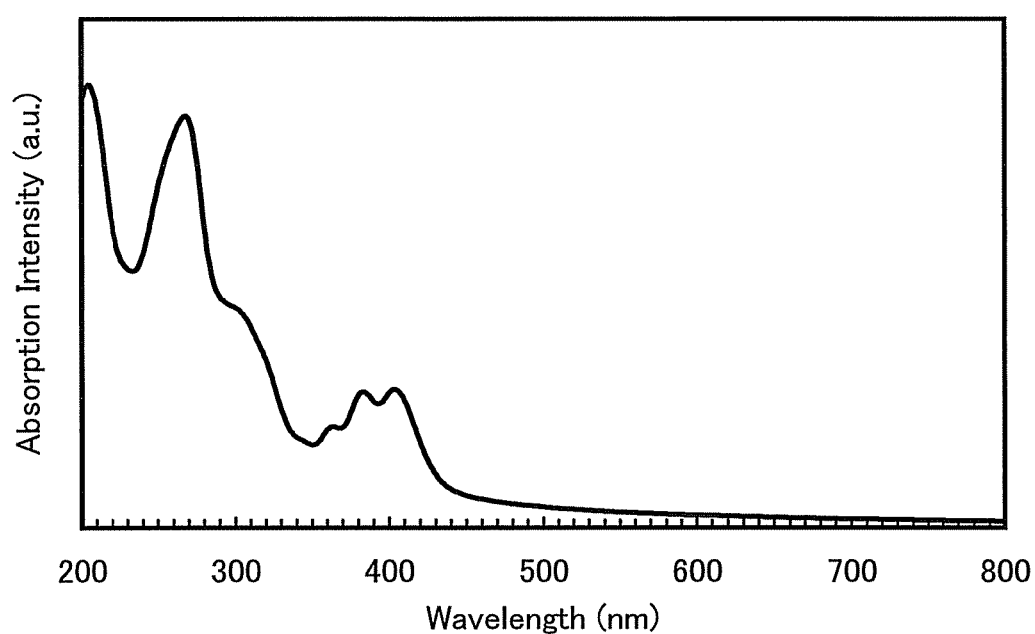
FIG. 47 shows an absorption spectrum of a thin film of 2-{4-[10-(biphenyl-4-yl)-9-anthryl]phenyl}benzoxazole (abbrev.: BPhABOx)
Figure 48:
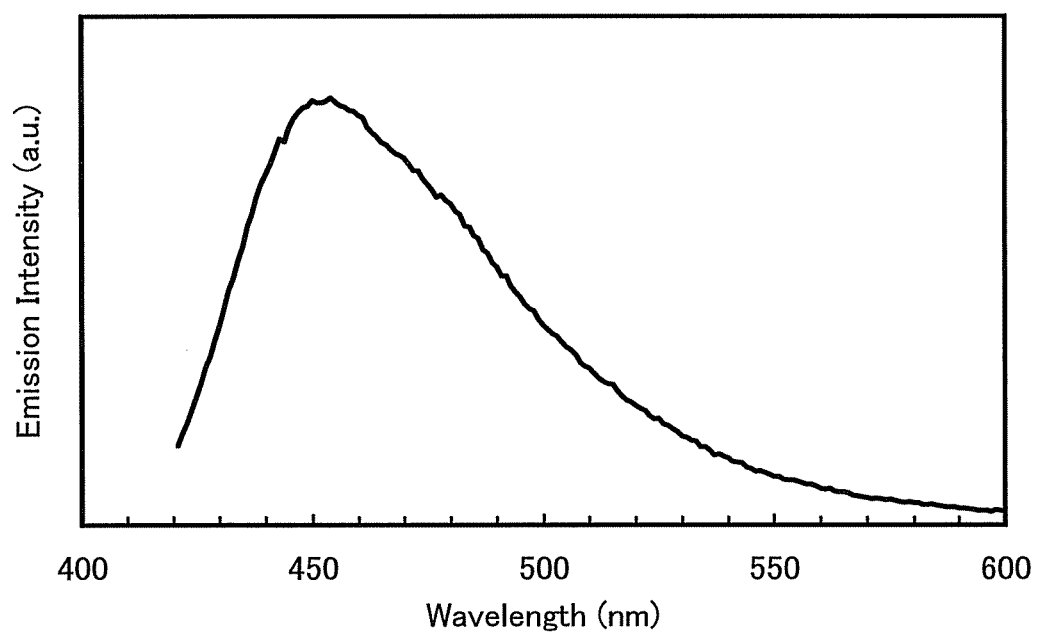
FIG. 48 shows an emission spectrum of a thin film of 2-{4-[10-(biphenyl-4-yl)-9-anthryl]phenyl}benzoxazole (abbrev.: BPhABOx)

FIG. 47 shows an absorption spectrum of a thin film of BPhABOx, and FIG. 48 shows an emission spectrum of a thin film of BPhABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 47. In FIG. 47, the horizontal axis indicates wavelength (nm) and the vertical axis indicates absorption intensity (arbitrary unit). In FIG. 48, the horizontal axis indicates wavelength (nm) and the vertical axis indicates emission intensity (arbitrary unit). In the case of the thin film, absorptions were observed at around 204 nm, 268 nm, 301 nm, 364 nm, 383 nm, and 404 nm. In addition, the maximum emission wavelength was 454 nm (excitation wavelength: 401 nm) in the case of the thin film.

In addition, the ionization potential of BPhABOx in the thin film state was 5.71 eV, which was measured by a photoelectron spectrometer (AC-2, manufactured by Riken Keiki Co., Ltd.) in air. As a result, the HOMO level was found to be −5.71 eV. Further, an absorption edge was obtained from a Tauc plot assuming direct transition with use of the data of the absorption spectrum of BPhABOx in the thin film state, and when the absorption edge was regarded as an optical energy gap, the energy gap was 2.90 eV A LUMO level of −2.81 eV was obtained from the obtained value of the energy gap and the HOMO level.

Further, oxidation-reduction characteristics of BPhABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, BPhABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristics of BPhABOx were measured as follows. The potential of the working electrode with respect to the reference electrode was changed from 0.00 V to 1.05 V, and then changed from 1.05 V to 0.00 V. This change in potential was regarded as one cycle, and measurement was carried out for 100 cycles. The reduction characteristics of BPhABOx were examined as follows. The potential of the working electrode with respect to the reference electrode was changed from −1.20 V to −2.30 V, and then changed from −2.30 V to −1.20 V. This change in potential was regarded as one cycle, and measurement was performed for 100 cycles. Further, the scanning speed of the CV measurement was set to be 0.1 V/s.

Figure 49:
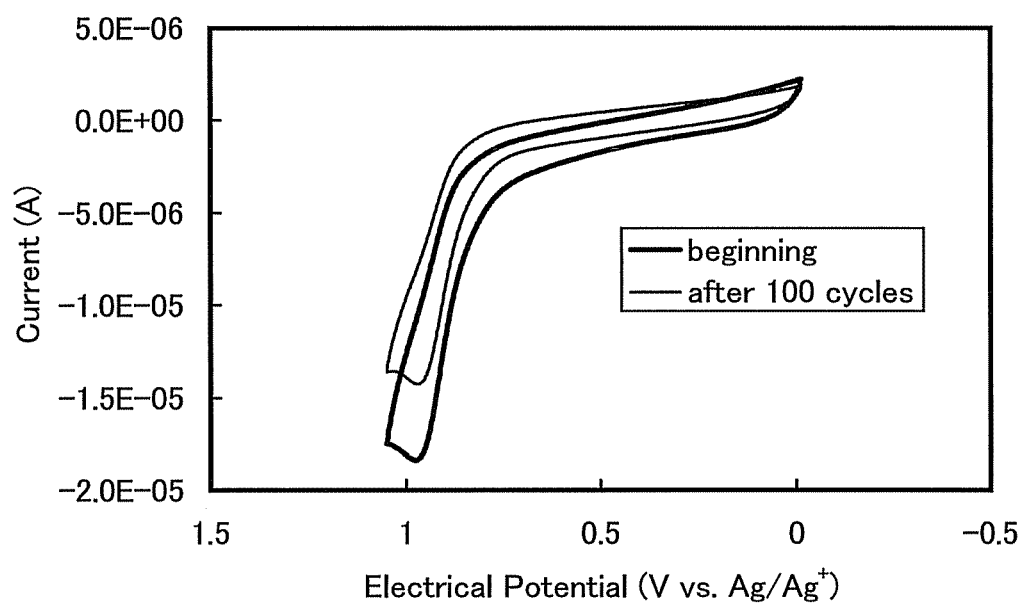
FIG. 49 shows CV measurement results of 2-{4-[10-(biphenyl-4-yl)-9-anthryl]phenyl}benzoxazole (abbrev.: BPhABOx)
Figure 50:
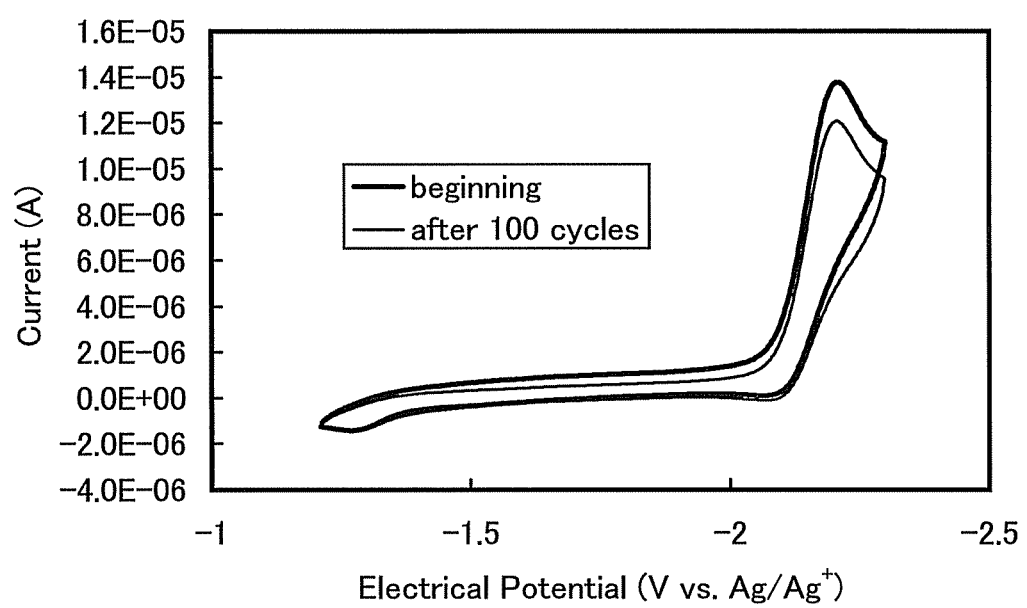
FIG. 50 shows CV measurement results of 2-{4-[10-(biphenyl-4-yl)-9-anthryl]phenyl}benzoxazole (abbrev.: BPhABOx)

FIG. 49 shows results of the CV measurement of BPhABOx on the oxidation side, and FIG. 50 shows results of the CV measurement of BPhABOx on the reduction side. In each of FIG. 49 and FIG. 50, the horizontal axis indicates a potential (V) of the working electrode with respect to the reference electrode, and the vertical axis indicates a current value (A) flowing between the working electrode and the auxiliary electrode. From FIG. 49, a current indicating oxidation was observed around 0.97 V (vs. Ag/Ag$^+$ electrode). In addition, from FIG. 50, a current indicating reduction was observed around −2.21 V (vs. Ag/Ag$^+$ electrode).

Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 7

In Example 7, a synthesis method of 2-(4-{10-[4-(1-naphthyl)phenyl]-9-anthryl}phenyl)benzoxazole (abbrev.: NPhABOx) represented by Structural Formula (131) will be described.

(131)

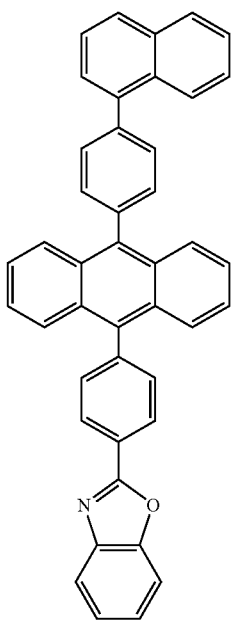

Step 1: Synthesis of 2-(4-{10-[4-(1-naphthyl)phenyl]-9-anthryl}phenyl)benzoxazole A synthesis scheme of 2-(4-{10-[4-(1-naphthyl)phenyl]-9-anthryl}phenyl)benzoxazole is shown in (F-1).

(F-1)

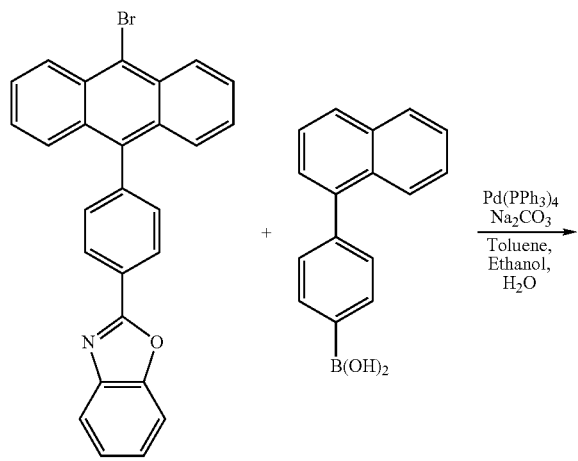

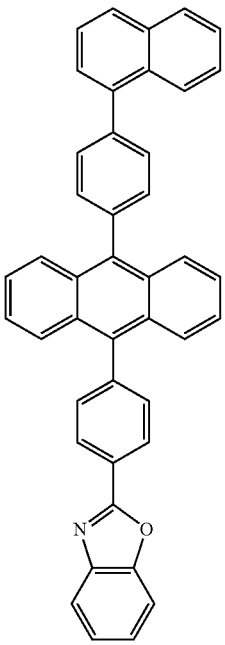

In a 50 mL three-neck flask, 0.97 g (2.2 mmol) of 2-[4-(10-bromo-9-anthryl)phenyl]benzoxazole, 0.57 g (2.3 mmol) of 4-(1-naphthyl)phenylboronic acid, 0.46 g (4.3 mmol) of sodium carbonate, 15 mL of toluene, 3 mL of ethanol, and 3 mL of water were placed. The mixture was degassed by being stirred under reduced pressure, and the air in the flask was replaced with nitrogen. To the mixture, 35 mg (0.030 mmol) of tetrakis(triphenylphosphine)palladium(0) was added, and the mixture was stirred under nitrogen stream at 100° C. for 18 hours. After a certain period, water was added to the mixture, and an aqueous layer was extracted with toluene. The obtained extracted solution and the organic layer were combined and washed with a saturated aqueous solution of sodium hydrogen carbonate and saturated saline, and the organic layer was dried with magnesium sulfate. The mixture was gravity filtered, and the obtained filtrate was condensed to give a solid. The solid was purified by silica gel column chromatograghy (toluene:hexane=2:1) and recrystallized with toluene/hexane, giving 1.2 g of the target white powder in a yield of 94%.

Then, 1.2 g of the target substance was subjected to sublimation purification at 385° C. under argon stream (flow rate: 3.0 mL/min) and a pressure of 10 Pa for 15 hours; thus, 1.1 g of the target substance was recovered in a yield of 91%. This compound was measured by nuclear magnetic resonance (NMR) spectrometry and identified as 2-(4-{10-[4-(1-naphthyl)phenyl]-9-anthryl}phenyl)benzoxazole (abbrev.: NPhABOx).

The $^1$H NMR data is shown below.

$^1$H NMR (300 MHz, CDCl$_3$): δ (ppm)=7.38-7.47 (m, 6H), 7.55-7.78 (m, 13H), 7.84-7.99 (m, 5H), 8.17-8.20 (m, 1H), 8.53 (d, J=8.1 Hz, 2H).

Figure 51A:
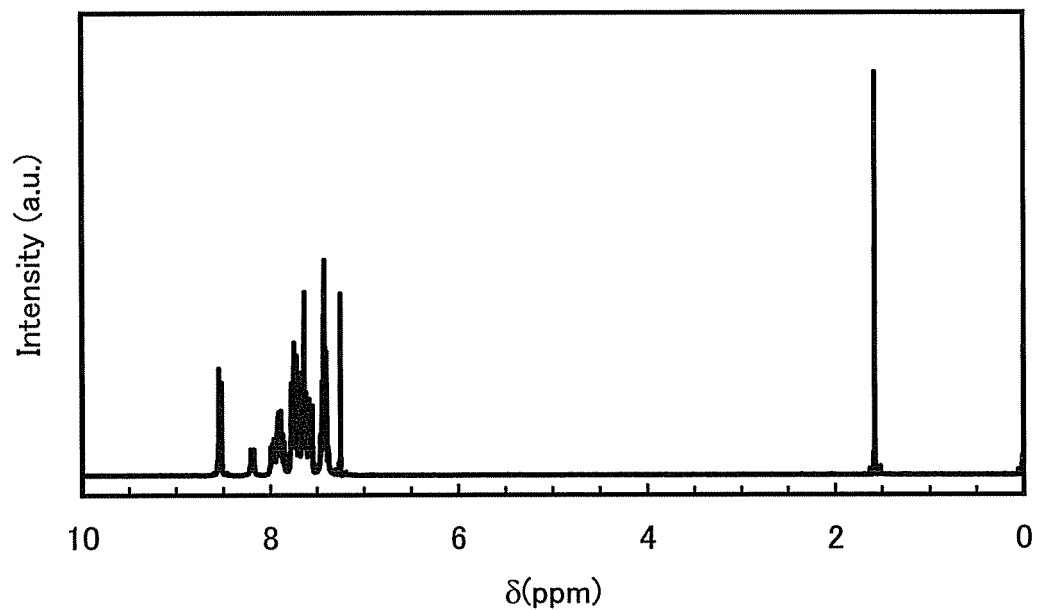
FIGS. 51A and 51B are each a $^1$H NMR chart of 2-(4-{10-[4-(1-naphthyl)phenyl]-9-anthryl}phenyl)benzoxazole (abbrev.: NPhABOx)
Figure 51B:
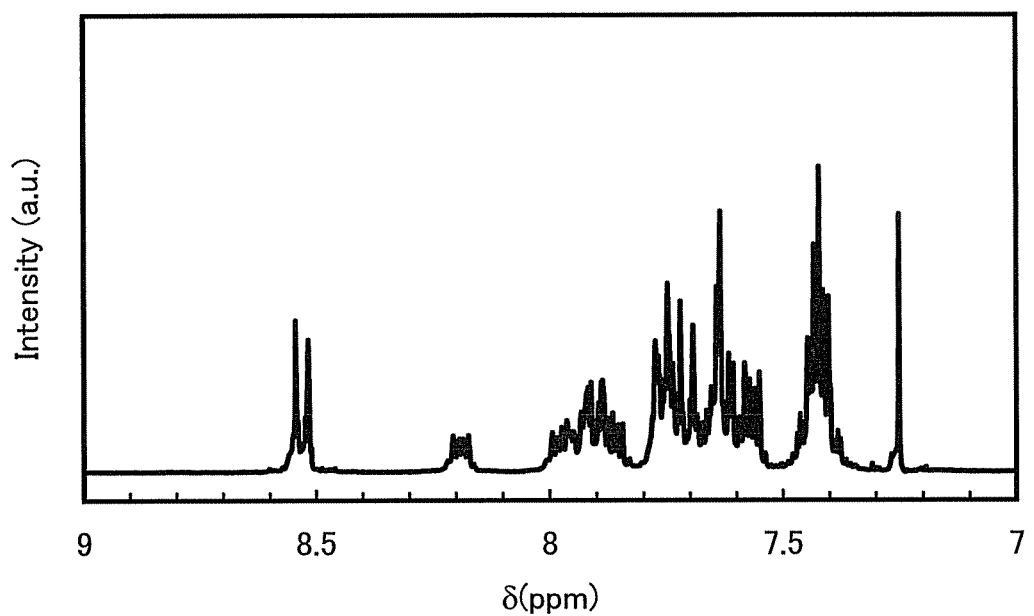

Further, the $^1$H NMR chart is shown in FIGS. 51A and 51B. Note that FIG. 51B is an enlarged chart showing the range from 7.0 ppm to 9.0 ppm in FIG. 51A.

Figure 52:
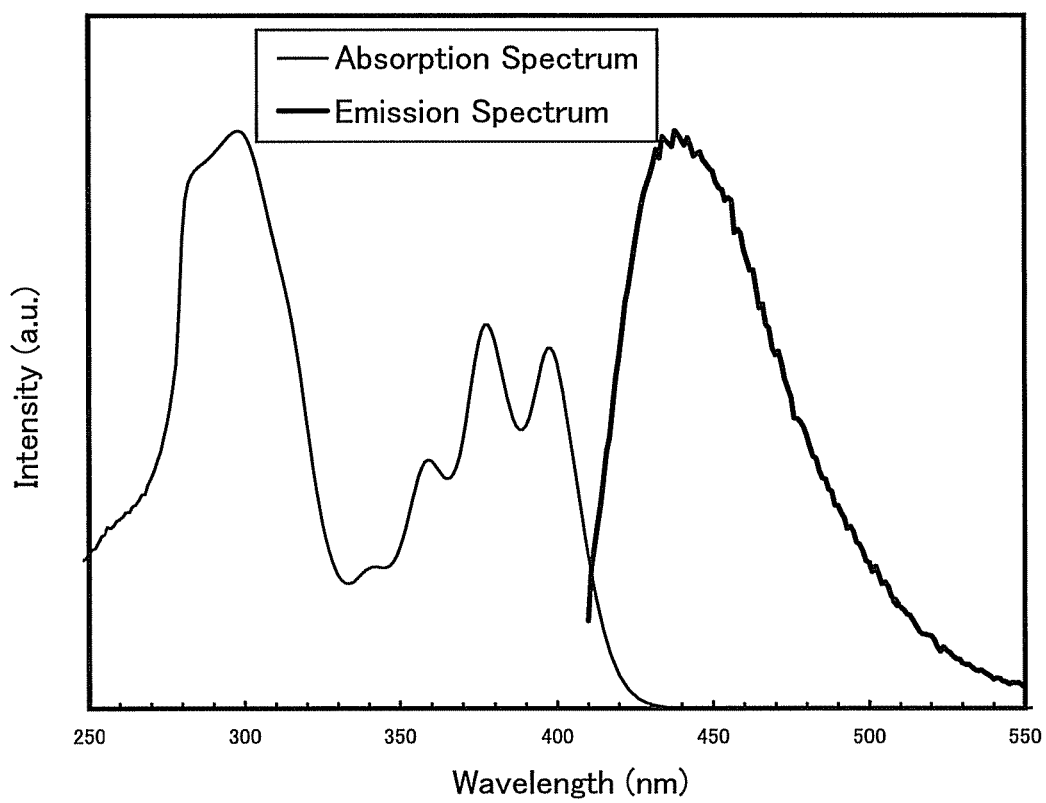
FIG. 52 shows an absorption spectrum and an emission spectrum of 2-(4-{10-[4-(1-naphthyl)phenyl]-9-anthryl}phenyl)benzoxazole in a toluene solution (abbrev.: NPhABOx)

Further, FIG. 52 shows an absorption spectrum and an emission spectrum of NPhABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 52. In FIG. 52, the horizontal axis indicates wavelength (nm) and the vertical axis indicates intensity (arbitrary unit). In the case of the toluene solution, absorptions were observed at around 341 nm, 359 nm, 377 nm, and 398 nm. In addition, the maximum emission wavelength was 438 nm (excitation wavelength: 397 nm) in the case of the toluene solution.

Figure 53:
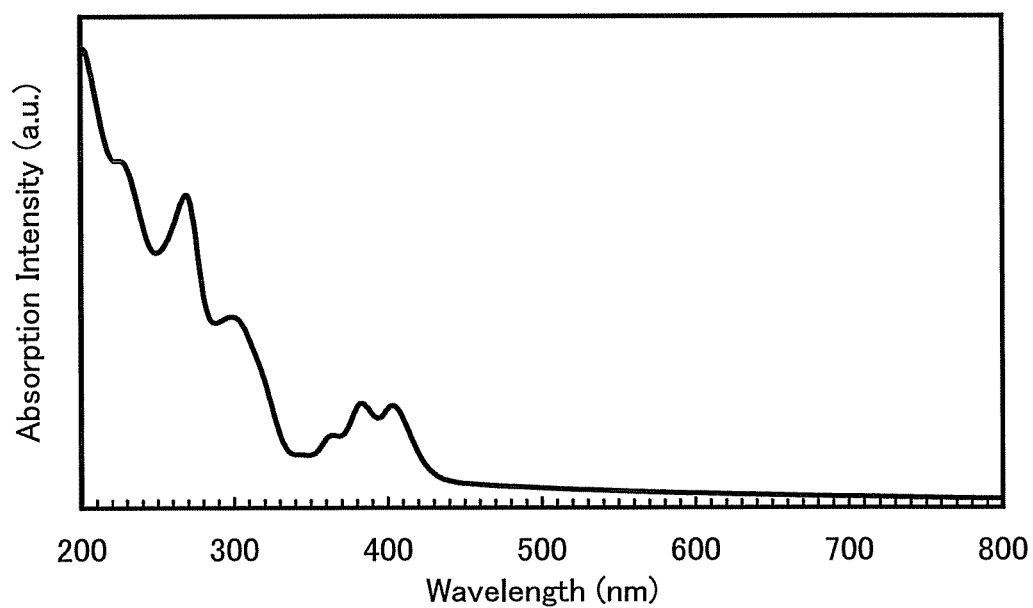
FIG. 53 shows an absorption spectrum of a thin film of 2-(4-{10-[4-(1-naphthyl)phenyl]-9-anthryl}phenyl)benzoxazole (abbrev.: NPhABOx)
Figure 54:
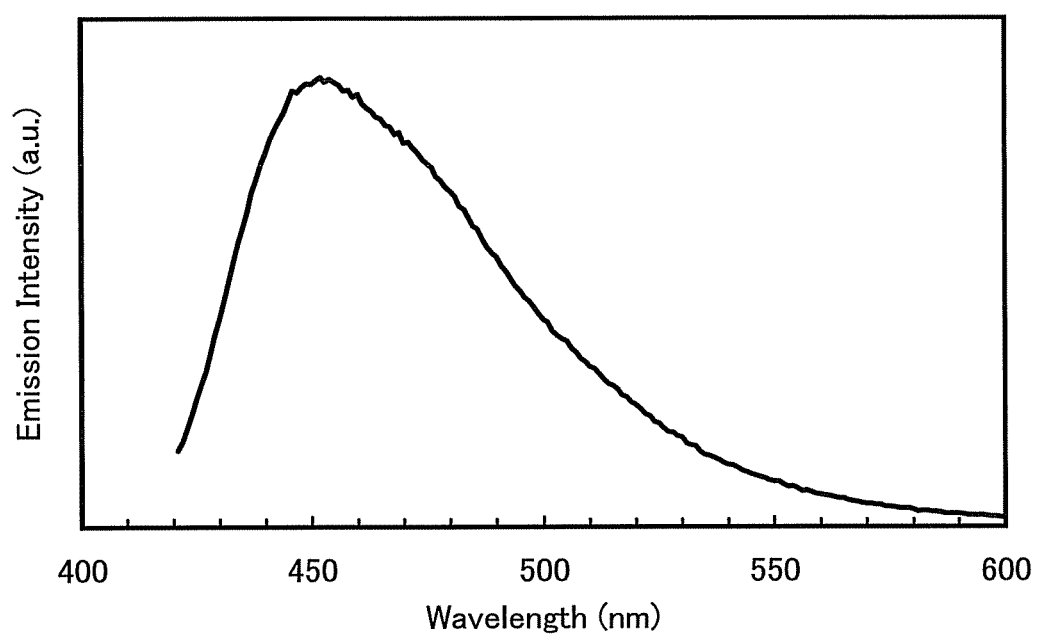
FIG. 54 shows an emission spectrum of a thin film of 2-(4-{10-[4-(1-naphthyl)phenyl]-9-anthryl}phenyl)benzoxazole (abbrev.: NPhABOx)

FIG. 53 shows an absorption spectrum of a thin film of NPhABOx, and FIG. 54 shows an emission spectrum of a thin film of NPhABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 53. In FIG. 53, the horizontal axis indicates wavelength (nm) and the vertical axis indicates absorption intensity (arbitrary unit). In FIG. 54, the horizontal axis indicates wavelength (nm) and the vertical axis indicates emission intensity (arbitrary unit). In the case of the thin film, absorptions were observed at around 225 nm, 269 nm, 299 nm, 364 nm, 383 nm, and 403 nm. In addition, the maximum emission wavelength was 452 nm (excitation wavelength: 404 nm) in the case of the thin film.

In addition, the ionization potential of NPhABOx in the thin film state was 5.69 eV, which was measured by a photoelectron spectrometer (AC-2, manufactured by Riken Keiki Co., Ltd.) in air. As a result, the HOMO level was found to be −5.69 eV. Further, an absorption edge was obtained from a Tauc plot assuming direct transition with use of the data of the absorption spectrum of NPhABOx in the thin film state, and when the absorption edge was regarded as an optical energy gap, the energy gap was 2.92 eV A LUMO level of −2.77 eV was obtained from the obtained value of the energy gap and the HOMO level.

Further, oxidation-reduction characteristics of NPhABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, NPhABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristics of BPhABOx were measured as follows. The potential of the working electrode with respect to the reference electrode was changed from −0.08 V to 1.07 V, and then changed from 1.07 V to −0.08 V. This change in potential was regarded as one cycle, and measurement was carried out for 100 cycles. The reduction characteristics of BPhABOx were examined as follows. The potential of the working electrode with respect to the reference electrode was changed from −1.37 V to −2.30 V, and then changed from −2.30 V to −1.37 V. This change in potential was regarded as one cycle, and measurement was performed for 100 cycles. Further, the scanning speed of the CV measurement was set to be 0.1 V/s.

Figure 55:
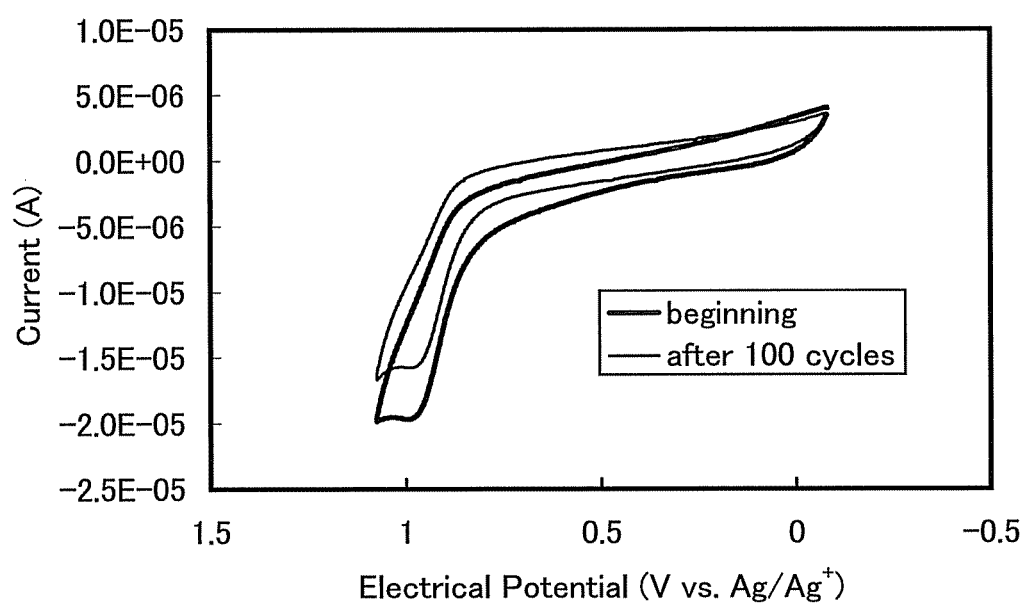
FIG. 55 shows CV measurement results of 2-(4-{10-[4-(1-naphthyl)phenyl]-9-anthryl}phenyl)benzoxazole (abbrev.: NPhABOx)
Figure 56:
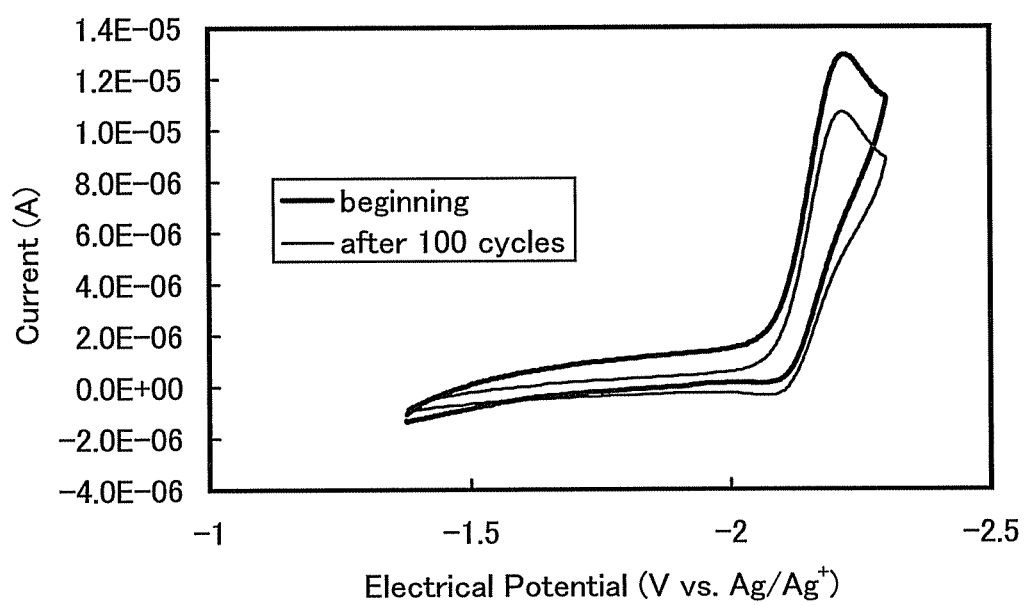
FIG. 56 shows CV measurement results of 2-(4-{10-[4-(1-naphthyl)phenyl]-9-anthryl}phenyl)benzoxazole (abbrev.: NPhABOx)

FIG. 55 shows results of the CV measurement of NPhABOx on the oxidation side, and FIG. 56 shows results of the CV measurement of NPhABOx on the reduction side. In each of FIG. 55 and FIG. 56, the horizontal axis indicates a potential (V) of the working electrode with respect to the reference electrode, and the vertical axis indicates a current value (A) flowing between the working electrode and the auxiliary electrode. From FIG. 55, a current indicating oxidation was observed around 0.99 V (vs. Ag/Ag$^+$ electrode). In addition, from FIG. 56, a current indicating reduction was observed around −2.22 V (vs. Ag/Ag$^+$ electrode).

Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 8

In Example 8, a synthesis method of 2-{4-[10-(2-naphthyl)-9-anthryl]phenyl}benzoxazole (abbrev.: 2NABOx) represented by Structural Formula (130) will be described.

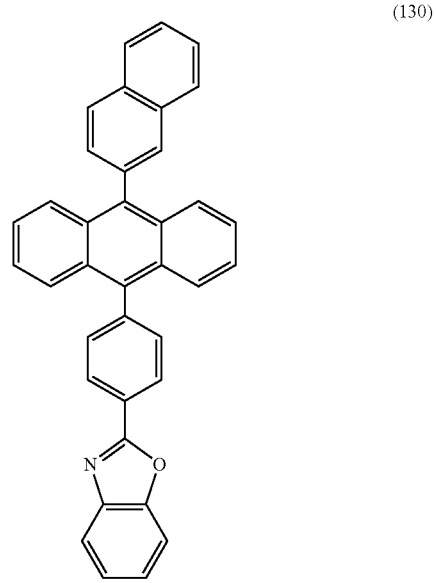 [SMILES: c1ccc2cc(-c3c4ccccc4c(-c4ccc(-c5nc6ccccc6o5)cc4)c4ccccc34)ccc2c1]

(130)

Step 1: Synthesis of 2-{4-[10-(2-naphthyl)-9-anthryl]phenyl}benzoxazole

A synthesis scheme of 2-{4-[10-(2-naphthyl)-9-anthryl]phenyl}benzoxazole is shown in (G-1).

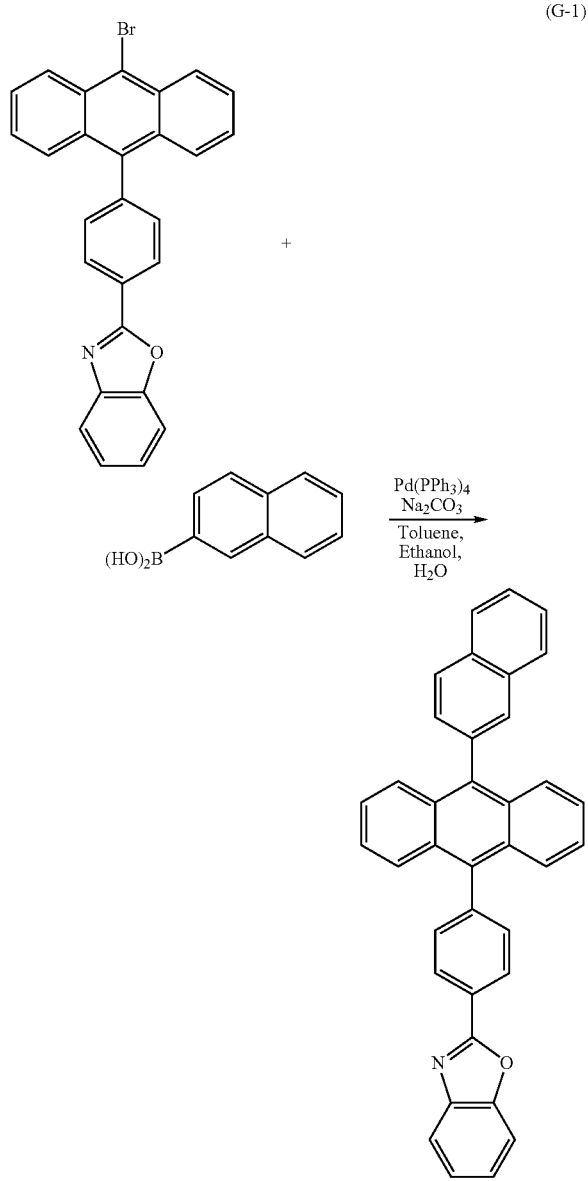

In a 50 mL three-neck flask, 0.90 g (2.0 mmol) of 2-[4-(10-bromo-9-anthryl)phenyl]benzoxazole, 0.37 g (2.2 mmol) of 2-naphthaleneboronic acid, 0.45 g (4.2 mmol) of sodium carbonate, 10 mL of toluene, 3 mL of ethanol, and 2 mL of water were placed. The mixture was degassed by being stirred under reduced pressure, and the air in the flask was replaced with nitrogen. To the mixture, 31 mg (0.027 mmol) of tetrakis(triphenylphosphine)palladium(0) was added, and the mixture was stirred under nitrogen stream at 80° C. for 7 hours. After a certain period, water was added to the mixture, and an aqueous layer was extracted with toluene. The obtained extracted solution and the organic layer were combined and washed with a saturated aqueous solution of sodium hydrogen carbonate and saturated saline, and the organic layer was dried with magnesium sulfate. The mixture was gravity filtered, and the obtained filtrate was condensed to give a solid. The solid was purified by silica gel column chromatograghy (toluene:hexane=2:1) and recrystallized with toluene/hexane, giving 0.92 g of the target yellow powder in a yield of 92%.

Then, 0.91 g of the target substance was subjected to sublimation purification at 255° C. under argon stream (flow rate: 3.0 mL/min) and a pressure of 10 Pa for 18 hours; thus, 0.81 g of the target substance was recovered in a yield of 89%. This compound was measured by nuclear magnetic resonance (NMR) spectrometry and identified as 2-{4-[10-(2-naphthyl)-9-anthryl]phenyl}benzoxazole (abbrev.: 2NABOx).

The $^1$H NMR data is shown below.

$^1$H NMR (300 MHz, CDCl$_3$): δ (ppm)=7.30-7.44 (m, 6H), 7.57-7.78 (m, 10H), 7.84-8.04 (m, 4H), 8.08 (d, J=8.4 Hz, 1H), 8.52 (d, J=8.4 Hz, 2H).

Figure 57A:
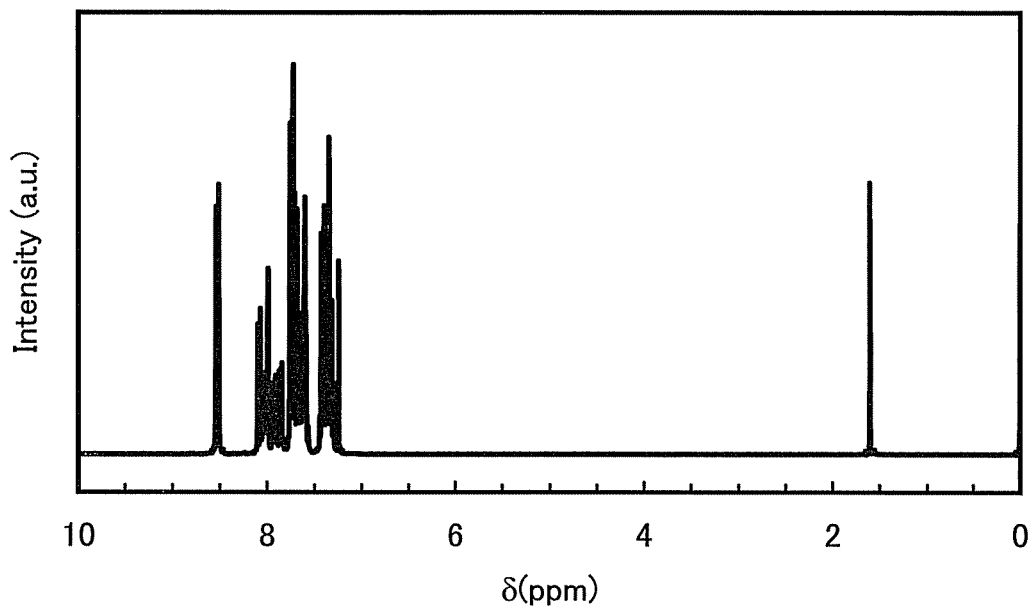
FIGS. 57A and 57B are each a $^1$H NMR chart of 2-{4-[10-(2-naphthyl)-9-anthryl]phenyl}benzoxazole (abbrev.: 2NABOx)
Figure 57B:
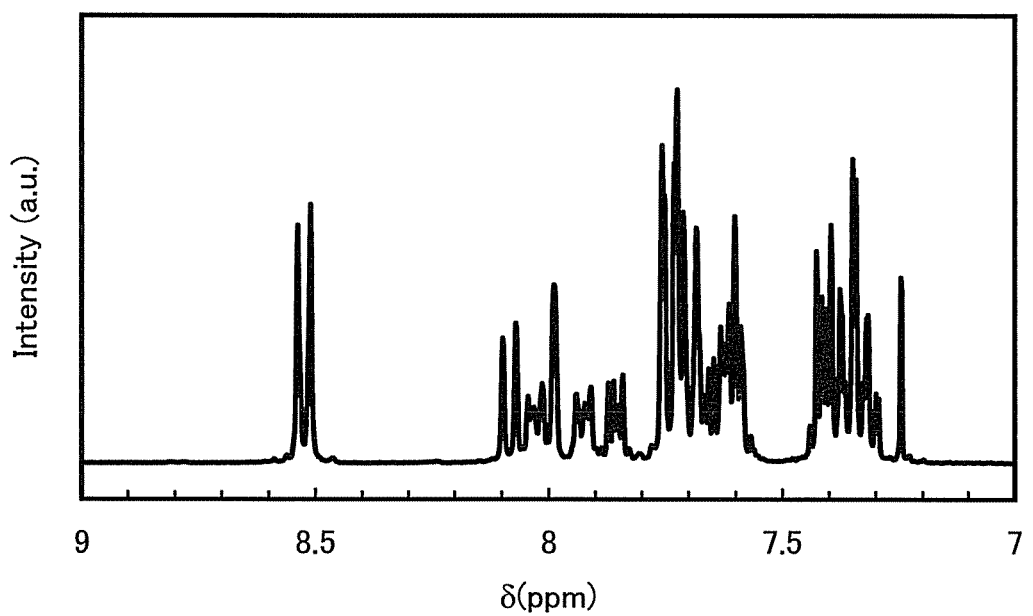

Further, the $^1$H NMR chart is shown in FIGS. 57A and 57B. Note that FIG. 57B is an enlarged chart showing the range from 7.0 ppm to 9.0 ppm in FIG. 57A.

Figure 58:
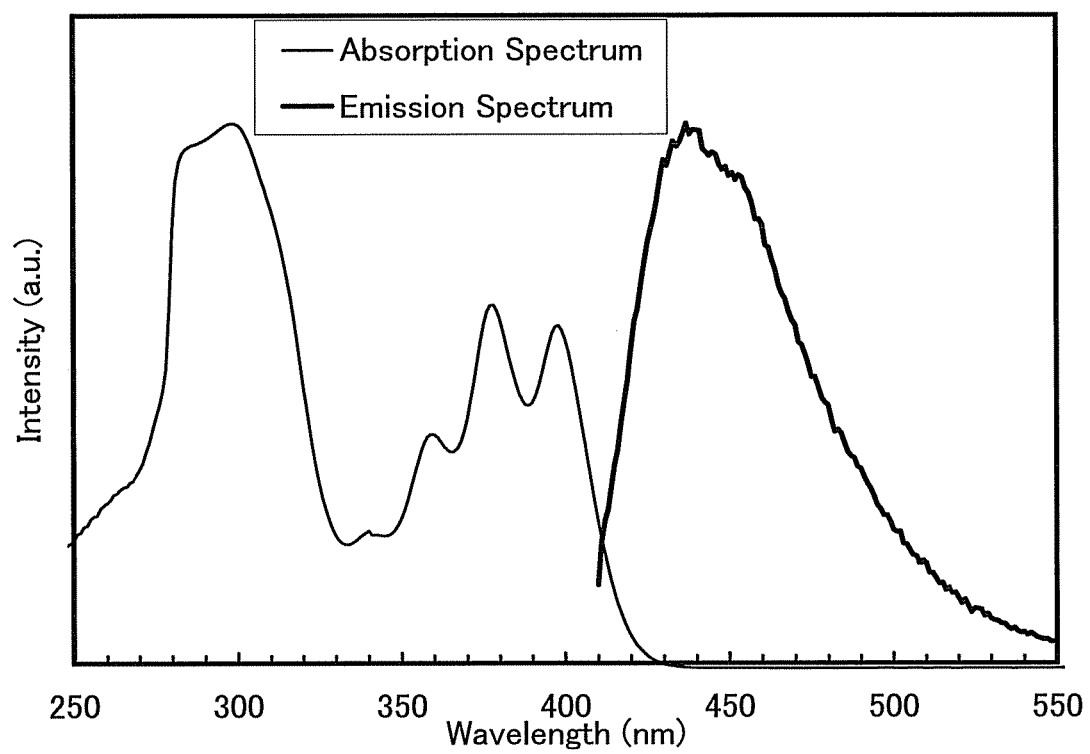
FIG. 58 shows an absorption spectrum and an emission spectrum of 2-{4-[10-(2-naphthyl)-9-anthryl]phenyl}benzoxazole in a toluene solution (abbrev.: 2NABOx)

Further, FIG. 58 shows an absorption spectrum and an emission spectrum of 2NABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 58. In FIG. 58, the horizontal axis indicates wavelength (nm) and the vertical axis indicates intensity (arbitrary unit). In the case of the toluene solution, absorptions were observed at around 340 nm, 359 nm, 378 nm, and 398 nm. In addition, the maximum emission wavelength was 437 nm (excitation wavelength: 398 nm) in the case of the toluene solution.

Figure 59:
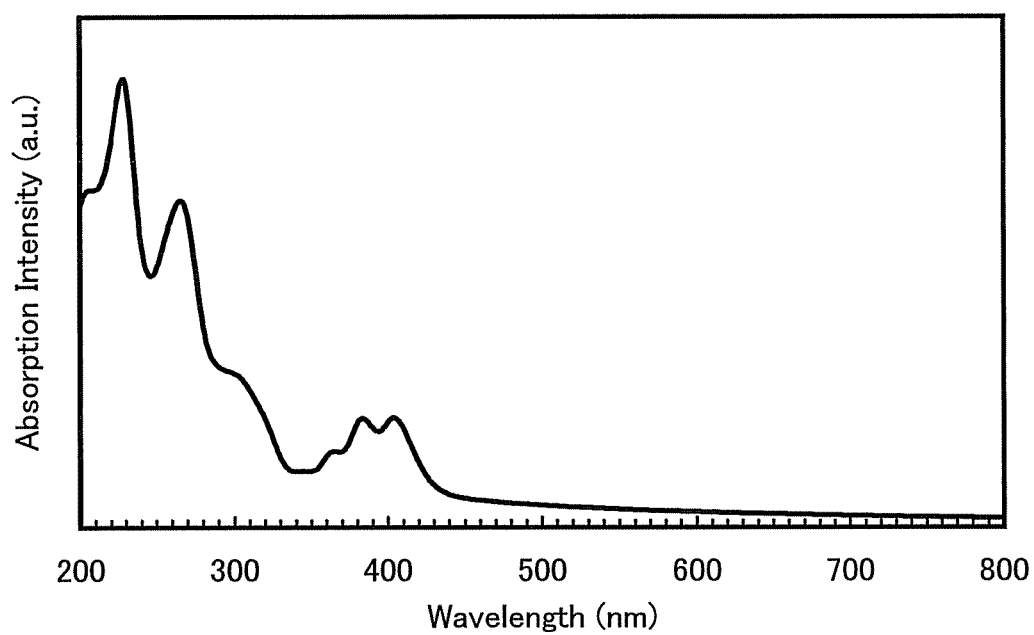
FIG. 59 shows an absorption spectrum of a thin film of 2-{4-[10-(2-naphthyl)-9-anthryl]phenyl}benzoxazole (abbrev.: 2NABOx)
Figure 60:
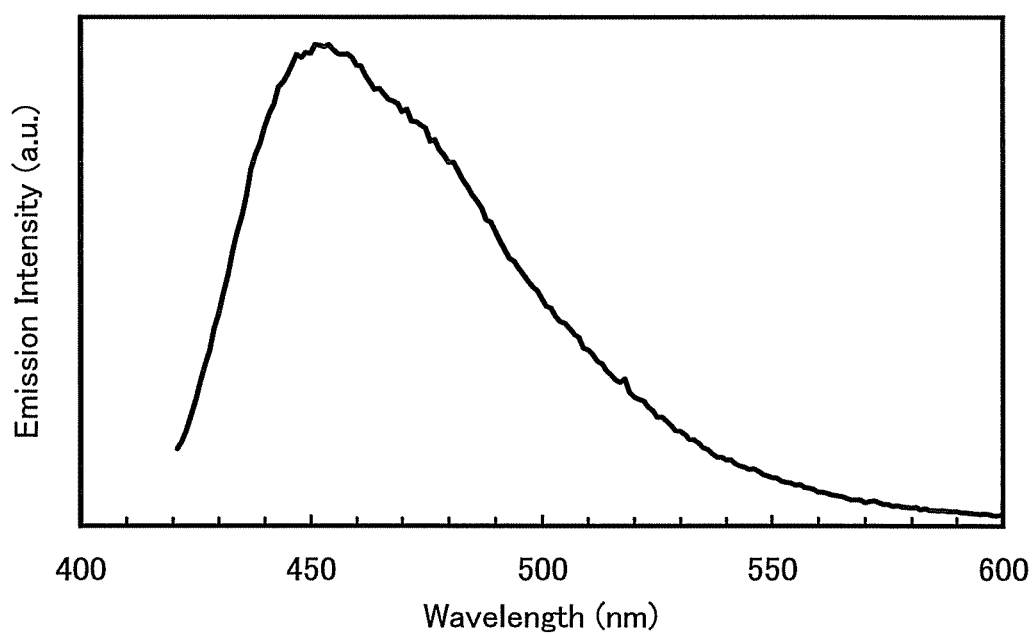
FIG. 60 shows an emission spectrum of a thin film of 2-{4-[10-(2-naphthyl)-9-anthryl]phenyl}benzoxazole (abbrev.: 2NABOx)

FIG. 59 shows an absorption spectrum of a thin film of 2NABOx, and FIG. 60 shows an emission spectrum of a thin film of 2NABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 59. In FIG. 59, the horizontal axis indicates wavelength (nm) and the vertical axis indicates absorption intensity (arbitrary unit). In FIG. 60, the horizontal axis indicates wavelength (nm) and the vertical axis indicates emission intensity (arbitrary unit). In the case of the thin film, absorptions were observed at around 228 nm, 266 nm, 300 nm, 365 nm, 383 nm, and 404 nm. In addition, the maximum emission wavelength was 453 nm (excitation wavelength: 405 nm) in the case of the thin film.

In addition, the ionization potential of 2NABOx in the thin film state was 5.82 eV, which was measured by a photoelectron spectrometer (AC-2, manufactured by Riken Keiki Co., Ltd.) in air. As a result, the HOMO level was found to be −5.82 eV. Further, an absorption edge was obtained from a Tauc plot assuming direct transition with use of the data of the absorption spectrum of 2NABOx in the thin film state, and when the absorption edge was regarded as an optical energy gap, the energy gap was 2.91 eV. A LUMO level of −2.91 eV was obtained from the obtained value of the energy gap and the HOMO level.

Further, oxidation-reduction characteristics of 2NABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, 2NABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristics of 2NABOx were measured as follows. The potential of the working electrode with respect to the reference electrode was changed from 0.23 V to 1.05 V, and then changed from 1.05 V to 0.23 V. This change in potential was regarded as one cycle, and measurement was carried out for 100 cycles. The reduction characteristics of 2NABOx were examined as follows. The potential of the working electrode with respect to the reference electrode was changed from −1.12 V to −2.45 V, and then changed from −2.45 V to −1.12 V. This change in potential was regarded as one cycle, and measurement was performed for 100 cycles. Further, the scanning speed of the CV measurement was set to be 0.1 V/s.

Figure 61:
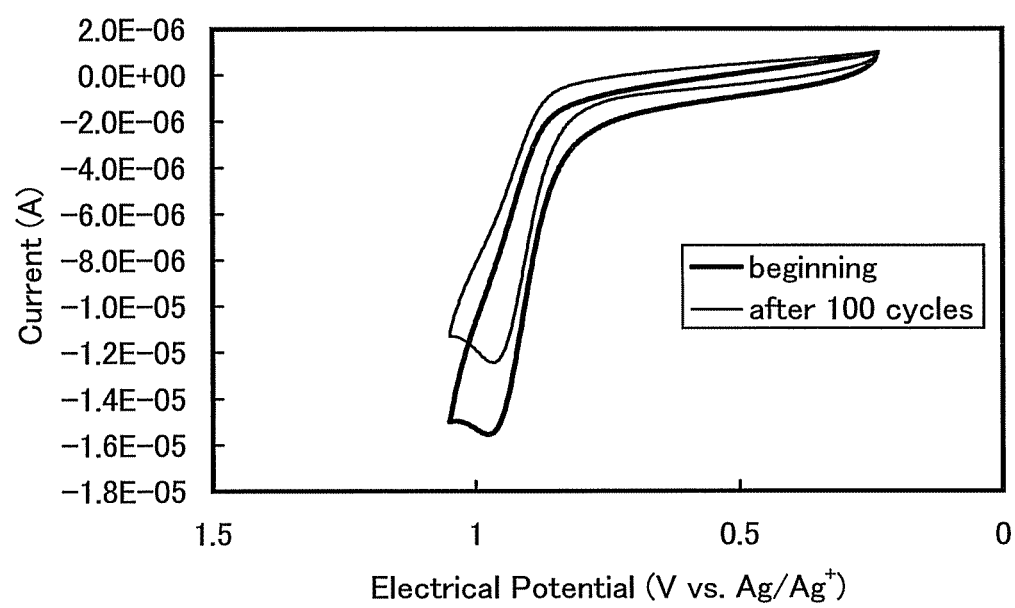
FIG. 61 shows CV measurement results of 2-{4-[10-(2-naphthyl)-9-anthryl]phenyl}benzoxazole (abbrev.: 2NABOx)
Figure 62:
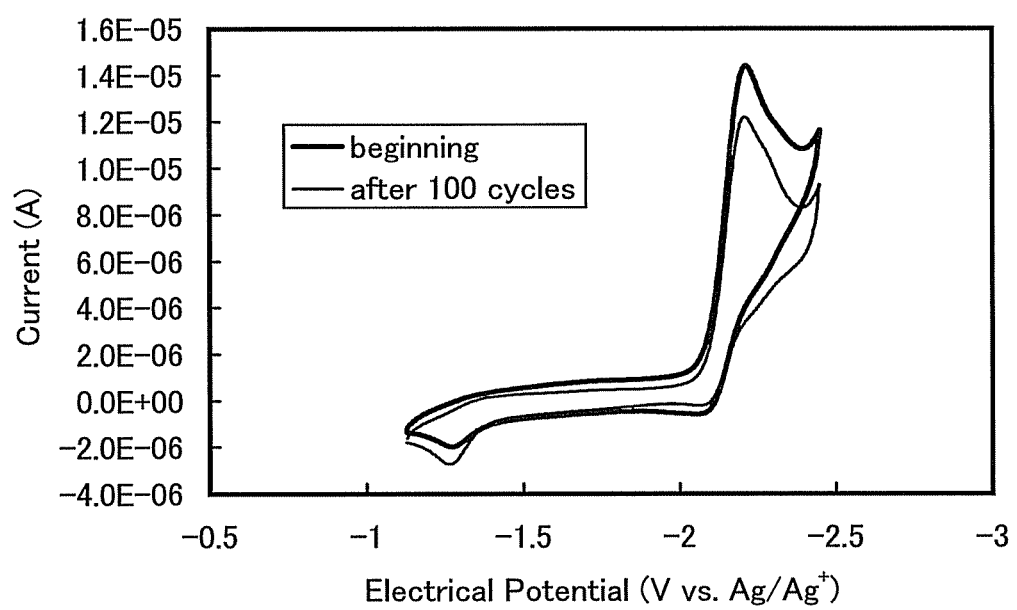
FIG. 62 shows CV measurement results of 2-{4-[10-(2-naphthyl)-9-anthryl]phenyl}benzoxazole (abbrev.: 2NABOx)

FIG. 61 shows results of the CV measurement of 2NABOx on the oxidation side, and FIG. 62 shows results of the CV measurement of 2NABOx on the reduction side. In each of FIG. 61 and FIG. 62, the horizontal axis indicates a potential (V) of the working electrode with respect to the reference electrode, and the vertical axis indicates a current value (A) flowing between the working electrode and the auxiliary electrode. From FIG. 61, a current indicating oxidation was observed around 0.98 V (vs. Ag/Ag$^+$ electrode). In addition, from FIG. 62, a current indicating reduction was observed around −2.21 V (vs. Ag/Ag$^+$ electrode).

Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 9

In Example 9, a synthesis method of 3-{10-[4-(benzoxazol-2-yl)phenyl]-9-anthryl}quinoline (abbrev.: 3 QABOx) represented by Structural Formula (158) will be described.

(158)

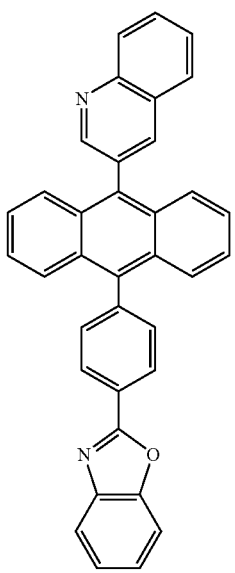

Step 1: Synthesis of 10-[4-(benzoxazol-2-yl)phenyl]-9-anthraceneboronic acid

A synthesis scheme of 10-[4-(benzoxazol-2-yl)phenyl]-9-anthraceneboronic acid is shown in (H-1).

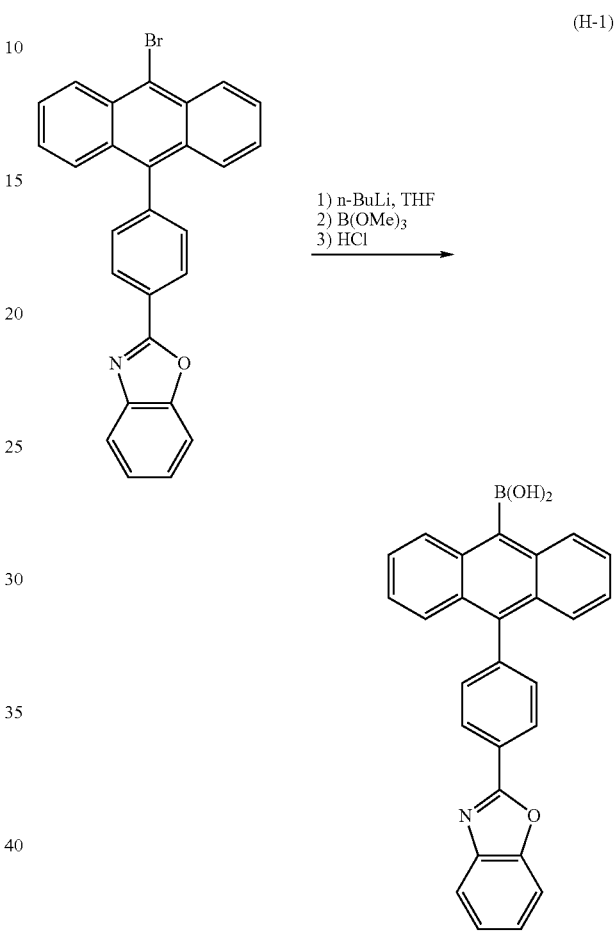

(H-1)

In a 300 mL three-neck flask, 5.2 g (11 mmol) of 2-[4-(10-bromo-9-anthryl)phenyl]benzoxazole was placed, and the air in the flask was replaced with nitrogen. Then, 130 mL of tetrahydrofuran was added in the flask, and the mixture was cooled to −78° C. under nitrogen stream. After cooling, 7.8 mL (13 mmol) of 1.7 M n-butyllithium was dripped into the solution, and the mixture was stirred at the same temperature for 2 hours. After a certain period, 1.7 mL (15 mmol) of trimethyl borate was added to the solution, and the temperature was raised to room temperature, and then, the solution was stirred for 20 hours. After a certain period, 100 mL of 1.0 M hydrochloric acid was added to the solution, and stirred for 1 hour. An aqueous layer of the obtained mixture was extracted with ethyl acetate. The obtained extracted solution and the organic layer were combined and washed with saturated saline, and the organic layer was dried with magnesium sulfate. The obtained mixture was gravity filtered, and the filtrate was condensed to give a solid. The solid was recrystallized with toluene, so that 2.0 g of target pale yellow powder was obtained in a yield of 41%.

[Step 2: Synthesis of 3-{10-[4-(benzoxazol-2-yl)phenyl]-9-anthryl}quinoline]

A synthesis scheme of 3-{10-[4-(benzoxazol-2-yl)phenyl]-9-anthryl}quinoline is shown in (H-2).

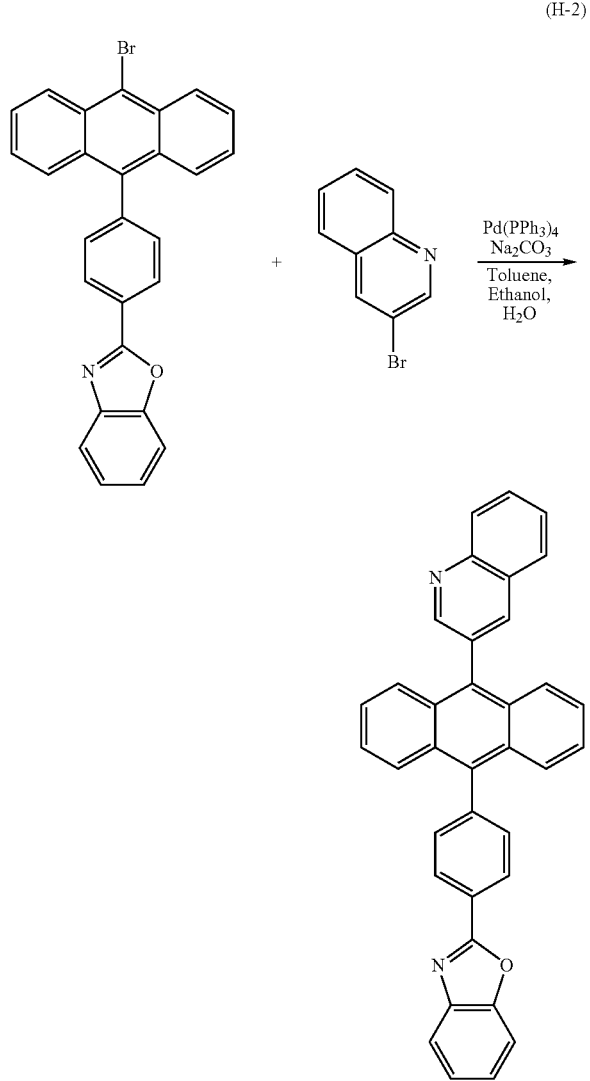

(H-2)

In a 100 mL three-neck flask, 1.0 g (2.4 mmol) of 10-[4-(benzoxazol-2-yl)phenyl]-9-anthraceneboronic acid, 0.61 g (2.9 mmol) of 3-bromoquinoline, 0.70 g (6.6 mmol) of sodium carbonate, 20 mL of toluene, 5 mL of ethanol, and 3 mL of water were placed. The mixture was degassed by being stirred under reduced pressure, and the air in the flask was replaced with nitrogen. To the mixture, 59 mg (0.051 mmol) of tetrakis(triphenylphosphine)palladium(0) was added, and the mixture was stirred under nitrogen stream at 100° C. for 5 hours. After a certain period, water was added to the mixture, and an aqueous layer was extracted with toluene. The obtained extracted solution and the organic layer were combined and washed with a saturated aqueous solution of sodium hydrogen carbonate and saturated saline, and the organic layer was dried with magnesium sulfate. The mixture was gravity filtered, and the obtained filtrate was condensed to give a solid. The solid was purified by silica gel column chromatograghy (hexane:ethyl acetate=5:1) and recrystal-lized with toluene/hexane, giving 0.75 g of the target pale yellow powder in a yield of 63%.

Then, 0.75 g of the target substance was subjected to sublimation purification at 240° C. under argon stream (flow rate: 3.0 mL/min) and a pressure of 10 Pa for 15 hours; thus, 0.56 g of the target substance was recovered in a yield of 74%. This compound was measured by nuclear magnetic resonance (NMR) spectrometry and identified as 3-{10-[4-(benzoxazol-2-yl)phenyl]-9-anthryl}quinoline (abbrev.: 3QABOx).

The $^1$H NMR data is shown below.

$^1$H NMR (300 MHz, CDCl$_3$): δ (ppm)=7.35-7.43 (m, 6H), 7.64-7.90 (m, 10H), 7.96 (dd, J=7.8 Hz, 1.5 Hz, 1H), 8.31-8.35 (m, 2H), 8.54 (d, J=8.7 Hz, 2H), 9.05 (d, J=1.8 Hz, 1H).

Figure 63A:
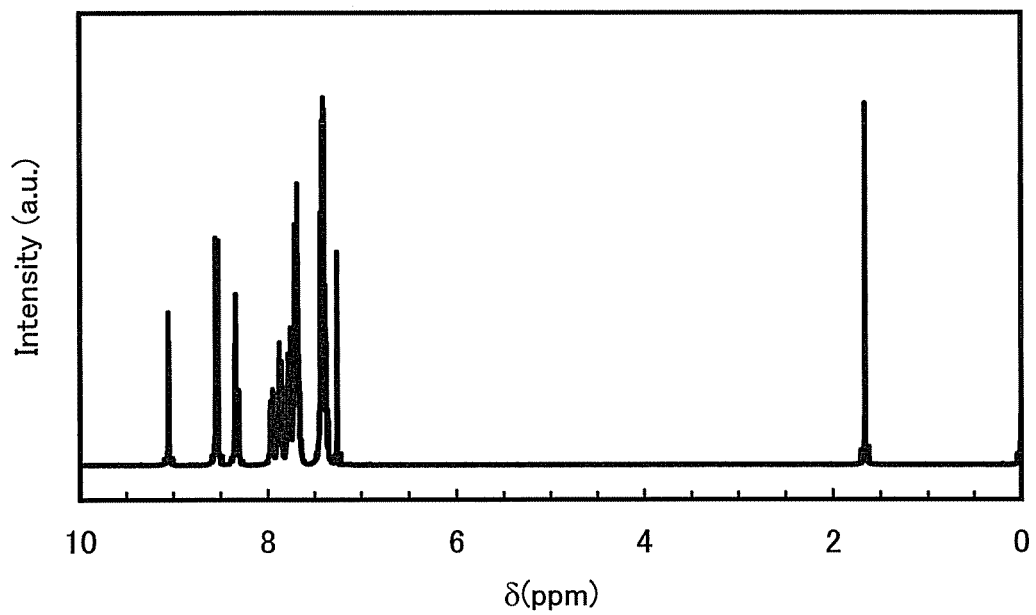
FIGS. 63A and 63B are each a $^1$H NMR chart of 3-{10-[4-(benzoxazol-2-yl)phenyl]-9-anthryl}quinoline (abbrev.: 3QABOx)
Figure 63B:
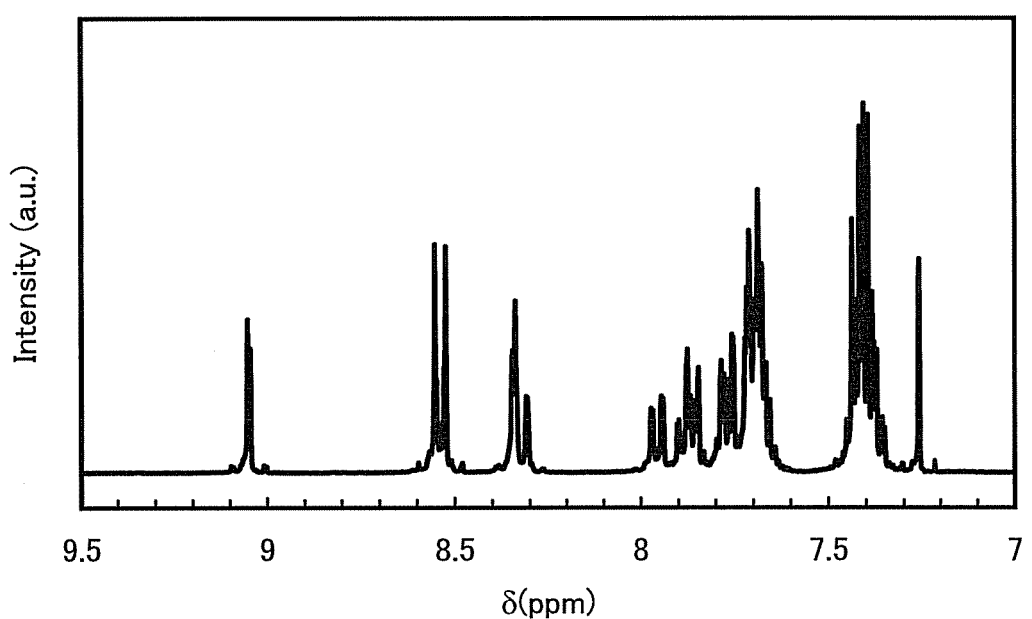

Further, the $^1$H NMR chart is shown in FIGS. 63A and 63B. Note that FIG. 63B is an enlarged chart showing the range from 7.0 ppm to 9.5 ppm in FIG. 63A.

Figure 64:
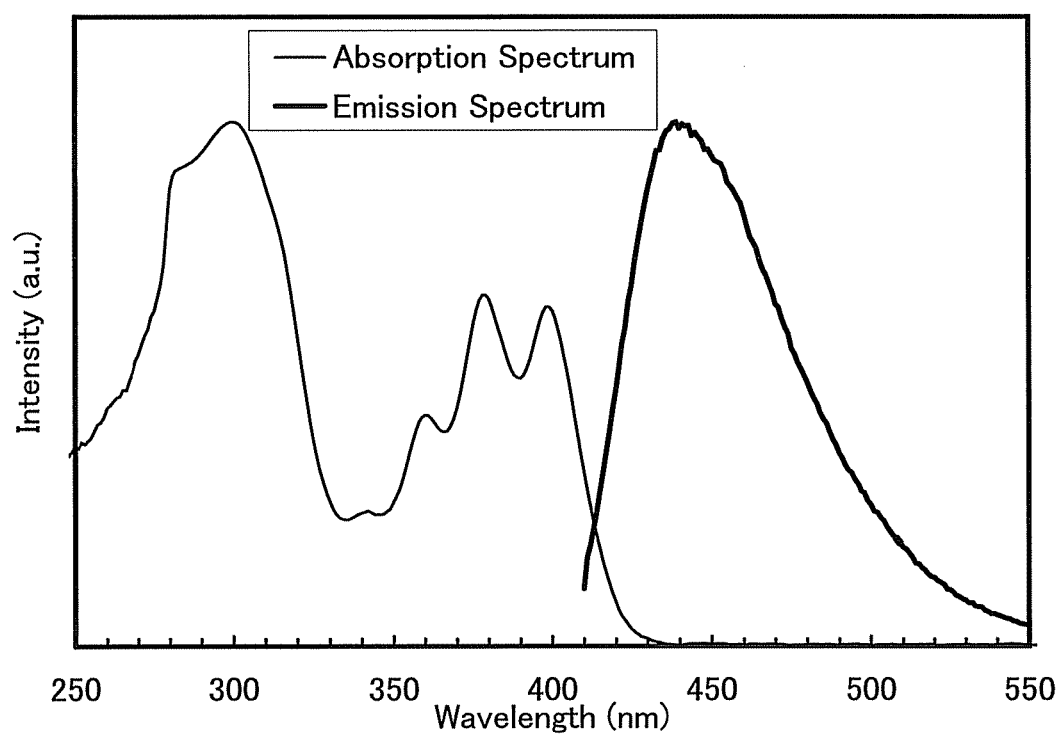
FIG. 64 shows an absorption spectrum and an emission spectrum of 3-{10-[4-(benzoxazol-2-yl)phenyl]-9-anthryl}quinoline in a toluene solution (abbrev.: 3QABOx)

Further, FIG. 64 shows an absorption spectrum and an emission spectrum of 3QABOx in a toluene solution. An ultraviolet-visible spectrophotometer (V-550, manufactured by JASCO Corporation) was used for the measurement. The solution was put into a quartz cell, and the absorption spectrum from which the absorption spectrum measured when only toluene was put into the quartz cell was subtracted is shown in FIG. 64. In FIG. 64, the horizontal axis indicates wavelength (nm) and the vertical axis indicates intensity (arbitrary unit). In the case of the toluene solution, absorptions were observed at around 342 nm, 360 nm, 379 nm, and 398 nm. In addition, the maximum emission wavelength was 439 nm (excitation wavelength: 399 nm) in the case of the toluene solution.

Figure 65:
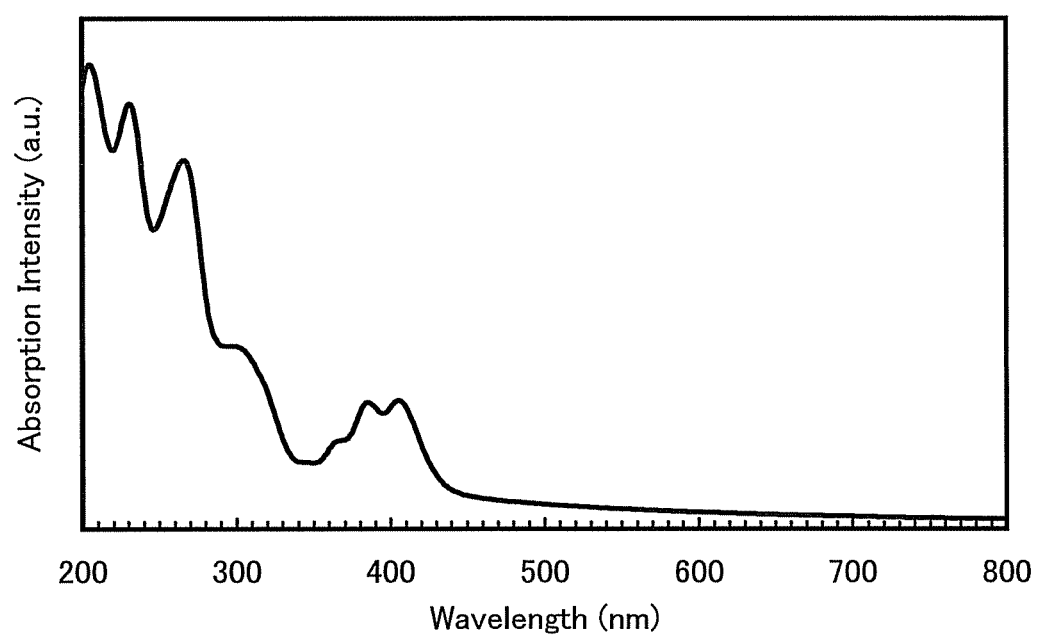
FIG. 65 shows an absorption spectrum of a thin film of 3-{10-[4-(benzoxazol-2-yl)phenyl]-9-anthryl}quinoline (abbrev.: 3QABOx)
Figure 66:
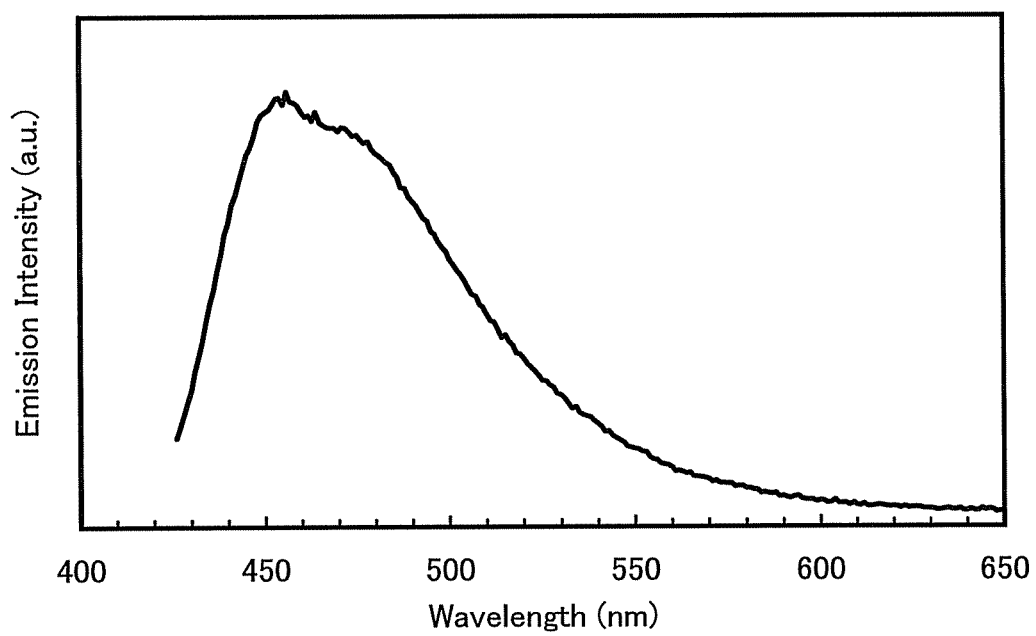
FIG. 66 shows an emission spectrum of a thin film of 3-{10-[4-(benzoxazol-2-yl)phenyl]-9-anthryl}quinoline (abbrev.: 3 QABOx)

FIG. 65 shows an absorption spectrum of a thin film of 3QABOx, and FIG. 66 shows an emission spectrum of a thin film of 3QABOx. An ultraviolet-visible spectrophotometer (V-550, manufactured by JASCO Corporation) was used for the measurement. A sample of the thin film was formed by evaporation on a quartz substrate, and the absorption spectrum thereof, from which the absorption spectrum of quartz is subtracted, is shown in FIG. 65. In FIG. 65, the horizontal axis indicates wavelength (nm) and the vertical axis indicates absorption intensity (arbitrary unit). In FIG. 66, the horizontal axis indicates wavelength (nm) and the vertical axis indicates emission intensity (arbitrary unit). In the case of the thin film, absorptions were observed at around 205 nm, 231 nm, 266 nm, 302 nm, 385 nm, and 405 nm. In addition, the maximum emission wavelength was 455 nm (excitation wavelength: 408 nm) in the case of the thin film.

In addition, the ionization potential of 3QABOx in the thin film state was 5.84 eV, which was measured by a photoelectron spectrometer (AC-2, manufactured by Riken Keiki Co., Ltd.) in air. As a result, the HOMO level was found to be −5.84 eV. Further, an absorption edge was obtained from a Tauc plot assuming direct transition with use of the data of the absorption spectrum of 3QABOx in the thin film state, and when the absorption edge was regarded as an optical energy gap, the energy gap was 2.99 eV A LUMO level of −2.85 eV was obtained from the obtained value of the energy gap and the HOMO level.

Further, oxidation-reduction characteristics of 3QABOx were measured. The oxidation-reduction characteristics were measured by cyclic voltammetry (CV) measurement. An electrochemical analyzer (ALS model 600A, manufactured by BAS Inc.) was used for the measurement.

The solution for the CV measurement was prepared as follows: tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, 3QABOx which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation characteristics of 3QABOx were measured as follows. The potential of the working electrode with respect to the reference electrode was changed from –0.03 V to 1.10 V, and then changed from 1.10 V to –0.03 V. This change in potential was regarded as one cycle, and measurement was carried out for 100 cycles. The reduction characteristics of 3QABOx were examined as follows. The potential of the working electrode with respect to the reference electrode was changed from –1.48 V to –2.35 V, and then changed from –2.35 V to –1.48 V. This change in potential was regarded as one cycle, and measurement was performed for 100 cycles. Further, the scanning speed of the CV measurement was set to be 0.1 V/s.

Figure 67:
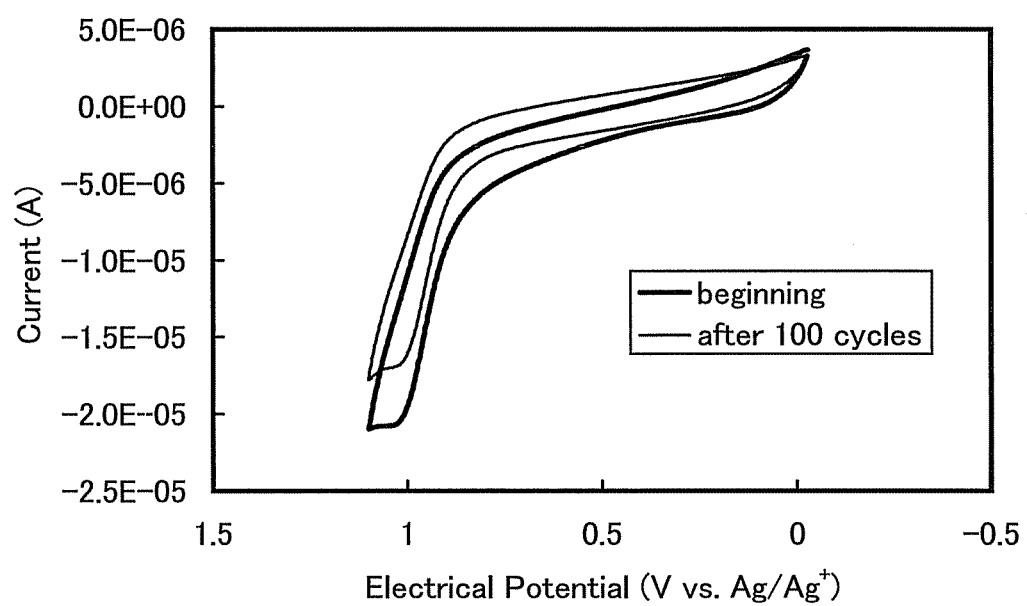
FIG. 67 shows CV measurement results of 3-{10-[4-(benzoxazol-2-yl)phenyl]-9-anthryl}quinoline (abbrev.: 3QABOx)
Figure 68:
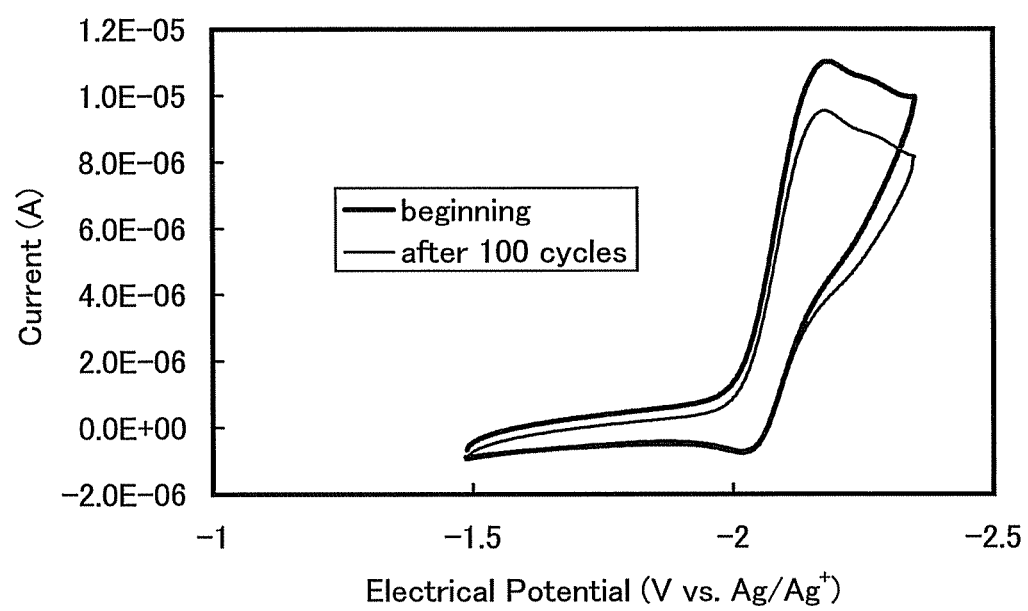
FIG. 68 shows CV measurement results of 3-{10-[4-(benzoxazol-2-yl)phenyl]-9-anthryl}quinoline (abbrev.: 3QABOx)

FIG. 67 shows results of the CV measurement of 3QABOx on the oxidation side, and FIG. 68 shows results of the CV measurement of 3QABOx on the reduction side. In each of FIG. 67 and FIG. 68, the horizontal axis indicates a potential (V) of the working electrode with respect to the reference electrode, and the vertical axis indicates a current value (A) flowing between the working electrode and the auxiliary electrode. From FIG. 67, a current indicating oxidation was observed around 1.04 V (vs. Ag/Ag$^+$ electrode). In addition, from FIG. 68, a current indicating reduction was observed around –2.18 V (vs. Ag/Ag$^+$ electrode).

Although the change in potential was repeated 100 times, changes in the peak position and peak intensity of the CV curve were scarcely observed in both the oxidation and reduction reactions. Accordingly, it is found that the benzoxazole derivative according to the present invention is significantly stable to repetitive oxidation-reduction reactions.

Example 10

In Example 10, a light-emitting element of the present invention will be described with reference to FIG. 26. A manufacturing method of the light-emitting element of this example will be described below.

(Light-Emitting Element 6)

First, a film of indium tin oxide containing silicon oxide (ITSO) was formed by a sputtering method over a glass substrate 2101 to form a first electrode 2102. The thickness of the first electrode 2102 was set to be 110 nm, and the area thereof was set to be 2 mm×2 mm.

Next, the substrate provided with the first electrode 2102 was fixed to a substrate holder provided in a vacuum evaporation apparatus such that the side on which the first electrode 2102 was formed faced downward. After the pressure in a film formation chamber was reduced to approximately 104 Pa, a layer 2111 containing a composite material of an organic compound and an inorganic compound was formed on the first electrode 2102 by co-evaporation of 4,4'-bis[N-(1-naphthyl)-N-phenylamino]biphenyl (abbrev.: NPB) and molybdenum(VI) oxide. The film thickness of the layer 2111 containing a composite material was set to be 50 nm and the weight ratio between NPB and molybdenum(VI) oxide was adjusted to be 4:1 (=NPB:molybdenum oxide). Note that the co-evaporation is an evaporation method in which evaporation is performed simultaneously from a plurality of evaporation sources in one chamber.

Next, a film of 4,4'-bis[N-(1-naphthyl)-N-phenylamino] biphenyl (abbrev.: NPB) was formed to a thickness of 10 nm on the layer 2111 containing a composite material by an evaporation method employing resistance heating to form a hole-transporting layer 2112.

Then, a light-emitting layer 2113 was formed to a thickness of 30 nm on the hole-transporting layer 2112 by co-evaporation of 9-[4-(10-phenyl-9-anthryl)phenyl]-9H-carbazole (abbrev.: CzPA) and 4-(10-phenyl-9-anthryl)-4'-(9-phenyl-9H-carbazol-3-yl)triphenylamine (abbrev.: PCBAPA). The weight ratio between CzPA and PCBAPA was adjusted so as to be 1:0.1 (=CzPA:PCBAPA).

Then, a film of 2-(4-{10-[4-(1-naphthyl)phenyl]-9-anthryl}phenyl)benzoxazole (abbrev.: NPhABOx) represented by Structural Formula (131) was formed to a thickness of 30 nm on the light-emitting layer 2113 by an evaporation method employing resistance heating, so that an electron-transporting layer 2114 was formed. Furthermore, a film of lithium fluoride was formed to a thickness of 1 nm on the electron-transporting layer 2114, so that an electron-injecting layer 2115 was formed.

Lastly, a film of aluminum was formed to a thickness of 200 nm on the electron-injecting layer 2115 by an evaporation method employing resistance heating, so that a second electrode 2104 was formed. Accordingly, a light-emitting element 6 was fabricated.

(Light-Emitting Element 7)

A light-emitting element 7 was fabricated in a similar manner to that of the light-emitting element 6 by using the same substrate and using 2-{4-[10-(biphenyl-4-yl)-9-anthryl]phenyl}benzoxazole (abbrev.: BPhABOx) represented by Structural Formula (126) instead of NPhABOx. That is, a film of 2-{4-[10-(biphenyl-4-yl)-9-anthryl]phenyl}benzoxazole (abbrev.: BPhABOx) represented by Structural Formula (126) was formed to a thickness of 30 nm to form the electron-transporting layer 2114. Except for the electron-transporting layer 2114, the light-emitting element 7 was fabricated in a similar manner to that of the light-emitting element 6.

(Comparative Light-Emitting Element 8)

A comparative light-emitting element 8 was fabricated in a similar manner to that of the light-emitting element 6 by using the same substrate and using tris(8-quinolinolato)aluminum (III) (abbrev.: Alq) instead of NPhABOx. That is, a film of tris(8-quinolinolato)aluminum(III) (abbrev.: Alq) was formed to a thickness of 30 nm to form the electron-transporting layer 2114. Except for the electron-transporting layer 2114, the comparative light-emitting element 8 was formed in a similar manner to that of the light-emitting element 6.

The light-emitting element 6, the light-emitting element 7, and the comparative light-emitting element 8 obtained in the above-described manner were placed in a nitrogen-atmosphere glove box and were sealed so that the light-emitting elements were not exposed to air. Then, the operating characteristics of the light-emitting elements were measured. The measurement was carried out at room temperature (in the atmosphere kept at 25° C.).

Figure 69:
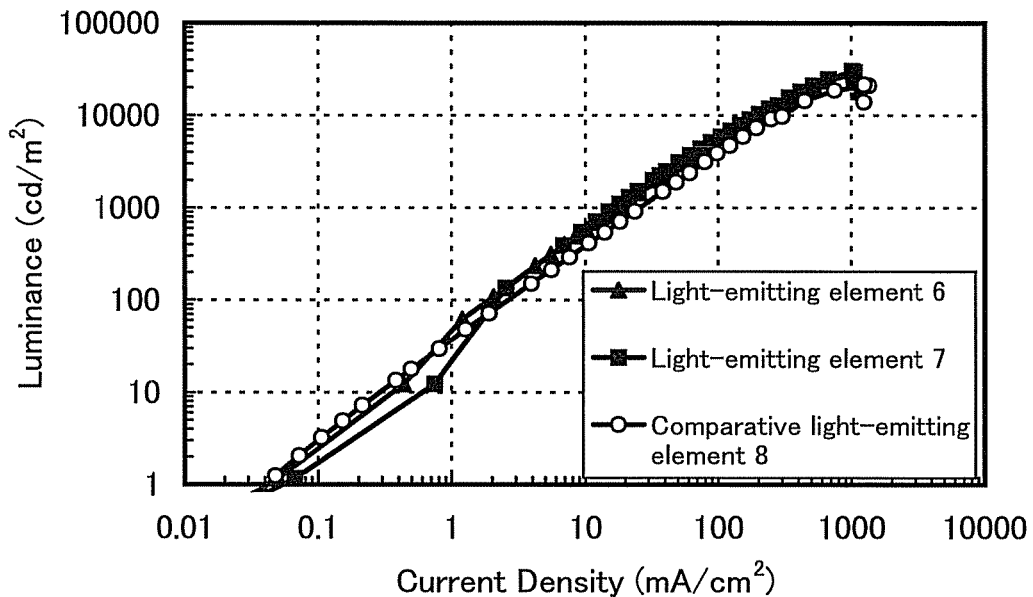
FIG. 69 shows current density-luminance characteristics of light-emitting elements fabricated in Example 10.
Figure 70:
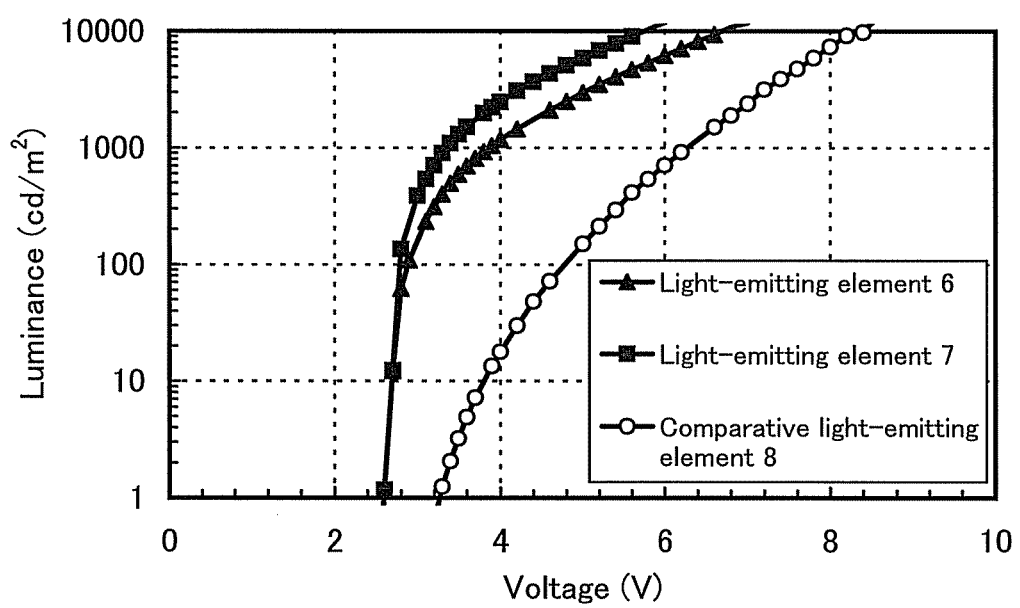
FIG. 70 shows voltage-luminance characteristics of the light-emitting elements fabricated in Example 10.
Figure 71:
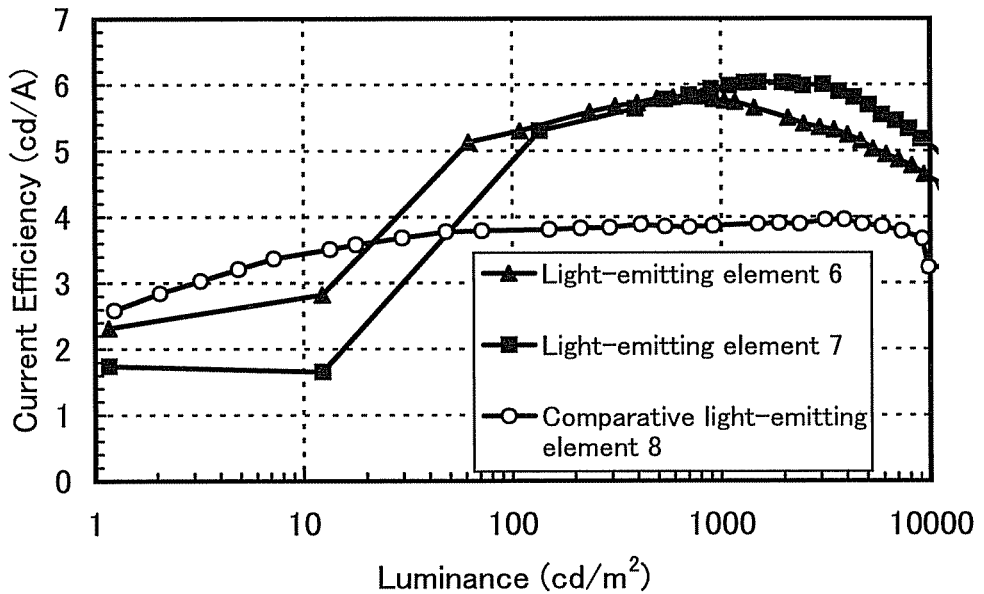
FIG. 71 shows luminance-current efficiency characteristics of the light-emitting elements fabricated in Example 10.
Figure 72:
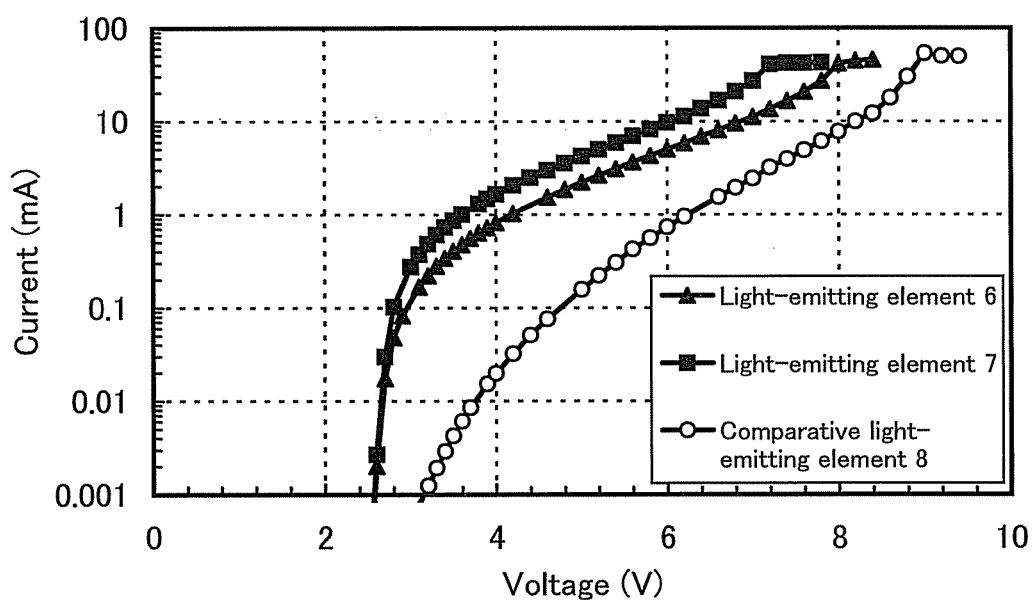
FIG. 72 shows voltage-current characteristics of the light-emitting elements fabricated in Embodiment 10.

FIG. 69 shows current density-luminance characteristics of the light-emitting element 6, the light-emitting element 7, and the comparative light-emitting element 8. FIG. 70 shows voltage-luminance characteristics. FIG. 71 shows luminance-current efficiency characteristics. FIG. 72 shows voltage-current characteristics.

Figure 73:
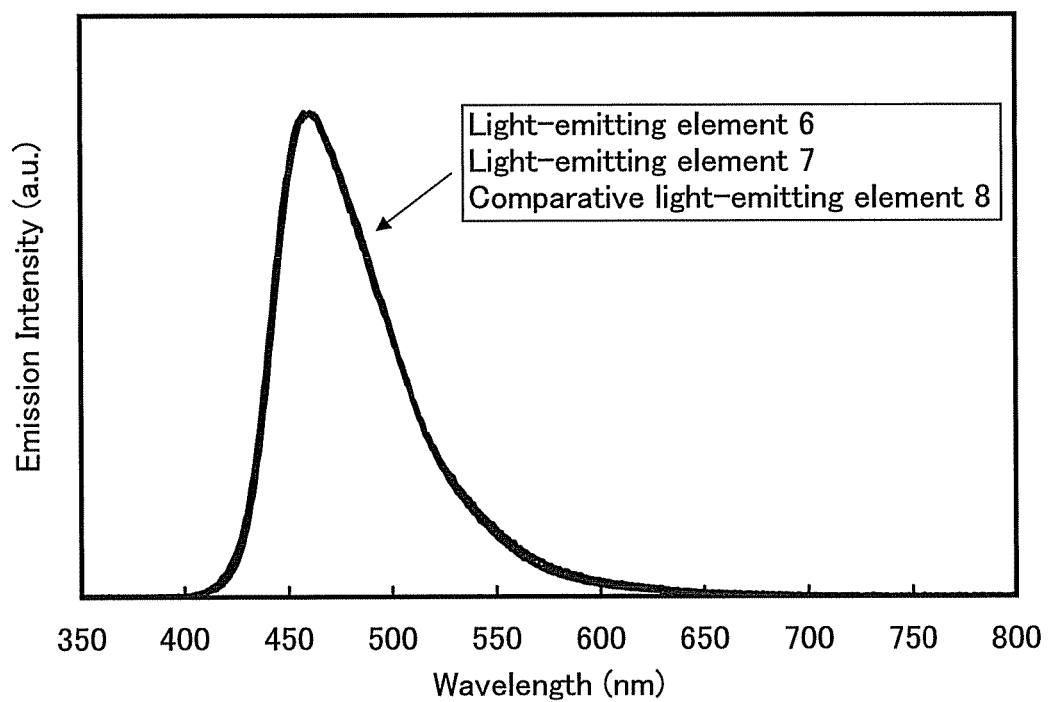
FIG. 73 shows emission spectra of the light-emitting elements fabricated in Example 10.

FIG. 73 shows the emission spectra when a current of 1 mA flows. It can be seen from FIG. 73 that light emission of each of the light-emitting element 6, the light-emitting element 7, and the comparative light-emitting element 8 results from PCBAPA.

The CIE chromaticity coordinates of the comparative light-emitting element 8 were x=0.15 and y=0.17 at a luminance of 920 cd/m$^2$, and the comparative light-emitting element 8 emitted blue light. In addition, the current efficiency at a luminance of 920 cd/m$^2$ was 3.9 cd/A. The voltage, the current density, and the power efficiency at a luminance of 920 cd/m$^2$ were 6.2 V, 23.7 mA/cm$^2$, and 2.0 μm/W, respectively.

On the contrary, the CE chromaticity coordinates of the light-emitting element 6 were x=0.15 and y=0.17 at a luminance of 1040 cd/m$^2$, and the light-emitting element 6 emitted blue light. In addition, the current efficiency at a luminance of 1040 cd/m$^2$ was 5.8 cd/A, which shows that the light-emitting element 6 has higher emission efficiency than the comparative light-emitting element 8. Since the voltage at a luminance of 1040 cd/m$^2$ was 3.9 V, it can be found that the driving voltage of the light-emitting element 6 is significantly lower than that of the comparative light-emitting element 8. Further, the current density was 18.1 mA/cm$^2$, and the power efficiency was as high as 4.6 lm/W.

The CIE chromaticity coordinates of the light-emitting element 7 were x=0.15 and y=0.17 at a luminance of 1100 cd/m$^2$, and the light-emitting element 7 emitted blue light. In addition, the current efficiency at a luminance of 1100 cd/m$^2$ was 6.0 cd/A, which shows that the light-emitting element 7 has higher emission efficiency than the comparative light-emitting element 8. Since the voltage at a luminance of 1100 cd/m$^2$ was 3.4 V, it can be found that the driving voltage of the light-emitting element 7 is significantly lower than that of the comparative light-emitting element 8. Further, the current density was 18.3 mA/cm$^2$, and the power efficiency was as high as 5.5 lm/W.

It can be seen from FIG. 72 that the light-emitting element 6 and the light-emitting element 7 require lower voltage than the comparative light-emitting element 8 to allow the same amount of current to flow. It can also be seen from FIG. 71 that the light-emitting element 6 and the light-emitting element 7 have higher current efficiency than the comparative light-emitting element 8. Accordingly, it can be understood that the light-emitting element 6 and the light-emitting element 7 require lower voltage and consume less power than the comparative light-emitting element 8 to provide the same luminance as shown in FIG. 70.

Therefore, the benzoxazole derivatives according to the present invention are excellent in an electron-transporting property. Further, by using the benzoxazole derivatives according to the present invention for light-emitting elements, light-emitting elements with low-voltage driving can be obtained. In addition, light-emitting elements with low power consumption can be obtained.

Example 11

In Example 11, a light-emitting element of the present invention will be described with reference to FIG. 26. A manufacturing method of the light-emitting element of this example will be described below.
(Light-Emitting Element 9)

First, a film of indium tin oxide containing silicon oxide (ITSO) was formed by a sputtering method over a glass substrate 2101 to form a first electrode 2102. The thickness of the first electrode 2102 was set to be 110 nm, and the area thereof was set to be 2 mm×2 mm.

Next, the substrate provided with the first electrode 2102 was fixed to a substrate holder provided in a vacuum evaporation apparatus such that the side on which the first electrode 2102 was formed faced downward. After the pressure in a film formation chamber was reduced to approximately 10$^{-4}$ Pa, a layer 2111 containing a composite material of an organic compound and an inorganic compound was formed on the first electrode 2102 by co-evaporation of 4,4'-bis[N-(1-naphthyl)-N-phenylamino]biphenyl (abbrev.: NPB) and molybdenum(VI) oxide. The film thickness of the layer 2111 containing a composite material was set to be 50 nm and the weight ratio between NPB and molybdenum(VI) oxide was adjusted to be 4:1 (=NPB:molybdenum oxide). Note that the co-evaporation is an evaporation method in which evaporation is performed simultaneously from a plurality of evaporation sources in one chamber.

Next, a film of 4,4'-bis[N-(1-naphthyl)-N-phenylamino]biphenyl (abbrev.: NPB) was formed to a thickness of 10 nm on the layer 2111 containing a composite material by an evaporation method employing resistance heating to form a hole-transporting layer 2112.

Then, a light-emitting layer 2113 was formed to a thickness of 30 nm on the hole-transporting layer 2112 by co-evaporation of 9-[4-(10-phenyl-9-anthryl)phenyl]-9H-carbazole (abbrev.: CzPA) and 4-(10-phenyl-9-anthryl)-4'-(9-phenyl-9H-carbazol-3-yl)triphenylamine (abbrev.: PCBAPA). The weight ratio between CzPA and PCBAPA was adjusted so as to be 1:0.1 (=CzPA:PCBAPA).

Then, a film of 2-{4-[10-(1-naphthyl)-9-anthryl]phenyl}benzoxazole (abbrev.: NABOx) represented by Structural Formula (129) was formed to a thickness of 30 nm on the light-emitting layer 2113 by an evaporation method employing resistance heating, so that an electron-transporting layer 2114 was formed.

Furthermore, a film of lithium fluoride was formed to a thickness of 1 nm on the electron-transporting layer 2114, so that an electron-injecting layer 2115 was formed.

Lastly, a film of aluminum was formed to a thickness of 200 nm on the electron-injecting layer 2115 by an evaporation method employing resistance heating, so that a second electrode 2104 was formed. Accordingly, a light-emitting element 9 was fabricated.
(Light-Emitting Element 10)

A light-emitting element 10 was fabricated in a similar manner to that of the light-emitting element 9 by using the same substrate and using 2-{4-[10-(2-naphthyl)-9-anthryl]phenyl}benzoxazole (abbrev.: 2NABOx) represented by Structural Formula (130) instead of NABOx. That is, a film of 2-{4-[10-(2-naphthyl)-9-anthryl]phenyl}benzoxazole (abbrev.: 2NABOx) represented by Structural Formula (130) was formed to a thickness of 30 nm to form the electron-transporting layer 2114. Except for the electron-transporting layer 2114, the light-emitting element 10 was fabricated in a similar manner to that of the light-emitting element 9.
(Comparative Light-Emitting Element 11)

A comparative light-emitting element 11 was fabricated in a similar manner to that of the light-emitting element 9 by using the same substrate and using tris(8-quinolinolato)aluminum(III) (abbrev.: Alq) instead of NABOx. That is, a film of tris(8-quinolinolato)aluminum(I) (abbrev.: Alq) was formed to a thickness of 30 nm to form the electron-transporting layer 2114. Except for the electron-transporting layer 2114, the comparative light-emitting element 11 was formed in a similar manner to that of the light-emitting element 9.

The light-emitting element 9, the light-emitting element 10, and the comparative light-emitting element 11 obtained in the above-described manner were placed in a nitrogen-atmosphere glove box and were sealed so that the light-emitting elements were not exposed to air. Then, the operating characteristics of the light-emitting elements were measured. The measurement was carried out at room temperature (in the atmosphere kept at 25° C.).

Figure 74:
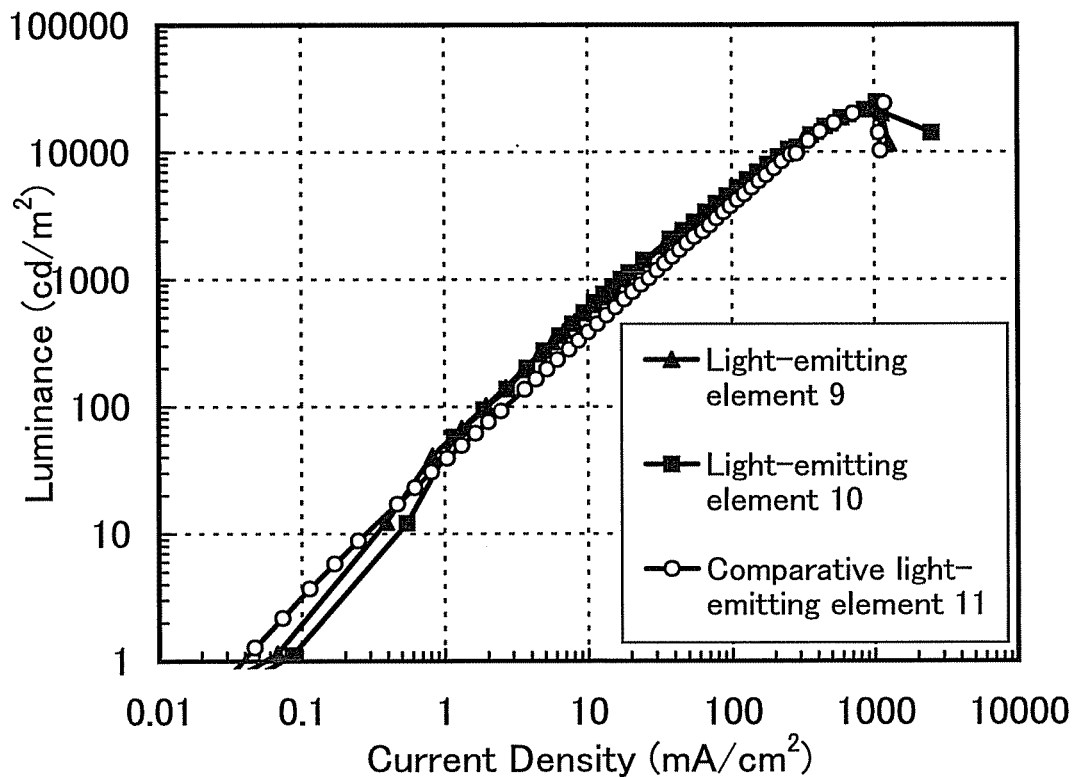
FIG. 74 shows current density-luminance characteristics of light-emitting elements fabricated in Example 11.
Figure 75:
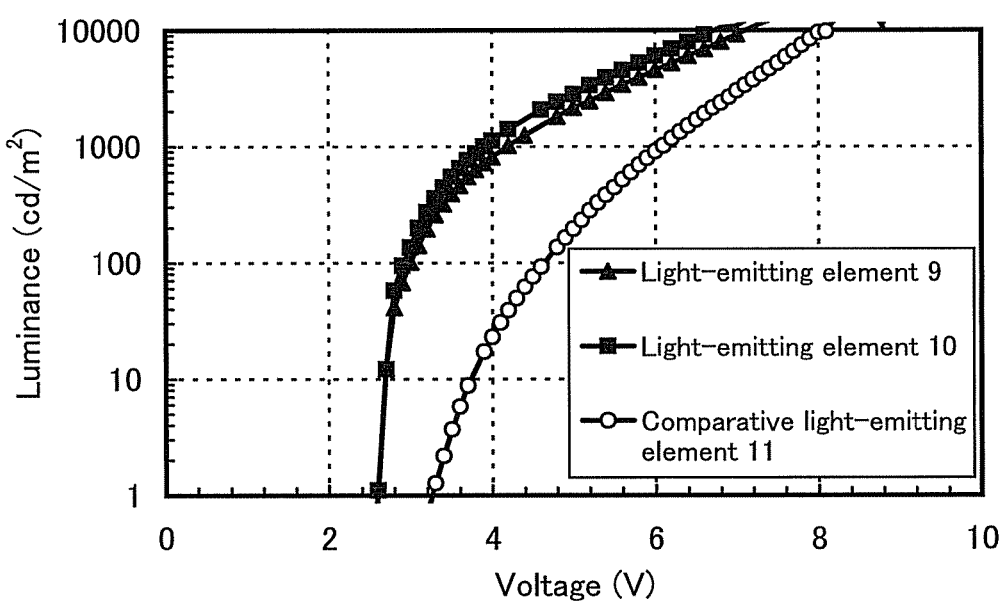
FIG. 75 shows voltage-luminance characteristics of the light-emitting elements fabricated in Example 11.
Figure 76:
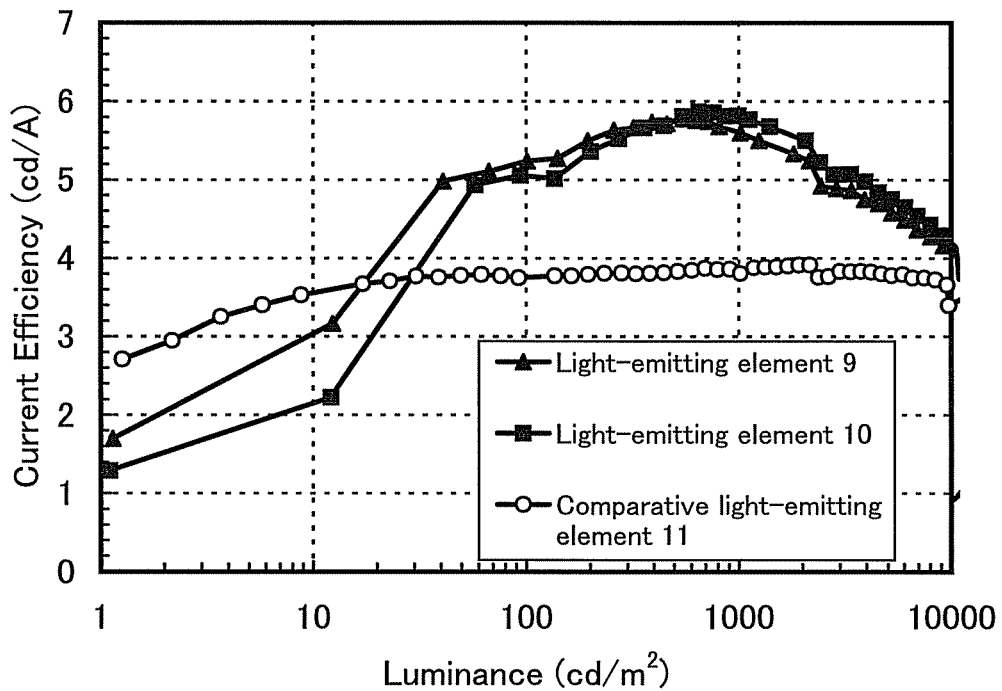
FIG. 76 shows luminance-current efficiency characteristics of the light-emitting elements fabricated in Example 11.
Figure 77:
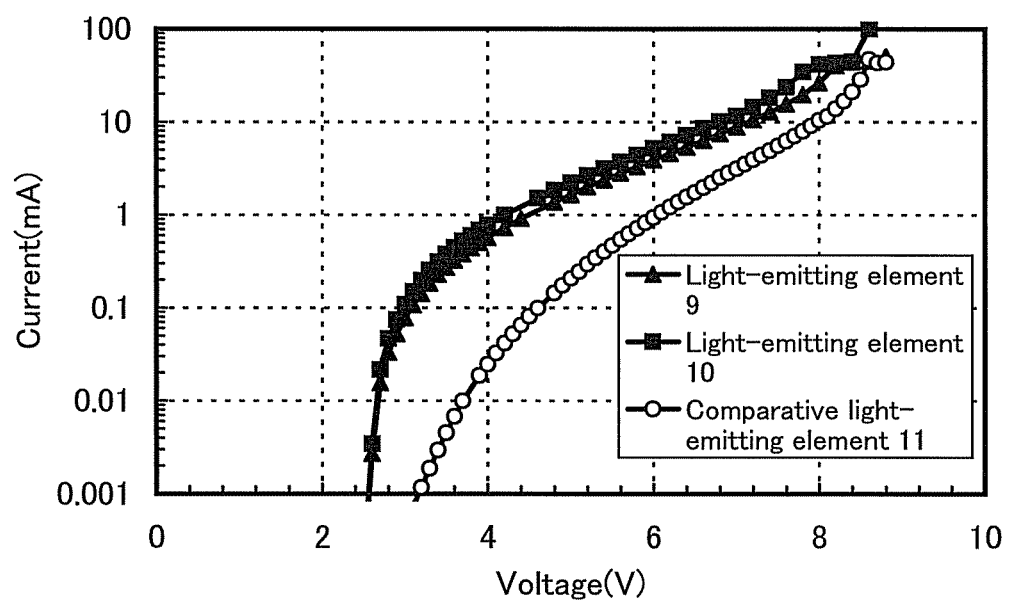
FIG. 77 shows voltage-current characteristics of the light-emitting elements fabricated in Example 11.

FIG. 74 shows current density-luminance characteristics of the light-emitting element 9, the light-emitting element 10, and the comparative light-emitting element 11. FIG. 75 shows voltage-luminance characteristics. FIG. 76 shows luminance-current efficiency characteristics. FIG. 77 shows voltage-current characteristics.

Figure 78:
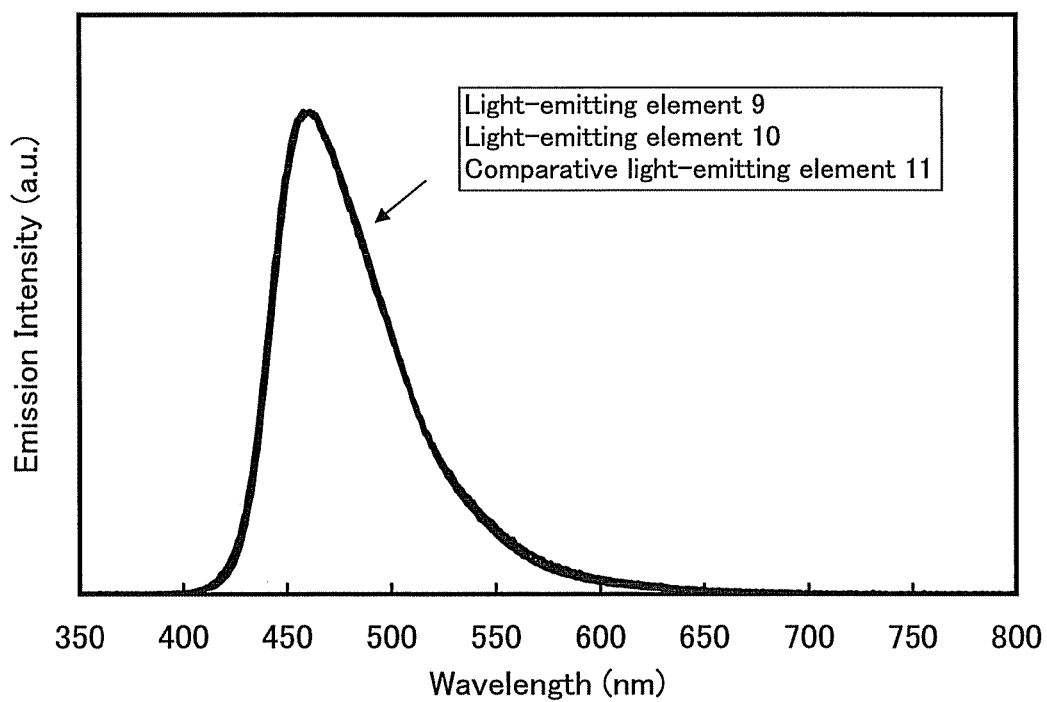
FIG. 78 shows emission spectra of the light-emitting elements fabricated in Example 11.

FIG. 78 shows the emission spectra when a current of 1 mA flows. It can be seen from FIG. 78 that light emission of each of the light-emitting element 9, the light-emitting element 10, and the comparative light-emitting element 11 results from PCBAPA.

The CIE chromaticity coordinates of the comparative light-emitting element 11 were x=0.16 and y=0.17 at a luminance of 910 cd/m$^2$, and the comparative light-emitting element 11 emitted blue light. In addition, the current efficiency at a luminance of 910 cd/m$^2$ was 3.9 cd/A. The voltage, the current density, and the power efficiency at a luminance of 910 cd/m$^2$ were 6.0 V, 23.5 mA/cm$^2$, and 2.0 lm/W, respectively.

On the contrary, the CIE chromaticity coordinates of the light-emitting element 9 were x=0.15 and y=0.17 at a luminance of 1020 cd/m$^2$, and the light-emitting element 9 emitted blue light. In addition, the current efficiency at a luminance of 1020 cd/m$^2$ was 5.6 cd/A, which shows that the light-emitting element 9 has higher emission efficiency than the comparative light-emitting element 11. Since the voltage at a luminance of 1020 cd/m$^2$ was 4.2 V, it can be found that the driving voltage of the light-emitting element 9 is significantly lower than that of the comparative light-emitting element 11. Further, the current density was 18.2 mA/cm$^2$, and the power efficiency was as high as 4.2 lm/W.

The CIE chromaticity coordinates of the light-emitting element 10 were x=0.15 and y=0.17 at a luminance of 1000 cd/m$^2$, and the light-emitting element 10 emitted blue light. In addition, the current efficiency at a luminance of 1000 cd/m$^2$ was 5.8 cd/A, which shows that the light-emitting element 10 has higher emission efficiency than the comparative light-emitting element 11. Since the voltage at a luminance of 1000 cd/m$^2$ was 3.9 V, it can be found that the driving voltage of the light-emitting element 10 is significantly lower than that of the comparative light-emitting element 11. Further, the current density was 17.2 mA/cm$^2$, and the power efficiency was as high as 4.7 lm/W.

It can be seen from FIG. 77 that the light-emitting element 9 and the light-emitting element 10 require lower voltage than the comparative light-emitting element 11 to allow the same amount of current to flow. It can also be seen from FIG. 76 that the light-emitting element 9 and the light-emitting element 10 have higher current efficiency than the comparative light-emitting element 11. Accordingly, it can be understood that the light-emitting element 9 and the light-emitting element 10 require lower voltage and consume less power than the comparative light-emitting element 11 to provide the same luminance as shown in FIG. 75.

Therefore, the benzoxazole derivatives according to the present invention are excellent in an electron-transporting property. Further, by using the benzoxazole derivatives according to the present invention for light-emitting elements, light-emitting elements with low-voltage driving can be obtained. In addition, light-emitting elements with low power consumption can be obtained.

Example 12

In Example 12, a light-emitting element of the present invention will be described with reference to FIG. 26. A manufacturing method of the light-emitting element of this example will be described below.

(Light-Emitting Element 12)

First, a film of indium tin oxide containing silicon oxide (ITSO) was formed by a sputtering method over a glass substrate 2101 to form a first electrode 2102. The thickness of the first electrode 2102 was set to be 110 nm, and the area thereof was set to be 2 mm×2 mm.

Next, the substrate provided with the first electrode 2102 was fixed to a substrate holder provided in a vacuum evaporation apparatus such that the side on which the first electrode 2102 was formed faced downward. After the pressure in a film formation chamber was reduced to approximately 110 Pa, a layer 2111 containing a composite material of an organic compound and an inorganic compound was formed on the first electrode 2102 by co-evaporation of 4,4'-bis[N-(1-naphthyl)-N-phenylamino]biphenyl (abbrev.: NPB) and molybdenum(VI) oxide. The film thickness of the layer 2111 containing a composite material was set to be 50 nm and the weight ratio between NPB and molybdenum(VI) oxide was adjusted to be 4:1 (=NPB:molybdenum oxide). Note that the co-evaporation is an evaporation method in which evaporation is performed simultaneously from a plurality of evaporation sources in one chamber.

Next, a film of 4,4'-bis[N-(1-naphthyl)-N-phenylamino]biphenyl (abbrev.: NPB) was formed to a thickness of 10 nm on the layer 2111 containing a composite material by an evaporation method employing resistance heating to form a hole-transporting layer 2112.

Then, a light-emitting layer 2113 was formed to a thickness of 30 nm on the hole-transporting layer 2112 by co-evaporation of 9-[4-(10-phenyl-9-anthryl)phenyl]-9H-carbazole (abbrev.: CzPA) and 4-(10-phenyl-9-anthryl)-4'-(9-phenyl-9H-carbazol-3-yl)triphenylamine (abbrev.: PCBAPA). The weight ratio between CzPA and PCBAPA was adjusted so as to be 1:0.1 (=CzPA:PCBAPA).

Then, a film of 3-{10-[4-(benzoxazol-2-yl)phenyl]-9-anthryl}quinoline (abbrev.: 3QABOx) represented by Structural Formula (158) was formed to a thickness of 30 nm on the light-emitting layer 2113 by an evaporation method employing resistance heating, so that an electron-transporting layer 2114 was formed.

Furthermore, a film of lithium fluoride was formed to a thickness of 1 nm on the electron-transporting layer 2114, so that an electron-injecting layer 2115 was formed.

Lastly, a film of aluminum was formed to a thickness of 200 nM on the electron-injecting layer 2115 by an evaporation method employing resistance heating, so that a second electrode 2104 was formed. Accordingly, a light-emitting element 12 was fabricated.

(Comparative Light-Emitting Element 13)

A comparative light-emitting element 13 was fabricated in a similar manner to that of the light-emitting element 12 by using the same substrate and using tris(8-quinolinolato)aluminum(II) (abbrev.: Alq) instead of 3QABOx. That is, a film of tris(8-quinolinolato)aluminum(III) (abbrev.: Alq) was formed to a thickness of 30 nm to form the electron-transporting layer 2114. Except for the electron-transporting layer 2114, the comparative light-emitting element 13 was formed in a similar manner to that of the light-emitting element 12.

The light-emitting element 12 and the comparative light-emitting element 13 obtained in the above-described manner were placed in a nitrogen-atmosphere glove box and were sealed so that the light-emitting elements were not exposed to air. Then, the operating characteristics of the light-emitting elements were measured. The measurement was carried out at room temperature (in the atmosphere kept at 25° C.).

Figure 79:
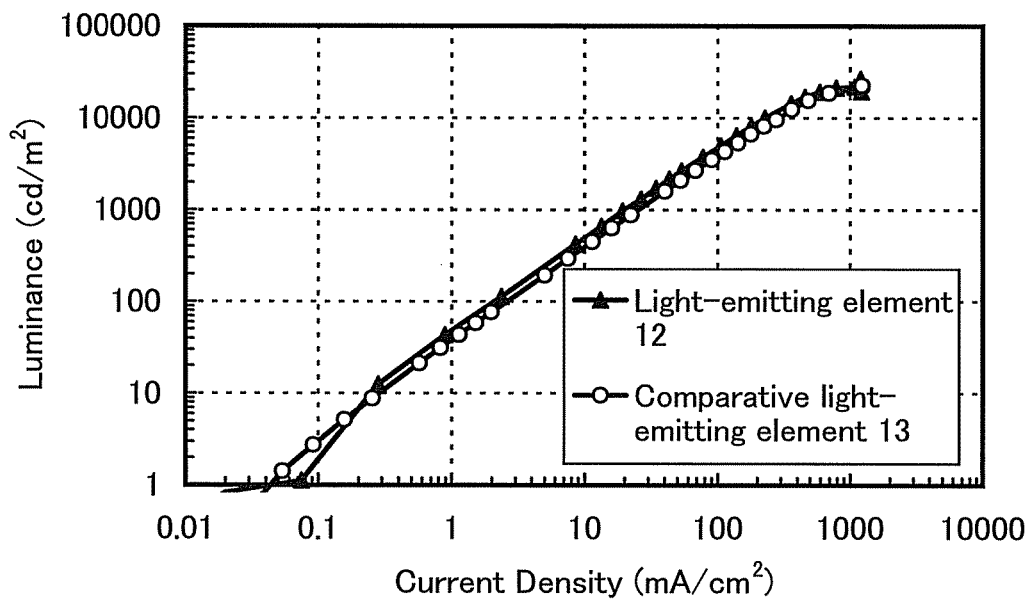
FIG. 79 shows current density-luminance characteristics of light-emitting elements fabricated in Example 12.
Figure 80:
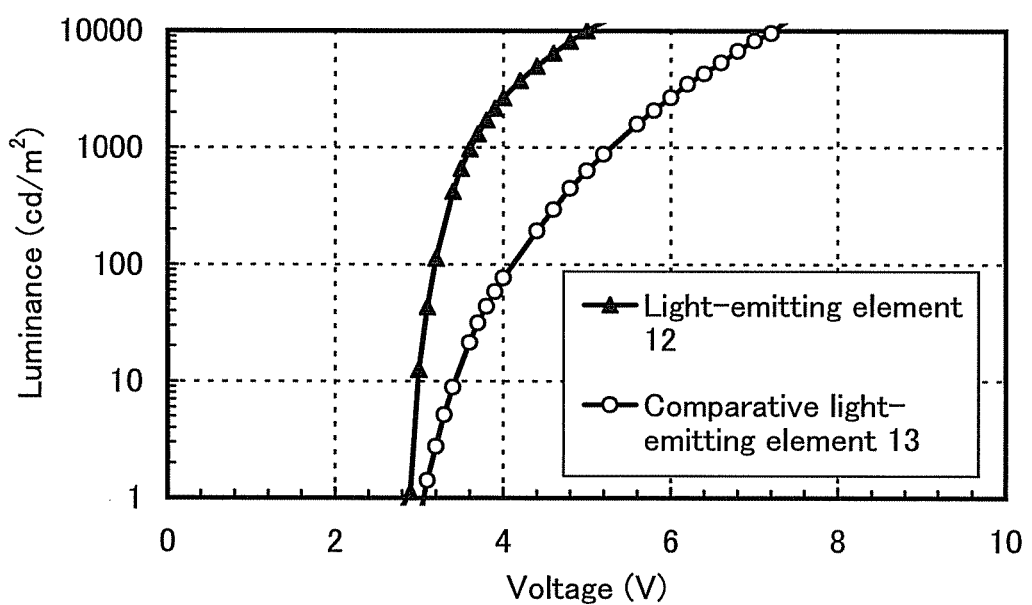
FIG. 80 shows voltage-luminance characteristics of the light-emitting elements fabricated in Example 12.
Figure 81:
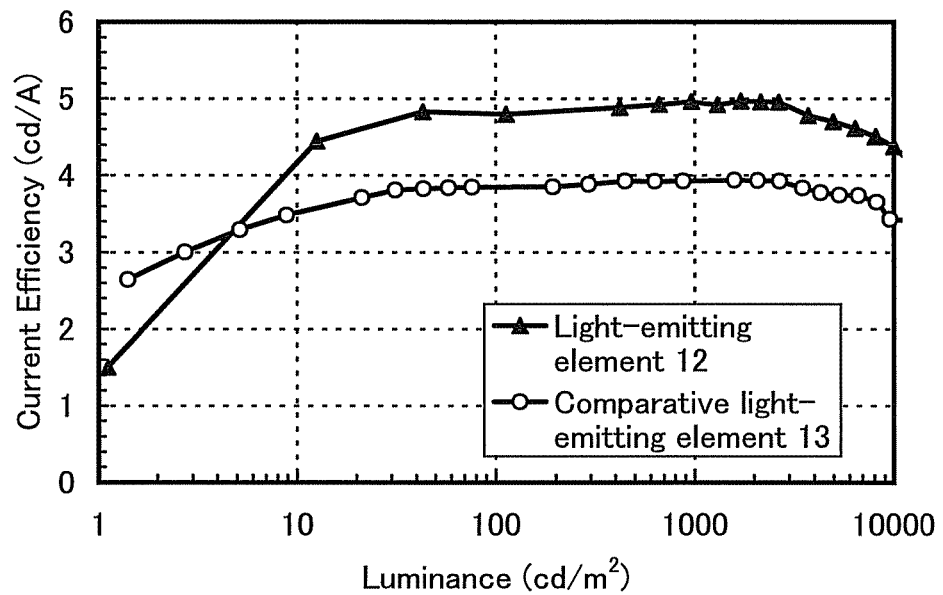
FIG. 81 shows luminance-current efficiency characteristics of the light-emitting elements fabricated in Example 12.
Figure 82:
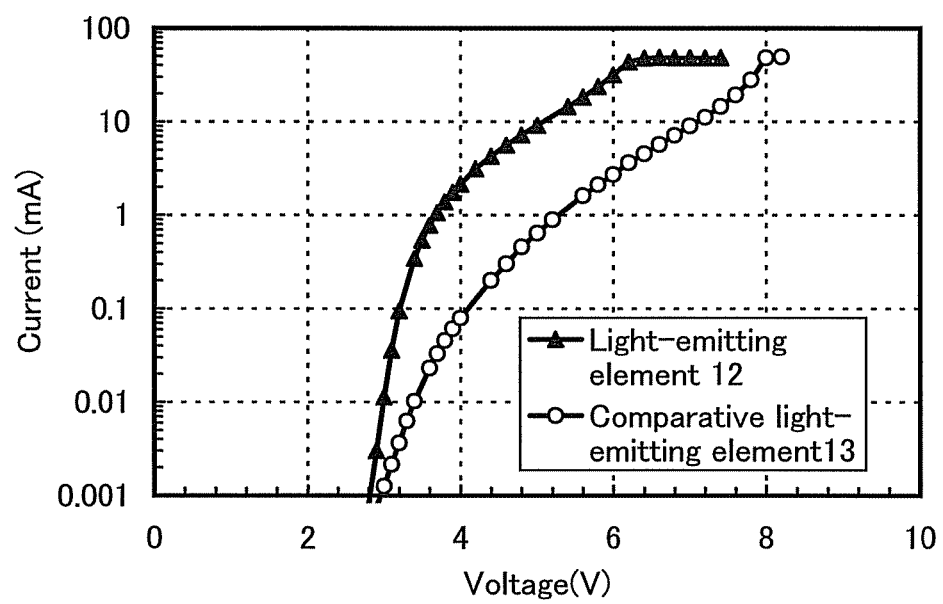
FIG. 82 shows voltage-current characteristics of the light-emitting elements fabricated in Example 12.

FIG. 79 shows current density-luminance characteristics of the light-emitting element 12 and the comparative light-emitting element 13. FIG. 80 shows voltage-luminance characteristics. FIG. 81 shows luminance-current efficiency characteristics. FIG. 82 shows voltage-current characteristics.

Figure 83:
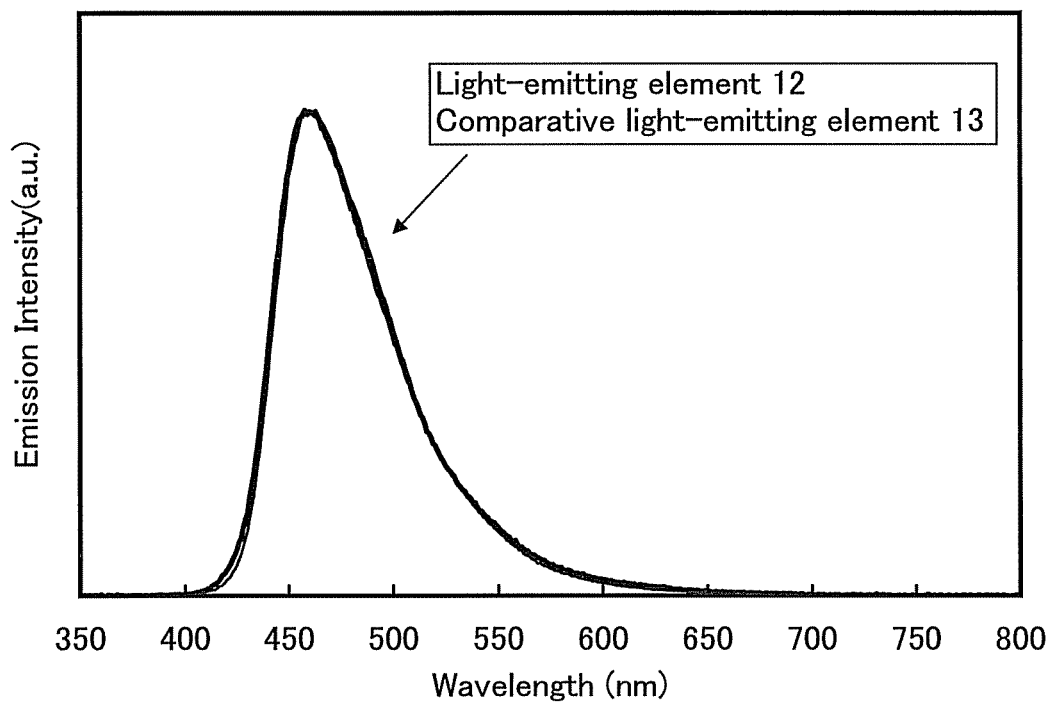
FIG. 83 shows emission spectra of the light-emitting elements fabricated in Example 12.

FIG. 83 shows the emission spectra when a current of 1 mA flows. It can be seen from FIG. 83 that light emission of each of the light-emitting element 12 and the comparative light-emitting element 13 results from PCBAPA.

The CIE chromaticity coordinates of the comparative light-emitting element 13 were x=0.16 and y=0.19 at a luminance of 880 cd/m², and the comparative light-emitting element 13 emitted blue light. In addition, the current efficiency at a luminance of 880 cd/m² was 3.9 cd/A. The voltage, the current density, and the power efficiency at a luminance of 880 cd/m² were 5.2 V, 22.3 mA/cm², and 2.4 lm/W, respectively.

On the contrary, the CIE chromaticity coordinates of the light-emitting element 12 were x=0.15 and y=0.19 at a luminance of 960 cd/m², and the light-emitting element 12 emitted blue light. In addition, the current efficiency at a luminance of 960 cd/m² was 5.0 cd/A, which shows that the light-emitting element 12 has higher emission efficiency than the comparative light-emitting element 13. Since the voltage at a luminance of 960 cd/m² was 3.6 V, it can be found that the driving voltage of the light-emitting element 12 is significantly lower than that of the comparative light-emitting element 13. Further, the current density was 19.4 mA/cm², and the power efficiency was as high as 4.3 lm/W.

It can be seen from FIG. 82 that the light-emitting element 12 requires lower voltage than the comparative light-emitting element 13 to allow the same amount of current to flow. It can also be seen from FIG. 81 that the light-emitting element 12 has higher current efficiency than the comparative light-emitting element 13. Accordingly, it can be understood that the light-emitting element 12 requires lower voltage and consumes less power than the comparative light-emitting element 13 to provide the same luminance as shown in FIG. 80.

Therefore, the benzoxazole derivative according to the present invention is excellent in an electron-transporting property. Further, by using the benzoxazole derivative according to the present invention for a light-emitting element, a light-emitting element with low-voltage driving can be obtained. In addition, a light-emitting element with low power consumption can be obtained.

This application is based on Japanese Patent Application serial no. 2008-129146 filed with Japan Patent Office on May 16, 2008, the entire contents of which are hereby incorporated by reference.

What is claimed is:

1. A benzoxazole derivative represented by General Formula (G1),

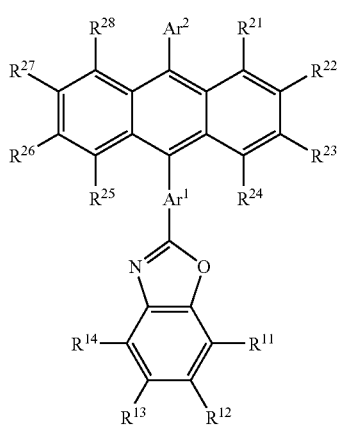

(G1)

wherein $Ar^1$ is a substituted or unsubstituted arylene group having 6 to 13 carbon atoms, wherein $Ar^2$ is any of an unsubstituted phenyl group, a substituted or unsubstituted pyridyl group, a substituted or unsubstituted quinolyl group, a substituted or unsubstituted pyrimidinyl group, a substituted or unsubstituted pyrazinyl group, a substituted or unsubstituted naphthyl group, or a substituted or unsubstituted isoquinolyl group, wherein $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and wherein $R^{21}$ to $R^{28}$ are independently either hydrogen or an alkyl group having 1 to 4 carbon atoms.

2. The benzoxazole derivative according to claim 1, wherein $Ar^1$ is a substituted or unsubstituted phenylene group.

3. The benzoxazole derivative according to claim 1, wherein $Ar^1$ is a substituted or unsubstituted 1,4-phenylene group.

4. The benzoxazole derivative according to claim 1, wherein $Ar^1$ is an unsubstituted 1,4-phenylene group, and wherein $R^{11}$ to $R^{14}$, and $R^{21}$ to $R^{28}$ are hydrogen.

5. A light-emitting device comprising a benzoxazole derivative represented by General Formula (G1),

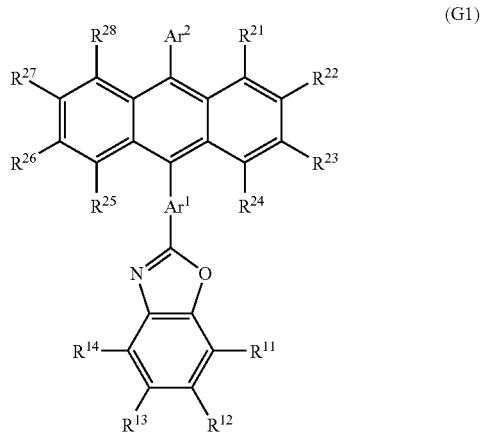

(G1)

wherein $Ar^1$ is a substituted or unsubstituted arylene group having 6 to 13 carbon atoms, wherein $Ar^2$ is any of an unsubstituted phenyl group, a substituted or unsubstituted pyridyl group, a substituted or unsubstituted quinolyl group, a substituted or unsubstituted pyrimidinyl group, a substituted or unsubstituted pyrazinyl group, a substituted or unsubstituted naphthyl group, or a substituted or unsubstituted isoquinolyl group, wherein $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and wherein $R^{21}$ to $R^{28}$ are independently either hydrogen or an alkyl group having 1 to 4 carbon atoms.

6. The light-emitting device according to claim 5, wherein $Ar^1$ is a substituted or unsubstituted phenylene group.

7. The light-emitting device according to claim 5, wherein $Ar^1$ is a substituted or unsubstituted 1,4-phenylene group.

8. The light-emitting device according to claim 4, wherein $Ar^1$ is an unsubstituted 1,4-phenylene group, and
wherein $R^{11}$ to $R^{14}$, and $R^{21}$ to $R^{28}$ are hydrogen.

9. An electronic device comprising a light-emitting device, the light-emitting device comprising a benzoxazole derivative represented by General Formula (G1),

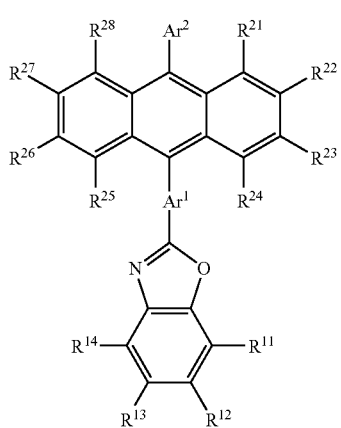

(G1)

wherein $Ar^1$ is a substituted or unsubstituted arylene group having 6 to 13 carbon atoms, wherein $Ar^2$ is any of an unsubstituted phenyl group, a substituted or unsubstituted pyridyl group, a substituted or unsubstituted quinolyl group, a substituted or unsubstituted pyrimidinyl group, a substituted or unsubstituted pyrazinyl group, a substituted or unsubstituted naphthyl group, or a substituted or unsubstituted isoquinolyl group, wherein $R^{11}$ to $R^{14}$ are independently any of hydrogen, an alkyl group having 1 to 4 carbon atoms, a haloalkyl group having 1 to 4 carbon atoms, a substituted or unsubstituted aryl group having 6 to 13 carbon atoms, and halogen, and wherein $R^{21}$ to $R^{28}$ are independently either hydrogen or an alkyl group having 1 to 4 carbon atoms.

10. The electronic device according to claim 9, wherein $Ar^1$ is a substituted or unsubstituted phenylene group.

11. The electronic device according to claim 9, wherein $Ar^1$ is a substituted or unsubstituted 1,4-phenylene group.

12. The electronic device according to claim 9, wherein $Ar^1$ is an unsubstituted 1,4-phenylene group, and
wherein $R^{11}$ to $R^{14}$, and $R^{21}$ to $R^{28}$ are hydrogen.

* * * * *

UNITED STATES PATENT AND TRADEMARK OFFICE
CERTIFICATE OF CORRECTION

PATENT NO. : 8,859,108 B2
APPLICATION NO. : 12/466116
DATED : October 14, 2014
INVENTOR(S) : Hiroshi Kadoma et al.

Page 1 of 2

It is certified that error appears in the above-identified patent and that said Letters Patent is hereby corrected as shown below:

In the Specification:

Column 27, Line 47, Chemical Structures (108) and (109);

Change

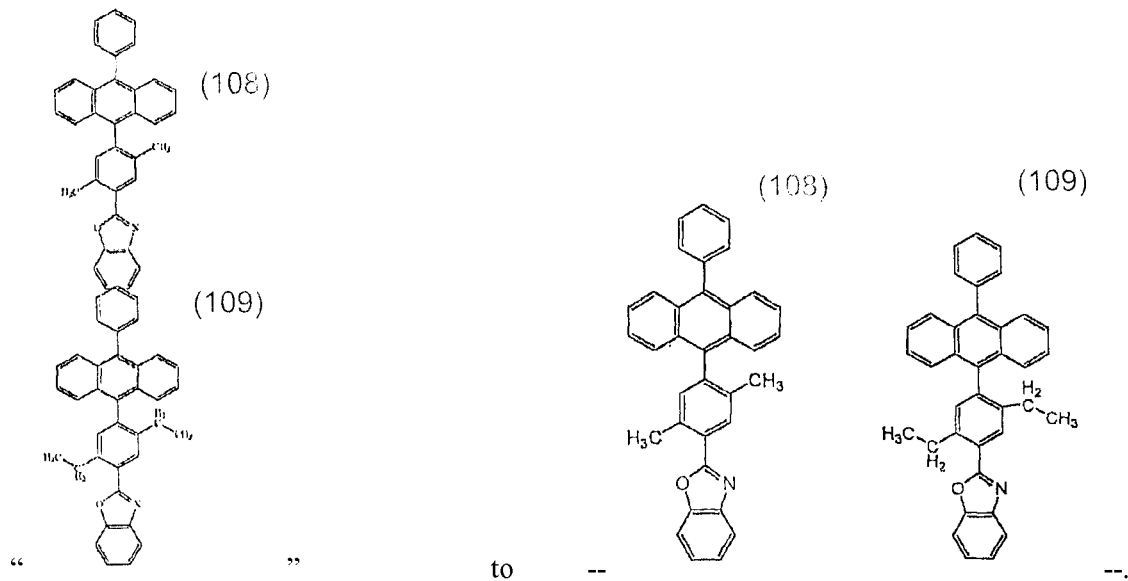

Column 94, Lines 10 to 11; Change "poly[N-(4-{1'-[" to --[N-(4-{N'-[--.

Column 94, Line 64; Change "iridium(II)" to --iridium(III)--.

Column 94, Line 65; Change "iridium(II)" to --iridium(III)--.

Column 94, Line 67; Change "iridium(II)" to --iridium(III)--.

Column 95, Line 11; Change "Ir(Pq)₃);" to --Ir(pq)₃);--.

Column 95, Line 15; Change "iridium(II)" to --iridium(III)--.

Column 95, Line 16; Change "iridium(II)" to --iridium(III)--.

Column 95, Line 18; Change "iridium(II)" to --iridium(III)--.

Signed and Sealed this
Eighteenth Day of August, 2015

Michelle K. Lee
*Director of the United States Patent and Trademark Office*

CERTIFICATE OF CORRECTION (continued)

U.S. Pat. No. 8,859,108 B2

Column 96, Line 36; Change "CZA1PA)," to --CzA1PA--.

Column 104, Line 55; Change "irradiation. An EL" to --irradiation.

[New paragraph] An EL--.

Column 105, Line 35; Change "or the like). The sealing" to --or the like).

[New paragraph] The sealing--.

Column 114, Line 51; Change "(m, 100H)," to --(m, 10H),--.

Column 119, Line 53; Change "211)," to --2H),--.

Column 120, Line 37; Change "2.90 eV A LUMO" to --2.90 eV. A LUMO--.

Column 122, Line 54; Change "104 Pa," to --$10^{-4}$ Pa,--.

Column 133, Line 32; Change "FIG. 45A. Further," to --FIG. 45A.

[New paragraph] Further,--.

Column 134, Line 6; Change "2.90 eV A LUMO" to --2.90 eV. A LUMO--.

Column 137, Line 39; Change "2.90 eV A LUMO" to --2.90 eV. A LUMO--.

Column 144, Line 55; Change "2.99 eV A LUMO" to --2.99 eV. A LUMO--.

Column 145, Line 59; Change "104 Pa," to --$10^{-4}$ Pa,--.

Column 145, Line 65; Change "50 m" to --50 nm--.

Column 147, Line 15; Change "2.0 μm/W," to --2.0 lm/W,--.

Column 147, Line 16; Change "CE" to --ClE--.

Column 148, Line 63; Change "aluminum(I)" to --aluminum(III)--.

Column 150, Line 13; Change "110 Pa," to --$10^{-4}$ Pa,--.

Column 150, Lines 44 to 45; Change "200 nM" to --200 nm--.

Column 150, Lines 51 to 52; Change "aluminum(II)" to --aluminum(III)--.

In the Claims:

Column 153, Line 1, Claim 8; Change "claim 4," to --claim 5,--.